United States Patent [19]
Wrobel et al.

[11] Patent Number: 6,110,962
[45] Date of Patent: Aug. 29, 2000

[54] 11-ARYL-BENZO[B]NAPHTHO[2,3-D]FURANS AND 11-ARYL-BENZO[B]NAPHTHO[2,3-D] THIOPHENES USEFUL IN THE TREATMENT OF INSULIN RESISTANCE AND HYPERGLYCEMIA

[75] Inventors: Jay E. Wrobel, Lawrenceville; Arlene J. Dietrich, Delran; Zenan Li, Plainsboro, all of N.J.

[73] Assignee: American Home Products Corporation, Madison, N.J.

[21] Appl. No.: 09/307,840

[22] Filed: May 10, 1999

Related U.S. Application Data

[60] Provisional application No. 60/098,554, May 12, 1998.

[51] Int. Cl.[7] .......................... A61K 31/34; A61K 31/38; C07D 307/77; C07D 33/52
[52] U.S. Cl. .......................... 514/443; 514/382; 514/397; 514/414; 514/337; 514/468; 546/281.1; 546/284.1; 548/252; 548/311.4; 548/454; 549/6; 549/220; 549/42; 549/457
[58] Field of Search ..................... 549/42, 457; 514/443, 514/468

[56] References Cited

U.S. PATENT DOCUMENTS

| | | | |
|---|---|---|---|
| 4,808,599 | 2/1989 | Dubroeucq et al. | 514/320 |
| 5,698,574 | 12/1997 | Riedl et al. | 514/376 |

FOREIGN PATENT DOCUMENTS

| | | |
|---|---|---|
| 0568289 | 11/1993 | European Pat. Off. . |
| 4016854 | 1/1992 | Japan . |

OTHER PUBLICATIONS

Hastings, John S. et al., *J. Chem.Soc., Perkins Trans. 1*, 1975, (14), pp. 1839–1842.
Ahmad, F. et al., Biochemica et Biophysica Acta, 1248, 1995, pp. 57–69.
Chang, A.Y. et al., Diabetes, 32, 1983, pp. 830–838.
Coleman, D. L., Diabetologia, 14, 1978, pp. 141–148.
DeFronzo, R. A. et al., Diabetes Care, 14:3, 1991, pp. 173–194.
Goldstein, B. J., Receptor, 3, 1993, pp. 1–15.
Goldstein, B. J. et al., Mol. and Cell. Biochem., 109, 1992, pp. 107–113.
Goldstein, B. J., J. Cell. Biochem., 48, 1992, pp. 33–42.
Haring, H. U., Diabetologia, 34, 1991, pp. 848–861.
Harris, M. I. et al., Diabetes in America, 1985, Chapter 29, pp. 1–48.

(List continued on next page.)

*Primary Examiner*—Bernard Dentz
*Attorney, Agent, or Firm*—Arnold S. Milowsky

[57] ABSTRACT

This invention provides compounds of Formula I having the structure

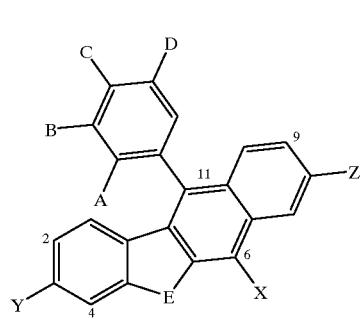

(I)

wherein
A is hydrogen, halogen, or OH;
B and D are each, independently, hydrogen, halogen, CN, alkyl of 1–6 carbon atoms, aryl, aralkyl of 6–12 carbon atoms, nitro, amino or OR;
R is hydrogen, alkyl of 1–6 carbon atoms, —$COR^1$, —$CH_2CO_2R^1$, —$CH(R^{1a})CO_2R^1$, or —$SO_2R^1$;
$R^1$ and $R^{1a}$ are each, independently, hydrogen, alkyl of 1–6 carbon atoms, aralkyl of 6–12 carbon atoms or aryl;
E is S, SO, $SO_2$, O;
X is hydrogen, halogen, alkyl of 1–6 carbon atoms, CN, perfluoroalkyl of 1–6 carbon atoms, alkoxy of 1–6 carbon atoms, aryloxy, arylalkoxy of 6–12 carbon atoms, nitro, amino, alkylsulfanyl of 1–6 carbon atoms, arylsulfanyl, pyridylsulfanyl, 2-N,N-dimethylaminoethylsulfanyl, or —$OCH_2CO_2R^{1b}$;
$R^{1b}$ is hydrogen or alkyl of 1–6 carbon atoms;
Y and Z are each, independently, hydrogen or $OR^2$;
$R^2$ is hydrogen, alkyl of 1–6 carbon atoms, aralkyl of 6–12 carbon atoms, or —$CH_2CO_2R^3$;
$R^3$ is hydrogen or alkyl of 1–6 carbon atoms;
C is hydrogen, halogen or $OR^4$;
$R^4$ is hydrogen, alkyl of 1–6 carbon atoms, —$CH(R^5)W$, —$C(CH_3)_2CO_2R^6$, 5-thiazolidine-2,4-dione, —$CH(R^7)CH_2CO_2R^6$, —$COR^6$, $PO_3(R^6)_2$, or —$SO_2R^6$;
$R^5$ is hydrogen, alkyl of 1–6 carbon atoms, aralkyl, aryl, $CH_2$(1H-imidazol-4-yl), —$CH_2$(3-1H-indolyl), —$CH_2CH_2$(1,3-dioxo-1,3-dihydro-isoindol-2-yl), —$CH_2CH_2$(1-oxo-1,3-dihydro-isoindol-2-yl), —$CH_2$(3-pyridyl), or —$CH_2CO_2H$;
W is —$CO_2R^6$, —$CONH_2$, —CONHOH, CN, —CONH$(CH_2)_2CN$, 5-tetrazole, —$PO_3(R^6)_2$, —$CH_2OH$, or —$CH_2Br$, —$CONR^6CHR^7CO2R^8$,
$R^6$ is hydrogen, alkyl of 1–6 carbon atoms, aryl or aralkyl;
$R^7$ is hydrogen, alkyl of 1–6 carbon atoms, aryl or aralkyl;
$R^8$ is hydrogen, alkyl of 1–6 carbon atoms, aryl or aralkyl;
or a pharmaceutically acceptable salt thereof, which are useful in treating metabolic disorders related to insulin resistance or hyperglycemia.

52 Claims, No Drawings

OTHER PUBLICATIONS

Jarrett, R. J., Diabetes/Metabolism Reviews, 5:7, 1989, pp. 547–558.
Lanzetta, P. A. et al., Analytical Biochem. 100, 1979, pp. 95–97.
McGuire, M. C. et al., Diabetes, 40, Jul. 1991, pp. 939–942.
Meyerovitch, J. et al., J. Clin. Invest., 87, Apr. 1991, pp. 1286–1294.
Meyerovitch, J. et al., J. Clin. Invest., 84, Sep. 1989, pp. 976–983.
Mitsunobu, O., Synthesis, Jan. 1981, pp. 1–28.
Nutaitis, C. F., Organic Preparations and Procedures Int., 23(4), 1991, pp. 403–411.
Perich, J. W. et al., Synthesis, Feb. 1988, pp. 142–144.
Phillion, D. P. et al., Tetrahedron, 27:13, 1986, pp. 1477–1480.
Pyorala, K. et al., Diabetes/Metabolism Reviews, 3:2, 1987, pp. 463–524.
Reaven, G. M. et al., Amer. J. Med., 60,1976, pp. 80–88.
Sredy, J. et al., Metabolism, 44:8, 1995, pp. 1074–1081.
Stout, R. W., Metabolism, 34:12 (Suppl 1), Dec. 1985, pp. 7–12.
Zask, A. et al., J. Med. Chem., 33, 1990, pp. 1418–1423.
Chen, H.–M. et al., Indian J. Chem., 35B, Dec. 1996, pp. 1304–1307.
d'Ishia, M. et al., Tetrahedron, 43:2, 1987, pp. 431–434.
Dryhurst, G. et al., J. Am. Chem. Soc., 111, 1989, pp. 719–726.
Guirguis, N. R. et al., J. Prakt. Chemie, 332:3, 1990, pp. 414–418.
Guirguis, N. R. et al., Liebigs Ann. Chem., 1986, pp. 1003–1011.
Han, B. H. et al., Tetrahedron Leter, 31:8, 1990, pp. 1181–1182.
Hashem, A. I., J. Prakt. Chemie, 319:4, 1977, pp. 689–692.
Konopelski, J. P. et al., Synlett, Letters, Jul. 1996, pp. 609–611.
Kuroda, T. et al., J. Org. Chem., 59, 1994, pp. 7353–7357.
Kuroda, T. et al., J. Chem. Soc., Chem. Commun., 1991, pp. 1635–1636.
Lefker, B. A. et al., Tetrahedron Letters, 35:29, 1994, pp. 5205–5208.
Molina, P. et al., Tetrahedron, 50:17, 1994, pp. 5027–5036.
Molina, P. et al., Tetrahedron Letters, 34:17, 1993, pp. 2809–2812.
Napolitano, A. et al., Tetrahedron, 45:21, 1989, pp. 6749–6760.
Schuster, I. I., et al., J. Org. Chem., 53, 1988, pp. 5819–5825.
Kano et al, Heterocycles vol. 19, No. 6, pp. 1033–1037, 1982.

11-ARYL-BENZO[B]NAPHTHO[2,3-D]FURANS AND 11-ARYL-BENZO[B]NAPHTHO[2,3-D] THIOPHENES USEFUL IN THE TREATMENT OF INSULIN RESISTANCE AND HYPERGLYCEMIA

This application claims the benefit of U.S. Provisional Application No. 60/098,554, which was converted from U.S. patent application Ser. No. 09/076,592, filed May 12, 1998, pursuant to a petition filed under 37 C.F.R. 1.53(c)(2)(i) on Jul. 6, 1998.

BACKGROUND OF THE INVENTION

The prevalence of insulin resistance in glucose intolerant subjects has long been recognized. Reaven et al (*American Journal of Medicine* 1976, 60, 80) used a continuous infusion of glucose and insulin (insulin/glucose clamp technique) and oral glucose tolerance tests to demonstrate that insulin resistance existed in a diverse group of nonobese, nonketotic subjects. These subjects ranged from borderline glucose tolerant to overt, fasting hyperglycemia. The diabetic groups in these studies included both insulin dependent (IDDM) and noninsulin dependent (NIDDM) subjects.

Coincident with sustained insulin resistance is the more easily determined hyperinsulinemia, which can be measured by accurate determination of circulating plasma insulin concentration in the plasma of subjects. Hyperinsulinemia can be present as a result of insulin resistance, such as is in obese and/or diabetic (NIDDM) subjects and/or glucose intolerant subjects, or in IDDM subjects, as a consequence of over injection of insulin compared with normal physiological release of the hormone by the endocrine pancreas.

The association of hyperinsulinemia with obesity and with ischemic diseases of the large blood vessels (e.g. atherosclerosis) has been well established by numerous experimental, clinical and epidemiological studies (summarized by Stout, *Metabolism* 1985, 34, 7, and in more detail by Pyorala et al, *Diabetes/Metabolism Reviews* 1987, 3, 463). Statistically significant plasma insulin elevations at 1 and 2 hours after oral glucose load correlates with an increased risk of coronary heart disease.

Since most of these studies actually excluded diabetic subjects, data relating the risk of atherosclerotic diseases to the diabetic condition are not as numerous, but point in the same direction as for nondiabetic subjects (Pyorala et al). However, the incidence of atherosclerotic diseases in morbidity and mortality statistics in the diabetic population exceeds that of the nondiabetic population (Pyorala et al; Jarrett *Diabetes/Metabolism Reviews* 1989,5, 547; Harris et al, Mortality from diabetes, in *Diabetes in America* 1985).

The independent risk factors obesity and hypertension for atherosclerotic diseases are also associated with insulin resistance. Using a combination of insulin/glucose clamps, tracer glucose infusion and indirect calorimetry, it has been demonstrated that the insulin resistance of essential hypertension is located in peripheral tissues (principally muscle) and correlates directly with the severity of hypertension (DeFronzo and Ferrannini, *Diabetes Care* 1991, 14, 173). In hypertension of the obese, insulin resistance generates hyperinsulinemia, which is recruited as a mechanism to limit further weight gain via thermogenesis, but insulin also increases renal sodium reabsorption and stimulates the sympathetic nervous system in kidneys, heart, and vasculature, creating hypertension.

It is now appreciated that insulin resistance is usually the result of a defect in the insulin receptor signaling system, at a site post binding of insulin to the receptor. Accumulated scientific evidence demonstrating insulin resistance in the major tissues which respond to insulin (muscle, liver, adipose), strongly suggests that a defect in insulin signal transduction resides at an early step in this cascade, specifically at the insulin receptor kinase activity, which appears to be diminished (reviewed by Haring, *Diabetalogia* 1991, 34, 848).

Protein-tyrosine phosphatases (PTPases) play an important role in the regulation of phosphorylation of proteins. The interaction of insulin with its receptor leads to phosphorylation of certain tyrosine molecules within the receptor protein, thus activating the receptor kinase. PTPases dephosphorylate the activated insulin receptor, attenuating the tyrosine kinase activity. PTPases can also modulate post-receptor signaling by catalyzing the dephosphorylation of cellular substrates of the insulin receptor kinase. The enzymes that appear most likely to closely associate with the insulin receptor and therefore, most likely to regulate the insulin receptor kinase activity, include PTP1B, LAR, PTPα and SH-PTP2 (B. J. Goldstein, *J. Cellular Biochemistry* 1992, 48, 33; B. J. Goldstein, *Receptor* 1993, 3, 1–15,; F. Ahmad and B. J. Goldstein *Biochim. Biophys Acta* 1995, 1248, 57–69).

McGuire et al. (*Diabetes* 1991, 40, 939), demonstrated that nondiabetic glucose intolerant subjects possessed significantly elevated levels of PTPase activity in muscle tissue vs. normal subjects, and that insulin infusion failed to suppress PTPase activity as it did in insulin sensitive subjects.

Meyerovitch et al (*J. Clinical Invest.* 1989, 84, 976) observed significantly increased PTPase activity in the livers of two rodent models of IDDM, the genetically diabetic BB rat, and the STZ-induced diabetic rat. Sredy et al (*Metabolism*, 44, 1074, 1995) observed similar increased PTPase activity in the livers of obese, diabetic ob/ob mice, a genetic rodent model of NIDDM.

The compounds of this invention have been shown to inhibit PTPases derived from rat liver microsomes and human-derived recombinant PTPase-1B (hPTP-1B) in vitro. They are useful in the treatment of insulin resistance associated with obesity, glucose intolerance, diabetes mellitus, hypertension and ischemic diseases of the large and small blood vessels.

K. Shinzo, et al., *Heterocylces* 1982, 19, 1033–1037 disclosed a synthesis of benzo[b]naphtho[2,3-d]thiophenes of which two examples also had a 11-phenyl substituent as shown by structure A below. None of the examples in this *Heterocylces* article contained the appropriate substitution, nor any subtitution on the 11-phenyl group necessary for in vitro PTPase inhibition activity or in vivo antidiabetic activity.

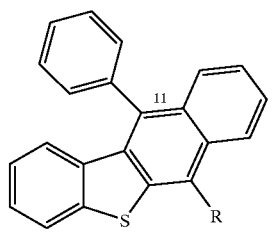

(A), R = H, CH₃

J. Hastings, et al.,*J. Chem. Soc., Perkin Trans.* 1 1975, 19, 1995–1998 and J. Hastings, et al., *J. Chem. Soc., Perkin*

Trans. 1 1972, 14, 1839–1842 disclosed three examples of benzo[b]naphtho[2,3-d]furans that also had a 11-phenyl substituent as shown by structure B below. None of the examples in these *J. Chem. Soc., Perkin Trans.* 1 articles contained the appropriate substitution on the 11-phenyl group necessary for in vitro PTPase inhibition activity or in vivo antidiabetic activity.

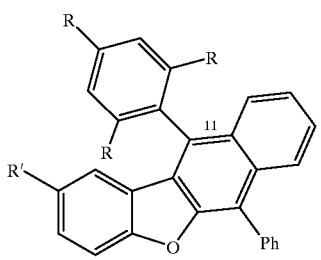

(B)

1) R = CH₃, R' = H
2) R, R' = H
3) R = H, R' = CH₃

DESCRIPTION OF THE INVENTION

This invention provides a compound of formula I having the structure

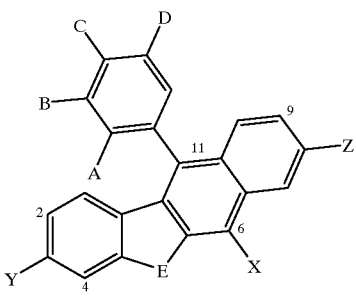

(I)

wherein

A is hydrogen, halogen, or OH;

B and D are each, independently, hydrogen, halogen, CN, alkyl of 1–6 carbon atoms, aryl, aralkyl of 6–12 carbon atoms, nitro, amino or OR;

R is hydrogen, alkyl of 1–6 carbon atoms, —$COR^1$, —$CH_2CO_2R^1$, —$CH(R^{1a})CO_2R^1$, or —$SO_2R^1$;

$R^1$ and $R^{1a}$ are each, independently, hydrogen, alkyl of 1–6 carbon atoms, aralkyl of 6–12 carbon atoms or aryl;

E is S, SO, $SO_2$, O;

X is hydrogen, halogen, alkyl of 1–6 carbon atoms, CN, perfluoroalkyl of 1–6 carbon atoms, alkoxy of 1–6 carbon atoms, aryloxy, arylalkoxy of 6–12 carbon atoms, nitro, amino, alkylsulfanyl of 1–6 carbon atoms, arylsulfanyl, pyridylsulfanyl, 2-N,N-dimethylaminoethylsulfanyl, or —$OCH_2CO_2R^{1b}$;

$R^{1b}$ is hydrogen or alkyl of 1–6 carbon atoms;

Y and Z are each, independently, hydrogen or $OR^2$;

$R^2$ is hydrogen, alkyl of 1–6 carbon atoms, aralkyl of 6–12 carbon atoms, or —$CH_2CO_2R^3$;

$R^3$ is hydrogen or alkyl of 1–6 carbon atoms;

C is hydrogen, halogen or $OR^4$;

$R^4$ is hydrogen, alkyl of 1–6 carbon atoms, —$CH(R^5)W$, —$C(CH_3)_2CO_2R^6$, 5-thiazolidine-2,4-dione, —$CH(R^7)CH_2CO_2R^6$, —$COR^6$, $PO_3(R^6)_2$, or —$SO_2R^6$;

$R^5$ is hydrogen, alkyl of 1–6 carbon atoms, aralkyl, aryl, $CH_2$(1H-imidazol-4-yl), —$CH_2$(3-1H-indolyl), —$CH_2CH_2$(1,3-dioxo-1,3-dihydro-isoindol-2-yl), —$CH_2CH_2$(1-oxo-1,3-dihydro-isoindol-2-yl), —$CH_2$(3-pyridyl), or —$CH_2CO_2H$;

W is —$CO_2R^6$, —$CONH_2$, —CONHOH, CN, —$CONH(CH_2)_2CN$, 5-tetrazole, —$PO_3(R^6)_2$, —$CH_2OH$, or —$CH_2Br$, —$CONR^6CHR^7CO2R^8$, $R^6$ is hydrogen, alkyl of 1–6 carbon atoms, aryl or aralkyl;

$R^7$ is hydrogen, alkyl of 1–6 carbon atoms, aryl or aralkyl;

$R^8$ is hydrogen, alkyl of 1–6 carbon atoms, aryl or aralkyl; or a pharmaceutically acceptable salt thereof, which are useful in treating metabolic disorders related to insulin resistance or hyperglycemia.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids when a compound of this invention contains a basic moiety, such as when $R^5$ is —$CH_2$(3-pyridyl) or contains similar basic moieties. Salts may also be formed from organic and inorganic bases, preferably alkali metal salts, for example, sodium, lithium, or potassium, when a compound of this invention contains a carboxylate or phenolic moiety.

Alkyl includes both straight chain as well as branched moieties. Halogen means bromine, chlorine, fluorine, and iodine. It is preferred that the aryl portion of the aryl or aralkyl substituent is a phenyl or naphthy; with phenyl being most preferred. The aryl moiety may be optionally mono-, di-, or tri- substituted with a substituent selected from the group consisting of alkyl of 1–6 carbon atoms, alkoxy of 1–6 carbon atoms, trifluoromethyl, halogen, alkoxycarbonyl of 2–7 carbon atoms, alkylamino of 1–6 carbon atoms, and dialkylamino in which each of the alkyl groups is of 1–6 carbon atoms, nitro, cyano, —$CO_2H$, alkylcarbonyloxy of 2–7 carbon atoms, and alkylcarbonyl of 2–7 carbon atoms.

The compounds of this invention may contain an asymmetric carbon atom and some of the compounds of this invention may contain one or more asymmetric centers and may thus give rise to optical isomers and diastereomers. While shown without respect to stereochemistry in Formula I, the present invention includes such optical isomers and diastereomers; as well as the racemic and resolved, enantiomerically pure R and S stereoisomers; as well as other mixtures of the R and S stereoisomers and pharmaceutically acceptable salts thereof.

The compounds of this invention may be atropisomers by virtue of possible restricted or slow rotation about the aryl-tetracyclic single bond. This restricted rotation creates additional chirality and leads to enantiomeric forms. If there is an additional chiral center in the molecule, diastereomers exist and can be seen in the NMR and via other analytical techniques. While shown without respect to atropisomer stereochemistry in Formula I, the present invention includes such atoropisomers (enantiomers and diastereomers; as well as the racemic, resolved, pure diastereomers and mixtures of diasteomers) and pharmaceutically acceptable salts thereof.

Preferred compounds of this invention include compounds of formula (I) in which

A and B are each, independently, hydrogen, or bromine;
C and D are OH;
E is S, or O;
X is hydrogen, halogen, alkyl of 1–6 carbon atoms, CN, alkoxy of 1–6 carbon atoms, aryloxy of 6–12 carbon atoms; arylalkoxy of 6–12 carbon atoms, arylsulfanyl, or pyridylsulfanyl;
Y and Z are H;
or a pharmaceutically acceptable salt thereof.

Other preferred compounds of this invention include compounds of formula (I) in which A is hydrogen;
B and D are each, independently, halogen, alkyl of 1–6 carbon atoms, aryl or aralkyl of 6–12 carbon atoms, or alkoxy of 1–6 carbon atoms;
C is $OR^4$
E is S, O;
X is hydrogen, halogen, alkyl of 1–6 carbon atoms, perfluoroalkyl of 1–6 carbon atoms, CN, alkoxy of 1–6 carbon atoms, aryloxy, arylalkoxy of 6–12 carbon atoms, arylsulfanyl, pyridylsulfanyl;
Y and Z are H;
$R^4$ is H, alkyl of 1–6 carbon atoms, —CH($R^5$)W, or 5-thiazolidine-2,4-dione;
$R^5$ is H, alkyl of 1–6 carbon atoms, aralkyl of 6–12 carbon atoms, aryl, —CH$_2$(3-1H-indolyl), —CH$_2$CH$_2$(1,3-dioxo-1,3-dihydro-isoindol-2-yl), —CH$_2$CH$_2$(1-oxo-1,3-dihydro-isoindol-2-yl), or —CH$_2$(3-pyridyl);
W is —CO$_2$R$^6$, —CONH$_2$, —CONHOH, -5-tetrazole, or —PO$_3$(R$^6$)$_2$;
$R^6$ is hydrogen or alkyl of 1–6 carbon atoms;
or a pharmaceutically acceptable salt thereof.

More preferred compounds of this invention include:
(R)-2-[2,6-dibromo-4-(6-bromo-benzo[b]naphtho[2,3-d]furan-11-yl)-phenoxy]-3-phenyl-propionic acid;
(R)-2-[2,6-dibromo-4-(6-bromo-benzo[b]naphtho[2,3-d]thiophen-11-yl)-phenoxy]-3-phenyl-propionic acid;
(5'-benzo[b]naphtho[2,3-d]thiophen-11-yl)-[1,1';3',1"]terphenyl-2'-yloxy)-acetic acid;
4-(6-bromo-benzo[b]naphtho[2,3-d]thiophen-11yl)-2,6-diisopropyl-phenoxy)-acetic acid;
(R)-2-[2,6-dibromo-4-(6-iodo-benzo[b]naphtho[2,3-d]thiophen-11-yl)-phenoxy]-3-phenyl-propionic acid;
2-[2,6-dibromo-4-(6-bromo-benzo[b]naphtho[2,3-d]thiophen-11-yl)-phenoxy]-3-(4-fluorophenyl-propionic acid;
(R)-2-[2-bromo-4-(6-bromo-benzo[b]naphtho[2,3-d]thiophen-11-yl)-6-methoxy-phenoxy]-3-phenyl-propionic acid;
(R)-2-[2,6-dibromo-4-(6-bromo-benzo[b]naphtho[2,3-d]thiophen-11-yl)-phenoxy]-propionic acid;
(R)-2-[2,6-dibromo-4-(6-iodo-benzo[b]naphtho[2,3-d]thiophen-11-yl)-phenoxy]-propionic acid;
2-[2,6-dibromo-4-(6-bromo-benzo[b]naphtho[2,3-d]thiophen-11-yl)-phenoxy]-hexanoic acid;
(R)-2-[2,6-dibromo-4-(6-methoxy-benzo[b]naphtho[2,3-d]thiophen-11-yl)-phenoxy]-3-phenyl-propionic acid;
(R)-2-[2,6-dibromo-4-(6-chloro-benzo[b]naphtho[2,3-d]thiophen-11-yl)-phenoxy]-3-phenyl-propionic acid;
(R)-2-[2,6-dibromo-4-(6-phenylsulfanyl-benzo[b]naphtho[2,3-d]thiophen-11-yl)-phenoxy]-propionic acid;
(R)-2-[2,6-dibromo-4-(6-phenylsulfanyl-benzo[b]naphtho[2,3-d]thiophen-11-yl)-phenoxy]-3-phenyl-propionic acid;
2-[2,6-dibromo-4-(6-bromo-benzo[b]naphtho[2,3-d]thiophen-11-yl)-phenoxy]-3-(1H-indol-3-yl)-propionic acid;
(R)-2-[2,6-diiodo-4-(benzo[b]naphtho[2,3-d]thiophen-11-yl)-phenoxy]-3-phenyl-propionic acid;
(R)-2-[2,6-dibromo-4-(6-bromo-benzo[b]naphtho[2,3-d]thiophen-11-yl)-phenoxy]-3-phenyl-butyric acid;
(R)-2-[2,6-dibromo-4-(6-trifluoromethyl-benzo[b]naphtho[2,3-d]thiophen-11-yl)-phenoxy]-3-phenyl-propionic acid;
(S)-2-[2,6-dibromo-4-(6-bromo-benzo[b]naphtho[2,3-d]thiophen-11-yl)-phenoxy]-3-phenyl-butyric acid;
(R)-2-(4-benzo[b]naphtho[2,3-d]thiophen-11-yl-2,6-dibromo-phenoxy)-4-(1,3-dioxo-1,3-dihydro-isoindol-2-yl)-butyric acid;
(R)-2-[2,6-dibromo-4-(6-bromo-benzo[b]naphtho[2,3-d]thiophen-11-yl)-phenoxy]-4-(1,3-dioxo-1,3-dihydro-isoindol-2-yl)-butyric acid;
{1-[2,6-dibromo-4-(6-bromo-benzo[b]naphtho[2,3-d]thiophen-11-yl)-phenoxy]-3-phenyl-propyl}-phosphonic acid;
(R)-2-[2,6-dibromo-4-(6-(pyridin-4-ylsulfanyl)-benzo[b]naphtho[2,3-d]thiophen-11-yl)-phenoxy]-3-phenyl-propionic acid;
(R)-2-[2,6-dibromo-4-(6-benzyloxy-benzo[b]naphtho[2,3-d]thiophen-11-yl)-phenoxy]-3-phenyl-propionic acid;
(S)-2-[2,6-dibromo-4-(6-bromo-benzo[b]naphtho[2,3-d]thiophen-11-yl)-phenoxy]-3-phenyl-propionic acid;
(R)-2-[2,6-dibromo-4-(6-bromo-benzo[b]naphtho[2,3-d]thiophen-11-yl)-phenoxy]-2-phenyl-acetic acid;
[2,6-dibromo-4-(6-bromo-benzo[b]naphtho[2,3-d]thiophen-11-yl)-phenoxy]-acetic acid;
[2,6-dibromo-4-(6-bromo-benzo[b]naphtho[2,3-d]thiophen-11-yl)-phenoxymethyl]-phosphonic acid;
(S)-2-[2,6-dibromo-4-(6-cyano-benzo[b]naphtho[2,3-d]thiophen-11-yl)-phenoxy]-3-phenyl-propionic acid;
2-[2,6-dibromo-4-(6-bromo-benzo[b]naphtho[2,3-d]thiophen-11-yl)-phenoxy]-3-(naphthalen-2yl)-propionic acid;
(R)-2-[2,6-dibromo-4-(6-bromo-benzo[b]naphtho[2,3-d]thiophen-11-yl)-phenoxy]-4-(1-oxo-1,3-dihydro-isoindol-2-yl)-butyric acid;
(R)-2-[2,6-dibromo-4-(6-methyl-benzo[b]naphtho[2,3-d]thiophen-11-yl)-phenoxy]-3-phenyl-propionic acid;
(R)-5-{1-[2,6-dibromo-4-(6-bromo-benzo[b]naphtho[2,3-d]thiophen-11-yl)-phenoxy]-2-phenyl-ethyl}-1H-tetrazole;
(R)-2-[2,6-dibromo-4-(6-bromo-benzo[b]naphtho[2,3-d]thiophen-11-yl)-phenoxy]-N-hydroxy-3-phenyl-propionamide;
5-[2,6-dibromo-4-(6-bromo-benzo[b]naphtho[2,3-d]thiophen-11-yl)-phenoxy]-thiazolidine-2,4-dione;
(R)-2-[2,6-diiodo-4-(benzo[b]naphtho[2,3-d]thiophen-11-yl)-phenoxy]--propionic acid;
2-[2,6-dibromo-4-(6-bromo-benzo[b]naphtho[2,3-d]thiophen-11-yl)-phenoxy]-3-pyridin-3-yl-propionic acid;
(R)-2-[4-(6-bromo-benzo[b]naphtho[2,3-d]thiophen-11-yl)-2,6-diisopropyl-phenoxy)-3-phenyl-propionic acid;

(R)-2-[4-(6-bromo-benzo[b]naphtho[2,3-d]thiophen-11-yl)-2,6-diisopropyl-phenoxy)-propionic acid;

4-(6-bromo-benzo[b]naphtho[2,3-d]thiophen-11-yl)-benzene-1,2-diol;

3-bromo-5-(6-bromo-benzo[b]naphtho[2,3-d]thiophen-11-yl)-benzene-1,2-diol;

4-bromo-5-(6-bromo-benzo[b]naphtho[2,3-d]thiophen-11-yl)-benzene-1,2-diol;

[2,6-dibromo-4-(6-bromo-benzo[b]naphtho[2,3-d]furan-11-yl)-phenoxy]-acetic acid;

2,6-dibromo-4-(6-bromo-benzo[b]naphtho[2,3-d]furan-11yl)-phenol;

or pharmaceutically acceptable salts thereof.

The compounds of this invention can be prepared according to the following schemes from commercially available starting materials or starting materials which can be prepared using to literature procedures. These schemes show the preparation of representative compounds of this invention.

Scheme IA

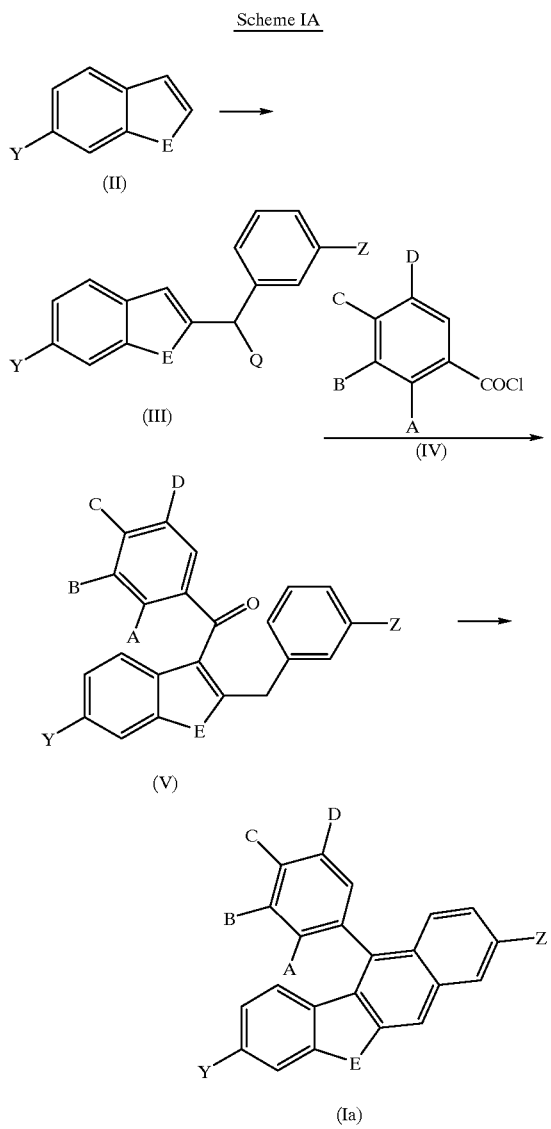

In Scheme 1A, commercially available thianaphthene (II: Y=H; E is S) or benzofuran (II: Y=H; E is O) is treated with one to 1.3 molar equivalents of an alkyl lithium reagent such as N-butyl lithium most preferably in a nonprotic solvent such as THF at temperatures ranging from −78° C. to room temperature under an inert atmosphere such as nitrogen or argon to provide the 2-lithiated-thianaphthene or benzofuran derivative. This lithiated analog is reacted in situ with one or more molar equivalents of benzaldehyde, generally at −78° C. to room temperature for 5 min to 3 h to provide the compound of formula (III: Y, Z=H; Q=OH; E is S or O). The hydroxy group (Q=OH) of (III) can be removed by a number of reduction procedures such as hydrogenation using palladium catalysts to produce the compound of formula (III: Q, Y, Z=H; E is S or O) but is most conveniently removed using the method of Nutaitis, et. al. (*Org. Prep. and Proceed. Int.*1991, 23, 403–411) in which (III: Y, Z=H; Q=OH; E is S or O) is stirred with one to ten molar equivalents of sodium borohydride in a suitable solvent such as ether, THF or dichloromethane at 0° C. to room temperature and one to fifty molar equivalents of trifluoroacetic acid is slowly added over a 15 min to 3 h period to produce the compound of formula (III: Q, Y, Z=H; E is S or O). Alternatively, the 2-lithiated analog of thianaphthene (II: Y=H; E is S) or benzofuran (II: Y=H; E is O), in a nonprotic solvent such as THF, can be reacted with one or more molar equivalents of a benzyl halide such as benzyl bromide (PhCH$_2$Br) at −78° C. to room temperature to directly provide the compound of formula (III: Q, Y, Z=H; E is S or O).

In an analogous fashion, 6-methoxythianapthene (II: Y=OMe; E is S, S. L. Graham, et al., *J. Med. Chem.* 1989, 32, 2548–2554) can be used as starting material using the above sequences to provide the compound of formula (III: Q, Z=H; Y=OMe; E is S). Still, alternatively, using the above sequences and starting from thianapthene (II: Y=H; E is S) or benzofuran (II: Y=H; E is O), 3-methoxybenzaldehyde (o-anisaldehyde) can be used in place of benzaldehyde to prepare the compound of formula (III: Q, Y=H; Z=OMe; E is S or O). The latter compound (III: Q, Y=H, Z=OMe; E is S or O) can also be prepared from a 3-methoxybenzyl halide such as 3-methoxybenzyl bromide and the 2-lithiated analog of thianaphthene (II: Y=H; E is S) or benzofuran (II: Y=H; E is O) as described above.

The compounds of formula (III: Q=H; Y, Z is H or OMe; E is S or O) can be acylated with one or more molar equivalents of a commercially available benzoic acid chloride of formula (IV: A, B, C, D is H or OMe; with the A, B, C, D, combination of substituents having at least one OMe group but not more than three OMe groups) to produce the acylated derivative of formula (V: A, B, C, D is H or OMe; with the A, B, C, D, combination of substituents having at least one OMe group but not more than three OMe groups; Y, Z is H or OMe; E is S or O). This acylation is accomplished most readily using a one to five molar equivalents of a Lewis acid catalyst such as tin tetrachloride or aluminum chloride in an inert solvent such as dichloromethane, 1,2-dichloroethane or carbon disulfide, generally at temperatures such as −78° C. to room temperature.

Cyclization of the compounds of formula (V: A, B, C, D is H or OMe; with the A, B, C, D, combination of substituents having at least one OMe group but not more than three OMe groups; Y, Z is H or OMe; E is S or O) is generally best accomplished using one to ten molar equivalents of a strong Lewis acid such as a trihaloborane, most conveniently tribromoborane. The reaction is best performed at −78° C. with warming to room temperature in a halocarbon solvent such as dichloromethane under an inert atmosphere such as nitrogen or argon. These procedures not only effect cyclization and aromatization with concomitant loss of water, but also result in demethylation of any pendant methoxy moieties and result in the production of compounds of formula (Ia: A, B, C, D is H or OH; with the A, B, C, D, combination of substituents having at least one OH group but not more than three OH groups; Y, Z is H or OH; E is S or O).

In the cases in which the compound of formula (III: Q, Y=H; Z=OMe; E is S or O) contains a methoxy moiety in position Z, acylation with the compound of formula (IV: A, B, D is H; C is OMe; E is S or O) is effected as usual with a Lewis acid catalyst such as tin tetrachloride to produce the compound of formula (V: A, B, D, Y is H; C, Z is OMe; E is S or O) in situ. This compound, by virtue of its Z=OMe moiety, is activated to further facile cyclization under the acylation conditions to provide directly the compound of formula (Ia: A, B, D, Y is H; C, Z is OMe; E is S or O). This compound can then be demethylated using boron tribromide or boron trichloride to produce the compound of formula (Ia: A, B, D, Y is H; C, Z is OH; E is S or O).

In an analogous fashion to the reactions above in Scheme 1A, the compounds of formula (Ia: A is H; B, D is alkyl of 1–6 carbon atoms; C is OH; Y, Z is H; E is S or O) can be prepared starting from the compound of formula (III: Q, Y, Z is H; E is S or O) and the appropriate benzoic acid chloride (IV: A is H; B, D is alkyl of 1–6 carbon atoms; C is OMe). The benzoic acid chloride (IV: A is H; B, D is alkyl of 1–6 carbon atoms; C is OMe) is prepared from the corresponding benzoic acid by standard procedures using reagents such as oxalyl chloride and thionyl chloride. The starting benzoic acid of the benzoic acid chloride (IV: A is H; B, D is alkyl of 1–6 carbon atoms; C is OMe) is commercially available or can be easily prepared by known procedures. For example, the acid starting material for benzoic acid chloride (IV: A is H; B, D is isopropyl; C is OMe) can be prepared using a modification of the method of Schuster, et al., *J. Org. Chem* 1988, 53, 5819. Thus commercially available 2,6-diisopropyl phenol is brominated in the 4-position (bromine/ acetic acid), methylated (iodomethane/potassium carbonate/ DMF), reacted with n-butyl lithium to effect lithium halogen exchange and the resultant organolithium species is reacted with carbon dioxide to provide 3,5-diisopropyl, 4-methoxy benzoic acid.

The compounds of formula (Ia: A, C is F; D is H; B is OH; Y, Z is H; E is S or O) can be prepared starting from the compound of formula (III: Q, Y, Z is H; E is S or O) and the appropriate benzoic acid chloride (IV: A, C is F; D is H; B is OMe). The benzoic acid chloride (IV: A, C is F; D is H; B is OMe) is prepared from the corresponding benzoic acid by standard procedures using reagents such as oxalyl chloride and thionyl chloride. The starting benzoic acid of the benzoic acid chloride (IV: A, C is F; D is H; B is OMe) can be easily prepared from the known, 4-bromo-2,6-difluoroaniline (L. I. Kruse, et al., *Biochemistry* 1986, 25, 7271–7278) by reacting the latter compound with n-butyl lithium to effect deprotonation ortho to the bromine and fluorine atoms, reaction of the resultant organolithium species with carbon dioxide to install the carboxy moiety ortho to the bromine and fluorine atoms, and further reaction with n-butyl lithium to effect lithium-bromine exchange and reaction of the final, resultant organolithium species with a proton source upon aqueous workup to provide 2,4-difluoro, 3-methoxy benzoic acid. Precedence for the fluorine directed ortholithiation reaction over lithium-bromine exchange reaction is found in the following paper: F. Mongin and M. Schlosser, *Tetrahedron Lett.* 1996, 37, 6551–6554.

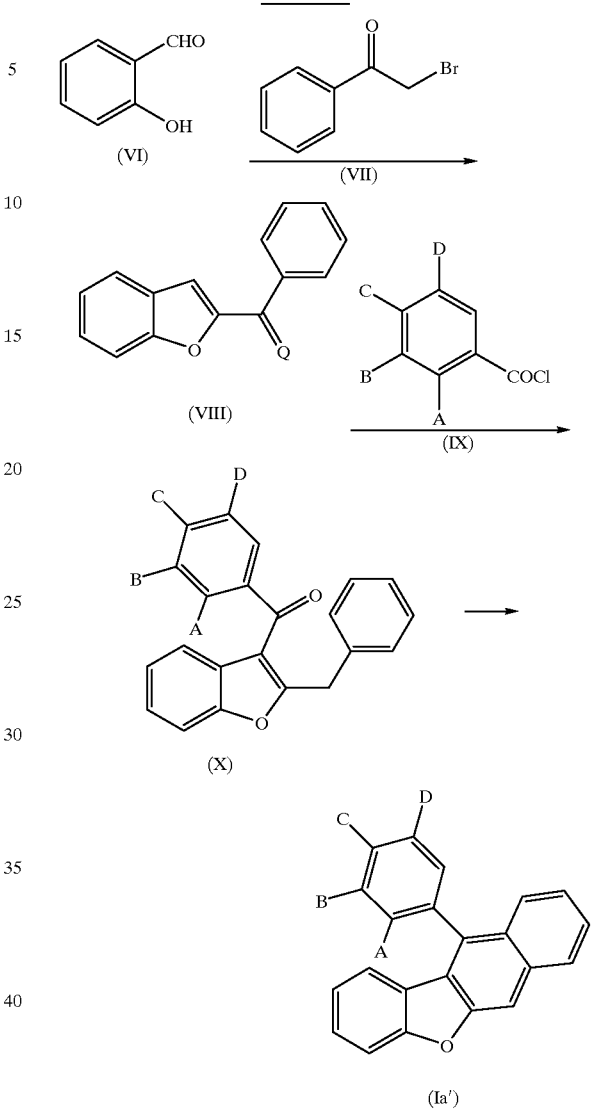

Scheme IB

In Scheme 1B, according to a procedure in *Syn. Comm.* 1987, 17, 341–354 commercially available salicylaldehyde (VI) is reacted with one molar equivalent of, 2-bromoacetophenone (VII), one or more molar equivalents of potassium carbonate and 5 mole % of tetrabutylammonium sulfate in a biphasic mixture of water and dichloromethane at room temperature to provide the compound of formula (VIII: Q=O). The ketone group (Q=O) of (VIII) can be reduced under Wolf-Kishner conditions (hydrazine, followed by potassium hydroxide in diethylene glycol reflux) to produce the compound of formula (VIII: Q=H₂).

The compounds of formula (VIII: Q=H₂) can be acylated with one or more molar equivalents of a commercially available benzoic acid chloride of formula (IX: A, B, C, D is H or OMe; with the A, B, C, D, combination of substituents having at least one OMe group but not more than three OMe groups) to produce the acylated derivative of formula (X: A, B, C, D is H or OMe; with the A, B, C, D, combination of substituents having at least one OMe group but not more than three OMe groups). This acylation is accomplished most readily using a one to five molar equivalents of a Lewis acid catalyst such as tin tetrachloride or aluminum chloride in an inert solvent such as dichloromethane, 1,2-dichloroethane or carbon disulfide, generally at temperatures such as −78° C. to room temperature.

Cyclization of the compounds of formula (X: A, B, C, D is H or OMe; with the A, B, C, D, combination of substituents having at least one OMe group but not more than three OMe groups) is generally best accomplished using one to ten molar equivalents of a strong Lewis acid such as a trihaloborane, most conveniently tribromoborane. The reaction is best performed at −78° C. with warming to room temperature in a halocarbon solvent such as dichloromethane under an inert atmosphere such as nitrogen or argon. These procedures not only effect cyclization and aromatization with concomitant loss of water, but also result in demethylation of any pendant methoxy moieties and result in the production of compounds of formula (Ia': A, B, C, D is H or OMe; with the A, B, C, D, combination of substituents having at least one OH group but not more than three OH groups).

In an analogous fashion to the reactions above in Scheme 1B, the compounds of formula (Ia': A is H; B, D is alkyl of 1–6 carbon atoms; C is OH) can be prepared starting from the compound of formula (VIII: Q is H₂) and the appropriate benzoic acid chloride (IX: A is H; B, D is alkyl of 1–6 carbon atoms; C is OMe). The benzoic acid chloride (IX: A is H; B, D is alkyl of 1–6 carbon atoms; C is OMe). is prepared from the corresponding benzoic acid by standard procedures using reagents such as oxalyl chloride and thionyl chloride. The starting benzoic acid of the benzoic acid chloride (IX is H; B, D is alkyl of 1–6 carbon atoms; C is OMe) is commercially available or can be easily prepared by known procedures. For example, the acid starting material for benzoic acid chloride (IX: A is H; B, D is isopropyl; C is OMe) can be prepared using a modification of the method of Schuster, et al., *J. Org. Chem* 1988, 53, 5819. Thus commercially available 2,6-diisopropyl phenol is brominated in the 4-position (bromine/acetic acid), methylated (iodomethane/potassium carbonate/DMF), reacted with n-butyl lithium to effect lithium halogen exchange and the resultant organolithium species is reacted with carbon dioxide to provide 3,5-diisopropyl, 4-methoxy benzoic acid.

Scheme 2

(Ib)

(Ic)

Further derivatives of the compounds of formula (I) in Scheme 2 can be prepared by the following methods. The phenol of formula (Ib: B, D, X is H; C is OH; E is S, O) can be brominated in three positions to afford the tribromophenol of formula (Ib: B, D, X is Br; C is OH; E is S, O) using at least 3 molar equivalents of molecular bromine in an appropriate solvent such as acetic acid. One to fifty molar equivalents of a salt of acetic acid such as potassium or sodium acetate can also be used as a co-reagent in this reaction although it is not absolutely required. The tribromophenol of formula (Ib: B, D, X is Br; C is OH; E is S, O) can be methylated to produce the methyl ether of formula (Ib: B, D, X is Br; C is OMe; E is S, O) by reacting the phenol moiety with a suitable methylating agent such as one or more molar equivalents of methyl iodide or dimethylsulfate employing a base such an alkali methyl carbonate or hydroxide such as potassium carbonate or sodium hydroxide in a suitable solvent such as THF, DMF or DMSO. The reaction is generally performed at temperatures ranging from 0° C. to 60° C.

The methyl ether of formula (Ib: B, D, X is Br; C is OMe; E is S, O) can be reacted with three or more molar equivalents of lower tetra-alkyltin in the presence of a palladium catalyst such as 1 to 10 mole % of bis(triphenylphosphine) palladium II chloride in a suitable solvent such as DMF, DMA or 1-methyl-2-pyrrolidinone at temperatures ranging from 140° C. to 200° C. to provide the trialkylmethoxy derivative of formula (Ib: B, D, X is alkyl of 1–6 carbon atoms; C is OMe; E is S, O). This methoxy analog can be converted to the corresponding phenol analog of formula (Ic: B, D, X is alkyl of 1–6 carbon atoms; E is S, O) using standard demethylation procedures including one or more molar equivalents of boron tribromide or boron trichloride in dichloromethane at −78° C. to room temperature; excess neat pyridinium hydrochloride at 190 to 280° C.; hydrobromic acid in acetic acid at 0° C. to 50° C.; excess trimethylsilylbromide or trimethylsilyliodide in dichloromethane, carbon tetrachloride or acetonitrile at −78° C. to 50° C.; lithium iodide in pyridine or quinoline at temperatures from 100° to 250° C. and one or more molar equivalents of ethyl, methyl or isopropyl mercaptan in the presence of one or more molar equivalents of a Lewis acid such as aluminum trichloride or boron trifluoride in a solvent such as dichloromethane at temperatures ranging from −78° C. to 50° C.

The phenol of formula (Ib: B, D, X is H; C is OH; E is S, O) (Scheme 2) can be conveniently iodinated to the diiodophenol of formula (Ib: B, D is I; X is H; C is OH; E is S, O) using at least two molar equivalents of iodine in the presence of two or more molar equivalents of an alkali metal hydroxide such as NaOH in an alcohol solvent such as methanol at −20° C. to room temperature. Similarly the monoiodophenol (Ib: B is I; X, D is H; C is OH; E is S, O)

can be prepared from the phenol of formula (Ib: B, D, X is H; C is OH; E is S, O) (Scheme 2) using one to 1.5 molar equivalents of iodine in the presence of at least one equivalent of an alkali metal hydroxide such as NaOH in an alcohol solvent such as methanol at −20° C. to room temperature. Either the monoiodophenol (Ib: B is I; X, D is H; C is OH; E is S, O) or the diiodophenol (Ib: B, D is I; X is H; C is OH; E is S, O) can be converted to the respective methyl ether derivatives of formula (Ib: B is I; X, D is H; C is OMe; E is S, O) or (Ib: B, D is I; X is H; C is OMe; E is S, O) by reacting the phenol moiety with a suitable methylating agent such as one or more molar equivalents of methyl iodide or dimethylsulfate employing a base such an alkali methyl carbonate or hydroxide such as potassium carbonate or sodium hydroxide in a suitable solvent such as THF, DMF or DMSO. The reaction is generally performed at temperatures ranging from 0° C. to 60° C.

The monoiodo methylether derivative of formula (Ib: B is I; X, D is H; C is OMe; E is S, O) or the diiodo methylether of formula (Ib: B, D is I; X is H; C is OMe; E is S, O) can be reacted with one or more molar equivalents of copper (I) cyanide for the monoiodo analog or two or more molar equivalents of copper (I) cyanide for the diiodo derivative to produce the monocyanomethyl ether of formula (Ib: B is CN; X, D is H; C is OMe; E is S, O) or the dicyanomethyl ether of formula (Ib: B, D is CN; X is H; C is OMe; E is S, O). The cyanation reaction is generally performed at temperatures ranging from 100° C. to 250° C. employing polar aprotic solvents such as DMF, 1-methyl-2-pyrrolidinone or HMPA. Quinoline or pyridine can also be used. The mono or dicyano methoxy analogs of formula (Ib: B is CN; D is H or CN; X is H; C is OMe; E is S, O) can be converted to the corresponding mono or dicyano phenol analogs of formula (Ic: B is CN; D is H or CN; X is H; E is S, O) (Scheme 2) using standard demethylation procedures including one or more molar equivalents of boron tribromide or boron trichloride in dichloromethane at −78° C. to room temperature; excess neat pyridinium hydrochloride at 190 to 280° C.; hydrobromic acid in acetic acid at 0° C. to 50° C.; excess trimethylsilylbromide or trimethylsilyliodide in dichloromethane, carbon tetrachloride or acetonitrile at −78° C. to 50° C.; lithium iodide in pyridine or quinoline at temperatures from 100° to 250° C. and one or more molar equivalents of ethyl, methyl or isopropyl mercaptan in the presence of one or more molar equivalents of a Lewis acid such as aluminum trichloride or boron trifluoride in a solvent such as dichloromethane at temperatures ranging from −78° C. to 50° C.

The monoiodo methylether derivative of formula (Ib: B is I; X, D is H; C is OMe; E is S, O) or the diiodo methylether of formula (Ib: B, D is I; X is H; C is OMe; E is S, O) (Scheme 2) can be reacted with one or more molar equivalents of copper (I) bromide for the monoiodo analog or two or more molar equivalents of copper (I) bromide for the diiodo derivative to produce the monobromo methyl ether of formula (Ib: B is Br; X, D is H; C is OMe; E is S, O) or the dibromo-methyl ether of formula (Ib: B, D is Br; X is H; C is OMe; E is S, O). The bromine/idodine exchange reaction is generally performed at temperatures ranging from 100° C. to 250° C. employing polar aprotic solvents such as DMF, 1-methyl-2-pyrrolidinone or HMPA. Quinoline or pyridine can also be used. The mono or dibromo methoxy analogs of formula (Ib: B is Br; D is H or Br; X is H; C is OMe; E is S, O) can be converted to the corresponding mono or dibromo phenol analogs of formula (Ic: B is Br; D is H or Br; X is H; E is S, O) (Scheme 2) using standard demethylation procedures including one or more molar equivalents of boron tribromide or boron trichloride in dichloromethane at −78° C. to room temperature; excess neat pyridinium hydrochloride at 190 to 280° C.; hydrobromic acid in acetic acid at 0° C. to 50° C.; excess trimethylsilylbromide or trimethylsilyliodide in dichloromethane, carbon tetrachloride or acetonitrile at −78° C. to 50° C.; lithium iodide in pyridine or quinoline at temperatures from 100° to 250° C. and one or more molar equivalents of ethyl, methyl or isopropyl mercaptan in the presence of one or more molar equivalents of a Lewis acid such as aluminum trichloride or boron trifluoride in a solvent such as dichloromethane at temperatures ranging from −78° C. to 50° C.

The monoiodo or monobromo methylether or phenol derivatives of formula (Ib: B is Br, I; X, D is H; C is , OH, OMe; E is S, O) or the diiodo or dibromo methylether or phenols of formula (Ib: B, D is Br, I; X is H; C is OH, OMe; E is S, O) (Scheme 2) can be reacted with one or more molar equivalents of an aryl boronic acid for the monoiodo or monobromo analog or two or more molar equivalents of aryl boronic acid for the diiodo or dbromo derivative to produce the monophenyl methyl ether or phenols of formula (Ib: B is phenyl; X, D is H; C is OH, OMe; E is S, O) or the dibromo-methyl ethers or phenols of formula (Ib: B, D is phenyl; X is H; C is OH, OMe; E is S, O). This reaction is best known as the Suzuki reaction (N. Miyaura, T. Yanagi, A Suzuki, *Synthetic Comm.* 1981, 11, 513–319) and further involves the use of 0.5 to 10 mol % of a palladium catalyst such as tetakis(triphenylphosphine) palladium or a palladium (II) species such as palladium acetate or [1,1'-bis (diphenyphosphino)ferrocene]palladium(II). One or more equivalents of an alkali-metal base is also needed and some of the more common bases include sodium, potassium or cesium carbonate; sodium, potassium, barium or thalium hydroxide and potassium phosphate. The reaction can be run in a variety of solvents including benzene, THF, dioxane, DME or DMF. For some of these solvents, such as THF and benzene, water or methanol can be used as a colvent. The reaction is generally run at temperatures ranging from room temperature to 120° C.

The mono or dibromo methoxy analogs of formula (Ib: B is Br; D is H or Br; X is H; C is OMe; E is S, O) and the mono and diphenyl methoxy analogs of formula (Ib: B is Ph; D is H or Ph; X is H; C is OMe; E is S, O) can be converted to the corresponding mono or dibromo phenol analogs of formula (Ic: B is Br; D is H or Br; X is H; E is S, O) or the mono and diphenyl phenol analogs of formula (Ib: B is Ph; D is H or Ph; X is H; C is OH; E is S, O) (Scheme 2) using standard demethylation procedures including one or more molar equivalents of boron tribromide or boron trichloride in dichloromethane at −78° C. to room temperature; excess neat pyridinium hydrochloride at 190 to 280° C.; hydrobromic acid in acetic acid at 0° C. to 50° C.; excess trimethylsilylbromide or trimethylsilyliodide in dichloromethane, carbon tetrachloride or acetonitrile at −78° C. to 50° C.; lithium iodide in pyridine or quinoline at temperatures from 100° to 250° C. and one or more molar equivalents of ethyl, methyl or isopropyl mercaptan in the presence of one or more molar equivalents of a Lewis acid such as aluminum trichloride or boron trifluoride in a solvent such as dichloromethane at temperatures ranging from −78° C. to 50° C.

Scheme 3

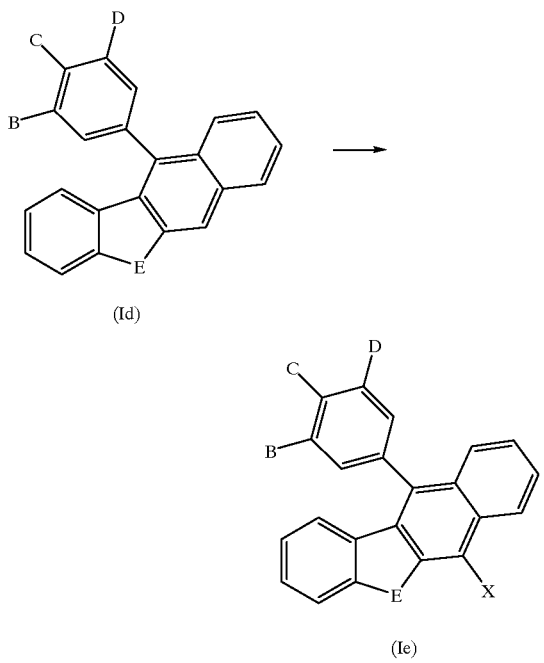

(Id)

(Ie)

Further derivatives of the compounds of formula (I) in Scheme 3 can be prepared by the following methods. The compounds of formula (Id: B, C, D is H or OH; with the B, C, D combination having at least one OH group; E is S, O) (Scheme 3) can be acylated on the phenolic oxygen using one or more molar equivalents of suitable acylating agent to provide the compounds of formula (Id: B, C, D is H or OCOR; with the B, C, D combination having at least one OCOR group; R is alkyl of 1–6 carbon atoms, aryl; E is S, O). The acylating agent is generally a alkyl of 1–6 carbon atoms or aryl carboxylic acid anhydride or a alkyl of 1–6 carbon atoms or aryl carboxylic acid chloride. The reaction is run under standard conditions, for example, the use of pyridine as solvent with or without a co-solvent such as dichloromethane at 0° C. to room temperature. The acylated phenols of formula (Id: B, C, D is H or OCOR; with the B, C, D combination having at least one OCOR group; R is alkyl of 1–6 carbon atoms, aryl; E is S, O) can then be brominated in the 6-position of the benzo[b]naphtho[2,3-d]thiophene or benzo[b]naphtho[2,3-d]furan ring to form the acylated bromophenols of formula (Ie: B, C, D is H or OCOR; with the B, C, D combination having at least one OCOR group; R is alkyl of 1–6 carbon atoms, aryl; X is Br; E is S, O) (Scheme 3). This bromination reaction is generally done using 1 to 1.3 molar equivalents of molecular bromine in an inert solvent such as dichloromethane or carbon tetrachloride at temperatures ranging from −78° C. to room temperature.

Using a similar bromination reaction, the phenols of formula (Id: B, D is alkyl of 1–6 carbon atoms, C is OH; E is S, O) can then be brominated in the 6-position of the benzo[b]naphtho[2,3-d]thiophene or benzo[b]naphtho[2,3-d]furan ring to form the bromophenols of formula (Ie: B, D is alkyl of 1–6 carbon atoms, C is OH; X is Br; E is S, O) (Scheme 3). This bromination reaction is generally done using 1 to 1.3 molar equivalents of molecular bromine in an inert solvent such as dichloromethane or carbon tetrachloride at temperatures ranging from −78° C. to room temperature.

The acyl group can then be removed from the acylated bromophenols of formula (Ie: B, C, D is H or OCOR; with the B, C, D combination having at least one OCOR group; R is alkyl of 1–6 carbon atoms, aryl; X is Br; E is S, O) to provide the bromophenols of formula (Ie: B, C, D is H or OH; with the B, C, D combination having at least one OH group; X is Br; E is S, O) (Scheme 3) using standard conditions. These conditions include aqueous base in which one or more molar equivalents of alkali metal hydroxide such as sodium hydroxide is used in water with a co-solvent such as THF, dioxane or a lower alcohol such as methanol or mixtures of THF and a lower alcohol at temperatures ranging from 0° C. to 40° C. acid conditions may also be employed in which the compound is reacted with one or more molar equivalents of a mineral acid such as HCl or sulfuric acid in water with or without a co-solvent such as THF at temperatures ranging from room temperature to 80° C.

The acylated phenols of formula (Id: B, C, D is H or OCOR; with the B, C, D combination having at least one OCOR group; R is alkyl of 1–6 carbon atoms, aryl; E is S, O) can be nitrated to provide the nitro compounds of formula (Ie: B, C, D is H or OCOR; with the B, C, D combination having at least one OCOR group; R is alkyl of 1–6 carbon atoms, aryl; X is $NO_2$; E is S, O) (Scheme 3). Dilute nitric acid at temperatures ranging from 0° C. to room temperature is suitable to effect this transformation. The nitro compounds of formula (Ie: B, C, D is H or OCOR; with the B, C, D combination having at least one OCOR group; R is alkyl of 1–6 carbon atoms, aryl; X is $NO_2$; E is S, O) can be further reduced to the primary amine of formula (1e: B, C, D is H or OCOR; with the B, C, D combination having at least one OCOR group; R is alkyl of 1–6 carbon atoms, aryl; X is $NH_2$; E is S, O) using a suitable reducing agent such as catalytic hydrogenation with a palladium or platinum catalyst, tin dichloride in aqueous HCl or in ethyl acetate. The acyl group of the compounds of formula (Ie: B, C, D is H or OCOR; with the B, C, D combination having at least one OCOR group; R is alkyl of 1–6 carbon atoms, aryl; X is $NO_2$ or $NH_2$; E is S, O) can be removed by using standard conditions to provide the phenols of formula (Ie: B, C, D is H or OH; with the B, C, D combination having at least one OH group; R is alkyl of 1–6 carbon atoms, aryl; X is $NO_2$ or $NH_2$; E is S, O).

The acylated bromophenols of formula (Ie: B, C, D is H or OCOR; with the B, C, D combination having at least one OCOR group; R is alkyl of 1–6 carbon atoms, aryl; X is Br; E is S, O) (Scheme 3) can be converted to the acylated cyanophenols of formula (Ie: B, C, D is H or OCOR; with the B, C, D combination having at least one OCOR group; R is alkyl of 1–6 carbon atoms, aryl; X is CN; E is S, O) by reaction with one or more molar equivalents of copper (I) cyanide. The cyanation reaction is generally performed at temperatures ranging from 100° C. to 250° C. employing polar aprotic solvents such as DMF, 1-methyl-2-pyrrolidinone or HMPA. Quinoline or pyridine can also be used. Often the acyl group of (Ie: B, C, D is H or OCOR; with the B, C, D combination having at least one OCOR group; R is alkyl of 1–6 carbon atoms, aryl; X is CN; E is S, O) is liberated under the cyanation reaction conditions to afford the cyanophenols of formula (Ie: B, C, D is H or OH; with the B, C, D combination having at least one OCOR group; X is CN; E is S, O). This liberation of the acyl group to afford the cyanophenols of formula (Ie: B, C, D is H or OH; with the B, C, D combination having at least one OH group; X is CN; E is S, O) can be effected most readily by addition of one or more molar equivalents of alkali metal hydroxide in water to the reaction mixture containing (Ie: B, C, D is H or OCOR; with the B, C, D combination having at least one OCOR group; R is alkyl of 1–6 carbon atoms, aryl; X is CN; E is S, O) prior to workup. The acyl group can also be removed from the isolated acylated cyanophenols of formula (Ie: B, C, D is H or OCOR; with the B, C, D combination having at least one OCOR group; R is alkyl of 1–6 carbon atoms, aryl; X is CN; E is S, O) to provide the cyanophenols of formula (Ie: B, C, D is H or OH; with the B, C, D combination having at least one OH group; X is CN; E is S, O) by using standard conditions. These conditions include aqueous base in which one or more molar equivalents of alkali metal hydroxide such as sodium hydroxide is used in water with a co-solvent such as THF, dioxane or a lower alcohol such as methanol or mixtures of THF and a lower alcohol at temperatures ranging from 0° C. to 40° C. acid conditions may also be employed in which the compound is reacted with one or more molar equivalents of a mineral acid such as HCl or sulfuric acid in water with or without a co-solvent such as THF at temperatures ranging from room temperature to 80° C.

The compounds of formula (Id: B, C, D is H or OH; with the B, C, D combination having at least one OH group; E is S, O) (Scheme 3) can be sulfonylated on the phenolic oxygen using one or more molar equivalents of suitable sulfonylating agent to provide the sulfonic acid esters of formula (Id: B, C, D is H or OSO$_2$R; with the B, C, D combination having at least one OSO$_2$R group; R is alkyl of 1–6 carbon atoms, aryl; E is S, O). The sulfonylating agent is generally a alkyl of 1–6 carbon atoms or aryl sulfonic acid anhydride or a alkyl of 1–6 carbon atoms or aryl sulfonic acid chloride. The reaction is run under standard conditions such as using pyridine as solvent with or without a co-solvent such as dichloromethane at 0° C. to room temperature.

The sulfonic acid esters of formula (Id: B, C, D is H or OSO$_2$R; with the B, C, D combination having at least one OSO$_2$R group; R is alkyl of 1–6 carbon atoms, aryl; E is S, O) can be treated with a chlorinating agent to effect chlorination at the 6-position of the benzo[b]naphtho[2,3-d] thiophene or benzo[b]naphtho[2,3-d]furan ring to afford the chloro-sulfonic acid esters of formula (Ie: B, C, D is H or OSO$_2$R; with the B, C, D combination having at least one OSO$_2$R group; R is alkyl of 1–6 carbon atoms, aryl; X is Cl; E is S, O). Suitable chlorinating agents include one or more molar equivalents of sulfuryl chloride, chlorine gas or N-chlorosuccinimide in suitable halocarbon solvents such as dichloromethane or chloroform at temperatures ranging from –78° C. to 40° C. The sulfonic ester group can then be removed from the chloro-sulfonic acid esters of formula (Ie: B, C, D is H or OSO$_2$R; with the B, C, D combination having at least one OSO$_2$R group; R is alkyl of 1–6 carbon atoms, aryl; X is Cl; E is S, O) to provide the chlorophenols of formula (Ie: B, C, D is H or OH; with the B, C, D combination having at least one OH group; X is Cl; E is S, O) (Scheme 3) using standard conditions. These conditions include aqueous base in which one or more molar equivalents of alkali metal hydroxide such as sodium hydroxide is used in water with a co-solvent such as THF, dioxane or a lower alcohol such as methanol or mixtures of THF and a lower alcohol at temperatures ranging from room temperature to 110° C.

The sulfonic acid esters of formula (Id: B, C, D is H or OSO$_2$R; with the B, C, D combination having at least one OSO$_2$R group; R is alkyl of 1–6 carbon atoms, aryl; E is S, O) can also be treated with iodinating reagents to effect iodination at the 6-position of the benzo[b]naphtho[2,3-d] thiophene or benzo[b]naphtho[2,3-d]furan ring to afford the iodo-sulfonic acid esters of formula (Ie: B, C, D is H or OSO$_2$R; with the B, C, D combination having at least one OSO$_2$R group; R is alkyl of 1–6 carbon atoms, aryl; X is I; E is S, O). A suitable iodinating reagent includes a mixture of 0.7 or more molar equivalents of molecular iodine and 0.25 or more molar equivalents of iodic acid in a mixture of THF and 80% aqueous acetic acid with a small amount of concentrated sulfuric acid at temperatures ranging from room temperature to 80° C. The sulfonic ester group can then be removed from the iodo-sulfonic acid esters of formula (Ie: B, C, D is H or OSO$_2$R; with the B, C, D combination having at least one OSO$_2$R group; R is alkyl of 1–6 carbon atoms, aryl; X is I; E is S, O) to provide the iodophenols of formula (Ie: B, C, D is H or OH; with the B, C, D combination having at least one OH group; X is I; E is S, O) (Scheme 3) using standard conditions. These conditions include aqueous base in which one or more molar equivalents of alkali metal hydroxide such as sodium hydroxide is used in water with a co-solvent such as THF, dioxane or a lower alcohol such as methanol or mixtures of THF and a lower alcohol at temperatures ranging from room temperature to 110° C.

Scheme 4

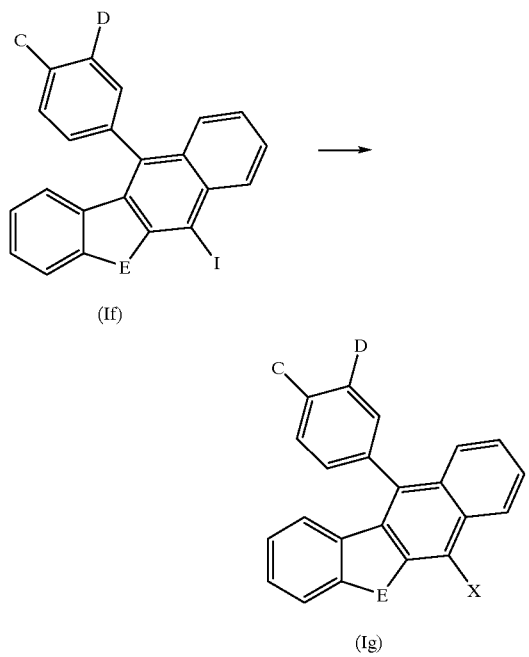

The iodo sulfonic acid esters of formula (If: C, D is H or OSO$_2$R; C, D cannot both be H; R is alkyl of 1–6 carbon atoms, aryl; E is S, O) were a convenient starting point for further derivatives of the compounds of formula (I) as shown in Scheme 4 and the methods below. The compounds (If: C, D is H or OSO$_2$R; C, D cannot both be H; R is alkyl of 1–6 carbon atoms, aryl; E is S, O) can be reacted with a reagent that catalyzes the exchange of the iodine atom in (If) with a perfluoroalkyl of 1–6 carbon atoms group to afford the compound of formula (Ig: C, D is H or OSO$_2$R; C, D cannot both be H; R is alkyl of 1–6 carbon atoms, aryl; X is perfluoroalkyl of 1–6 carbon atoms; E is S, O) (Scheme 4). The reagent and conditions to effect this exchange include reacting (If) under anhydrous conditions with one to ten molar molar equivalents of a sodium perfluorocarboxylate ($RCO_2Na$: R is perfluoroalkyl) and one to five molar molar equivalents of copper (I) iodide in a high boiling inert solvent such as DMF, DMA or 1-methyl-2-pyrrolidinone at temperatures ranging from 140° C. to 200° C. Alternatively, the compound of formula (Ig: C, D is H or $OSO_2R$; C, D cannot both be H; R is alkyl of 1–6 carbon atoms, aryl; X is perfluoroalkyl of 1–6 carbon atoms; E is S, O) can be prepared from the compound of formula (If: C, D is H or $OSO_2R$; C, D cannot both be H; R is alkyl of 1–6 carbon atoms, aryl; E is S, O) by reacting the former with one to ten molar molar equivalents of a perfluoroalkyl iodide and one to five molar molar equivalents of activated $Cu^0$ in a high boiling inert solvent such as DMF, DMA or 1-methyl-2-pyrrolidinone at temperatures ranging from 140° C. to 200° C. Still, alternatively, the compound of formula (If: C, D is H or $OSO_2R$; C, D cannot both be H; R is alkyl of 1–6 carbon atoms, aryl; E is S, O) can be reacted with 0.5 to two molar equivalents of bis(trifluoromethylmercury) and two to four molar equivalents of activated $Cu^0$ in a high boiling inert solvent such as DMF, DMA or 1-methyl-2-pyrrolidinone at temperatures ranging from 140° C. to 200° C. to produce the compound of (Ig: C, D is H or $OSO_2R$; C, D cannot both be H; R is alkyl of 1–6 carbon atoms, aryl; X is $CF_3$; E is S, O).

6-Alkyl of 1–6 carbon atoms derivatives of the compound of formula (Ig: C, D is H or $OSO_2R$; C, D cannot both be H; R is alkyl of 1–6 carbon atoms, aryl; X is alkyl of 1–6 carbon atoms; E is S, O) (Scheme 4) can be prepared by reaction of (If: C, D is H or $OSO_2R$; C, D cannot both be H; R is alkyl of 1–6 carbon atoms, aryl; E is S, O) with three or more molar equivalents of lower tetra-alkyltin in the presence of a palladium catalyst such as 1 to 10 mole % of bis (triphenylphosphine)palladium II chloride in a suitable solvent such as DMF, DMA or 1-methyl-2-pyrrolidinone at temperatures ranging from 140° C. to 200° C.

The sulfonic ester group can then be removed from the sulfonic acid esters of formula (Ig: C, D is H or $OSO_2R$; C, D cannot both be H; R is alkyl of 1–6 carbon atoms, aryl; X is alkyl of 1–6 carbon atoms or perfluoroalkyl of 1–6 carbon atoms; E is S, O) to provide the phenols of formula (Ig: C, D is H or OH; C, D cannot both be H; X is alkyl of 1–6 carbon atoms or perfluoroalkyl of 1–6 carbon atoms; E is S, O) using standard conditions. These conditions include aqueous base in which one or more molar equivalents of alkali metal hydroxide such as sodium hydroxide is used in water with a co-solvent such as THF, dioxane or a lower alcohol such as methanol or mixtures of THF and a lower alcohol at temperatures ranging from room temperature to 110° C.

6-Alkoxy derivatives of the compound of formula (Ig: C, D is H, OH; C, D cannot both be H; X is alkoxy of 1–6 carbon atoms; E is S, O) can be prepared by reaction of (If: C, D is H or $OSO_2R$; C, D cannot both be H; R is alkyl of 1–6 carbon atoms, aryl; E is S, O) with three or more molar equivalents of lower alkali metal alkoxide in the presence of a copper (I) or copper (II) catalyst such as 1 to 10 mole % copper (II) chloride in a suitable solvent such as DMF, DMA or 1-methyl-2-pyrrolidinone at temperatures ranging from 80° C. to 180° C. Under the reaction conditions, the sulfonic acid group of (If: C, D is H or $OSO_2R$; C, D cannot both be H; R is alkyl of 1–6 carbon atoms, aryl; E is S, O) is removed.

6-Sulfanyl derivatives of the compound of formula (Ig: C, D is H or OH; C, D cannot both be H; X is alkylsulfanyl of 1–6 carbon atoms, arylsulfanyl, pyridylsulfanyl, 2-N,N-dimethylaminoethylsulfanyl; E is S, O) can be prepared by reaction of (If: C, D is H or $OSO_2R$; C, D cannot both be H; R is alkyl of 1–6 carbon atoms, aryl; E is S, O) with one or more molar equivalents of the appropriate alkyl of 1–6 carbon atomsthiol, arylthiol, thiopyridine or 2-N,N-dimethylaminoethyl-mercaptan, one or more molar equivalents of an alkali metal hydroxide such as sodium hydroxide, one or more molar equivalents of a copper (I) or copper (II) catalyst such as copper (I) oxide in a suitable solvent such as DMF, DMA or 1-methyl-2-pyrrolidinone at temperatures ranging from 100° C. to 180° C. Under the reaction conditions, the sulfonic acid group of (If: C, D is H or $OSO_2R$; C, D cannot both be H; R is alkyl of 1–6 carbon atoms, aryl; E is S, O) is removed.

Scheme 5

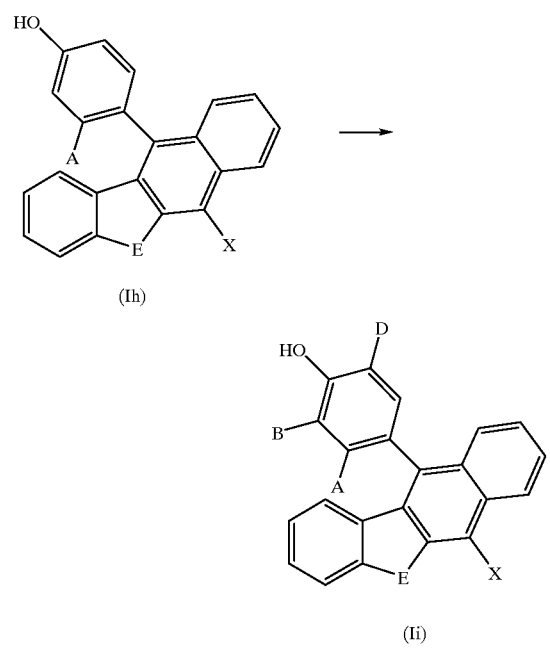

Further derivatives of the compounds of formula (I) in Scheme 5 can be prepared by the following methods. The phenols of formula (Ih: A is H or OH; X is H, halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; E is S, O) can be brominated in two positions to afford the dibromphenols of formula (Ii: A is H or OH; B, D is Br; X is H, halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; E is S, O) using at least 2 molar equivalents of molecular bromine in an appropriate solvent such as acetic acid. One to fifty molar equivalents of a salt of acetic acid such as potassium or sodium acetate can also be used as a co-reagent in this reaction although it is not absolutely required.

The phenols of formula (Ih: A is H or OH; X is H, halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; E is S, O) can be chlorinated in two positions to afford the dichlorophenols of formula (Ii: A is H or OH; B, D is Cl; X is H, halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; E is S, O) using two or more molar equivalents of chlorine in an appropriate solvent such as a lower alcohol solvent, most conveniently, methanol. The reaction is run at temperatures ranging from −78° C. to room temperature.

The phenols of formula (Ih: A is H; X is H, halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; E is S, O) can be mononitrated to the phenols of formula (Ii: A is H; B is NO$_2$; D is H; X is H, halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; E is S, O) most conveniently using iron (III) trinitrate in a lower alcohol solvent.

The nitro compounds of formula (Ii: A is H; B is NO$_2$; D is H; X is H, halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; E is S, O) can be reduced to the amino compounds of formula (Ii: A is H; B is NH$_2$; D is H; X is H, halogen, alkyl of 1–6 carbon atoms, CN, perfluoroalkyl of 1–6 carbon atoms, alkoxy of 1–6 carbon atoms, aralkoxy, amino, alkylsulfanyl of 1–6 carbon atoms, arylsulfanyl, pyridylsulfanyl, 2-N,N-dimethylamino-ethylsulfanyl; E is S, O) most readily using tin dichloride in ethyl acetate at 40 to 100° C. or with hydrazine and Montmorillinite clay in ethanol at 40 to 100° C.

The nitro compounds of formula (Ii: A is H; B is NO$_2$; D is H; X is H, halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; E is S, O) can also be brominated to the compounds of formula (Ii: A is H; B is NO$_2$; D is Br; X is H, halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; E is S, O) using at least 2 molar equivalents of molecular bromine in an appropriate solvent such as acetic acid. One to fifty molar equivalents of a salt of acetic acid such as potassium or sodium acetate can also be used as a co-reagent in this reaction although it is not absolutely required. The bromo nitro compounds of formula (Ii: A is H; B is NO$_2$; D is Br; X is H, halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; E is S, O) can be reduced to the bromo amino compounds of formula (Ii: A is H; B is NH$_2$; D is Br; X is H, halogen, alkyl of 1–6 carbon atoms, CN, perfluoroalkyl of 1–6 carbon atoms, alkoxy of 1–6 carbon atoms, aralkoxy, amino, alkylsulfanyl of 1–6 carbon atoms, arylsulfanyl, pyridylsulfanyl, 2-N,N-dimethylaminoethylsulfanyl; E is S, O) most readily using tin dichloride in ethyl acetate at 40 to 100° C. or with hydrazine and Montmorillinite clay in ethanol at 40 to 100° C.

The dibromo-bisphenols of formula (Ii: A is OH; B, D is Br; X is H; E is S, O) can be further brominated in the 6-position of the benzo[b]naphtho[2,3-d]thiophene ring to form the bisphenols of formula (Ii: A is OH; B, D, X is Br; E is S, O). This bromination reaction is generally done using 1 to 1.3 molar equivalents of molecular bromine in an inert solvent such as dichloromethane or carbon tetrachloride at temperatures ranging from −78° C. to room temperature.

Scheme 6

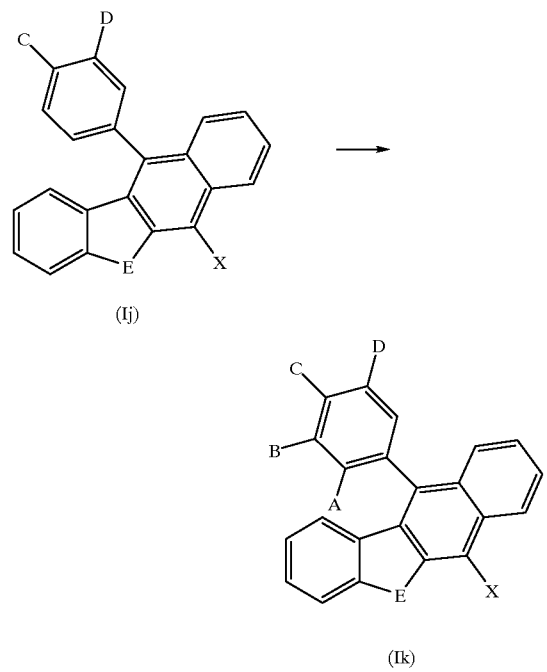

Further derivatives of the compounds of formula (I) in Scheme 6 can be prepared by the following methods. The phenols of formula (Ij: C is H; D is OH; X is halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; E is S, O) can be monobrominated to provide the provide the bromophenols of formula (Ik: A, B is H; C is Br; D is OH; X is halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; E is S, O) using at least 1 molar equivalent of molecular bromine in an appropriate solvent such as acetic acid or dibrominated to provide the bromophenols of formula (Ik: B is H; A, C is Br; D is OH; X is halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; E is S, O) using at least 2 molar equivalents of molecular bromine in an appropriate solvent such as acetic acid. Similarly, the bisphenols of formula (Ij: C, D is OH; X is halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; E is S, O) can be monobrominated to provide a mixture of the bromobisphenols of formula (Ik: A is H; B is Br; C, D is OH; X is halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; E is S, O) and (Ik: A is Br; B is H; C, D is OH; X is halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; E is S, O) using at 1 molar equivalent of molecular bromine in an appropriate solvent such as acetic acid. This mixture can be separated into pure monobromo products by conventional means.

The bromobisphenols of formula (Ik: A is H; B is Br; C, D is OH; X is halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; E is S, O) can be alkylated regioselectively with a alkyl of 1–6 carbon atoms, allyl or benzyl halide on the phenolic hydroxyl occupied by position C to provide the monoalkylated products of formula (Ik: A is H; B is Br; C is alkoxy of 1–6 carbon atomsl, allyloxy or benzyloxy, D is OH; X is halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; E is S, O) using one or more molar equivalents of an alkali metal carbonate such as potassium carbonate in a polar aprotic solvent such as DMF.

The monobenzylated products of formula (Ik: A is H; B is Br; C is benzyloxy, D is OH; X is halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; E is S, O) can be further alkylated with a alkyl of 1–6 carbon atoms halide to provide the dialkylated product of formula (Ik: A is H; B is Br; C is benzyloxy, D is alkoxy of 1–6 carbon atoms; X is halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; E is S, O) using one or more molar equivalents of an alkali metal carbonate such as potassium carbonate in a polar aprotic solvent such as DMF.

The benzyl group of the compounds of formula (Ik: A is H; B is Br; C is benzyloxy, D is alkoxy of 1–6 carbon atoms; X is halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; E is S, O) can be removed using standard hydrogenolysis conditions, for example, hydrogen gas with a 5 to 10% palladium on carbon catalyst in a lower alcohol solvent or in ethyl acetate ir THF to provide the phenols of formula (Ik: A is H; B is Br; C is OH, D is alkoxy of 1–6 carbon atoms; X is halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; E is S, O).

Scheme 7

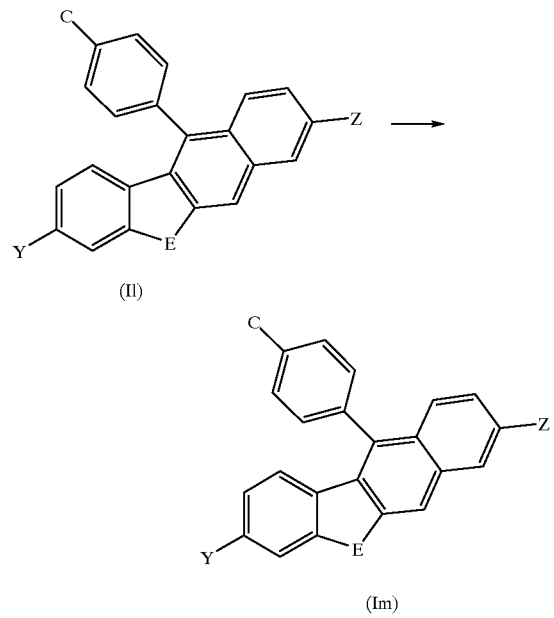

Further derivatives of the compounds of formula (I) in Scheme 7 can be prepared by the following methods. The bisphenol of formula (Il: Y, C is OH; Z is H; E is S) can be reacted with one molar equivalent of methyl bromoacetate and with one or more molar equivalents of an alkali metal carbonate such as potassium carbonate in a polar aprotic solvent such as DMF to afford the monoalkylated product of formula (Im: Y is $OCH_2CO_2CH_3$; C is OH; Z is H; E is S). This product may be contaminated with small amounts (<10%) of the regioisomer of formula (Im: C is $OCH_2CO_2CH_3$; Y is OH; Z is H; E is S). The regioisomers can be separated by conventional means.

Alternatively, the bisphenols of formula (Il: Y, C is OH; Z is H; E is S) or (Z, C is OH; Y is H; E is S or O) can be diaklylated with two or more molar equivalents of an alkyl haloacetate of formula ($X^2CH_2CO_2R^6$ where $X^2$ is Cl, Br or I and $R^6$ is alkyl of 1–6 carbon atoms) and with two or more molar equivalents of an alkali metal carbonate such as potassium carbonate in a polar aprotic solvent such as DMF to afford the dialkylated product of formula (Im: Y, C is $OCH_2CO_2R^6$; Z is H; E is S; $R^6$ is alkyl of 1–6 carbon atoms) or (Z, C is $OCH_2CO_2R^6$; Y is H; E is S or O; $R^6$ is alkyl of 1–6 carbon atoms).

The monoesters of formula (Im: Y is $OCH_2CO_2CH_3$; C is OH; Z is H; E is S) as well as the diesters of formula (Im: Y, C is $OCH_2CO_2R^6$; Z is H; E is S; E is S) or (Z, C is $OCH_2CO_2R^6$; Y is H; E is S or O) can be transformed into their carboxylic acid analogs using standard conditions to afford the moncarboxylic acids of formula (Im: Y is $OCH_2CO_2H$; C is OH; Z is H; E is S) and the dicarboxylic acids of formula (Im: Y, C is $OCH_2CO_2H$; Z is H; E is S) or (Z, C is $OCH_2CO_2H$; Y is H; E is S or O). The conditions to effect these transformations include aqueous base in which one or more molar equivalents of alkali metal hydroxide such as sodium hydroxide is used in water with a co-solvent such as THF, dioxane or a lower alcohol such as methanol or mixtures of THF and a lower alcohol at temperatures ranging from 0° C. to 40° C.

Scheme 8

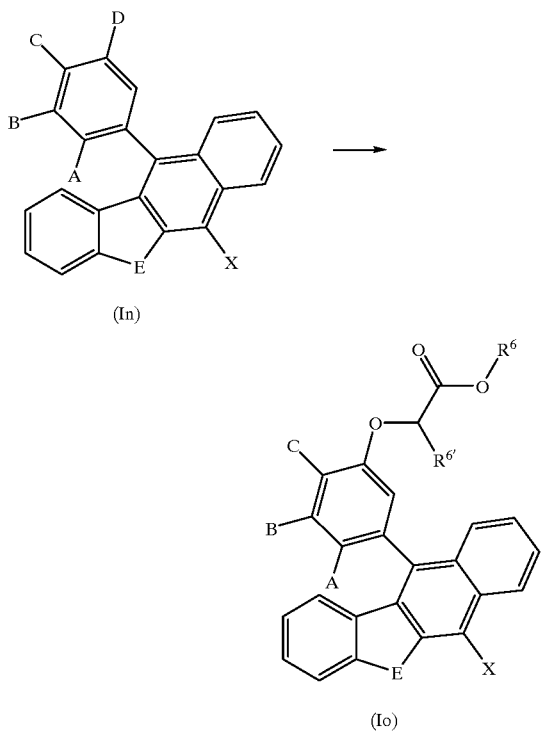

(In)

(Io)

Further derivatives of the compounds of formula (I) in Scheme 8 can be prepared by the following methods. The phenols of formula (In: B is H; A, C is H, Br or alkoxy of 1–6 carbon atoms; D is OH; X is halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; E is S, O) can be alkylated with one or more molar equivalents of an alkyl haloacetate of formula ($X^2CHR^{6'}CO_2R^6$ where $X^2$ is Cl, Br or I and $R^6$ is alkyl of 1–6 carbon atoms, $R^{6'}$ is H) and with one or more molar equivalents of an alkali metal carbonate such as potassium carbonate in a polar aprotic solvent such as DMF to afford the alkylated product of formula (Io: B is H; A, C is H, Br or alkoxy of 1–6 carbon atoms; X is halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; $R^6$ is alkyl of 1–6 carbon atoms, $R^{6'}$ is H; E is S, O).

Alternatively the bisphenols of formula (In: A, B is H or Br; C, D is OH; X is halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; E is S, O) can be diaklylated with two or more molar equivalents of an alkyl haloacetate of formula ($X^2CHR^{6'}CO_2R^6$ where $X^2$ is Cl, Br or I and $R^6$ is alkyl of 1–6 carbon atoms, $R^{6'}$ is H) and with two or more molar equivalents of an alkali metal carbonate such as potassium carbonate in a polar aprotic solvent such as DMF to afford the dialkylated esters of formula (Io: A, B is H or Br; C is $OCHR^6CO_2R^{6'}$; X is halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; $R^6$ is alkyl of 1–6 carbon atoms, $R^{6'}$ is H; E is S, O).

Still alternatively, the phenols of formula (In: B is H or halogen; A is H or halogen; C is H, Br or alkoxy of 1–6 carbon atoms; D is OH; X is halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; E is S, O) can be reacted with a 2-hydroxy carboxylic acid ester of formula $CH(OH)(R^{6'})CO_2R^6$ ($R^6$, $R^{6'}$ is alkyl of 1–6 carbon atoms, aralkyl, aryl) to afford the esters of formula (Io: B is H or halogen; A is H or halogen; C is H, Br or alkoxy of 1–6 carbon atoms; X is halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; $R^6$, $R^{6'}$ is alkyl of 1–6 carbon atoms, aralkyl, aryl; E is S, O) under the conditions of the Mitsunobu Reactions (for a review see Oyo Mitsunobu *Synthesis.* 1981, 1–27). The other co-reagents necessary to effect the Mitsunobu Reaction include one or more molar equivalents of a alkyl of 1–6 carbon atoms azodicarboxylate diester such as diethyl azodicarboxylate or diisopropyl azodicarboxylate and one or more molar equivalents of triarylphosphine such as triphenylphosphine in a suitable solvent such as diethyl ether, THF, benzene or toluene at temperatures ranging from –20° C. to 120° C.

The monoesters of formula (Io: A, B is H or halogen; C is H, Br or alkoxy of 1–6 carbon atoms; X is halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; $R^6$, $R^{6'}$ is alkyl of 1–6 carbon atoms, aralkyl, aryl; E is S, O) as well as the diesters of formula (Io: A, B is H or Br; C is $OCHR^{6'}CO_2R^6$, X is halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; $R^6$ is alkyl of 1–6 carbon atoms, $R^{6'}$ is H; E is S, O) can be transformed into their carboxylic acid analogs using standard conditions to afford the moncarboxylic acids of formula (Io: A, B is H or halogen; C is H, Br or alkoxy of 1–6 carbon atoms; X is halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; $R^6$ is H; $R^{6'}$ is alkyl of 1–6 carbon atoms, aralkyl, aryl; E is S, O) and the dicarboxylic acids of formula (Io: A, B is H or Br; C is $OCHR^{6'}CO_2R^6$, X is halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; $R^6$, $R^{6'}$ is H; E is S, O). The conditions to effect these transformations include aqueous base in which one or more molar equivalents of alkali metal hydroxide such as sodium hydroxide is used in water with a co-solvent such as THF, dioxane or a lower alcohol such as methanol or mixtures of THF and a lower alcohol at temperatures ranging from 0° C. to 40° C.

Scheme 9

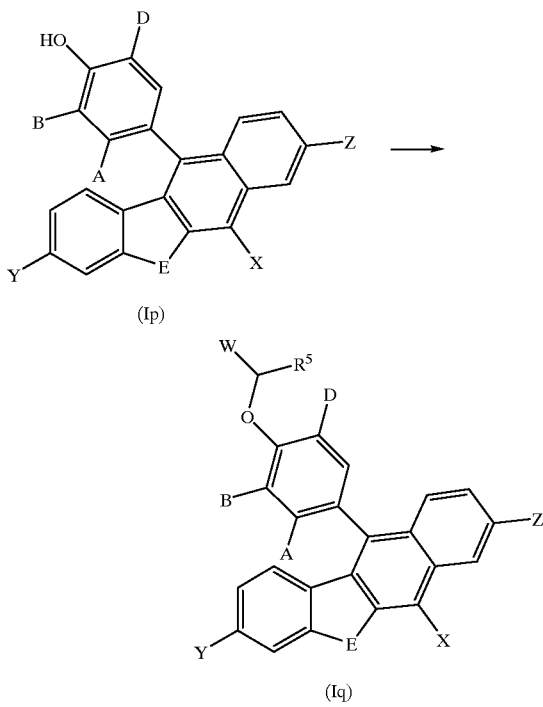

Further derivatives of the compounds of formula (I) in Scheme 9 can be prepared by the following methods. The phenols of formula (Ip: A is H; B, D is H, halogen, CN, alkyl of 1–6 carbon atoms, aryl, aralkyl, alkoxy of 1–6 carbon atoms, nitro; Y, Z is H or $OCH_2CO_2R^6$, but Y and Z are not concurrently $OCH_2CO_2R^6$; X is H, halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; $R^6$ is alkyl of 1–6 carbon atoms; E is S, O) can be alkylated with one or more molar equivalents of an alkyl haloacetate of formula ($X^2CH_2CO_2R^6$ where $X^2$ is Cl, Br or I and $R^6$ is alkyl of 1–6 carbon atoms) and with one or more molar equivalents of an alkali metal carbonate such as potassium carbonate in a polar aprotic solvent such as DMF to afford the alkylated product of formula (Iq: A is H; B, D is H, halogen, CN, alkyl of 1–6 carbon atoms, aryl, aralkyl, alkoxy of 1–6 carbon atoms, nitro; Y, Z is H or $OCH_2CO_2R^6$, but Y and Z are not concurrently $OCH_2CO_2R^6$; X is H, halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; W is $CO_2R^6$; $R^5$ is H; $R^6$ is alkyl of 1–6 carbon atoms; E is S, O).

The phenols of formula (Ip: A is H or OH; B, D is H, halogen, CN, alkyl of 1–6 carbon atoms, aryl, aralkyl, alkoxy of 1–6 carbon atoms, nitro; Y, Z is H or $OCH_2CO_2R^6$, but Y and Z are not concurrently $OCH_2CO_2R^6$; X is H, halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; $R^6$ is alkyl of 1–6 carbon atoms; E is S, O) can be reacted with a 2-hydroxy carboxylic acid ester of formula $CH(OH)(R^5)$ $CO_2R^6$ ($R^5$ is H, alkyl of 1–6 carbon atoms, aralkyl, aryl, $CH_2$(1H-imidazol-4-yl), $CH_2$(3-1H-indolyl), $CH_2CH_2$(1,3-dioxo-1,3-dihydro-isoindol-2-yl), $CH_2CH_2$(1-oxo-1,3-dihydro-isoindol-2-yl), $CH_2$(3-pyridyl), $CH_2CO_2R^6$, $R^6$ is alkyl of 1–6 carbon atoms) to afford the esters of formula (Iq: A is H or OH; B, D is H, halogen, CN, alkyl of 1–6 carbon atoms, aryl, aralkyl, alkoxy of 1–6 carbon atoms, nitro; Y, Z is H or $OCH_2CO_2R^6$, but Y and Z are not concurrently $OCH_2CO_2R^6$; X is H, halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; W is $CO_2R^6$; $R^5$ is H, alkyl of 1–6 carbon atoms, aralkyl, aryl, $CH_2$(1H-imidazol-4-yl), $CH_2$(3-1H-indolyl), $CH_2CH_2$(1,3-dioxo-1,3-dihydro-isoindol-2-yl), $CH_2CH_2$(1-oxo-1,3-dihydro-isoindol-2-yl), $CH_2$(3-pyridyl), $CH_2CO_2R^6$, $R^6$ is alkyl of 1–6 carbon atoms; E is S, O) under the conditions of the Mitsunobu Reactions (for a review see Oyo Mitsunobu *Synthesis.* 1981, 1–27). The other co-reagents necessary to effect the Mitsunobu Reaction include one or more molar equivalents of a alkyl of 1–6 carbon atoms azodicarboxylate diester such as diethyl azodicarboxylate or diisopropyl azodicarboxylate and one or more molar equivalents of triarylphosphine such as triphenylphosphine in a suitable solvent such as diethyl ether, THF, benzene or toluene at temperatures ranging from −20° C. to 120° C.

The 2-hydroxy carboxylic acid ester of formula $CH(OH)$ $(R^5)CO_2R^6$ ($R^5$ is H, alkyl of 1–6 carbon atoms, aralkyl, aryl, $CH_2$(1H-imidazol-4-yl), $CH_2$(3-1H-indolyl), $CH_2CH_2$ (1,3-dioxo-1,3-dihydro-isoindol-2-yl), $CH_2CH_2$(1-oxo-1,3-dihydro-isoindol-2-yl), $CH_2$(3-pyridyl), $CH_2CO_2R^6$, $R^6$ is alkyl of 1–6 carbon atoms) are commercially available or can be prepared from commercially available carboxylic acid precursors under standard esterification conditions. (S)-(+)-2-Hydroxy-1-oxo-3-dihydro-2-isoindolinebutyric acid, methyl ester can be prepared from (S)-(+)-2-hydroxy-1,3-dioxo-2-isoindolinebutyric acid, methyl ester via sequential treatment with 1) sodium borohydride in THF-water; 2) trifluoroacetic acid/chloroform; 3) triethylsilane/trifluoroacetic acid and 4) aqueous sodium bicarbonate. 3-(Pyridin-3-yl)-phenyllactic acid, ethyl ester can be prepared according to the two step procedure of B. A. Lefker, W. A. Hada, P. J. McGarry *Tetrahedron Lett.* 1994, 35, 5205–5208, from commericially available 3-pyridinecarboxaldehyde and ethyl chloroacetate.

The esters of formula (Iq: A is H; B, D is H, halogen, alkyl of 1–6 carbon atoms, aryl, aralkyl, alkoxy of 1–6 carbon atoms; Y, Z is H; X is H, halogen, alkyl of 1–6 carbon atoms, CN, perfluoroalkyl of 1–6 carbon atoms, alkoxy of 1–6 carbon atoms, aralkoxy, alkylsulfanyl of 1–6 carbon atoms, arylsulfanyl; W is $CO_2tBu$; $R^5$ is H; E is S, O) can be treated with one or more molar equivalents of a strong base such as lithium diisopropyl amide in a suitable solvent such as THF at temperatures ranging from −78° C. to room temperature. This procedure produces an anion alpha to the ester carbonyl. The resultant anion is treated with one or more molar equivalents of an alkyl halide of formula $X^2R^5$ (where is $X^2$ is halogen; $R^5$ is alkyl and aralkyl) and warmed to room temperature to produce the alkylated ester of formula (Iq: A is H; B, D is H, halogen, alkyl of 1–6 carbon atoms, aryl, aralkyl alkoxy of 1–6 carbon atoms; Y, Z is H; X is H, halogen, alkyl of 1–6 carbon atoms, CN, perfluoroalkyl of 1–6 carbon atoms, alkoxy of 1–6 carbon atoms, aralkoxy, alkylsulfanyl of 1–6 carbon atoms, arylsulfanyl; W is $CO_2tBu$; $R^5$ is alkyl and aralkyl; E is S, O).

The esters of formula (Iq: A is H or OH; B, D is H, halogen, CN, alkyl of 1–6 carbon atoms, aryl, aralkyl, alkoxy of 1–6 carbon atoms, nitro; Y, Z is H or $OCH_2CO_2R^6$, but Y and Z are not concurrently $OCH_2CO_2R^6$; X is H, halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; W is $CO_2R^6$; $R^5$ is H, alkyl of 1–6 carbon atoms, aralkyl, aryl, $CH_2$(1H-imidazol-4-yl), $CH_2$(3-1H-indolyl), $CH_2CH_2$(1,3-dioxo-1,3-dihydro-isoindol-2-yl), $CH_2CH_2$(1-oxo-1,3-dihydro-isoindol-2-yl), $CH_2$(3-pyridyl), $CH_2CO_2R^6$, $R^6$ is alkyl of 1–6 carbon atoms; E is S, O) can be transformed into their carboxylic acid analogs using standard conditions to afford the carboxylic acids of formula (Iq: A is H or OH; B, D is H, halogen, alkyl of 1–6 carbon atoms, aryl, aralkyl, alkoxy of 1–6 carbon atoms, nitro; Y, Z is H or $OCH_2CO_2H$, but Y and Z are not concurrently $OCH_2CO_2H$; X is H, halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; W is $CO_2H$; $R^5$ is H, alkyl of 1–6 carbon atoms, aralkyl, aryl, $CH_2$(1H-imidazol-4-yl), $CH_2$(3-1H-indolyl), $CH_2CH_2$(1,3-dioxo-1,3-dihydro-isoindol-2-yl), $CH_2CH_2$(1-oxo-1,3-dihydro-isoindol-2-yl), $CH_2$(3-pyridyl), $CH_2CO_2H$; E is S, O). The conditions to effect these transformations include aqueous base in which one or more molar equivalents of alkali metal hydroxide such as sodium hydroxide is used in water with a co-solvent such as THF, dioxane or a lower alcohol such as methanol or mixtures of THF and a lower alcohol at temperatures ranging from 0° C. to 40° C. Alternatively, acid conditions may also be employed in which the above mentioned carboxylic acid ester of formula (Iq) is reacted with one or more molar equivalents of a mineral acid such as HCl or sulfuric acid in water with or without a co-solvent such as THF at temperatures ranging from room temperature to 80° C. Still alternatively, many other conditions may be employed to effect the above mentioned ester to acid transformation leading to (Iq). These include reacting the carboxylic acid ester of formula (Iq) with one or more molar equivalents of boron tribromide or boron trichloride in dichloromethane at –78° C. to room temperature; one or more molar equivalents hydrobromic acid in acetic acid at 0° C. to 50° C.; one or more molar equivalents trimethylsilylbromide or trimethylsilyliodide in dichloromethane, carbon tetrachloride or acetonitrile at –78° C. to 50° C.; one or more molar equivalents lithium iodide in pyridine or quinoline at temperatures from 100° to 250° C.

When the esters of formula (Iq: A is H; B, D is H, halogen, CN, alkyl of 1–6 carbon atoms, aryl, aralkyl, alkoxy of 1–6 carbon atoms, nitro; Y, Z is H; X is Br or I; W is $CO_2R^6$; $R^5$ is H, alkyl of 1–6 carbon atoms, aralkyl, aryl, $CH_2$(1H-imidazol-4-yl), $CH_2$(3-1H-indolyl), $CH_2CH_2$(1,3-dioxo-1,3-dihydro-isoindol-2-yl), $CH_2CH_2$(1-oxo-1,3-dihydro-isoindol-2-yl), $CH_2$(3-pyridyl), $CH_2CO_2R^6$, $R^6$ is alkyl of 1–6 carbon atoms; E is S, O) are reacted with two or more molar equivalents of trimethylsilyliodide in dichloromethane at temperatures ranging from 0° C. to room temperature, conversion to the carboxylic acids takes place (i.e., W is $CO_2H$) but also the 6-halogen (X is Br or I) is reduced to give the carboxylic acids of formula (Iq: A is H; B, D is H, halogen, CN, alkyl of 1–6 carbon atoms, aryl, aralkyl, alkoxy of 1–6 carbon atoms, nitro; Y, Z is H; X is H; W is $CO_2H$; $R^5$ is H, alkyl of 1–6 carbon atoms, aralkyl, aryl, $CH_2$(1H-imidazol-4-yl), $CH_2$(3-1H-indolyl), $CH_2CH_2$(1,3-dioxo-1,3-dihydro-isoindol-2-yl), $CH_2CH_2$(1-oxo-1,3-dihydro-isoindol-2-yl), $CH_2$(3-pyridyl), $CH_2CO_2H$; E is S, O).

The phenols of formula (Ip: A is H; B, D is H, halogen, CN, alkyl of 1–6 carbon atoms, aryl, aralkyl, alkoxy of 1–6 carbon atoms, nitro; Y, Z is H or $OCH_2CO_2R^6$, but Y and Z are not concurrently $OCH_2C_2R^6$; X is H, halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; $R^6$ is alkyl of 1–6 carbon atoms; E is S, O) can be alkylated with one or more molar equivalents of diethyl trifluoromethylsulfonyloxymethylphosphanate (D. P. Phillion and S. S. Andrew *Tet. Lett.* 1986, 1477–1480) and with one or more molar equivalents of an alkali metal hydride such as sodium hydride in a suitable solvent such as THF or DMF to afford the diethylphosphonate product of formula (Iq: A is H; B, D is H, halogen, CN, alkyl of 1–6 carbon atoms, aryl, aralkyl, alkoxy of 1–6 carbon atoms, nitro; Y, Z is H or $OCH_2CO_2R^6$, but Y and Z are not concurrently $OCH_2CO_2R^6$; X is H, halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; W is $PO_3Et_2$; $R^5$ is H; $R^6$ is alkyl of 1–6 carbon atoms; E is S, O).

The phenols of formula (Ip: A is H or OH; B, D is H, halogen, CN, alkyl of 1–6 carbon atoms, aryl, aralkyl, alkoxy of 1–6 carbon atoms, nitro; Y, Z is H or $OCH_2CO_2R^6$, but Y and Z are not concurrently $OCH_2CO_2R^6$; X is H, halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; $R^6$ is alkyl of 1–6 carbon atoms; E is S, O) can be reacted with a 2-hydroxy phosphonic acid diester of formula $CH(OH)(R^5)PO_3(R^6)_2$, ($R^5$ is H, alkyl of 1–6 carbon atoms, aralkyl, aryl, $R^6$ is alkyl of 1–6 carbon atoms) to afford the phosphonic acid diesters of formula (Iq: A is H or OH; B, D is H, halogen, CN, alkyl of 1–6 carbon atoms, aryl, aralkyl, alkoxy of 1–6 carbon atoms, nitro; Y, Z is H or $OCH_2CO_2R^6$, but Y and Z are not concurrently $OCH_2CO_2R^6$; X is H, halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; W is $PO_3(R^6)_2$; $R^5$ is H, alkyl of 1–6 carbon atoms, aralkyl, aryl, $R^6$ is alkyl of 1–6 carbon atoms; E is S, O) under the conditions of the Mitsunobu Reactions (for a review see Oyo Mitsunobu *Synthesis* 1981, 1–27). The other co-reagents necessary to effect the Mitsunobu Reaction include one or more molar equivalents of a alkyl of 1–6 carbon atoms azodicarboxylate diester such as diethyl azodicarboxylate or diisopropyl azodicarboxylate and one or more molar equivalents of triarylphosphine such as triphenylphosphine in a suitable solvent such as diethyl ether, THF, benzene or toluene at temperatures ranging from –20° C. to 120° C. The 2-hydroxy phosphonic acid diester of formula $CH(OH)(R^5)PO_3R^6$ ($R^5$ is H, alkyl of 1–6 carbon atoms, aralkyl, aryl, $R^6$ is alkyl of 1–6 carbon atoms) can be prepared by reacting a dialklylphosphonate of formula $HP(O)(OR^6)_2$ ($R^6$ is alkyl of 1–6 carbon atoms) with an aldehyde of formula $R^5CHO$ ($R^5$ is alkyl of 1–6 carbon atoms, aryl, aralkyl) under standard conditions.

The phosphonic acid diesters of formula (Iq: A is H or OH; B, D is H, halogen, CN, alkyl of 1–6 carbon atoms, aryl, aralkyl, alkoxy of 1–6 carbon atoms, nitro; Y, Z is H or $OCH_2CO_2R^6$, but Y and Z are not concurrently $OCH_2CO_2R^6$; X is H, halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; W is $PO_3(R^6)_2$; $R^5$ is H, alkyl of 1–6 carbon atoms, aralkyl, aryl, $R^6$ is H, alkyl of 1–6 carbon atoms; E is S, O) can be transformed into their phosphonic acid analogs using standard conditions to afford the phosphonic acids acids of formula (Iq: A is H or OH; B, D is H, halogen, CN, alkyl of 1–6 carbon atoms, aryl, aralkyl, alkoxy of 1–6 carbon atoms, nitro; Y, Z is H or $OCH_2CO_2R^6$, but Y and Z are not concurrently $OCH_2CO_2R^6$; X is H, halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; W is $PO_3H_2$; $R^5$ is H, alkyl of 1–6 carbon atoms, aralkyl, aryl, $R^6$ is alkyl of 1–6 carbon atoms; E is S, O). The conditions that may also be employed in which the above mentioned phosphonic acid diester of formula (Iq) is reacted with two or more molar equivalents of a mineral acid such as HCl or sulfuric acid in water with or without a co-solvent such as THF at temperatures ranging from 40 to 100° C. Still alternatively, many other conditions may be employed to effect the above mentioned diester to acid transformation leading to (Iq). These include reacting the phosphonic acid diester of formula (Iq) with two or more molar equivalents of boron tribromide or boron trichloride in dichloromethane at –78° C. to room temperature; two or more molar equivalents hydrobromic acid in acetic acid at 0° C. to 50° C.; two or more molar equivalents trimethylsilyl-bromide or trimethylsilyliodide in dichloromethane, carbon tetrachloride or acetonitrile at –78° C. to 50° C.; two or more molar equivalents lithium iodide in pyridine or quinoline at temperatures from 60° to 250° C.

The esters of formula (Iq: A is H or OH; B, D is H, halogen, CN, alkyl of 1–6 carbon atoms, aryl, aralkyl, alkoxy of 1–6 carbon atoms, nitro; Y, Z is H; X is H, halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; W is $CO_2R^6$; $R^5$ is H, alkyl of 1–6 carbon atoms, aralkyl, aryl, $CH_2$(1H-imidazol-4-yl), $CH_2$(3-1H-indolyl), $CH_2CH_2$(1-oxo-1,3-dihydro-isoindol-2-yl), $CH_2$(3-pyridyl), $R^6$ is alkyl of 1–6 carbon atoms; E is S, O) can be transformed into their primary carboxylic acid amide analogs of formula (Iq: A is H or OH; B, D is H, halogen, alkyl of 1–6 carbon atoms, aryl, aralkyl, alkoxy of 1–6 carbon atoms, nitro; Y, Z is H; X is H, halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; W is $CONH_2$; $R^5$ is H, alkyl of 1–6 carbon atoms, aralkyl, aryl, $CH_2$(1H-imidazol-4-yl), $CH_2$(3-1H-indolyl), , $CH_2CH_2$(1-oxo-1,3-dihydro-isoindol-2-yl), $CH_2$(3-pyridyl); E is S, O) by reacting the ester starting material with ammonia gas dissolved in a lower alcohol solvent such as methanol or ethanol at temperatures ranging from 0° C. to 100° C.

Alternatively, the carboxylic acids of formula (Iq: A is H or OH; B, D is H, halogen, CN, alkyl of 1–6 carbon atoms, aryl, aralkyl, alkoxy of 1–6 carbon atoms, nitro; Y, Z is H; X is H, halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; W is $CO_2H$; $R^5$ is H, alkyl of 1–6 carbon atoms, aralkyl, aryl, $CH_2$(1H-imidazol-4-yl), $CH_2$(3-1H-indolyl), $CH_2CH_2$(1,3-dioxo-1,3-dihydro-isoindol-2-yl), $CH_2CH_2$(1-oxo-1,3-dihydro-isoindol-2-yl), $CH_2$(3-pyridyl); E is S, O) can be transformed into their carboxylic acid amide analogs of formula (Iq: A is H or OH; B, D is H, halogen, alkyl of 1–6 carbon atoms, aryl, aralkyl, alkoxy of 1–6 carbon atoms, nitro; Y, Z is H; X is H, halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; W is $CONH_2$, CONHOH, $CONH(CH_2)_2CN$; $R^5$ is H, alkyl of 1–6 carbon atoms, aralkyl, aryl, $CH_2$(1H-imidazol-4-yl), $CH_2$(3-1H-indolyl), $CH_2CH_2$(1,3-dioxo-1,3-dihydro-isoindol-2-yl), $CH_2CH_2$(1-oxo-1,3-dihydro-isoindol-2-yl), $CH_2$(3-pyridyl); E is S, O). This transformation can be accomplished using standard methods to effect carboxylic acid to carboxylic acid amide transformations. These methods include converting the acid to an activated acid and reacting with one or more molar equivalents of the desired amine. Amines in this category include ammonia in the form of ammonium hydroxide, hydroxyl amine and 2-aminopropionitrile. Methods to activate the carboxylic acid include reacting said acid with one or more molar equivalents of oxalyl chloride or thionyl chloride to afford the carboxylic acid chloride in a suitable solvent such as dichloromethane, chloroform or diethyl ether. This reaction is often catalyzed by adding small amounts (0.01 to 0.1 molar equivalents) of dimethylformamide. Other methods to activate the carboxylic acid include reacting said acid with one or more molar equivalents dicyclohexylcarbodiimide with or without one or more molar equivalents of hydroxybenzotriazole in a suitable solvent such as dichloromethane or dimethylformamide at temperatures ranging from 0° C. to 60° C.

The phenols of formula (Ip: A is H; B, D is H, halogen, CN, alkyl of 1–6 carbon atoms, aryl, aralkyl, alkoxy of 1–6 carbon atoms, nitro; Y, Z is H; X is H, halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; E is S, O) can be alkylated with one or more molar equivalents of a haloacetonitrile of formula ($X^2CH_2CN$ where $X^2$ is Cl, Br or I) and with one or more molar equivalents of an alkali metal carbonate such as potassium carbonate in a polar aprotic solvent such as DMF to afford the nitriles of formula (Iq: A is H; B, D is H, halogen, CN, alkyl of 1–6 carbon atoms, aryl, aralkyl, alkoxy of 1–6 carbon atoms, nitro; Y, Z is H; X is H, halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; W is CN; $R^5$ is H; E is S, O).

Alternatively, the carboxylic acid amide analogs of formula (Iq: A is H or OH; B, D is H, halogen, alkyl of 1–6 carbon atoms, aryl, aralkyl, alkoxy of 1–6 carbon atoms, nitro; Y, Z is H; X is H, halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; W is $CONH_2$; $R^5$ is H, alkyl of 1–6 carbon atoms, aralkyl, aryl, $CH_2$(1H-imidazol-4-yl), $CH_2$(3-1H-indolyl), $CH_2CH_2$(1,3-dioxo-1,3-dihydro-isoindol-2-yl), $CH_2CH_2$(1-oxo-1,3-dihydro-isoindol-2-yl), $CH_2$(3-pyridyl); E is S, O) can be converted to their nitrile analogs of formula (Iq: A is H or OH; B, D is H, halogen, alkyl of 1–6 carbon atoms, aryl, aralkyl, alkoxy of 1–6 carbon atoms, nitro; Y, Z is H; X is H, halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; W is CN; $R^5$ is H, alkyl of 1–6 carbon atoms, aralkyl, aryl, CH$_2$(1H-imidazol-4-yl), CH$_2$(3-1H-indolyl), CH$_2$CH$_2$(1,3-dioxo-1,3-dihydro-isoindol-2-yl), CH$_2$CH$_2$(1-oxo-1,3-dihydro-isoindol-2-yl), CH$_2$(3-pyridyl); E is S, O) by using reagents that dehydrate the primary carboxamide function to the nitrile function. One set of conditions to effect this transformation include reacting the said primary carboxylic acid amide with one or more molar equivalents of trifluoroacetic anhydride and two or more molar equivalents of pyridine in a suitable solvent such as dioxane at temperatures ranging from 60° C. to 120° C. The nitrile analogs of formula (Iq: A is H or OH; B, D is H, halogen, alkyl of 1–6 carbon atoms, aryl, aralkyl, alkoxy of 1–6 carbon atoms, nitro; Y, Z is H; X is H, halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; W is CN; $R^5$ is H, alkyl of 1–6 carbon atoms, aralkyl, aryl, CH$_2$(1H-imidazol-4-yl), CH$_2$(3-1H-indolyl), CH$_2$CH$_2$(1,3-dioxo-1,3-dihydro-isoindol-2-yl), CH$_2$CH$_2$(1-oxo-1,3-dihydro-isoindol-2-yl), CH$_2$(3-pyridyl); E is S, O) can be converted to the tetrazoles of formula (Iq: A is H or OH; B, D is H, halogen, alkyl of 1–6 carbon atoms, aryl, aralkyl, alkoxy of 1–6 carbon atoms, nitro; Y, Z is H; X is H, halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; W is 5-tetrazole; $R^5$ is H, alkyl of 1–6 carbon atoms, aralkyl, aryl, CH$_2$(1H-imidazol4-yl), CH$_2$(3-1H-indolyl), CH$_2$CH$_2$(1,3-dioxo-1,3-dihydro-isoindol-2-yl), CH$_2$CH$_2$(1-oxo-1,3-dihydro-isoindol-2-yl), CH$_2$(3-pyridyl); E is S, O) by reacting the nitrile function with one or more molar equivalents of trimethylaluminum and one or more molar equivalents of trimethylsilyl azide in a suitable solvent such as benzene or toluene at temperatures ranging from 60° C. to 120° C. Alternatively, the nitrile fuction can be reacted with one or more molar equivalents of ammonium azide in a suitable solvent such as dimethylformamide at temperatures ranging from 60° C. to 160° C.

The esters of formula (Iq: A is H; B, D is H, halogen, alkyl of 1–6 carbon atoms, aryl, aralkyl, alkoxy of 1–6 carbon atoms; Y, Z is H; X is H, halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; W is CO$_2$R$^6$; $R^5$ is H, alkyl of 1–6 carbon atoms, aralkyl, aryl; $R^6$ is alkyl of 1–6 carbon atoms; E is S, O) can be transformed into their primary alcohol analogs of formula (Iq: A is H; B, D is H, halogen, alkyl of 1–6 carbon atoms, aryl, aralkyl, alkoxy of 1–6 carbon atoms; Y, Z is H; X is H, halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; W is CH$_2$OH; $R^5$ is H, alkyl of 1–6 carbon atoms, aralkyl, aryl; $R^6$ is alkyl of 1–6 carbon atoms; E is S, O) by reacting said ester with one or more molar equivalents of lithium aluminum hydride and one or more molar equivalents of aluminum chloride in a suitable solvent such as THF at temperatures ranging from –78 to room temperature.

The primary alcohol analogs of formula (Iq: A is H; B, D is H, halogen, alkyl of 1–6 carbon atoms, aryl, aralkyl, alkoxy of 1–6 carbon atoms; Y, Z is H; X is H, halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; W is CH$_2$OH; $R^5$ is H, alkyl of 1–6 carbon atoms, aralkyl, aryl; $R^6$ is alkyl of 1–6 carbon atoms; E is S, O) can be converted to the primary bromides of formula (Iq: A is H; B, D is H, halogen, alkyl of 1–6 carbon atoms, aryl, aralkyl, alkoxy of 1–6 carbon atoms; Y, Z is H; X is H, halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; W is CH$_2$Br; $R^5$ is H, alkyl of 1–6 carbon atoms, aralkyl, aryl; $R^6$ is alkyl of 1–6 carbon atoms; E is S, O) by reacting the said primary alcohol with one or more molar equivalents of lithium bromide with one or more molar equivalents of a alkyl of 1–6 carbon atoms azocarboxylate diester such as diethyl azodicarbxylate or diisopropyl azodicarboxylate and one or more molar equivalents of triarylphosphine such as triphenylphosphine in a suitable solvent such as diethyl ether, THF, benzene or toluene at temperatures ranging from –20° C. to 120° C.

Scheme 10

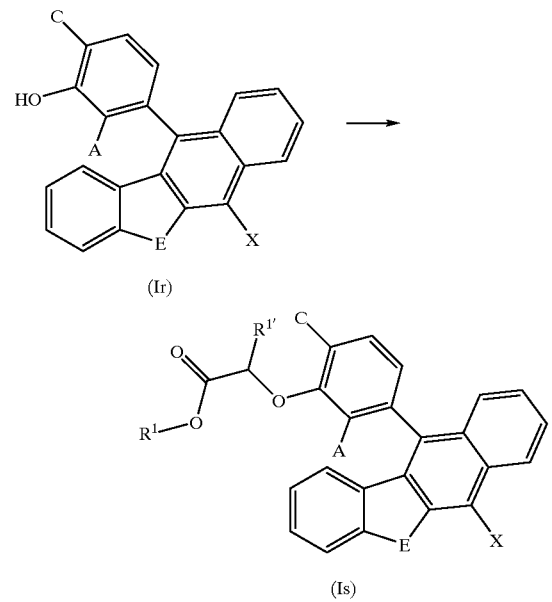

Further derivatives of the compounds of formula (I) in Scheme 10 can be prepared by the following methods. The phenols of formula (Ir: A is H or halogen; C is halogen or methoxy; X is halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; E is S, O) can be reacted with a 2-hydroxy carboxylic acid ester of formula CH(OH)(R$^{1a}$)CO$_2$R$^1$ (R$^1$, R$^{1a}$ is alkyl of 1–6 carbon atoms, aralkyl, aryl) to afford the esters of formula (Is: A is H or halogen; C is halogen or methoxy; X is halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; R$^1$ is alkyl of 1–6 carbon atoms, aralkyl, aryl; R$^{1a}$ is H or alkyl of 1–6 carbon atoms, aralkyl, aryl; E is S, O) under the conditions of the Mitsunobu Reactions (for a review see Oyo Mitsunobu *Synthesis* 1981, 1–27). The other co-reagents necessary to effect the Mitsunobu Reaction include one or more molar equivalents of a alkyl of 1–6 carbon atoms azodicarboxylate diester such as diethyl azodicarboxylate or diisopropyl azodicarboxylate and one or more molar equivalents of triarylphosphine such as triphenylphosphine in a suitable solvent such as diethyl ether, THF, benzene or toluene at temperatures ranging from −20° C. to 120° C. at temperatures ranging from −20° C. to 120° C.

The 2-hydroxy carboxylic acid ester of formula CH(OH)(R$^{1a}$)CO$_2$R$^1$ (R$^1$, R$^{1a}$ s alkyl of 1–6 carbon atoms, aralkyl, aryl) are commercially available or can be prepared from commercially available carboxylic acid precursors under standard esterification conditions.

The esters of formula (Is: A is H or halogen; C is halogen or methoxy; X is halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl R$^1$ is alkyl of 1–6 carbon atoms, aralkyl, aryl; R$^{1a}$ is H or alkyl of 1–6 carbon atoms, aralkyl, aryl; E is S, O) can be transformed into their carboxylic acid analogs using standard conditions to afford the carboxylic acids of formula (Is: A is H or halogen; C is halogen or methoxy; X is halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; R$^1$H; R$^{1a}$ is H or alkyl of 1–6 carbon atoms, aralkyl, aryl; E is S, O). The conditions to effect these transformations include aqueous base in which one or more molar equivalents of alkali metal hydroxide such as sodium hydroxide is used in water with a co-solvent such as THF, dioxane or a lower alcohol such as methanol or mixtures of THF and a lower alcohol at temperatures ranging from 0° C. to 40° C.

Scheme 11

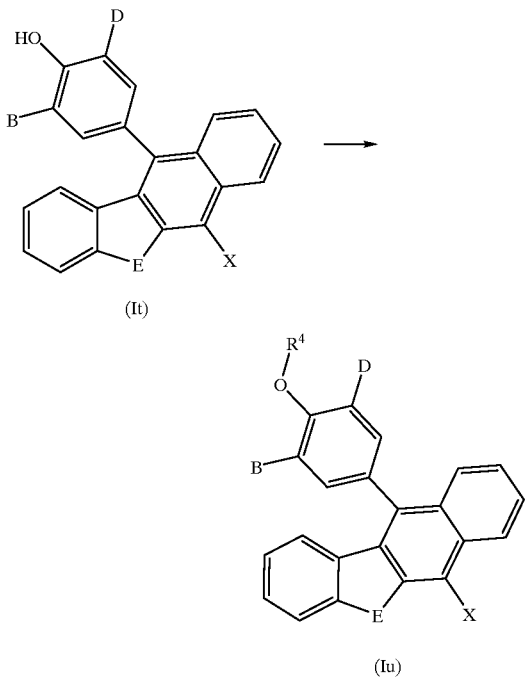

Further derivatives of the compounds of formula (I) in Scheme 11 can be prepared by the following methods. The phenols of formula (It: B, D is H, halogen, CN, alkyl of 1–6 carbon atoms, aryl, aralkyl, alkoxy of 1–6 carbon atoms, nitro; X is halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; E is S, O) can be reacted with one or more molar equivalents of lithium(bis)trimethylsilylamide at temperautres ranging from −78° C. to room temperature and the lithium salt can be further reacted with one or more molar equivalents of 5-bromothiazolidine-2,4-dione (prepared according to the method of Zask, et al., *J. Med Chem,* 1990, 33, 1418–1423) using a suitable solvent such as THF under an inert atmosphere at temperautres ranging from −78° C. to room temperature to provide the compounds of formula (Iu: R$^4$ is (R, S)-5-thiazolidine-2,4-dione; B, D is H, halogen, CN, alkyl of 1–6 carbon atoms, aryl, aralkyl, alkoxy of 1–6 carbon atoms, nitro; X is halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; E is S, O).

Alternatively, the phenols of formula (It: B, D is H, halogen, CN, alkyl of 1–6 carbon atoms, aryl, aralkyl, alkoxy of 1–6 carbon atoms, nitro; X is halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; E is S, O) can be reacted with one or more molar equivalents of tetrazole and di-tert-butyl N,N-diethylphosporamidate in THF at room temperature followed by addition of one or more molar equivalents of meta-chlorobenzoic acid at −40° C. according to the procedure of J. W. Perich and R. B. Johns, *Synthesis,* 1988, 142–144) to afford the phosphate diesters of formula (Iu: R$^4$ is P(O)(OtBu)$_2$; B, D is H, halogen, CN, alkyl of 1–6 carbon atoms, aryl, aralkyl, alkoxy of 1–6 carbon atoms, nitro; X is halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; E is S, O). These phosphate diesters are then treated with one or more molar equivalents hydrochloric acid in a suitable solvent such as dioxane to provide the phosphonic acids of formula (Iu: R$^4$ is P(O)(OH)$_2$; B, D is H, halogen, CN, alkyl of 1–6 carbon atoms, aryl, aralkyl, nitro; X is halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; E is S, O).

The phenols of formula (It: B, D is H, halogen, CN, alkyl of 1–6 carbon atoms, aryl, aralkyl, alkoxy of 1–6 carbon atoms, nitro; X is halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; E is S, O) can be transformed to the carboxylic acids of formula (Iu: R$^4$ is C(CH$_3$)$_2$CO$_2$H; B, D is H, halogen, CN, alkyl of 1–6 carbon atoms, aryl, aralkyl, alkoxy of 1–6 carbon atoms, nitro; X is halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; E is S, O) by treatment of the phenols with two or more molar equivalents of solid sodium hydroxide followed by one or more molar equivalents of 1,1,1-trichloro-2-methyl-2-propanol tetrahydrate in the presence of a large excess of acetone which also serves as solvent.

The phenols of formula (It: B, D is H, halogen, CN, alkyl of 1–6 carbon atoms, aryl, aralkyl, alkoxy of 1–6 carbon atoms, nitro; X is halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; E is S, O) can be transformed to the carboxylic acids of formula (Iu: $R^4$ is $CH_2CH_2CO_2H$; B, D is H, halogen, CN, alkyl of 1–6 carbon atoms, aryl, aralkyl, alkoxy of 1–6 carbon atoms, nitro; X is halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; E is S, O) by treatment with one or more molar equivalents of β-propiolactone and treatment with one or more molar equivalents of potassium tert-butoxide in a suitable solvent such as THF.

The phenols of formula (It: B, D is H, halogen, CN, alkyl of 1–6 carbon atoms, aryl, aralkyl, alkoxy of 1–6 carbon atoms, nitro; X is halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; E is S, O) can be reacted with a 3-hydroxy carboxylic acid ester of formula $CH(OH)(R^7)CH_2CO_2R^6$ ($R^7$ is H or alkyl of 1–6 carbon atoms; $R^6$ is alkyl of 1–6 carbon atoms) to afford the esters of formula (Iu: $R^4$ is (R)—$CH(R^7)CH_2CO_2R^6$; B, D is H, halogen, CN, alkyl of 1–6 carbon atoms, aryl, aralkyl, alkoxy of 1–6 carbon atoms, nitro; X is halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; $R^7$ is H or alkyl of 1–6 carbon atoms; $R^6$ is alkyl of 1–6 carbon atoms; E is S, O) under the conditions of the Mitsunobu Reactions (for a review see Oyo Mitsunobu *Synthesis* 1981, 1–27). The other co-reagents necessary to effect the Mitsunobu Reaction include one or more molar equivalents of a alkyl of 1–6 carbon atoms azodicarboxylate diester such as diethyl azodicarboxylate or diisopropyl azodicarboxylate and one or more molar equivalents of triarylphosphine such as triphenylphosphine in a suitable solvent such as diethyl ether, THF, benzene or toluene at temperatures ranging from –20° C. to 120° C. at temperatures ranging from –20° C. to 120° C.

The 3-hydroxy carboxylic acid ester of formula $CH(OH)(R^7)CH_2CO_2R^6$ ($R^7$ is H or alkyl of 1–6 carbon atoms; $R^6$ is alkyl of 1–6 carbon atoms) are commercially available or can be prepared from commercially available carboxylic acid precursors under standard esterification conditions.

The esters of formula (Iu: $R^4$ is (R)—$CH(R^7)CH_2CO_2R^6$; B, D is H, halogen, CN, alkyl of 1–6 carbon atoms, aryl, aralkyl, alkoxy of 1–6 carbon atoms, nitro; X is halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; $R^7$ is H or alkyl of 1–6 carbon atoms; $R^6$ is alkyl of 1–6 carbon atoms; E is S, O) can be transformed to the acids of formula (Iu: $R^4$ is (R)—$CH(R^7)CH_2CO_2H$; B, D is H, halogen, CN, alkyl of 1–6 carbon atoms, aryl, aralkyl, alkoxy of 1–6 carbon atoms, nitro; X is halogen, alkyl of 1–6 carbon atoms, CN, perfluoroalkyl of 1–6 carbon atoms, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; $R^7$ is H or alkyl of 1–6 carbon atoms; E is S, O) by several standard conditions which include reacting the ester of formula (Iu) with two or more molar equivalents of a mineral acid such as HCl or sulfuric acid in one or more solvents or a combination of two or more solvents such as water, THF or dioxane at temperatures ranging from 40 to 120° C. Still alternatively, many other conditions may be employed to effect the above mentioned ester to acid transformation leading to (Iu). These include reacting the esters of formula (Iu) with two or more molar equivalents of boron tribromide or boron trichloride in dichloromethane at –78° C. to room temperature; two or more molar equivalents hydrobromic acid in acetic acid at 0° C. to 50° C.; two or more molar equivalents trimethylsilylbromide or trimethylsilyliodide in dichloromethane, carbon tetrachloride or acetonitrile at –78° C. to 50° C.; two or more molar equivalents lithium iodide in pyridine or quinoline at temperatures from 60° to 250° C.

Scheme 12

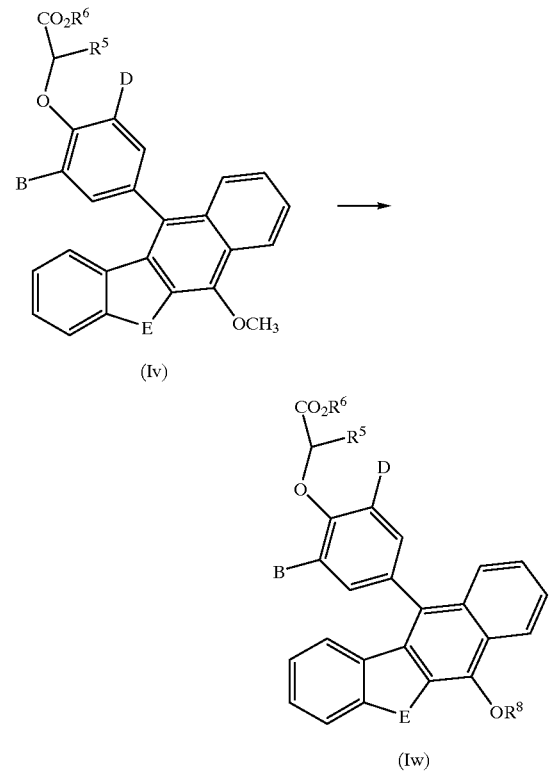

Further derivatives of the compounds of formula (I) in Scheme 12 can be prepared by the following methods. The esters of formula (Iv: B, D is H, halogen, alkyl of 1–6 carbon atoms; $R^5$ is H, alkyl of 1–6 carbon atoms, aryl or aralkyl; $R^6$ is alkyl of 1–6 carbon atoms; E is S, O) can be reacted with one or more molar equivalents of boron tribromide in a halocarbon solvent such as dichloromethane at temperatures ranging from –78 to room temperature to provide the phenols of formula (Iw: B, D is H, halogen, alkyl of 1–6 carbon atoms; $R^5$ is H, alkyl of 1–6 carbon atoms, aryl or aralkyl; $R^6$ is alkyl of 1–6 carbon atoms; $R^8$ is H; E is S, O).

The phenols of formula (Iw: B, D is H, halogen, alkyl of 1–6 carbon atoms; $R^5$ is H, alkyl of 1–6 carbon atoms, aryl or aralkyl; $R^6$ is alkyl of 1–6 carbon atoms; $R^8$ is H; E is S, O) can be alkylated with one or more molar equivalents of an alkylating agent of formula $R^8X$ ($R^8$ is alkyl of 1–6 carbon atoms, lower aralkyl and $CH_2CO_2CH_3$; X is halogen; E is S, O) and with one or more molar equivalents of an alkali metal carbonate such as potassium carbonate in a polar aprotic solvent such as DMF to afford the alkylated phenol of formula (Iw: B, D is H, halogen, alkyl of 1–6 carbon atoms; $R^5$ is H, alkyl of 1–6 carbon atoms, aryl or aralkyl; $R^6$ is alkyl of 1–6 carbon atoms; $R^8$ is alkyl of 1–6 carbon atoms, lower aralkyl, $CH_2CO_2CH_3$; E is S, O).

The esters of formula (Iw: B, D is H, halogen, alkyl of 1–6 carbon atoms; $R^5$ is H, alkyl of 1–6 carbon atoms, aryl or aralkyl; $R^6$ is alkyl of 1–6 carbon atoms; $R^8$ is alkyl of 1–6 carbon atoms, lower aralkyl, $CH_2CO_2CH_3$; E is S, O) can be transformed into their carboxylic acid analogs using standard conditions to afford the carboxylic acids of formula (Iw: B, D is H, halogen, alkyl of 1–6 carbon atoms; $R^5$ is H, alkyl of 1–6 carbon atoms, aryl or aralkyl; $R^6$ is H; $R^8$ is alkyl of 1–6 carbon atoms, lower aralkyl, $CH_2CO_2H$; E is S, O). The conditions to effect these transformations include aqueous base in which one or more molar equivalents of alkali metal hydroxide such as sodium hydroxide is used in water with a co-solvent such as THF, dioxane or a lower alcohol such as methanol or mixtures of THF and a lower alcohol at temperatures ranging from 0° C. to 40° C.

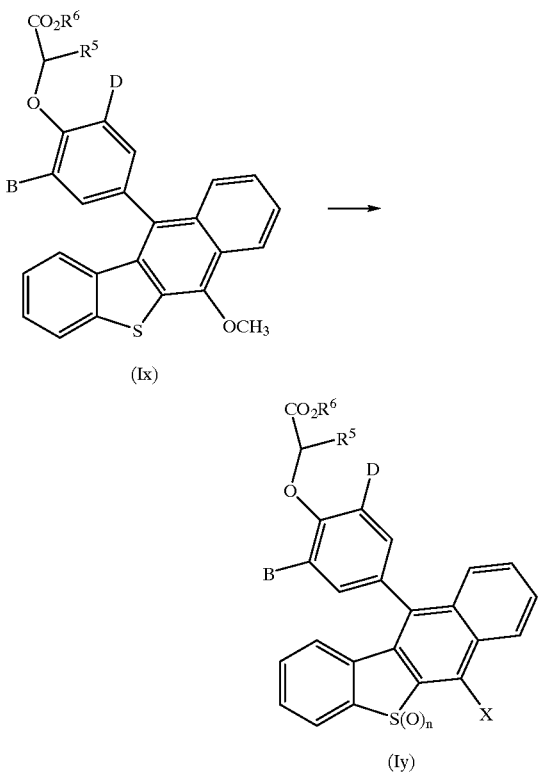

Scheme 13

Further derivatives of the compounds of formula (I) in Scheme 13 can be prepared by the following methods. The compounds of formula (Ix: B, D is H, halogen, alkyl of 1–6 carbon atoms, alkoxy of 1–6 carbon atoms; X is halogen, alkyl of 1–6 carbon atoms, CN, perfluoroalkyl of 1–6 carbon atoms, alkoxy of 1–6 carbon atoms, aralkoxy, $R^5$ is H, alkyl of 1–6 carbon atoms, aryl or aralkyl; $R^6$ is H, alkyl of 1–6 carbon atoms) can be transformed into their sulfoxide derivatives of formula (Iy: n is 1; B, D is H, halogen, alkyl of 1–6 carbon atoms, alkoxy of 1–6 carbon atoms; X is halogen, alkyl of 1–6 carbon atoms, CN, perfluoroalkyl of 1–6 carbon atoms, alkoxy of 1–6 carbon atoms, aralkoxy, $R^5$ is H, alkyl of 1–6 carbon atoms, aryl or aralkyl; $R^6$ is H, alkyl of 1–6 carbon atoms) using one molar equivalent of an oxidizing agent such as m-chloroperbenzoic acid in dichloromethane at temperatures ranging from –20° C. to 40° C. or peracetic acid in acetic acid and water at temperatures ranging from room temperature to 100° C.

The compounds of formula (Ix: B, D is H, halogen, alkyl of 1–6 carbon atoms, alkoxy of 1–6 carbon atoms; X is halogen, alkyl of 1–6 carbon atoms, CN, perfluoroalkyl of 1–6 carbon atoms, alkoxy of 1–6 carbon atoms, aralkoxy, $R^5$ is H, alkyl of 1–6 carbon atoms, aryl or aralkyl; $R^6$ is H, alkyl of 1–6 carbon atoms) can be transformed into their sulfone derivatives of formula (Iy: n is 2; B, D is H, halogen, alkyl of 1–6 carbon atoms, alkoxy of 1–6 carbon atoms; X is halogen, alkyl of 1–6 carbon atoms, CN, perfluoroalkyl of 1–6 carbon atoms, alkoxy of 1–6 carbon atoms, aralkoxy, $R^5$ is H, alkyl of 1–6 carbon atoms, aryl or aralkyl; $R^6$ is H, alkyl of 1–6 carbon atoms) using two or more molar equivalents of an oxidizing agent such as m-chloroperbenzoic acid in dichloromethane at temperatures ranging from –20° C. to 60° C. or peracetic acid in acetic acid and water at temperatures ranging from room temperature to 100° C.

The compounds of this invention are useful in treating metabolic disorders related to insulin resistance or hyperglycemia, typically associated with obesity or glucose intolerance. The compounds of this invention are therefore, particularly useful in the treatment or inhibition of type II diabetes. The compounds of this invention are also useful in modulating glucose levels in disorders such as type I diabetes.

The ability of compounds of this invention to treat or inhibit disorders related to insulin resistance or hyperglycemia was established with representative compounds of this invention in the following two standard pharmacological test procedures which measure the inhibition of PTPase.

Inhibition of Tri-Phosphorylated Insulin Receptor Dodecaphosphopeptide Dephosphorylation by Rat Hepatic Protein-Tyrosine Phosphatases (PTPases)

This standard pharmacological test procedure assess the inhibition of rat hepatic microsomal PTPase activity using, as substrate, the phosphotyrosyl dodecapeptide corresponding to the 1142–1153 insulin receptor kinase domain, phosphorylated on the 1146, 1150 and 1151 tyrosine residues. The procedure used and results obtained are briefly outlined below.

Preparation of Microsomal Fraction: Rats (Male Sprague-Dawley rats (Charles River, Kingston, N.Y.) weighing 100–150 g, maintained on standard rodent chow (Purina)) are sacrificed by asphyxiation with CO2 and bilateral thoracotomy. The liver is removed and washed in cold 0.85% (w/v) saline and weighed. The tissue is homogenized on ice in 10 volumes of Buffer A and the microsomes are isolated essentially as described by Meyerovitch J, Rothenberg P, Shechter Y, Bonner-Weir S, Kahn C R. Vanadate normalizes hyperglycemia in two mouse models of non-insulin-dependent diabetes mellitus. *J Clin Invest* 1991; 87:1286–1294 and Alberts B, Bray D, Lewis J, Raff M, Roberts K, Watson J D, editors. Molecular biology of the cell. New York: Garland Publishing, Inc., 1989 with minor modifications. The liver homogenate is filtered through silk to remove any remaining tissue debris and then is centrifuged at 10,000×g for 20 minutes at 40 C. The supernatant is decanted and centrifuged at 100,000×g for 60 minutes at 40 C. The pellet, microsomes and small vesicles, is resuspended and lightly homogenized in: 20 mM TRIS-HCl (pH 7.4), 50 mM 2-mercaptoethanol, 250 mM sucrose, 2 mM EDTA, 10 mM EGTA, 2 mM AEBSF, 0.1 mM TLCK, 0.1 mM TPCK, 0.5 mM benzamidine, 25 ug/ml leupeptin, 5 ug/ml pepstatin A, 5 ug/ml; H5B antipain, 5 ug/ml chymostatin, 10 ug/ml aprotinin (Buffer A), to a final concentration of approximately 850 ug protein/ml. Protein concentration is determined by the Pierce Coomassie Plus Protein Assay using crystalline bovine serum albumin as a standard (Pierce Chemical Co., Rockford, Ill.).

Measurement of PTPase activity: The malachite green-ammonium molybdate method, as described by Lanzetta P A, Alvarez L J, Reinach P S, Candia O A was used. An improved assay for nanomolar amounts of inorganic phosphate. Anal. Biochem. 1979;100:95–97, and adapted for the platereader, is used for the nanomolar detection of liberated phosphate by rat hepatic microsomal PTPases. The test procedure uses, as substrate, a dodecaphosphopeptide custom synthesized by AnaSpec, Inc. (San Jose, Calif.). The peptide, TRDIYETDYYRK, corresponding to the 1142–1153 catalytic domain of the insulin receptor, is tyrosine phosphorylated on the 1146, 1150 and 1151 tyrosine residues. The microsomal fraction (83.25 ul) is preincubated for 10 min at 37 deg.C. with or without test compound (6.25 ul) and 305.5 ul of the 81.83 mM HEPES reaction buffer, pH 7.4. Peptide substrate, 10.5 ul at a final concentration of 50 uM, is equilibrated to 37 deg.C. in a LABLINE Multi-Blok heater equipped with a titerplate adapter. The preincubated microsomal preparation (39.5 ul) with or without drug is added to initiate the dephosphorylation reaction, which proceeds at 37 deg.C. for 30 min. The reaction is terminated by the addition of 200 ul of the malachite green-ammonium molybdate-Tween 20 stopping reagent (MG/AM/Tw). The stopping reagent consists of 3 parts 0.45% malachite green hydrochloride, 1 part 4.2% ammonium molybdate tetrahydrate in 4 N HCl and 0.5% Tween 20. Sample blanks are prepared by the addition of 200 ul MG/AM/Tw to substrate and followed by 39.5 ul of the preincubated membrane with or without drug. The color is allowed to develop at room temperature for 30 min and the sample absorbances are determined at 650 nm using a platereader (Molecular Devices). Samples and blanks are prepared in quadruplicates. Screening activity of 50 uM (final) drug is accessed for inhibition of microsomal PTPases.

Calculations: PTPase activities, based on a potassium phosphate standard curve, are expressed as nmoles of phosphate released/min/mg protein. Test compound PTPase inhibition is calculated as percent of control. A four parameter non-linear logistic regression of PTPase activities using SAS release 6.08, PROC NLIN, is used for determining IC50 values of test compounds. All compounds were administered at a concentration of 50 $\mu$M. The following results were obtained using representative compounds of this invention.

| Example | % Change from Control |
| --- | --- |
| 7 | 1.03 |
| 14 | −34.19 |
| 15 | −43.68 |
| 18 | −15.22 |
| 20 | −26.86 |
| 21 | −32.41 |
| 22 | −16.83 |
| 23 | −8.92 |
| 24 | 3.16 |
| 25 | −38.31 |
| 26 | −8.68 |
| 27 | −35.78 |
| 30 | 1.00 |

-continued

| Example | % Change from Control |
| --- | --- |
| 32 | −58.12 |
| 34 | −3.40 |
| 37 | −3.02 |
| 40 | −1.40 |
| 41 | −39.32 |
| 42 | −21.28 |
| 43 | −14.62 |
| 47 | −3.50 |
| 58 | −43.32 |
| 59 | −35.46 |
| 60 | −25.07 |
| 61 | −54.82 |
| 62 | −40.14 |
| 63 | −47.53 |
| 64 | −15.90 |
| 68 | −26.32 |
| 70 | −29.03 |
| 71 | −35.74 |
| 74 | −21.61 |
| 76 | −18.89 |
| 79 | −82.58 |
| 81 | −47.69 |
| 82 | −39.80 |
| 83 | −57.89 |
| 84 | −73.91 |
| 85 | −71.67 |
| 86 | −69.35 |
| 87 | −63.18 |
| 88 | −67.03 |
| 89 | −61.04 |
| 90 | −79.04 |
| 91 | −97.10 |
| 92 | −98.16 |
| 93 | −58.35 |
| 94 | −95.80 |
| 95 | −75.45 |
| 108 | −72.94 |
| 109 | −66.67 |
| 110 | −12.78 |
| 111 | −76.45 |
| 113 | −101.01 |
| 114 | −68.03 |
| 115 | −55.43 |
| 116 | −61.89 |
| 117 | −79.06 |
| 118 | −82.00 |
| 119 | −75.29 |
| 120 | −17.35 |
| 121 | −74.70 |
| 122 | −85.46 |
| 123 | −87.44 |
| 124 | −70.01 |
| 125 | −73.96 |
| 126 | −78.77 |
| 127 | −37.08 |
| 128 | −50.94 |
| 129 | −59.03 |
| 130 | −72.14 |
| 131 | −66.21 |
| 132 | −49.27 |
| 133 | −27.89 |
| 134 | −69.86 |
| 135 | −59.75 |
| 136 | −63.42 |
| 137 | −64.92 |
| 138 | −69.13 |
| 139 | −64.89 |
| 140 | −71.19 |
| 141 | −76.58 |
| 142 | −104.68 |
| 143 | −76.98 |
| 144 | −85.24 |
| 146 | −71.95 |
| 147 | −66.60 |
| 148 | −82.62 |
| 149 | −59.82 |

| Example | % Change from Control |
|---|---|
| 150 | −92.46 |
| 152 | −95.22 |
| 155 | −82.25 |
| 156 | −71.12 |
| 161 | −8.03 |
| 162 | −60.67 |
| 163 | −38.40 |
| 164 | −70.32 |
| 165 | −3.12 |
| 166 | −26.86 |
| 167 | −16.99 |
| 168 | −17.85 |
| 169 | −9.30 |
| 170 | −18.79 |
| 171 | −71.04 |
| 172 | −70.95 |
| 174 | 0.39 |
| 175 | −69.20 |
| 177 | −69.35 |
| 178 | −42.41 |
| 179 | −66.27 |
| 180 | −50.64 |
| 184 | −46.44 |
| 185 | −98.45 |
| 186 | −74.87 |
| 187 | −57.64 |
| 189 | −89.32 |
| 194 | −79.35 |
| 195 | −29.34 |
| 196 | −80.08 |
| 200 | −50.62 |
| 201 | −75.75 |
| 203 | −86.47 |
| 210 | −51.55 |
| 211 | −36.82 |
| 213 | −54.40 |
| 215 | −80.93 |
| 216 | −60.67 |
| 217 | −80.42 |
| Phenylarsine oxide (reference standard) | −57.06 |

Inhibition of Tri-Phosphorylated Insulin Receptor Dodecaphosphopeptide Dephosphorylation by hPTP1B This standard pharmacological test procedure assess the inhibition of recombinant rat protein tyrosine phosphatase, PTP1B, activity using, as substrate, the phosphotyrosyl dodecapeptide corresponding to the 1142–1153 insulin receptor kinase domain, phosphorylated on the 1146, 1150 and 1151 tyrosine residues. The procedure used and results obtained are briefly described below.

Human recombinant PTP1B was prepared as described by Goldstein (see Goldstein et al. *Mol. Cell. Biochem.* 109, 107, 1992). The enzyme preparation used was in microtubes containing 500–700 μg/ml protein in 33 MM Tris-HCl, 2 mM EDTA, 10% glycerol and 10 mM 2-mercaptoethanol.

Measurement of PTPase activity. The malachite green-ammonium molybdate method, as described (Lanzetta et al. *Anal. Biochem.* 100, 95, 1979) and adapted for a platereader, is used for the nanomolar detection of liberated phosphate by recombinant PTP1B. The test procedure uses, as substrate, a dodecaphosphopeptide custom synthesized by AnaSpec, Inc. (San Jose, Calif.). the peptide, TRDIYETDYYRK, corresponding to the 1142–1153 catalytic domain of the insulin receptor, is tyrosine phosphorylated on the 1146, 1150, and 1151 tyrosine residues. The recombinant rPTP1B is diluted with buffer (pH 7.4, containing 33 mM Tris-HCl, 2 mM EDTA and 50 mM b-mercaptoethanol) to obtain an approximate activity of 1000–2000 nmoles/min/mg protein. The diluted enzyme (83.25 mL) is preincubated for 10 min at 37° C. with or without test compound (6.25 mL) and 305.5 mL of the 81.83 mM HEPES reaction buffer, pH 7.4 peptide substrate, 10.5 ml at a final concentration of 50 mM, and is equilibrated to 37° C. in a LABLINE Multi-Blok heater equipped with a titerplate adapter. The preincubated recombinant enzyme preparation (39.5 ml) with or without drug is added to initiate the dephosphorylation reaction, which proceeds at 37° C. for 30 min. The reaction is terminated by the addition of 200 mL of the malachite green-ammonium molybdate-Tween 20 stopping reagent (MG/AM/Tw). The stopping reagent consists of 3 parts 0.45% malachite green hydrochloride, 1 part 4.2% ammonium molybdate tetrahydrate in 4 N HCl and 0.5% Tween 20. Sample blanks are prepared by the addition of 200 mL MG/AM/Tw to substrate and followed by 39.5 ml of the preincubated recombinant enzyme with or without drug. The color is allowed to develop at room temperature for 30 min. and the sample absorbances are determined at 650 nm using a platereader (Molecular Devices). Sample and blanks are prepared in quadruplicates.

Calculations: PTPase activities, based on a potassium phosphate standard curve, are expressed as nmoles of phosphate released/min/mg protein. Inhibition of recombinant PTP1B by test compounds is calculated as percent of phosphatase control. A four parameter non-linear logistic regression of PTPase activities using SAS release 6.08, PROC NLIN, is used for determining $IC_{50}$ values of test compounds. The following results were obtained.

| Example | IC50 ($\mu$M) |
|---|---|
| 18 | 0.554 |
| 21 | 0.384 |
| 37 | 1.18 |
| 40 | 1.10 |
| 41 | 1.08 |
| 42 | 1.50 |
| 43 | 0.189 |
| 58 | 1.01 |
| 59 | 0.612 |
| 60 | 0.129 |
| 62 | 0.654 |
| 63 | 0.904 |
| 64 | 0.347 |
| 68 | 1.02 |
| 70 | 0.074 |
| 71 | 0.079 |
| 79 | 0.386 |
| 81 | 1.99 |
| 82 | 2.00 |
| 87 | 1.68 |
| 89 | 0.126 |
| 91 | 1.30 |
| 92 | 0.644 |
| 108 | 0.061 |
| 109 | 0.071 |
| 110 | 1.52 |
| 111 | 0.062 |
| 113 | 0.045 |
| 114 | 0.589 |
| 115 | 0.279 |
| 116 | 0.765 |
| 117 | 1.51 |
| 118 | 0.031 |
| 120 | 0.541 |
| 121 | 0.184 |
| 122 | 0.036 |

-continued

| Example | IC50 (µM) |
|---|---|
| 123 | 0.082 |
| 124 | 0.085 |
| 126 | 0.298 |
| 127 | 0.064 |
| 128 | 0.025 |
| 129 | 0.046 |
| 130 | 0.80 |
| 132 | 0.311 |
| 133 | 0.506 |
| 134 | 0.093 |
| 135 | 0.209 |
| 136 | 0.050 |
| 137 | 0.341 |
| 138 | 0.636 |
| 139 | 0.061 |
| 140 | 0.204 |
| 141 | 0.126 |
| 142 | 0.103 |
| 143 | 1.17 |
| 144 | 1.13 |
| 146 | 0.064 |
| 148 | 1.23 |
| 150 | 0.207 |
| 152 | 0.994 |
| 155 | 0.056 |
| 156 | 0.026 |
| 162 | 0.145 |
| 165 | 0.665 |
| 166 | 0.565 |
| 168 | 0.994 |
| 169 | 1.22 |
| 170 | 0.607 |
| 171 | 0.302 |
| 172 | 0.076 |
| 177 | 1.08 |
| 178 | 0.480 |
| 179 | 0.203 |
| 180 | 0.384 |
| 184 | 0.045 |
| 189 | 1.39 |
| 190 | 2.00 |
| 191 | 0.118 |
| 194 | 0.217 |
| 195 | 0.889 |
| 196 | 0.174 |
| 200 | 1.17 |
| 203 | 0.402 |
| 210 | 1.06 |
| 215 | 0.49 |
| 216 | 0.083 |
| Phenylarsine oxide (reference standard) | 39.7 |
| Sodium orthovanadate (reference standard) | 244.8 |
| Ammonium molybdate tetrahydrate (reference standard) | 8.7 |

The blood glucose lowering activity of representative compounds of this invention were determined in an in vivo standard procedure using diabetic (ob/ob) mice. The procedures used and results obtained are briefly described below.

The non-insulin dependent diabetic (NIDDM) syndrome can be typically characterizes by obesity, hyperglycemia, abnormal insulin secretion, hyperinsulinemia and insulin resistance. The genetically obese-hyperglycemic ob/ob mouse exhibits many of these metabolic abnormalities and is thought to be a useful model to search for hypoglycemic agents to treat NIDDM [Coleman, D.: Diabetologia 14: 141–148, 1978].

In each test procedure, mice [Male or female ob/ob (C57 B1/6J) and their lean litermates (ob+ or +/+, Jackson Laboratories) ages 2 to 5 months (10 to 65 g)] of a similar age were randomized according to body weight into 4 groups of 10 mice. The mice were housed 5 per cage and are maintained on normal rodent chow with water ad libitum. Mice received test compound daily by gavage (suspended in 0.5 ml of 0.5% methyl cellulose); dissolved in the drinking water; or admixed in the diet. The dose of compounds given ranges from 2.5 to 200 mg/kg body weight/day. The dose is calculated based on the fed weekly body weight and is expressed as active moiety. The positive control, ciglitazone (5-(4-(1-methylcyclohexylmethoxy)benzyl)-2,4-dione; see Chang, A., Wyse, B., Gilchrist, B., Peterson, T. and Diani, A. Diabetes 32: 830–838, 1983.) was given at a dose of 100 mg/kg/day, which produces a significant lowering in plasma glucose. Control mice received vehicle only.

On the morning of Day 4, 7 or 14 two drops of blood (approximetly 50 ul) were collected into sodium fluoride containing tubes either from the tail vein or after decapitation. For those studies in which the compound was administered daily by gavage the blood samples were collected two hours after compound administration. The plasma was isolated by centrifugation and the concentration of glucose is measured enzymatically on an Abbott V. P. Analyzer.

For each mouse, the percentage change in plasma glucose on Day 4, 7 or 14 is calculated relative to the mean plasma glucose of the vehicle treated mice. Analysis of variance followed by Dunett's Comparison Test (one-tailed) are used to estimate the significant difference between the plasma glucose values from the control group and the individual compound treated groups (CMS SAS Release 5.18).

The results shown in the table below shows that the compounds of this invention are antihyperglycemic agents as they lower blood glucose levels in diabetic mice.

| Example | Dose (mg/Kg) | % Change Glucose from Vehicle | % Change Insulin from Vehicle |
|---|---|---|---|
| 70 | 25 | −28.55 | 45.68(a) |
| 79 | 100 | −22.6 | −60.9 |
| 79 | 100 | −22.60 | −60.85 |
| 87 | 100 | −15.77(a) | −87.97 |
| 89 | 10 | −24.9 | (b) |
| 108 | 100 | −45.83 | −72.56 |
| 108 | 75 | −49.74 | −89.61 |
| 108 | 50 | −34.79 | −84.77 |
| 108 | 25 | −25.66 | −71.03 |
| 108 | 10 | −26.09 | −30.33(a) |
| 109 | 25 | −26.31 | −71.64 |
| 111 | 100 | −39.36 | −17.85(a) |
| 113 | 25 | −0.50(a) | −55.84 |
| 115 | 100 | −33.9 | 52.00 |
| 117 | 100 | −14.5(a) | −83.8 |
| 121 | 100 | −54.57 | −87.76 |
| 121 | 10 | 1.37(a) | −41.81 |
| 122 | 100 | −28.13 | −37.40 |
| 123 | 75 | −23.96 | −40.94 |
| 125 | 95 | −27.58 | −89.68 |
| 126 | 25 | −28.55 | −62.39 |
| 127 | 25 | −18.75(a) | −76.54 |
| 128 | 25 | 3.10(a) | −38.83 |
| 129 | 25 | −14.86(a) | −54.58 |
| 131 | 25 | −3.63(a) | −67.55 |
| 135 | 25 | −15.83(a) | −57.43 |
| 136 | 25 | −23.63 | −52.05 |
| 138 | 25 | −13.84(a) | −91.90 |
| 139 | 25 | −18.5(a) | −22.00 |
| 146 | 100 | −45.79 | −56.19 |
| 155 | 25 | −28.89 | −63.23 |
| 172 | 100 | 5.62(a) | −52.05 |
| 189 | 100 | −46.8 | 11.00(a) |
| 191 | 25 | −36.5 | −64.3 |

-continued

| Example | Dose (mg/Kg) | % Change Glucose from Vehicle | % Change Insulin from Vehicle |
|---------|--------------|-------------------------------|-------------------------------|
| 191 | 10 | −22.8 | (b) |
| 194 | 25 | −32.0 | (b) |
| 203 | 100 | −16.1(a) | −91.0 |
| 215 | 100 | −39.36 | −4.66(a) |
| 216 | 25 | −42.4 | −85.6 |
| 216 | 25 | −38.7 | −84.0 |
| 216 | 10 | −28.7 | −69.4 |
| 216 | 5 | −14.8(a) | −55.9 |
| Ciglitazone (reference) standard | 100 | −43 | −39 |

(a)—no significant activity (p < 0.05) at this dose.
(b)—not measured

Based on the results obtained in the standard pharmacological test procedures, representative compounds of this invention have been shown to inhibit PTPase activity and lower blood glucose levels in diabetic mice, and are therefore useful in treating metabolic disorders related to insulin resistance or hyperglycemia, typically associated with obesity or glucose intolerance. More particularly, the compounds of this invention useful in the treatment or inhibition of type II diabetes, and in modulating glucose levels in disorders such as type I diabetes. As used herein, the term modulating means maintaining glucose levels within clinically normal ranges.

Effective administration of these compounds may be given at a daily dosage of from about 1 mg/kg to about 250 mg/kg, and may given in a single dose or in two or more divided doses. Such doses may be administered in any manner useful in directing the active compounds herein to the recipient's bloodstream, including orally, via implants, parenterally (including intravenous, intraperitoneal and subcutaneous injections), rectally, vaginally, and transdermally. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Oral formulations herein may utilize standard delay or time release formulations to alter the absorption of the active compound(s). Suppository formulations may be made from traditional materials, including cocoa butter, with or without the addition of waxes to alter the suppository's melting point, and glycerin. Water soluble suppository bases, such as polyethylene glycols of various molecular weights, may also be used.

It is understood that the dosage, regimen and mode of administration of these compounds will vary according to the malady and the individual being treated and will be subject to the judgment of the medical practitioner involved. It is preferred that the administration of one or more of the compounds herein begin at a low dose and be increased until the desired effects are achieved.

The following procedures describe the preparation of representative examples of this invention.

EXAMPLE 1

Benzo[b]thiophene-2-yl-(phenyl)-methanol n-Butyl lithium (35 ml, 2.5 N in hexanes) was added dropwise to a stirred solution of thianaphthene (11.5 g, 85.6 mmol) in THF (300 mL) at −78° C. under a dry N2 atmosphere. After 1 h, benzaldehyde (9.6 mL, 94.4 mmol) was added and the cold bath was removed. After an additional 30 minutes, sat. aq. NH4Cl was added and the reaction mixture was partitioned between water and ether. The ether phase was washed with brine and concentrated. The resultant solid was triturated with pet. ether and filtered to provide the title compound as a white solid (17.7 g, 86%): NMR (CDCl3); δ 7.78 (m, 1H, thiopheneH), 7.68 (m, 1H, thiopheneH), 7.22–7.56 (m, 7H), 7.12 (s, 1H, thiopheneH), 6.12 (d, 1H, OH), 2.51 (d, 1H, CH).

EXAMPLE 2

(6-Methoxy-benzo[b]thiophene-2-yl-(phenyl)-methanol n-Butyl lithium (12.5 ml, 2.5 N in hexanes) was added dropwise to a stirred solution of 6-methoxythianaphthene (5.0 g, 30.4 mmol, S. L. Graham, et al., *J. Med. Chem.* 1989, 32, 2548–2554) in THF (70 mL) at −78° C. under a dry N2 atmosphere. After 1 h, benzaldehyde (3.42 mL, 33.4 mmol) was added. After an additional 45 minutes, sat. aq. NH4Cl was added and the reaction mixture was partitioned between water and ether. The ether phase was washed with brine and silica gel was added to it. The solvent was removed and the adsorbate was flash chromatographed (eluent: 9:1 petroleum ether: ethyl acetate) to provide the title compound as a white solid (5.5 g, 66%): mp 79–80: NMR (CDCl3); δ 7.55 (d, J=9 Hz, 1H), d 7.49 (ddd, J=7, 1, 1 Hz, 2H), 7.39 (ddd, J=7, 7, 1 Hz, 2H), 7.26 (m, 1H), 7.01 (s, 1H), 6.94 (d, J=8 Hz, 1H), 6.09 (d, J=4 Hz, 1H), 3.85 (s, 3H), 2.46 (d, J=4 Hz, 1H); MS (EI): 270 (25%, MI).

EXAMPLE 3

Benzo[b]thiophen-2-yl-(3-methoxy-phenyl)-methanol

Prepared according to the procedure of Example 1 and substituing m-anisaldehyde for bezaldehyde. White solid: mp 63–65° C.; MS (+FAB): [M+] 270; Anal. Calc. for C16H14O2S: C, 71.08, H, 5.22, N, 0.00. Found: C, 71.07, H, 5.16, N, 0.13.

EXAMPLE 4

2-Benzyl-benzo[b]thiophene

Trifluoroacetic acid (105 mL) was added dropwise over a 35 minute period to a stirred suspension of benzo[b]

thiophene-2-yl-(phenyl)-methanol (17.6 g, 73.2 mmol), sodium borohydride (13.75 g, 364 mmol) and ether (1.3 L). After an additional 5 hours the reaction mixture was added to 10% aqueous sodium hydroxide (1.3 L) and stirred for 30 minutes. The layers were separated and the ether phase was washed with brine (500 mL) and dried (MgSO4). The ether phase was concentrated to provide the title compound as a white solid (15.2 g, 92%): NMR (CDCl3); δ 7.73 (d, J=6 Hz, 1H, thiopheneH), 7.65 (d, J=7 Hz, 1H, thiopheneH), 7.20–7.38 (m, 7H), 7.00 (s, 1H, thiopheneH), 4.22 (s, 2H, CH2).

EXAMPLE 5

2-Benzyl-6-methoxy-benzo[b]thiophene

Prepared from (6-methoxy-benzo[b]thiophene-2-yl-(phenyl)-methanol (Example 2) according to the procedure in Example 4. White solid: mp 60–61° C.: NMR (CDCl3); δ 7.53 (d, J=9 Hz, 1H), d 7.35–7.22 (m, 6H), 6.93 (dd, J=8, 2 Hz, 1H), 6.91 (d, J=1 Hz, 1H), 4.19 (s, 2H), 3.84 (s, 3H); MS (EI): 254 (50%, MI); Anal. Calc. for C16H14OS: C, 75.56, H, 5.55, N, 0.00. Found: C, 75.62, H, 5.44, N, 0.02.

EXAMPLE 6

2-(3-Methoxy-benzyl)-benzo[b]thiophene

Prepared from benzo[b]thiophen-2-yl-(3-methoxy-phenyl)-methanol (Example 3) according to the procedure in Example 4. White solid: mp 74–75.5° C.: MS (+FAB): [M+]254; Anal. Calc. for C16H14OS: C, 75.56, H, 5.55, N, 0.00. Found: C, 75.85, H, 5.48, N, 0.01.

EXAMPLE 7

(2-Benzyl-benzo[b]thiophen-3-yl)-(4-methoxy-phenyl)-methanone

Tin tetrachloride (9.0 mL, 76.91 mmol) was added dropwise over a 25 minute period to a stirred solution of 2-benzyl-benzo[b]thiophene (14.87 g, 96.79 mmol), p-anisoyl chloride (11.75 g, 68.87 mmol) and carbon disulfide (75 mL) under a dry nitrogen atmosphere. After 6 hours, the reaction mixture was added to water and extracted with dichloromethane. The dichloromethane extract was washed with sat. aq. sodium bicarbonate and brine. The solvent was removed and the resultant solid was triturated with pet. ether to give the title compound as a white solid (20.2 g, 85%): mp 135–137° C.: NMR (CDCl3); δ 7.85 (dm, J=9 Hz, 2H), 7.73 (dm, 1H), 7.42 (dm, 1H), 7.18–7.30 (m, 7H), 6.93 (dm, J=9 Hz, 2H), 4.21 (s, 2H, CH2), 3.88 (s, 3H, CH3): IR (KBr, cm–1): 1650; MS (EI): 358 (100%, MI), 343 (15%), 327 (75%); Anal. Calc. for C23H18O2S: C, 77.07, H, 5.06, N, 0.00. Found: C, 76.91, H, 5.02, N, –0.12.

EXAMPLE 8

(2-Benzyl-6-methoxy-benzo[b]thiophen-3-yl)-(4-methoxy-phenyl)-methanone

Tin tetrachloride (2.0 mL, 17.09 mmol) was added dropwise over a 10 minute period to a stirred, –78° C. solution of 2-benzyl-6-methoxy-benzo[b]thiophene (2.71 g, 10.65 mmol), anisoyl chloride (1.93 g, 11.29 mmol) and dichloromethane (41 mL) under a dry nitrogen atmosphere. After 1 hours at –78° C., the reaction mixture was slowly warmed to room temperature and stirred for 16 h period. The reaction mixture was added to water and extracted with ether. The ether phase was washed with brine and silica gel was added to it. The solvent was removed and the adsorbate was flash chromatographed (eluent: 9:1 petroleum ether: ethyl acetate) to provide the title compound as a white solid (2.42 g, 58%): mp 110–112° C.: NMR (CDCl3); δ 7.84 (d, J=9 Hz, 2H), 7.31–7.18 (m, 7H), 7.92 (d, J=9 Hz, 2H), 6.97 (dd, J=9, 2 Hz, 1H), 4.17 (s, 2H), 3.88 (s, 3H), 3.883 (s, 3H); MS (FAB+): 389 (80%, M+H); Anal. Calc. for C24H20O3S: C, 74.20, H, 5.19, N, 0.00. Found: C, 74.94, H, 5.10, N, 0.03.

EXAMPLE 9

4-Bromo-2,6-diisopropylanisole

This is a modification of the procedure of Schuster, Ingeborg I.; Parvez, Masood; Freyer, Alan J. *J. Org. Chem.* 1988, 53, 5819. A solution of bromine (6.3 mL, 119 mmol) in acetic acid (40 mL) was added dropwise to a stirred, room temperature solution of 2,6-diisopropylphenol (20 mL, 97.1 mmol of 90% tech. grade) in acetic acid (280 mL). After 6 h, water was added and the mixture was extracted with ether. The ether phase was dried and concentrated and the residue was flash chromatographed (petroleum ether: eluent) to provide 4-bromo-2,6-diisopropylphenol (16.2 g, 65%) as a red oil. This oil was dissolved in DMF (50 mL), iodomethane (11.7 mL, 189 mmol) and potassium carbonate (26.3 g, 117 mL) were added to it. This reaction mixture was stirred for 5 h and diluted with water. This mixture was extracted with ether and the ether extracts were dried, concentrated and flash chromatographed (petroleum ether: eluent) to provide the title compound as a colorless oil (15.4 g, 90%): NMR (CDCl3); δ 7.17 (s, 2H), 3.70 (s, 3H), 3.29 (septet, 1H), 1.20 (d, 12 H).

EXAMPLE 10

3,5-Diisopropyl, 4-methoxybenzoic acid

This is a modification of the procedure of Schuster, Ingeborg I.; Parvez, Masood; Freyer, Alan J. *J. Org. Chem.* 1988, 53, 5819. A solution of n-butyllithium (2.5 N in hexanes, 13.0 mL, 32.5 mmol) was added dropwise over 20 min to a stirred, –78° C. solution of 4-bromo-2,6-diisopropylanisole (8.0 g, 29.5 mmol) in THF (185 mL). After 2 h at –78° C., the reaction mixture was cautiously added to finely ground dry ice. The resulting suspension was stirred for 20 min at room temperature and cautiously added to water. The water phase was acidified with 10% aqueous HCl and extracted with ether. The ether extracts were dried and concentrated. The resulting oil solidified upon standing. This solid was triturated with petroleum ether to provide the title compound as a white solid (5.38 g, 77%): NMR (CDCl3); δ 7.87 (s, 2H), 3.76 (s, 3H), 3.35 (septet, 1H), 1.25 (d, 12 H).

EXAMPLE 11

(2-Benzyl-benzo[b]thiophen-3 -yl)-(3,5-diisopropyl-4-methoxy-phenyl)-methanone A drop of DMF was added to a solution of oxalyl chloride (1.4 mL, 16.2 mmmol), 3,5-diisopropyl-4-methoxybenzoic acid (4.0 g, 14.7 mmol) in dichloromethane under a dry nitrogen atmosphere. After 4 h the solvent was removed and the resulting solid was triturated with petroleum ether and dried in vacuo. To this solid was added 2-benzyl-benzo[b]thiophene (3.32 g, 13.4 mmol) and dichloromethane (75 mL). The resulting solution was stirred under a dry nitrogen atmosphere and cooled to –78° C. Tin tetrachloride (3.44 mL, 29.48 mmol) was added dropwise over a 20 minute period.

The reaction mixture was warmed to room temperature and stirred overnight. The reaction mixture was added to water and extracted with ether. The ether extract was washed with water and brine. Silica gel was added and the solvent was removed. The adsorbate was flash chromatographed (gradient, petroleum ether to 95:5 petroleum ether:ethyl acetate). The solvent was removed and the solid was triturated with ether to give the title compound as a a white solid (3.68 g, 62%): mp 124–125° C.; NMR (CDCl3); δ 7.75 (ddd, J=8, 2, 1 Hz, 1H), 7.64 (s, 2H), 7.48 (ddd, J=8, 2, 1, 1H), 7.30–7.19 (m, 7H), 4.22 (s, 2H), 3.80 (s, 3H) 3.35 (septuplet, J=7 Hz, 2H), 1.19 (d, J=7 Hz, 12H); MS (+FAB): 443 (100%, M+H); Anal. Calc. for C29H30O2S: C, 78.69, H, 6.83, N, 0.00. Found: C, 78.57, H, 6.88, N, 0.14.

EXAMPLE 12

(2-Benzyl-benzo[b]thiophen-3-yl)-(3-methoxy-phenyl)-methanone

Prepared from 2-benzyl-benzo[b]thiophene and m-anisoyl chloride according to the procedure in Example 8. White solid: MS (EI): [M+], 358.

EXAMPLE 13

(2-Benzyl-benzo[b]thiophen-3-yl)-(3,4-dimethoxy-phenyl)-methanone

Prepared from 2-benzyl-benzo[b]thiophene and 3,4-dimethoxybenzoyl chloride according to the procedure in Example 8. White solid: MS (EI): [M+], 388.

EXAMPLE 14

4-Benzo[b]naphtho[2,3-d]thiophen-11-yl-phenol

A 1.0 M solution of boron tribromide in dichloromethane (130 mL, 130 mmol) was added slowly to a stirrred solution of (2-benzyl-benzo[b]thiophen-3-yl)-(4-methoxy-phenyl)-methanone (14.5 g, 40.45 mmol) in dichloromethane (130 mL) at −78° C. under a dry nitrogen atomosphere. The solution was allowed to warm to ambient temperature and was stirred overnight. The reaction mixture was quenched with water and partitioned between water and dichloromethane. Silica gel was added to the dichloromethane phase and the solvent was removed, The adsorbate was flash chromatographed (eluent 4:1 pet. ether:ethyl acetate) to provide a white solid (9.75 g). This solid was recrystalized from acetic acid to provide off-white needles (8.78, 56%): mp: 112–116° C.; NMR (CDCl3); δ 8.33 (s, 1H), 7.94 (dt, J=8 Hz, 1H), 7.77 (dm, J=8 Hz, 1H), 7.64 (dm, J=8 Hz, 1H), 7.52 (ddd, J=8, 7, 1 Hz, 1H), 7.37 (m, 2H), 7.29 (d, J=9 Hz, 2H), 7.11 (d, J=9 Hz, 2H), 7.08 (m, 1H), 6.85 (dm, J=8 Hz, 1H), 2.11 (s, 3H, acetic acid CH3); MS (EI): 326 (100%, MI); Anal. Calc. for C22H14OS.C2H4O2: C, 74.59, H, 4.69, N, 0.00. Found: C, 74.40, H, 4.59, N, 0.15.

EXAMPLE 15

11-(4-Hydroxy-phenyl)-benzo[b]naphtho[2,3-d]thiophen-3-ol

Boron tribromide (5 mL, 52.9 mmol) was added slowly to a stirrred solution of (2-benzyl-6-methoxy-benzo[b]thiophen-3-yl)-(4-methoxy-phenyl)-methanone (2.30 g, 5.92 mmol) in dichloromethane (30 mL) at −78° C. under a dry nitrogen atomosphere. The solution was allowed to warm to ambient temperature and was stirred for 4 h. The reaction mixture was quenched with water and partitioned between water and ether. Silica gel was added to the ether phase and the solvent was removed, The adsorbate was flash chromatographed (eluent 7:3 pet. ether:ethyl acetate) to provide the title compound as a white solid (2.08 g, 96%): mp: 197–199° C.; NMR (CDCl3); δ 8.28 (s, 1H), 7.92 (d, J=8 Hz, 1H), 7.59 (dm, J=8 Hz, 1H), 7.50 (ddd, J=8, 7, 1 Hz, 1H), 7.39–7.25 (m, 5H), 7.21 (d, J=2 Hz, 1H), 7.11 (d, J=9 Hz, 2H), 6.69 (d, J=9 Hz, 1H), 6.57 (dd, J=9, 2 Hz, 1H), 5.03 (s, 1H), 4.94 (s, 1H); MS (FAB+): 343 (15%, M+H); Anal. Calc. for C22H14O2S: C, 77.17, H, 4.12, N, 0:00. Found: C, 76.74, H, 4.04, N, 0.02.

EXAMPLE 16

4-(6-Benzo[b]naphtho[2,3-d]thiophen-11-yl)-2,6-diisopropyl-phenol

Neat boron tribromide (4.3 mL, 45.2 mmol) was added dropwise to a stirrred suspension of (2-benzyl-benzo[b]thiophen-3-yl)-(3,5-diisopropyl-4-methoxy-phenyl)-methanone (3.57 g, 8.07 mmol) in dichloromethane (30 mL) at −78° C. under a dry nitrogen atomosphere. The solution was allowed to warm to ambient temperature and was stirred for 1.5 h. The reaction mixture was cooled to 0° C. and carefully quenched with water. The reaction mixture was partitioned between water and ether. The ether phase was washed with water and brine. Silica gel was added to the ether phase and the solvent was removed. The adsorbate was flash chromatographed (gradient: 99:1 to 97:1 petroleum ether:ethyl acetate) to provide the title compound as a white solid (1.46 g, 44%): NMR (CDCl3); δ 8.33 (s, 1H), 7.95 (ddd, J=8, 1, 1, 1H), 7.77 (ddd, J=8, 1, 1 Hz, 1H), 7.73 (ddd, J=8, 1, 1 Hz, 1H), 7.53 (ddd, J=8, 8, 1, 1H), 7.40 (ddd, J=8, 8, 1 Hz, 1H), 7.34 (ddd, J=8, 8, 1 Hz, 1H), 7.10 (s, 2H), 7.04 (ddd, J=8, 8, 1 Hz, 1H), 6.75 (ddd, J=8, 1, 1 Hz, 1H), 5.01 (s, 1H), 3.31 (septuplet, J=7 Hz, 2H), 1.29 (s, J=7 Hz, 6H), 1.27 (s, J=7 Hz, 6H); MS (+FAB): 411 (100%, M+H); Anal. Calc. for C28H26OS: C, 81.91, H, 6.38, N, 0.00. Found: C, 81.10, H, 6.54, N, 0.40.

EXAMPLE 17

3-Benzo[b]naphtho[2,3-d]thiophen-11-yl)-phenol

Prepared from (2-benzyl-benzo[b]thiophen-3-yl)-(3-methoxy-phenyl)-methanone (Example 12) according to the procedure for Example 15. White solid: mp 92–94° C.: MS (EI): [M+], 326; Anal. Calc. for C22H14OS: C, 80.95, H, 4.32, N, 0.00. Found: C, 80.01, H, 4.18, N, 0.04.

EXAMPLE 18

4-(Benzo[b]naphtho[2,3-d]thiophen-11-yl)-benzene-1,2-diol

Prepared from (2-benzyl-benzo[b]thiophen-3-yl)-(3,4-dimethoxy-phenyl)-methanone (Example 13) according to the procedure for Example 15. White solid: mp 188–189° C.: MS (EI): [M+], 342; Anal. Calc. for C22H14O2S: C, 77.17, H, 4.12, N, 0.00. Found: C, 76.47, H, 3.85, N, 0.00.

EXAMPLE 19

8-Methoxy-11-(4-methoxy-phenyl)-benzo[b]naphtho[2,3-d]thiophene

To a cold (−78° C.) solution of 2-(3-methoxybenzyl)-benzo[b]thiophene (2.10 g, 8.26 mmol) and p-anisoyl chloride (1.48 g, 8.67 mmol) in anhydrous methylene chloride (31 mL) was added tin IV chloride (2.90 mL, 24.8 mmol, 3 eq) dropwise over a period of 24 minutes. After stirring overnight in the warming dry ice bath and at ambient temperature for 7 hours the reaction mixture was poured onto water (175 mL) and the organics were extracted with diethyl ether (2×300 mL). The extracts were combined, and washed with brine. Silica gel was added and the solvent was removed. The adsorbate was flash chromatographed (97/3 petroleum ehter/ethyl acetate) to give the title compound as a white solid (1.92 g, 63%): mp 158–159° C.; MS (+FAB): [M+] 370; Anal. Calc. for C24H18O2S: C, 77.81, H, 4.90, N, 0.00. Found: C, 78.00, H, 4.76, N, 0.03.

EXAMPLE 20

11-(4-Hydroxy-phenyl)-benzo[b]naphtho[2,3-d]thiophen-8-ol

To a cold (−75° C.) solution of 8-methoxy-11-(4-methoxy-phenyl)-benzo[b]naphtho[2,3-d]thiophene (1.92 g, 5.18 mmol) in anhydrous methylene chloride was added a solution of boron tribromide (1 M in methylene chloride, 6.74 mL, 6.74 mmol, 1.3 eq) dropwise over a period of 18 minutes. After stirring in the cold for 3.5 hours and at ambient temperature for approximately 19 hours the reaction mixture was quenched with water (100 mL), diluted with methylene chloride (50 mL) and the organics were extracted with diethyl ether (1×100 mL, 1×75 mL). The extracts were combined, washed with brine, and combined with silica gel. The solvents were removed and the adsorbate was flash chromatographed (74/26 petrolem ether/ethyl acetate) and dried at 92° C. overnight to the title compound as an off-white solid (1.07 g, 91%): mp 233–235° C.; NMR (DMSO-d6); δ 9.91 (broad s, 1H), 9.77 (broad s, 1H), 8.30 (s, 1H), 7.88 (d, J=8 Hz, 1H), 7.40 (d, J=8 Hz, 1H), 7.35 (ddd, J=8, 8, 1 Hz, 1H), 7.23 (d, J=2 Hz, 1H), 7.15 (d, J=8 Hz, 2H), 7.09 (ddd, J=8, 8, 1 Hz, 1H), 7.06–7.00 (multiplet containing a doublet at 7.05, J=8 Hz, 3 H), 6.71 (d, J=8 Hz, 1H); MS (+FAB): [M+] 343; Anal. Calc. for C22H14O2S: C, 77.17, H, 4.12, N, 0.00. Found: C, 76.43, H, 3.82, N, 0.01.

EXAMPLE 21

2,6-Dibromo-4-(6-bromo-benzo[b]naphtho[2,3-d]thiophen-11-yl)-phenol

A solution of bromine (3.1 mL, 60.17 mmol) in glacial acetic acid (30 mL) was added over a five minute period to a stirred cloudy solution of 4-benzo[b]naphtho[2,3-d]thiophen-11-yl-phenol (5.0 g, 15.32 mmol) and potassium acetate (15.0 g, 153 mmol) in acetic acid (92 mL) at ambient temperature. An exotherm was noted and yellow precipitate resulted. After 45 minutes, the reaction mixture was added to water (1 L), solid sodium thiosulfate (2 g) was added and the suspension was stirred for five minutes. The solid was filtered and washed with water (1L), pet. ether (2×300 mL), 3:1 pet. ether:ether (3×50 mL) and pet. ether (2×300 mL) and dried in vacuo to provide a tan solid (7.00 g). An additional amount crystallized from the mother liquor and was added to the total (tan solid, 8.31 g, 96%). The product was 95% pure at this stage, however it could be further purified by recrystallization from acetic acid to provide the title compound as a white solid: mp 226.5–227° C.: NMR (CDCl3); δ 8.35 (ddd, J=8, 1, 1 Hz, 1H), 7.84 (ddd, J=8, 1, 1 Hz, 1H), 7.67 (ddd, J=8, 7, 1 Hz, 1H), 7.60 (ddd, J=8, 1, 1 Hz, 1H), 7.55 (s, 2H), 7.49 (ddd, J=8, 7, 1 Hz, 1H), 7.45 (ddd, J=8, 7, 1 Hz, 1H), 7.21 (ddd, J=8, 7, 1 Hz, 1H), 6.87 (ddd, J=8, 1, 1 Hz, 1H), 6.19 (s, 1H, OH); MS (−APCI): [M—H]—, 3 bromine isotope pattern, 559 (25%), 561 (75%) 563 (100%) 565 (45%); Anal. Calc. for C22H11Br3OS: C, 46.92, H, 1.97, N, 0.00. Found: C, 46.67, H, 1.85, N, 0.03.

EXAMPLE 22

11-(3,5-dibromo-4-methoxy-phenyl)-benzo[b]naphtho[2,3-d]thiophene

Iodomethane (0.383 mL, 6.16.mmol) was added to a stirred suspension of 2,6-dibromo-4-(6-bromo-benzo[b]naphtho[2,3-d]thiophen-11-yl)-phenol (2.13 g, 4.4 mmol), potassium carbobnate (0.669 g, 4.34 mmol) and DMF (15 mL) at room temperature under a dry nitrogen atmosphere. After 3 h, the reaction mixture was diluted with water and the resulting solid was filtered and washed with water. The solid was taken up in dichloromethane and silica gel (40 mL) was added. The solvent was removed and the adsorbate was flash chromatographed (90:10 petroleum ether:dichloromethane) to provide the title compound as a white solid (2.0 g, 91%): mp 238.5–239.5° C.: NMR (CDCl3); δ 8.36 (ddd, J=8, 1, 1 Hz, 1H), 7.84 (ddd, J=8, 1, 1 Hz, 1H), 7.67 (ddd, J=8, 7, 1 Hz, 1H), 7.60 (s, 2H), 7.58 (ddd, J=8, 1, 1 Hz, 1H), 7.50 (ddd, J=8, 7, 1 Hz, 1H), 7.45 (ddd, J=8, 7, 1 Hz, 1H), 7.20 (ddd, J=8, 7, 1 Hz, 1H), 6.80 (ddd, J=8, 1, 1 Hz, 1H), 4.11 (s, 3H, CH3); MS (EI): [M+], 3 bromine isotope pattern, 574 (35%), 576 (95%) 578 (100%) 580 (45%); Anal. Calc. for C23H13Br3OS: C, 47.87, H, 2.27, N, 0.00. Found: C, 47.73, H, 1.88, N, 0.03.

EXAMPLE 23

11-(4-Methoxy-phenyl)-benzo[b]naphtho[2,3-d]thiophene

Prepared from benzo[b]naphtho[2,3-d]thiophen-11-yl-phenol (Example 14) according to the procedure in Example 22. White solid (0.516 g, 50%): mp: 220–221° C.; NMR (DMSO-d6); δ 8.60 (s, 1H), 8.04 (d, J=8 Hz, 1H), 7.96 (d, J=8 Hz, 1H), 7.57 (ddd, J=8, 7, 1 Hz, 1H), 7.50 (ddd, J=8, 1, 1 Hz, 1H), 7.46–7.40 (m, 3H), 7.33 (d, J=9 Hz, 2H), 7.24 (d, J=9 Hz, 2H), 7.14 (ddd, J=8, 7, 1 Hz, 1H), 6.75 (d, J=8 Hz, 1H), 3.33 (s, 3H); MS (EI): 340 (100%, MI); Anal. Calc. for C23H16OS: C, 81.14, H, 4.74, N, 0.00. Found: C, 81.11, H, 4.57, N, 0.14.

EXAMPLE 24

11-(4-Methoxy-3,5-dimethyl-phenyl)-6-methyl-benzo[b]naphtho[2,3-d]thiophene

A suspension of 6-bromo-11-(3,5-dibromo-4-methoxy-phenyl)-benzo[b]naphtho[2,3-d]thiophene (1.0 g, 1.733 mmol), tetramethyl tin (2.0 mL, 14.38 mmol), bis(triphenylphosphine)palladium II chloride (100 mg, 8 mol %) and DMF (8 mL) was heated in a sealed pressure vessel under argon at 100° C. for 17 hours (dissolution occured after 30 min). The reaction mixture was added water and the water was extracted with ether. Silica gel was added to the ether phase and the ether was removed. The adsorbate was flash chromatographed (96:4 petroleum ether:ethyl acetate) to provide the title compound as a white solid (0.63 g, 86%): mp 154–156° C.: NMR (CDCl3); δ 8.16 (ddd, J=8, 1, 1 Hz, 1H), 7.80 (dd, J=8, 1 Hz, 1H), 7.70 (dd, J=8, 1 Hz, 1H), 7.57 (ddd, J=8, 7, 1 Hz, 1H), 7.41 (ddd, J=8, 7, 1 Hz, 1H), 7.35 (ddd, J=8, 8, 1 Hz, 1H), 7.07 (ddd, J=8, 7, 1 Hz, 1H), 7.04 (s, 2H), 6.79 (dd, J=8, 1 Hz, 1H), 3.92 (s, 3H), 2.97 (s, 3H), 2.39 (s, 6H); MS (EI): 382 (100%, MI); Anal. Calc. for C26H22OS: C, 81.64, H, 5.80, N, 0.00. Found: C, 81.30, H, 5.99, N, 0.38.

EXAMPLE 25

2,6-Dimethyl-4-(6-methyl-benzo[b]naphtho[2,3-d]thiophen-11-yl)-phenol

A mixture of 11-(4-methoxy-3,5-dimethyl-phenyl)-6-methyl-benzo[b]naphtho[2,3-d]thiophene (0.55 g, 1.44 mmol) and pyridinium hydrochloride (1.0 g, 8.64 mmol) was heated in a 240° C. oil bath for 1.25 hour. During this time an additional amount of pyridinium hydrochloride was added (1.0 g, 8.64 mmol). The reaction mixture was cooled to room temperature and partitioned between dilute HCl and ether. Silica gel was added to the ether phase and the solvent was removed. The adsorbate was flash chromatographed (9:1 petroleum ether:ethyl acetate) to provide a light yellow solid (340 mg). This solid was recrystallized from acetic acid to provide the title compound as a light yellow solid (0.215 g, 41%): mp 147–149° C.: NMR (CDCl3); δ 8.15 (ddd, J=8, 1, 1 Hz, 1H), 7.80 (ddd, J=8, 1, 1 Hz, 1H), 7.71 (ddd, J=8, 1, 1 Hz, 1H), 7.56 (ddd, J=8, 7, 1 Hz, 1H), 7.39 (ddd, J=8, 7, 1 Hz, 1H), 7.35 (ddd, J=8, 8, 1 Hz, 1H), 7.09 (ddd, J=8, 7, 1 Hz, 1H), 7.01 (s, 2H), 6.79 (ddd, J=8, 1, 1 Hz, 1H), 2.96 (s, 3H), 2.36 (s, 6H); MS (EI): 368 (100%, MI); Anal. Calc. for C25H20OS: C, 81.49, H, 5.47, N, 0.00. Found: C, 81.62, H, 5.32, N, –0.03.

EXAMPLE 26

4-(Benzo[b]naphtho[2,3-d]thiophen-11-yl)-2,6-diiodo-phenol

Iodine (4.5 g, 17.6 mmol) was added portionwise to a stirred, 0° C. solution of 4-(benzo[b]naphtho[2,3-d]thiophen-11-yl-phenol (2.3 mL, 7.05 mmol), sodium hydroxide (97%, 0.581 g, 14.1 mmol) in methanol (46 mL) over a period of one hour and the mixture was stirred at 0° C. for 1 h. and at ambient temperature for 6 h. The reaction mixture was diluted with water (200 mL) and aqueous mixture was extracted with ethyl ether (2×200 mL). The ethyl ether extracts were washed with 5% sodium bisulfite and water, dried with brine and anhydrous MgSO4. Silica gel (50 mL) was added. Solvent was removed and the adsorbate was flash chromatographed (eluent 8:2 petroleum ether: methylene chloride) to provide the title compound as a white solid (2.2 g, 54%): mp 213–214° C.: MS (–FAB): [M—H]—, 576.8; Anal. Calc. for C22H12I2OS: C, 45.70, H, 2.09, N, 0.00. Found: C, 45.82, H, 2.07, N, 0.30.

EXAMPLE 27

4-(Benzo[b]naphtho[2,3-d]thiophen-11-yl)-2-iodo-phenol

Iodine (4.5 g, 17.6 mmol) was added portionwise to a stirred, 0° C. solution of 4-(benzo[b]naphtho[2,3-d]thiophen-11-yl-phenol (2.3 mL, 7.05 mmol), sodium hydroxide (97%, 0.581 g, 14.1 mmol) in methanol (46 mL) over a period of one hour and the mixture was stirred at 0° C. for 1 h. and at ambient temperature for 6 h. The reaction mixture was diluted with water (200 mL) and aqueous mixture was extracted with ethyl ether (2×200 mL). The ethyl ether extracts were washed with 5% sodium bisulfite and water, dried with brine and anhydrous MgSO4. Silica gel (50 mL) was added. Solvent was removed and the adsorbate was flash chromatographed (eluent 8:2 petroleum ether:methylene chloride) to provide a off-white solid (0.624 g, 20%): mp 125–128° C.: MS (EI): [M+], 452; Anal. Calc. for C22H13IOS: C, 58.42, H, 2.90, N, 0.00. Found: C, 58.46, H, 3.00, N, 0.09.

EXAMPLE 28

11-(4-Methoxy-3,5-diiodo-phenyl)-benzo[b]naphtho[2,3-d]thiophene

Prepared from 4-(benzo[b]naphtho[2,3-d]thiophen-11-yl)-2,6-diiodo-phenol (Example 26) according to the procedure on Example 22. White solid: mp 228–230° C.: MS (EI): [M+], 592; Anal. Calc. for C23H14I2OS: C, 46.65, H, 2.38, N, 0.00. Found: C, 45.95, H, 2.25, N, 0.19.

EXAMPLE 29

11-(3-Iodo-4-methoxy-phenyl)-benzo[b]naphtho[2,3-d]thiophene

Prepared from 4-(benzo[b]naphtho[2,3-d]thiophen-11-yl)-2-iodo-phenol (Example 27) according to the procedure on Example 22. White solid: mp 274–275° C.: MS (EI): [M+], 466 (100%, MI); Anal. Calc. for C23H15IOS: C, 59.24, H, 3.24, N, 0.00. Found: C, 58.53, H, 3.11, N, 0.11.

EXAMPLE 30

5-Benzo[b]naphtho[2,3-d]thiophen-11-yl-2-methoxy-isophthalonitrile

A suspension of 11-(3,5-diiodo-4-methoxy-phenyl)-benzo[b]naphtho[2,3-d]thiophene (4.55 g, 7.68 mmol) and copper (I) cyanide 3.13 g, 38.4 mmol) in 1-methyl-2-pyrrolidinone (18 mL) was heated in an 150° C. oil bath under a dry nitrogen atmosphere. After 1 h the solution was added to water (200 mL) and acidified with 10% aqueous HCl. The solid was filtered and flash chromatographed (silica gel: eluent: methylene chloride) to provide the title compound as a yellow solid (2.47 g, 82%): mp 214–215° C.: MS (EI): [M+], 390 (100%, MI); Anal. Calc. for C25H14N2OS: C, 76.90, H, 3.61, N, 7.17. Found: C, 76.48, H, 3.46, N, 7.17.

EXAMPLE 31

5-(Benzo[b]naphtho[2,3-d]thiophen-11-yl)-2-methoxy-benzonitrile

Prepared from 11-(3-iodo-4-methoxy-phenyl)-benzo[b]naphtho[2,3-d]thiophene (Example 29) according to the procedure on Example 30. White solid: mp 230–232° C.: MS (EI): [M+], 365 (100%, MI); Anal. Calc. for C24H15NOS: C, 78.88, H, 4.41, N, 3.83. Found: C, 77.61, H, 4.23, N, 4.10.

EXAMPLE 32

5-Benzo[b]naphtho[2,3-d]thiophen-11-yl-2-hydroxy-isophthalonitrile

Prepared from 5-benzo[b]naphtho[2,3-d]thiophen-11-yl-2-methoxy-isophthalonitrile (Example 30) according to the procedure on Example 20. White solid: mp 274–276° C.: MS (EI): [M+], 376 (80%, MI); Anal. Calc. for C24H12N2OS: C, 76.58, H, 3.21, N, 7.44. Found: C, 76.20, H, 3.19, N, 7.35.

EXAMPLE 33

5-Benzo[b]naphtho[2,3-d]thiophen-11-yl-2-hydroxy-benzonitrile

Prepared from 5-(benzo[b]naphtho[2,3-d]thiophen-11-yl)-2-methoxy-benzonitrile (Example 31) according to the procedure on Example 20. White solid: mp 231–232° C.: MS (EI): [M+], 351 (100%, MI); Anal. Calc. for C23H13NOS: C, 78.61, H, 3.73, N, 3.99. Found: C, 78.27, H, 3.59, N, 3.89.

EXAMPLE 34

4-(Benzo[b]naphtho[2,3-d]thiophen-11-yl-phenol) acetate ester

Acetic anhydride (0.62 mL, 6.57 mmol) was added to a 0° C., stirred solution of 4-benzo[b]naphtho[2,3-d]thiophen-11-yl-phenol (2.0 g, 6.13 mmol) in pyridine (8 mL). After 7 h the reaction mixture was added to water and the resulting solid was filtered and washed with water and dried in vacuo to provide the title compound as a white solid (2.23 g, 99%): mp: 160–161° C.; NMR (CDCl3); δ 8.36 (s, 1H), 7.95 (d, J=8 Hz, 1H), 7.78 (d, J=8 Hz, 1H), 7.61 (d, J=8 Hz, 1H), 7.53 (ddd, J=8, 7, 1 Hz, 1H), 7.47–7.33 (m, 6H), 7.08 (ddd, J=8, 7, 1 Hz, 1H), 6.76 (d, J=8 Hz, 1H), 2.42 (s, 3H, CH3); MS (EI): 368 (100%, MI); Anal. Calc. for C24H16O2S: C, 78.24, H, 4.38, N, 0.00. Found: C, 77.99, H, 4.29, N, 0.02.

EXAMPLE 35

Acetic acid 3-Benzo[b]naphtho[2,3-d]thiophen-11-yl)-phenyl ester

Prepared from 3-benzo[b]naphtho[2,3-d]thiophen-11-yl)-phenol (Example 17) according to the procedure of Example 34. White solid: mp 122–124° C.: MS (EI): [M+], 368; Anal. Calc. for C24H16O2S: C, 78.24, H, 4.38, N, 0.00. Found: C, 77.47, H, 4.19, N, 0.27.

EXAMPLE 36

Acetic acid 2-Acetoxy-4-(benzo[b]naphtho[2,3-d]thiophen-11-yl)-phenyl ester

Prepared from 4-(benzo[b]naphtho[2,3-d]thiophen-11-yl)-benzene-1,2-diol (Example 18) according to the procedure of Example 34. White solid: mp 179–180° C.: MS (EI): [M+], 426; Anal. Calc. for C26H18O4S: C, 73.22, H, 4.25, N, 0.00. Found: C, 73.17, H, 4.30, N, 0.12.

EXAMPLE 37

4-(6-Bromo-benzo[b]naphtho[2,3-d]thiophen-11-yl-phenol)acetate(ester)

A solution of bromine (0.35 mL, 6.63 mmol) in dichloromethane (10 mL) was added dropwise over a 15 min. period to a stirred, -20° C. solution of 4-(benzo[b]naphtho[2,3-d]thiophen-11-yl-phenol)acetate(ester) (2.22 g, 6.03 mmol) in dichloromethane (45 mL). This solution was stirred for 1.5 h then quenched with dilute aqueous sodium thiosulfate. The organic solvents were removed, water was added and the resulting solid was filtered, washed with water, triturated with pet. ether and dried in vacuo to provide the title compound as a white solid (2.60, 96%): mp: 204–205° C.; NMR (CDCl3); δ 8.35 (ddd, J=8, 1, 1 Hz, 1H), 7.81 (ddd, J=8, 1, 1 Hz, 1H), 7.68–7.61 (m, 2H), 7.47–7.36 (m, 6H), 7.08 (ddd, J=8, 8, 1 Hz, 1H), 6.69 (ddd, J=8, 1, 1 Hz, 1H), 2.42 (s, 3H, CH3); MS (EI): [M+], 1 bromine isotope pattern, 446 (60%, MI), 448 (65%, MI), 404 (100%), 406 (95%); Anal. Calc. for C24H15BrO2S: C, 64.44, H, 3.38, N, 0.00. Found: C, 64.18, H, 3.34, N, −0.03.

EXAMPLE 38

Acetic acid 3-(6-Bromo-benzo[b]naphtho[2,3-d]thiophen-11-yl)-phenyl ester

Prepared from acetic acid 3-benzo[b]naphtho[2,3-d]thiophen-11-yl)-phenyl ester (Example 35) according to the procedure of Example 37. White solid: mp 74–76° C.: MS (EI): [M+], 1 bromine isotope pattern, 446, 448; Anal. Calc. for C24H15BrO2S: C, 64.44, H, 3.38, N, 0.00. Found: C, 63.77, H, 3.08, N, 0.12.

EXAMPLE 39

Acetic acid 2-Acetoxy-4-(6-bromo-benzo[b]naphtho[2,3-d]thiophen-11-yl)-phenyl ester Prepared from acetic acid 2-acetoxy-4-(benzo[b]naphtho[2,3-d]thiophen-11-yl)-phenyl ester (Example 36) according to the procedure of Example 37. White solid: mp 178–179° C.: MS (EI): [M+], 1 bromine isotope pattern, 504, 506; Anal. Calc. for C26H17BrO4S: C, 61.79, H, 3.39, N, 0.00. Found: C, 61.37, H, 3.32, N, 0.11.

EXAMPLE 40

4-(6-Bromo-benzo[b]naphtho[2,3-d]thiophen-11-yl)-2,6-diisopropyl-phenol

A solution of bromine (0.185 mL, 3.50 mmol) in dichloromethane (7 mL) was added dropwise over a 40 minute period to a solution of 4-(6-benzo[b]naphtho[2,3-d]thiophen-11-yl)-2,6-diisopropyl-phenol (1.31 g, 3.18 mmol) in dichloromethane (26 mL) at −20° C. under a dry nitrogen atmosphere that was stirred in the absence of light. After 15 minutes, a dilute aqueous sodium bisulfite solution was added and the reaction mixture was partitioned between water and ether. The ether phase was washed with brine and concentrated to provide the title compound as a white solid (1.65 g, 100%): mp: 189–190° C.; NMR (CDCl3); δ 8.35 (ddd, J=8, 1, 1, 1H), 7.80 (ddd, J=8, 1, 1 Hz, 1H), 7.74 (ddd, J=8, 1, 1 Hz, 1H), 7.65 (ddd, J=8, 8, 1, 1H), 7.45 (ddd, J=8, 8, 1 Hz, 1H), 7.37 (ddd, J=8, 8, 1 Hz, 1H), 7.08 (s, 2H), 7.06 (ddd, J=8, 8, 1 Hz, 1H), 6.68 (ddd, J=8, 1, 1 Hz, 1H), 5.03 (s, 1H), 3.31 (septuplet, J=7 Hz, 2H), 1.29 (d, J=7 Hz, 6H), 1.26 (d, J=7 Hz, 6H); MS (EI): 488 (90%), 490 (100); Anal. Calc. for C28H25BrOS: C, 68.71, H, 5.15, N, 0.00. Found: C, 67.74, H, 5.02, N, 0.07.

EXAMPLE 41

4-(6-Bromo-benzo[b]naphtho[2,3-d]thiophen-11-yl)-phenol

Aqueous potassium hydroxide (6.0 mL, 6.0 mmol) was added to a stirred, room temperature suspension of 4-(6-bromo-benzo[b]naphtho[2,3-d]thiophen-11-yl-phenol) acetate(ester) (2.60 g, 5.81 mmol) in THF (20 mL)/methanol (15 mL). Dissolution occurred immediately and the reaction mixture turned green. After 1 h, the organic solvents were removed, water was added, the reaction mixture was acidified with 10% HCl and the resulting solid was washed with water and triturated with pet. ether and then dried in vacuo to provide the title compound as a white solid (2.18 g, 93%). A portion of this solid (0.5 g) was recrystalized from acetic acid/water and then cyclohexane/acetonitrile: mp: 211–213° C.; NMR (CDCl3); δ 8.34 (ddd, J=8, 1, 1 Hz, 1H), 7.80 (ddd, J=8, 1, 1 Hz, 1H), 7.67–7.62 (m, 2H), 7.43 (ddd, J=8, 8, 1 Hz, 1H), 7.39 (ddd, J=8, 8, 1 Hz, 1H), 7.27 (d, J=9 Hz, 2H), 7.12 (d, J=9 Hz, 2H), 7.11 (m, 1H), 6.78 (ddd, J=8, 1, 1 Hz, 1H) 4.99 (s, 1H, OH); MS (EI): [M+], 1 bromine isotope pattern, 404 (100%, MI), 406 (96%, MI); Anal. Calc. for C22H13BrOS: C, 65.19, H, 3.23, N, 0.00. Found: C, 64.87, H, 3.00, N, 0.03.

EXAMPLE 42

3-(6-Bromo-benzo[b]naphtho[2,3-d]thiophen-11-yl)-phenol

Prepared from acetic acid 3-(6-bromo-benzo[b]naphtho[2,3-d]thiophen-11-yl)-phenyl ester (Example 38) according to the procedure for Example 41. White solid: mp 110–111° C.: NMR (CDCl3); δ 8.35 (dd, J=8, 1 Hz, 1H), 7.81 (d, J=8, Hz, 1H), 7.67–7.63 (m, 2H), 7.53 (dd, J=8, 7 Hz, 1H), 7.44 (ddd, J=8, 7, 1 Hz, 1H), 7.39 (ddd, J=8, 7, 1 Hz, 1H), 7.13–7.09 (m, 2H), 7.00 (dd, J=8, 1 Hz, 1H), 6.88 (dd, J=1, 1 Hz, 1H), 6.78 (dd, J=8, 1 Hz, 1H), 4.99 (s, 1H, OH); MS (EI): [M+], 1 bromine isotope pattern, 404 (95%), 406 (100%); Anal. Calc. for C22H13BrOS: C, 65.19, H, 3.23, N, 0.00. Found: C, 64.85, H, 3.51, N, 0.43.

EXAMPLE 43

4-(6-bromo-benzo[b]naphtho[2,3-d]thiophen-11-yl)-benzene-1,2-diol

Prepared from acetic acid 2-acetoxy-4-(6-bromo-benzo[b]naphtho[2,3-d]thiophen-11-yl)-phenyl ester (Example 39) according to the procedure for Example 41. White solid: mp 181–182° C.: MS (EI): [M+], 1 bromine isotope pattern, 420 (95%); Anal. Calc. for C22H13BrO2S: C, 62.72, H, 3.11, N, 0.00. Found: C, 62.11, H, 3.10, N, 0.13.

EXAMPLE 44

11-(4-Hydroxy-phenyl)-benzo[b]naphtho[2,3-d]thiophene-6-carbonitrile

A suspension of 4-(6-bromo-benzo[b]naphtho[2,3-d]thiophen-11-yl-phenol)acetate(ester) (2.0 g, 4.47 mmol), copper (I) cyanide (2.0 g, 22.3 mmol) and N-methylpyrrolidinone (10 mL) was heated in a sealed vessel in a 150° C. oil bath for 9 h. The reaction mixture was cooled to room temperature, added to water and extracted with ethyl acetate. The aqueous phase was filtered and the resulting solid was taken up in THF. The THF and ethyl acetate phases were combined and concentrated. THF (100 mL), methanol (50 mL) and aqueous potassium hydroxide (1.0 N, 4.5 mL, 4.5 mmol) were added to the residue. After 5 minutes, water was added and the reaction mixture was acidified with 10% HCl and the resulting solid was filtered, washed with water and tritrurated with ether (3×) and then pet. ether. The solid was dried in vacuo to provide the title compound as a tan solid (1.27 g, 82%): mp: 307–309° C.; NMR (CDCl3); δ 8.35 (ddd, J=8, 1, 1 Hz, 1H), 7.84 (ddd, J=8, 1, 1 Hz, 1H), 7.76–7.69 (m, 2H), 7.51 (ddd, J=8, 8, 1 Hz, 1H), 7.44 (ddd, J=8, 8, 1 Hz, 1H), 7.27 (d, J=9 Hz, 2H), 7.15 (d, J=9 Hz, 2H), 7.14 (m, 1H), 6.82 (ddd, J=8, 1, 1 Hz, 1H), 5.08 (s, 1H); IR (KBr, cm−1): 2210 (CN); MS (EI): [M+], 451 (40%, MI); Anal. Calc. for C23H13NOS: C, 78.61, H, 3.73, N, 3.99. Found: C, 77.84, H, 3.46, N, 3.89.

EXAMPLE 45

Methanesulfonic acid 4-Benzo[b]naphtho[2,3-d]thiophen-11-yl-phenyl Ester

Methylsulfonyl chloride (0.63 mL, 8.14 mmol) was added dropwise to a cold (ice bath) solution of 4-benzo[b]naphtho[2,3-d]thiophen-11-yl-phenol (2.00 g, 5.43 mmol) in dry methylene chloride (10 mL) and pyridine (2.08 mL). After stiring at ambient temperature for ca. 36 h. the reaction mixture was combined with water (100 mL). The organics were extracted with ether (100 mL), washed with 10% HCl (100 mL) and concentrated to give the title compound as a white solid (2.51 g, 100%); mp 136–139° C.; NMR (CDCl3); δ 8.38 (s, 1H), 7.97–7.95 (m, 1H), 7.80–7.78 (m, 1H), 7.60–7.50 (m, 6H), 7.43–7.35 (m, 2H), 7.07 (ddd, J=8, 7, 1 Hz, 1H), 6.68 (d, J=8 Hz, 1H), 3.33 (s, 3H); MS (EI): [M+] 404 (100%); Anal. calc. for C23H16O3S2+0.07 C6H14, C, 68.52, H, 4.17, N, 0.03. Found: C, 67.91, H, 3.85, N, 0.06.

EXAMPLE 46

Methanesulfonic acid 4-(6-Chloro-benzo[b]naphtho[2,3-d]thiophen-11-yl)-phenyl ester To a solution of methanesulfonic acid 4-benzo[b]naphtho[2,3-d]thiophen-11-yl-phenyl ester (1.00 g, 2.47 mmol) in chloroform (10 mL) was added sulfuryl chloride (0.21 mL, 2.60 mmol, 1.05 eq) dropwise at room temperature under a dry nitrogen atmosphere. After stirring 19 hours the reaction mixture was added to water (100 mL) and the organics were extracted with ether (2×100 mL). The extracts were combined, washed with brine, combined with silica gel and the solvent was removed. The adsorbate was flash chromatographed (85/15 petroleum ether/ethyl acetate) to give the title compound as a white solid (0.957 g, 88%): mp 155–158° C.; NMR (CDCl3); δ 8.41 (ddd, J=8, 1, 1 Hz, 1H), 7.82 (ddd, J=8, 1, 1 Hz, 1H), 7.67 (ddd, J=8, 7, 1 Hz, 1H), 7.61–7.56 (m, 3H), 7.51–7.45 (m, 3H), 7.42–7.38 (ddd, J=8, 7, 1 Hz, 1H), 7.10 (ddd, J=8, 7, 1 Hz, 1H), 6.64 (d, J=8 Hz, 1H), 3.34 (s, 3H); MS (+EI) : [M+], 1 chlorine isotope pattern, 438 (100%), 440 (40%); Anal. Calc. for C23H15ClO3S2: C, 62.93, H, 3.49, N, 0.00. Found: C, 62.72, H, 3.25, N, 0.03.

EXAMPLE 47

Methanesulfonic acid 4-(6-Iodo-benzo[b]naphtho[2,3-d]thiophen-11-yl)-phenyl ester To a solution of methanesulfonic acid 4-benzo[b]naphtho[2,3-d]thiophen-11-yl-phenyl ester (2.24 g, 5.54 mmole) in tetrahydrofuran (22.4 mL), 80% aqueous acetic acid (11.2 mL) and sulfuric acid (0.6 mL) was added iodine (0.984 g, 3.87 mmol) and iodic acid (0.244 g, 1.39 mmol). The reaction mixture was stirred for 88 h at room temperature then combined with an aqueous solution of sodium bisulfite (100 mL). The organics were extracted with ether (500 mL). The extracts were concentrated and chased with benzene and pet ether to provide the title compound as a yellow solid (2.75 g, 94%): mp 176–186° C.; NMR (CDCl3); δ 8.24 (ddd, J=8, 1, 1 Hz, 1H), 7.81 (ddd, J=8, 1, 1 Hz, 1H), 7.65–7.58 (m, 3H), 7.52–7.38 (m, 5H), 7.11–7.07 (ddd, J=8, 7, 1 Hz, 1H), 6.57 (ddd, J=8, 1, 1 Hz, 1H), 3.33 (s, 3H); MS (+FAB): [M+] m/z 530 (65%), [M+H]+m/z 531 (25%); Anal. calc. for C23H15IO3S2: C, 52.08, H, 2.85, N, 0.00. Found: C, 51.75, H, 2.75, N, 0.06.

EXAMPLE 48

Methanesulfonic acid 4-(6-trifluoromethyl-benzo[b]naphtho[2,3-d]thiophen-11-yl)-phenyl ester A mixture of freshly activated copper (0.359 g, 5.66 mmol) and bis(trifluoromethyl)mercury (0.993 g, 3.78 mmol) in N,N-dimethylacetamide (12 mL) was heated at 144° C. under a dry nitrogen atmosphere for 2 hours with stirring. After cooling a solution of methanesulfonic acid 4-(6-iodo-benzo[b]naphtho[2,3-d]thiophen-11-yl)-phenyl ester (1.00 g, 1.89 mmol) in N,N-dimethylacetamide (12 mL) was added and the mixture was heated at 160–168° C. for 3 hours 20 min. After cooling the mixture was poured into water and the organics were extracted with ether (2×200 mL). The extracts were combined, silica gel (ca. 30 mL) was added and the solvent was removed. The adsorbate was flash chromatographed (eluant: 80:20 pet ether:ethyl acetate) to provide the title compound as a white solid (0.697 g, 85%): mp 215–216° C.; NMR (CDCl3); δ 8.39–8.36 (m, 1H), 7.81–7.79 (m, 1H), 7.71–7.67 (m, 1H), 7.61–7.59 (m, 3H), 7.51–7.46 (m, 3H), 7.41 (ddd, J=8, 7, 1 Hz, 1H), 7.08 (ddd, J=8, 7, 1 Hz), 6.54 (d, J=8 Hz, 1H), 3.35 (s, 3H); MS+FAB [M+H]+m/z 473 and m+472; Anal. Calc. for C24H15F3O3S2.0.15C6H6: C, 61.76, H, 3.31, N, 0.00. Found: C, 61.20, H, 3.11, N, 0.16.

EXAMPLE 49

Methanesulfonic acid 4-(6-methyl-benzo[b]naphtho[2,3-d]thiophen-11-yl)-phenyl ester A suspension of methanesulfonic acid 4-(6-iodo-benzo[b]naphtho[2,3-d]thiophen-11-yl)-phenyl ester (1.65 g, 3.11 mmole), tetramethyltin (3.58, 25.8 mmole), and bis(triphenylphosphine)palladium II chloride (0.218 g, 0.311 mmole 10 mole %) in dry N,N dimethylformamide (16 mL) was heated in a sealed vessel under argon at 103° C. for 4 hours and left at room temperature overnight. The reaction mixture was added to water (200 mL) and extracted with ether. Silica gel (40 mL) was added and the solvent removed. The adsorbate was flash chromatographed (85:15 Petroleum ether:ethyl acetate) to give the title compound as a pale yellow solid (1.12 g, 86%): mp 172–173° C.; NMR (CDCl3); δ 8.18 (ddd, J=8, 1, 1 Hz, 1H), 7.81 (ddd, J=1, 1, 8 Hz, 1H), 7.62–7.55 (m, 3H), 7.50–7.48 (m, 2H), 7.44–7.34 (m, 2H), 7.06 (ddd, J=8, 7, 1 Hz, 1H), 6.64 (ddd, J=8, 1, 1 Hz), 3.32 (s, 3H), 2.99 (s, 3H); MS: EI [m/z] 418 (100%); Anal. Calcd. for C24H18O3S2: C, 68.87, H, 4.34, N, 0.00. Found: C, 68.60, H, 4.26, N, 0.02.

EXAMPLE 50

4-(6-Chloro-benzo[b]naphtho[2,3-d]thiophen-11-yl)-phenol

A biphasic mixture of methanesulfonic acid 4-(6-chloro-benzo[b]naphtho[2,3-d]thiophen-11-yl)-phenyl ester (0.917 g, 2.09 mmol) in dioxane (13 mL) and a solution of sodium hydroxide (2.5 N, 6.7 mL, 16.7 mmol, 8 eq) was heated at reflux overnight. After cooling to room temperature the reaction mixture was combined with water (50 mL), acidified with concentrated hydrochloric acid, and stirred for 15 minutes. The crude white solid product was collected by filtration, redissolved in ether, combined with silica gel, and the solvent was removed. The adsorbate was flash chromatographed (gradient 85/15–80/20 petroleum ether/ethyl acetate) to give the title compound as a white solid (0.705 g, 94%); mp 193–195° C.; NMR (CDCl3); δ 8.37 (ddd, J=8, 1, Hz, 1H), 7.81 (ddd, J=8, 1, 1 Hz, 1H), 7.68–7.63 (m, 2H), 7.44 (ddd, J=8, 7, 1 Hz, 1H), 7.39 (ddd, J=8, 7, 1 Hz, 1H), 7.29–7.26 (m, 2H,), 7.14–7.09 (m, 3H), 6.81 (ddd, J=8, 1, 1 Hz, 1H), 5.01 (d, J=4 Hz, 1H); MS (+EI): [M+], 1 chlorine isotope pattern, 360 (100%), 362 (45%); Anal. calc. for C22H13ClOS: C, 73.23, H, 3.63, N, 0.00. Found: C, 72.86, H, 3.24, N, 0.04.

EXAMPLE 51

4-(6-Iodo-benzo[b]naphtho[2,3-d]thiophen-11-yl)-phenol

To a solution of methanesulfonic acid 4-(6-iodo-benzo[b]naphtho[2,3-d]thiophen-11-yl)-phenyl ester (1.00 g, 1.89 mmol) in tetrahydrofuran (5 mL) was added a 2.5 N aqueous solution of sodium hydroxide (6.0 mL) and the biphasic reaction mixture was heated at reflux for 5 hours and then heated in a sealed pressure tube at 110 C. for about 18 hours. The reaction mixture was diluted with water (100 mL), acidified with 10% hydrochloric acid and the organics were extracted with ether (2×100 mL). The extracts were combined, washed with water (100 mL), concentrated and chased with petroleum ether to give the title compound (0.869 g, over theoretical); NMR (DMSO-d6); δ 9.85 (s, 1H, OH), 8.15 (d, J=8 Hz, 1H), 8.02 (d, J=8 Hz, 1H), 7.73 (ddd, J=8, 7, 1 Hz, 1H), 7.69–7.44 (m, 3H), 7.21–7.16 (m, 3H), 7.09–7.06 (m, 2H), 6.68 (d, J=8Hz, 1H).

EXAMPLE 52

4-(6-Trifluoromethyl-benzo[b]naphtho[2,3-d]thiophen-11-yl)-phenol

Prepared from methanesulfonic acid 4-(6-trifluoromethyl-benzo[b]naphtho[2,3-d]thiophen-11-yl)-phenyl ester (Example 48) according to the procedure of Example 51. White solid: mp 210–211° C.; NMR (CDCl3); δ 8.35 (m, 1H), 7.80–7.77 (m, 1H), 7.72–7.64 (m, 2H), 7.47 (ddd, J=8, 7, 1 Hz, 1H), 7.39 (ddd, J=8, 7, 1 Hz, 1H), 7.28–7.24 (m, 2H), 7.16–7.08 (m, 3H), 6.75 (d, J=8 Hz, 1H), 5.03 (s, 1H); MS: (+) EI (direct probe) [M+]: 394 (100%); Anal. Calc. for: C23H13F3OS: C, 70.04, H, 3.32, N, 0.00. Found: C, 69.68, 3.12, N, 0.10.

EXAMPLE 53

4-(6-Methyl-benzo[b]naphtho[2,3-d]thiophen-11-yl)-phenol

Prepared from methanesulfonic acid 4-(6-methyl-benzo[b]naphtho[2,3-d]thiophen-11-yl)-phenyl ester (Example 49) according to the procedure of Example 51. White solid: mp 184–185° C.; NMR (CDCl3); δ 8.16 (ddd, J=8, 1, 1 Hz, 1H), 7.81 (ddd, J=8, 1, 1 Hz, 1H), 7.67 (ddd, J=8, 1, 1 Hz, 1H), 7.58 (ddd, J=8, 7, 1 Hz, 1H), 7.42–7.34 (m, 2H), 7.29–7.26 (m, 3H), 7.12–7.06 (m, 3H), 6.82 (ddd, J=8, 1, 1 Hz, 1H), 4.94 (s, 1H), 2.98 (s, 3H); MS(EI): [M+], 340 (100%); Anal. Calcd. for C23H16OS: C, 81.14, H, 4.74, N, 0.00, Found C, 81.47, H, 4.59, N, 0.02.

EXAMPLE 54

4-(6-Methoxy-benzo[b]naphtho[2,3-d]thiophen-11-yl)-phenol

To cold (ice bath) anhydrous methanol (13.2 mL) was added sodium hydride (80% by weight suspension in mineral oil, 1.70 g, 56.6 mmol) in three portions. After stirring in the cold for 0.5 hours and at ambient temperature for 50 minutes copper II chloride (0.251 g, 1.87 mmol) and solution of methanesulfonic acid 4-(6-iodo-benzo[b]naphtho[2,3-d]thiophen-11-yl)-phenyl ester (3.00 g, 5.66 mmol) in dry N,N-dimethylformamide (24 mL) were added. The reaction mixture was heated at reflux for approximately 3 hours, cooled to room temperature, diluted with water (400 mL), acidified with 10% hydrochloric acid and extracted with diethyl ether. The extracts were combined, silica gel was added and the solvent removed. The adsorbate was flash chromatographed (40/60 petroleum ether/methylene chloride) to provide the title compound as a white solid (1.82 g, 90%): mp 218–223° C. (dec); NMR (CDCl3); δ 8.27 (ddd, J=8, 1, 1 Hz, 1H), 7.80 (ddd, J=8, 1, 1 Hz, 1H), 7.65 (ddd, J=8, 1, 1 Hz, 1H), 7.57 (ddd, J=8, 7, 1 Hz, 1H), 7.40 (ddd, J=8, 7, 1 Hz, 1H), 7.36 (ddd, J=8, 7, 1 Hz, 1H), 7.30–7.26 (m, 2H), 7.13–7.07 (m, 3H), 6.85 (ddd, J=8, 1, 1 Hz, 1H), 4.98 (s, 1H), 4.21 (S, 3H); MS (EI): [M+], 356 (100%); Anal. Calc. for C23H16O2S: C, 77.50, H, 4.52, N, 0.00; Found C, 76.79, H, 4.61, N, 0.11.

EXAMPLE 55

4-(6-Phenylsufanyl-benzo[b]naphtho[2,3-d]thiophen-11-yl)-phenol

Sodium hydroxide (0.183 g, 4.58 mmol) was added to a stirred, room temperature solution of methanesulfonic acid 4-(6-iodo-benzo[b]naphtho[2,3-d]thiophen-11-yl)-phenyl ester (1.04 g, 1.95 mmol), thiophenol (0.47 mL, 4.578 mmol), copper (I) oxide (0.326, 2.28 mmol) and dimethylformamide (20 mL). The vessel was heated in a 155–160° C. oil bath under an argon atmosphere. After 7 h, the reaction mixture was cooled to room temperature, added to water, acidified with 10% HCl and extracted with ether. The ether extract was filtered to remove copper salts and silica gel was added. The solvent was removed and the adsorbate was flash chromatographed (eluent:gradient: 9:1 to 85:15 petroleum ether:ethyl acetate) to provide the title compound as a white solid (0.721 g, 86%): mp 162–164° C.; NMR (DMSO-d6); δ 9.87 (s, 1H), 8.48 (ddd, J=8, 1, 1 Hz, 1H), 7.95 (ddd, J=8, 1, 1 Hz, 1H), 7.66 (m, 2H), 7.52 (ddd, J=8, 7, 1 Hz, 1H), 7.44 (ddd, J=8, 7, 1 Hz, 1H), 7.27–7.07 (m, 10H), 6.76 (d, J=8 Hz, 1H); MS (EI): 434 (M+, 100%); Anal. Calc. for C28H18OS: C, 77.39, H, 4.19, N, 0.00. Found: C, 76.82, H, 3.95, N, 0.16.

EXAMPLE 56

4-[6-(2-Dimethylamino-ethylsulfanyl)-benzo[b]naphtho[2,3-d]thiophen-11-yl]-phenol To a suspension of methanesulfonic acid 4-(6-iodo-benzo[b]naphtho[2,3-d]thiophen-11-yl)-phenyl ester (1.00 g, 1.89 mmol), dimethylaminoethanethiol hydrochloride (0.614 g, 4.34 mmol, 2.3 eq) and copper I oxide (0.316 g, 8.69 mmol, 1.17 eq) in anhydrous N,N-dimethylformamide (24 mL) was added finely ground sodium hydroxide (0.348 g, 8.69 mmol, 4.6 eq) at room temperature in a pressure vessel. The vessel was flushed with argon, sealed and heated with stirring at 155° C. (oil bath) for 6 hours and at ambient temperature for 12 hours. The reaction mixture was poured into water (100 mL) and extracted with ether. The solid which remained as a suspension in the aqueous phase was filtered. The filtrate was extracted once more with ether. The extracts were combined and silica gel was added. The solvents were removed and the adsorbate was flash chromatographed (gradient 94/6–95/5) methylene chloride:isopropanol to give the title compound as a solid (0.707 g, 87%): NMR (DMSO-d6); δ 9.83 (s, 1H, OH), 8.65 (d, J=8 Hz, 1H), 7.98 (d, J=8 Hz, 1H), 7.71 (ddd, J=8, 7, 1 Hz, 1H), 7.61 (d, J=8 Hz, 1H), 7.50 (ddd, J=8, 7, 1 Hz, 1H), 7.43 (ddd, J=8, 7, 1 Hz, 1H), 7.21–7.05 (m, 3H), 7.08–7.04 (m, 2H), 6.73 (d, J=8 Hz, 1H), 3.35–3.27 (m,), 3.10 (t, J=6 Hz, 2H), 2.21–2.08 (broad singlet, 6H); MS(EI): [M+] 429.

EXAMPLE 57

4-[6-(Pyridin-4-ylsulfanyl)-benzo[b]naphtho[2,3-d]thiophen-11-yl]-phenol

To a suspension of methanesulfonic acid 4-(6-iodo-benzo[b]naphtho[2,3-d]thiophen-11-yl)-phenyl ester (1.00 g, 1.89 mmol), 4 mercaptopyridine (0.614 g, 4.34 mmol, 2.3 eq) and copper I oxide (0.316 g, 2.21 mmol, 1.17 eq) in dry N,N-dimethyformamide (24 mL) was added finely ground sodium hydroxide (0.174 g, 4.34 mmol, 2.3 eq) and the mixture was heated in a pressure bottle at 157° C. (oil bath) under argon for 5 hours and then stirred at ambient temperature overnight. The reaction mixture was poured into water (100 mL) and the organics were extracted with ether (2.300 mL). The extracts were combined, dried with brine, and silica gel was added. The solvent was removed and the adsorbate was flash chromatographed (97/3 methylene chloride/isopropanol) to give a solid which was stirred in water (100 mL) overnight and collected on a sintered glass funnel and air dried to give the title compound as a solid (0.587 g, 73%); NMR (DMSO-d6); δ 9.90 (s, 1H), 8.37 (d, J=8 Hz, 1H), 8.30 (d, J=5 Hz, 2H), 7.95 (d, J=8 Hz, 1H), 7.70 (m, 2H), 7.57 (m, 1H), 7.45 (t, J=8 Hz, 1H), 7.28 (d, J=Hz, 2H), 7.20 (t, J=8 Hz, 1H), 7.11 (d, J=8 Hz, 2H), 6.96 (d, J=6 Hz, 2H), 6.77 (d, J=8 Hz, 1H); MS (EI): [M+] 435.

EXAMPLE 58

11-(3,5-Dibromo-4-hydroxy-phenyl)-benzo[b]naphtho[2,3-d]thiophene-6-carbonitrile A solution of bromine (0.21 mL, 4.07 mmol) in acetic acid (3 mL) was added dropwise to a room temperature, stirred suspension of 11-(4-hydroxy-phenyl)-benzo[b]naphtho[2,3-d]thiophene-6-carbonitrile (650 mg, 1.85 mmol), potassium acetate (1.82 g, 18.5 mmol) and acetic acid (17 mL). After 35 minutes, water (100 mL) and a small amount of solid sodium sulfite were added. The suspension was filtered and the solid was washed with water, triturated with pet. ether and dried in vacou to provide the title compound as a tan solid (1.04 g, 96%): mp 321–323° C.: NMR (CDCl3); δ 8.36 (ddd, J=8, 1, 1 Hz, 1H), 7.87 (ddd, J=8, 1, 1 Hz, 1H), 7.76 (ddd, J=8, 7, 1 Hz, 1H), 7.67 (ddd, J=8, 1, 1 Hz, 1H), 7.56 (ddd, J=8, 7, 1 Hz, 1H), 7.54 (s, 2H), 7.50 (ddd, J=8, 7, 1 Hz, 1H), 7.27 (ddd, J=8, 7, 1 Hz, 1H), 6.90 (ddd, J=8, 1, 1 Hz, 1H), 6.24 (s, 1H, OH); MS (EI): [M+], 2 bromine isotope pattern, 507 (55%), 509 (100%), 511 (55%); Anal. Calc. for C23H11Br2NOS.0.5 H2O: C, 53.31, H, 2.33, N, 2.70. Found: C, 53.51, H, 2.28, N, 2.70.

The compounds in Examples 59–66 were prepared using the procedure in Example 58 and the appropriate starting material.

EXAMPLE 59

2,6-Dibromo-4-(6-iodo-benzo[b]naphtho[2,3-d]thiophen-11-yl)-phenol

From 4-(6-iodo-benzo[b]naphtho[2,3-d]thiophen-11-yl)-phenol (Example 51). White solid: mp 221–222° C.; NMR (CDCl3); δ 8.22 (d, J=8 Hz, 1H), 7.83 (d, J=8 Hz, 1H), 7.63 (ddd, J=8, 7, 1 Hz, 1H), 7.55 (d, J=8 Hz, 1H), 7.54 (s, 2H), 7.50–7.43 (m, 2H), 7.20 (ddd, J=8, 7, 1 Hz, 1H), 6.83 (d, J=8 Hz, 1H); MS (+FAB): [M+], 2 bromine isotope pattern, 608 (25%), 609.7 (100%), 612 (35%); Anal. Calc. for C22H11Br2IOS: C, 43.31, H, 1.82, N, 0.00. Found: C, 42.98, H, 1.93, N, 0.26.

EXAMPLE 60

2,6-Dibromo-4-(6-chloro-benzo[b]naphtho[2,3-d]thiophen-11-yl)-phenol

From 4-(6-chloro-benzo[b]naphtho[2,3-d]thiophen-11-yl)-phenol (Example 50). White solid: mp 222–223° C.; NMR (CDCl3); δ 8.39 (ddd, J=8, 1, 1 Hz, 1H), 7.84 (ddd, J=8, 1, 1 Hz, 1H), 7.67 (ddd, J=8, 7, 1 Hz, 1H), 7.61 (ddd, J=8, 1, 1 Hz, 1H), 7.55 (s, 2H,), 7.52–7.43 (m, 2H), 7.23 (ddd, J=8, 7, 1 Hz, 1H), 6.89 (ddd, J=8, 1, 1 Hz,), 6.19 (s, 1H); MS (EI): [M+], 2 bromine, 1 chlorine isotope pattern, 516 (38%), 518 (100%), 520 (72%), 521 (20%); Anal. Calc. for C22H11Br2ClOS: C, 50.95, H, 2.14. Found: C, 51.12, H, 2.20.

EXAMPLE 61

2,6-Dibromo-4-(6-trifluoromethyl-benzo[b]naphtho[2,3-d]thiophen-11-yl)-phenol

From 4-(6-trifluoromethyl)-benzo[b]naphtho[2,3-d]thiophen-11-yl-phenol (Example 52). White solid: mp 223–225° C.; NMR (CDCl3); δ 8.37 (ddd, J=8, 1, 1 Hz, 1H), 7.82 (m, 2H), 7.54–7.50 (m, 2H), 7.53 (s, 2H), 7.45 (ddd, J=8, 7, 1 Hz, 1H), 7.20 (ddd, J=8, 7, 1 Hz, 1H), 6.83 (d, J=8 Hz, 1H), 6.22 (s, 1H, OH); MS: (+)EI (direct probe) [M+], 2 bromine isotope pattern, 550 (52%), 552 (100%) 554 (58%); Anal. Calc. for C23H11Br2F3OS: C, 50.03, H, 2.01, N, 0.00. Found: C, 49.66, H, 2.07, N, 0.08.

EXAMPLE 62

2,6-Dibromo-4-(6-methyl-benzo[b]naphtho[2,3-d]thiophen-11-yl)-phenol

From 4-methyl[b]naphtho[2,3-d]thiophen-11-yl-phenol (Example 53). White solid: mp 224–226° C.: NMR (CDCl3); δ 8.17 (ddd, J=8, 1, 1 Hz, 1H), 7.84 (ddd, J=8, 1, 1 Hz, 1H), 7.62–7.58 (m, 2H), 7.55 (s, 2H), 7.47–7.39 (m, 3H), 7.18 (ddd, J=8, 7, 1 Hz, 1H), 6.89 (ddd, J=8, 1, 1 Hz, 1H), 6.16 (s, 1H,); MS (–ESI): m/z 495.2 (40%), 497.1 (100%) 499.2 (27%); Anal. Calc. for C23H14Br2OS: C, 55.45, H, 2.83, N, 0.00. Found: C, 56.17, H, 2.78, N, 0.13.

EXAMPLE 63

2,6-Dibromo-4-(6-methoxybenzo[b]naphtho[2,3-d]thiophen-11-yl-phenol

From 4-(6-methoxy-benzo[b]naphtho[2,3-d]thiophen-11-yl)-phenol (Example 54). White solid: mp 233–234° C.; NMR (DMSO-d6); δ 10.35 (broad s, 1H), 8.23 (d, J=8 Hz, 1H), 8.03 (d, J=8 Hz, 1H), 7.69–7.64 (m, 1H), 7.64 (s, 2H), 7.54 (d, J=4 Hz, 2H), 7.48 (ddd, J=8, 7, 1 Hz, 1H), 7.26 (ddd, J=8, 7, 1 Hz, 1H), 6.84 (d, J=8 Hz, 1H), 4.13 (s, 3H); MS (EI): [M+], 2 bromine isotope pattern, 512 (48%), 514 (100%), 516 (54%); Anal. Calc. for C23H14Br2O2S: C, 53.72, H, 2.74, N, 0.00. Found: C, 53.62, H, 2.55, N, 0.18.

EXAMPLE 64

2,6-Dibromo-4-(6-phenylsulfanyl-benzo[b]naphtho[2,3-d]thiophen-11-yl)-phenol

From 4-(6-phenylsulfanyl-benzo[b]naphtho[2,3-d]thiophen-11-yl)-phenol (Example 55). White solid: mp 152–155° C.: NMR (DMSO-d6); δ 10.42 (s, 1H), 8.49 (d, J=8 Hz, 1H), 7.99 (d, J=8, Hz, 1H), 7.75 (s, 2H), 7.69 (ddd, J=8, 7, 1 Hz, 1H), 7.63 (d, J=8 Hz, 1H), 7.57 (ddd, J=8, 7, 1 Hz, 1H), 7.48 (ddd, J=8, 7, 1 Hz, 1H), 7.28 (ddd, J=8, 7, 1 Hz, 1H), 7.25–7.21 (m, 2H), 7.14 (ddd, J=8, 7, 1 Hz, 1H), 7.09 (d, J=8 Hz, 2H), 6.81 (d, J=8 Hz, 1H), 1.90 (s, 3H, AcOH); MS (EI): [M+], 2 bromine isotope pattern, 590 (50%), 592 (100%), 594 (60%); Anal. Calc. for C28H16Br2OS2.1.0 CH3CO2H.0.5 H2O; C, 54.48, H, 3.20, N, 0.00. Found: C, 54.56, H, 2.91, N, 0.23.

EXAMPLE 65

2,6-Dibromo-4-[6-(pyridin-4-ylsulfanyl)-benzo[b]naphtho[2,3-d]thiophen-11-yl]-phenol From 4-[6-(pyridin-4-ylsulfanyl)-benzo[b]naphtho[2,3-d]thiophen-11-yl]-phenol (Example 57). Yellow solid: mp 225–270° C. (dec); NMR (DMSO-d6); δ 10.48 (s, 1H, —OH), 8.40 (dd, J=8, 1 Hz, 2H), 8.37 (d, J=8 Hz, 1H), 8.00 (d, J=8 Hz, 1H), 7.76 (s, 2H), 7.75–7.68 (m, 2H), 7.62 (ddd, J=8, 7, 1 Hz, 1H), 7.50 (ddd, J=8, 7, 1 Hz, 1H), 7.31 (ddd, J=8, 7, 1 Hz, 1H), 7.20 (dd, J=6, 1 Hz, 2H), 6.83 (d, J=8 Hz, 1H); Anal. Calc. for C27H15Br2NOS2: C, 54.65, H, 2.55, N, 2.36. Found: C, 48.94, H, 2.46, N, 2.22.

EXAMPLE 66

2,6-Dibromo-4-[6-(2-dimethylaminoethylsulfanyl)-benzo[b]naphtho[2,3-d]thiophen-11-yl]-phenol From 4-[6-(2-dimethylaminoethylsulfanyl)-benzo[b]naphtho[2,3-d]thiophen-11-yl]-phenol (Example 56). Yellow solid: NMR (DMSO-d6); δ 8.65 (d, J=8 Hz, 1H), 8.04 (d, J=8 Hz, 1H), 7.77 (septet, J=3 Hz, 1H), 7.65 (s, 2H), 7.60–7.58 (m, 2H), 7.50 (dd, J=8, 1 Hz, 1H), 7.27 (ddd, J=8, 7, 1 Hz 1H), 6.86 and 6.63 (s, isomers, 1H), 6.79 (d, J=8 Hz, 1H), 3.24 (d, m, 2H), 2.85 (m, 2H); MS (EI): [M+], 2 bromine isotope pattern, 585 (3%), 587 (7%), 589 (4%).

EXAMPLE 67

2,6-Dichloro-4-(6-bromo-benzo[b]naphtho[2,3-d]thiophen-11-yl)-phenol

Methanol (20 mL) was purged with chlorine gas for 2 min. This solution was cooled to −78° C. and added to a −78° C. solution of 4-(6-bromo-benzo[b]naphtho[2,3-d]thiophen-11-yl)-phenol (0.609 g, 1.50 mmol) in methanol (15 mL). After 25 min, the solution was added to a rapidly stirred biphasic mixture of dilute aqueous sodium thiiosulfate and ether. The layers were separated and silica gel was added to the ether phase. The ether was removed and the adsorbate was flashed (gradient: 9:1 to 1:1 petroleum ether-:ethyl acetate). Silica gel was added to the fractions containing the desired product and the solvent was removed. The adsorbate was flashed (9:1 petroleum ether:ethyl acetate). Silica gel was added to the fractions containing the desired product and the solvent was removed. The adsorbate was flash chromatographed (7:3 petroleum ether:dichloromethane) to provide the title compound as a white solid (0.082 g, 12%): NMR (DMSO-d6); δ 10.65 (s, 1H), 8.28 (ddd, J=8, 1, 1 Hz, 1H), 8.07 (ddd, J=8, 1, 1 Hz, 1H), 7.78 (ddd, J=9, 5, 2 Hz, 1H), 7.63–7.58 (m, 2 H), 7.53 (s, 2 H), 7.52 (ddd, J=8, 8, 1 Hz, 1 H), 7.31 (ddd, J=8, 7, 1 Hz, 1 H), 6.69 (d, J=8 Hz, 1 H):MS (EI):[M+], 1 bromine, 2 chlorine isotope pattern, 472 (60%), 474 (100%), 476 (50%).

EXAMPLE 68

2-Bromo-5-(6-bromo-benzo[b]naphtho[2,3-d]thiophen-11-yl)-phenol

Prepared from 3-(6-bromo-benzo[b]naphtho[2,3-d]thiophen-11-yl)-phenol (Example 42) according to the procedure of Example 58. White solid: mp 111–112° C.: MS (+FAB): [M+], 482; Anal. Calc. for C22H12Br2OS: C, 54.57, H, 2.50, N, 0.00. Found: C, 53.72, H, 2.35, N, 0.41.

EXAMPLE 69

2,4-Dibromo-5-(6-bromo-benzo[b]naphtho[2,3-d]thiophen-11-yl)-phenol

Prepared from 3-(6-bromo-benzo[b]naphtho[2,3-d]thiophen-11-yl)-phenol (Example 42) according to the procedure of Example 58. White solid: 269–270° C.: MS (+FAB): [M+], 560, 562, 564, 566; Anal. Calc. for C22H11Br3OS: C, 46.93, H, 1.97, N, 0.00. Found: C, 46.43, H, 2.20, N, 0.11.

EXAMPLE 70

3-Bromo-5-(6-bromo-benzo[b]naphtho[2,3-d]thiophen- 11 -yl)-benzene- 1,2-diol

Prepared from 4-(6-bromo-benzo[b]naphtho[2,3-d]thiophen-11-yl)-benzene-1, 2-diol (Example 43) according to the procedure of Example 58. White solid: mp 212–213° C.: MS (EI): [M+], 2 bromine isotope pattern, 498, 500, 502; Anal. Calc. for C22H12Br2O2S:C, 52.83, H, 2.42, N, 0.00. Found: C, 52.08, H, 2.55, N, 0.01.

EXAMPLE 71

4-Bromo-5-(6-bromo-benzo[b]naphtho[2,3-d]
thiophen- 11-yl)-benzene- 1,2-diol

Prepared from 4-(6-bromo-benzo[b]naphtho[2,3-d]
thiophen-11-yl)-benzene-1, 2-diol (Example 43) according
to the procedure of Example 58. White solid: mp 138–140°
C.: MS (EI): [M+], 2 bromine isotope pattern, 498, 500, 502;
Anal. Calc. for C22H12Br2O2S: C, 52.83, H, 2.42, N, 0.00.
Found: C, 52.17, H, 2.71, N, 0.05.

EXAMPLE 72

[11-(4-Hydroxy-phenyl)-benzo[b]naphtho[2.3-d]
thiophen-3-yloxy]-acetic acid methyl ester 11-(4-Hydroxy-phenyl)-benzo[b]naphtho[2,3-d]
thiophen-3-ol (1.36 g, 3.96 mmol), methyl bromoacetate
(0.38 mL, 4.01 mmol), potassium carbonate (0.548 g, 3.97
mmol) and N,N-dimethylformamide (21 mL) were combined and stirred at ambient temperatures for 2.5 h. The
reaction mixture was added to water and extracted with ethyl
acetate and THF. Silica gel was added to the organic phase
and the solvent was removed. The adsorbate was flash
chromatographed (eluent:gradient dichloromethane to 98:2
dichloromethane:acetonitrile) to provide the title compound
as a white solid (0.953 g, 58%): mp: 229–231° C: NMR
(DMSO-d6); δ9.78 (s, 1 H), 8.51 (s, 1 H), 8.00 (d, J=8 Hz,
1 H), 7.56-7.39 (m, 4 H), 7.18 (d, J=9 Hz, 2 H), 7.05 (d, J=9
Hz, 2 H), 6.79 (dd, J=9, 2 Hz, 1 H), 6.66 (d, J=9 Hz, 1 H),
4.86 (s, 2 H), 3.68 (s, 3 H); MS (EI): 414 (100%, M+); Anal.
Calc. for C25 H18O4S: C, 72.45, H, 4.38, N, 0.00. Found:
C, 71.78, H, 4.41, N, 0.13.

EXAMPLE 73

[11-(4-Methoxycarbonylmethoxy-phenyl)-benzo[b]
naphtho[2.3-d]thiophen-3-yloxy]-acetic acid methyl
ester 11-(4-Hydroxy-phenyl)-benzo[b]naphtho[2,3-d]
thiophen-3-ol (0.60 g, 1.752 mmol), methyl bromoacetate
(0.70 mL, 7.39 mmol), potassium carbonate (1.2 g, 8.76
mmol) and N,N-dimethylformamide (8 mL) were combined
and stirred at ambient temperatures overnight. The reaction
mixture was added to water and filtered. The solid was
washed with water and dried in vacuo to provide the title
compound as a white solid (0.82 g, 96%): mp: 152–154° C.:
NMR (CDCl3); 6 8.27 (s, 1 H), 7.91 (dt, J =8, 1 Hz, 1 H),
7.61 (dm, J=8 Hz, 1 H), 7.49 (ddd, J=8, 7, 1 Hz, 1 H),
7.39-7.26 (m, 3 H), 7.18 (d, J=9 Hz, 2 H), 6.66 (dd, J=1 Hz,
2 H), 4.82 (s, 2 H), 4.67 (s, 2 H), 3.90 (s, 3 H), 3.81 (s, 3 H);
MS (FAB+): 487 (10%, M+H); Anal. Calc. for C28
H22O6S: C, 69.12, H, 4.56, N, 0.00. Found: C, 67.52, H,
4.40, N, 0.07.

EXAMPLE 74

[11-(4-Carboxymethoxy-phenyl)-benzo[b]naphtho[2,
3-d]thiophen-3-yloxy]-acetic acid 1.0 N Aqueous potassium hydroxide (8.0 mL, 8.0 mmol)
was added to a stirred suspension of [11 -(4-
methoxycarbonylmethoxy-phenyl)-benzo[b]naphtho[2,3-d
]thiophen-3-yloxy]-acetic acid methyl ester (0.750 g, 1.54
mmol) in THF (20 mL) and methanol (13 mL). Dissolution
occurred. After 3 h at ambient temperature, the reaction
mixture was diluted with water and extracted with ether (100
mL). The aqueous phase was acidified with 10% aqueous
HCl and filtered. The solid was washed with water and
triturated with pet. ether. The solid was dried in vacuo at 70°
C. to provide a grey solid. This solid was recrystalized from
acetic acid to provide the title compound as a white solid
(0.502, 71%): mp 220–222° C.: NMR (DMSO-d6); δ12.8
(broad s, 2 H), 8.54 (s, 1 H), 8.02 (d, J=8 Hz, 1 H), 7.56-7.40
(m, 4 H), 7.31 (d, J=8 Hz, 2 H), 7.23 (d, J=8 Hz, 2 H), 6.73
(dd, J=9, 1 Hz, 1 H), 6.56 (d, J=9 Hz, 1 H), 4.85 (s, 2 H), 4.74
(s, 2 H), 1.97 (s, 2.49 H, 0.83 mol acetic acid); MS (FAB+):
459 (20%, M+H); Anal. Calc. for
C26H18O6S.0.83CH3CO2 H: C, 65.46, H, 4.24, N, 0.00.
Found: C, 64.47, H, 4.05, N, 0.03.

EXAMPLE 75

[11-(4-Methoxycarbonylmethoxy-phenyl)-benzo[b]
naphtho[2.3-d]thiophen-8-yloxy]-acetic acid, methyl
ester To a suspension of 11-(4-hydroxy-phenyl)-benzo[b]
naphtho[2,3-d]thiophen-8-ol (0.600 g, 1.75 mmol) and
potassuim carbonate (0.605 g, 4.38 mmol, 2.5 eq) in anhydrous N,N-dimethylformamide (3 mL) was added methylbromoacetate (0.50 mL, 5.26 mmol) dropwise at room
temperature. After stirring 26 hours additional methylbromoacetate (0.166 mL, 1.75 mmol) was added and stirring
continued for 64 hours. The solvents were removed and
water (100 mL) was added. The solid was dissolved in a
mixture of diethyl ether and methylene chloride and combined with silica gel. The solvents were removed and the
adsorbate was flash chromatographed (70/30 petroleum ether/
ethyl acetate) to give the title compound as a yellow solid
(0.300 , 35%).

EXAMPLE 76

[11-(4-Carboxymethoxy-phenyl)-benzo[b]naphtho
[2.3-d]thiophen-8-yloxy]-acetic acid To a solution of [11-(4-methoxycarbonylmethoxy-
phenyl)-benzo [b]naphtho[2,3-d]thiophen-8-yloxy]-acetic
acid, methyl ester (0.268 g, 0.551 mmol) in tetrahydrofuran
(8 mL) and methanol (5 mL) was added an aqueous solution
of potassuim hydroxide (1 N, 2.2 mL, 2.2 mmol) dropwise
at room temperature. After stirring 2 hours an addition of
potassuim hydroxide (1 N, 1 mL, 1 mmol) was introduced.
After stirring another 14 hours the solvents were removed
and the residue was disolved in water (50 mL) and was
acidified with 10% aqueous hydrochloric acid, and the
organics were extracted with diethyl ether. The solvent was
removed and chased with benzene and petroleum ether and
dried at 53° C. to give the title compound as a white solid
(0.18 g, 43%): mp 245–246° C.; NMR (DMSO-d6); δ13.08
(broad s, 2 H), 8.44 (s, 1 H), 7.93 (d, J=8 Hz, 1 H), 7.45 -
7.35 (m, 3 H), 7.31 (d, J=9 Hz, 2 H), 7.22 (d, J=9 Hz, 2 H),
7.17 (dd, J=3,9 Hz, 1 H), 7.10 (ddd, J=9, 9, 1 Hz, 1 H), 6.67
(d, J=8 Hz, 1 H), 4.84 (d, J=7 Hz, 4 H); MS (EI): [M+] 458;
Anal. Calc. for C26 H18O6S: C, 68.11, H, 3.96, N, 0.00.
Found: C, 66.41, H, 3.95, N, 0.05.

EXAMPLE 77

[2,6-Dibromo-4-(6-bromo-benzo[b]naphtho[2,3-d]
thiophen-11-yl)-phenoxy]-acetic acid, methyl ester 2,6-Dibromo-4-(6-bromo-benzo[b]naphtho[2,3-d]
thiophen- 11 -yl)-phenol (1.0 g, 1.78 mmol), methyl bromoacetate (0.35 mL, 3.70 mmol), potassium carbonate (0.50
g, 3.62 mmol) and N,N-dimethylformamide (5 mL) were combined and stirred at ambient temperatures overnight. The reaction mixture was added to water and filtered. The solid was washed with water and dried in vacuo to provide the title compound as a white solid (1.11 g, 98%): mp 183–184° C.: NMR (CDCl3); δ8.36 (ddd, J=8, 1, 1 Hz, 1 H), 7.84 (ddd, J=8, 1, 1 Hz, 1 H), 7.68 (ddd, J=8, 7, 1 Hz, 1 H), 7.62 (s, 2 H), 7.57 (ddd, J=8, 1, 1 Hz, 1 H), 7.51 (ddd, J=8, 7, 1 Hz, 1 H), 7.42 (ddd, J=8, 7, 1 Hz, 1 H), 7.18 (ddd, J=8, 7, 1 Hz, 1 H), 6.72 (ddd, J=8, 1, 1 Hz, 1 H), 4.88 (s, 2 H), 3.94 (s, 3 H); MS (EI): [M+], 3 bromine isotope pattern, 632 (30%), 634 ( 90%) 636 (100%) 638 (35%); Anal. Calc. for C25H15Br3O3S: C, 47.27, H, 2.38, N, 0.00. Found: C, 47.17, H, 2.19, N, 0.09.

EXAMPLE 78

[2,6-Dibromo-4-(6-bromo-benzo[b]naphtho[2,3-d]thiophen- 11-yl)-phenoxy]-acetic acid, tert-butyl ester To a suspension of 2,6-dibromo-4-(6-bromo-benzo[b]naphtho[2,3-d]thiophen-11 -yl)-phenol (1.50 g, 2.66 mmol) in anhydrous DMF (10 mL) was added potassium carbonate (0.496 g, 3.59 mmol) followed by the dropwise addition of tert-butyl bromo acetate (0.79 mL, 3.59 mmol) at room temperature under a dry nitrogen atmosphere. After stirring for 3 h. the reaction mixture was poured into water (250 mL) and filtered. The white solid was washed with water then taken up in methylene chloride and silica gel was added. The solvent was removed and the silica adsorbate was flash chromatographed (96:4 petroleum ether:ethyl acetate) to provide the title compound as a white solid (1.14 g, 64%): NMR (CDCl3); δ8.36 (d, J=8 Hz, 1 H, ArH), 7.85 (d, J=8 Hz, 1 H, ArH), 7.67 (ddd, J=8, 7, 1 Hz, 1 H, ArH), 7.60 (s, 2 H, ArH), 7.59-7.36 (m, 3 H, ArH), 7.19 (t, J=7 Hz, 1 H, ArH), 6.75 (d, J=7 Hz, 1 H, ArH), 4.73 (s, 2 H, CH2), 1.60 (s, 9 H, 3(CH3); MS (EI): [M+], 3 bromine pattern 674 (29%), 676 (85%), 678 (85%), 680 (35%); Anal. Calc. for C28H21Br3O3S: C, 49.66, H, 3.12, N, 0.00; found: C, 49.55, H, 2.84, N, 0.06.

EXAMPLE 79

[2,6-Dibromo-4-(6-bromo-benzo[b]naphtho[2,3-d]thiophen- 11-yl)-phenoxy]-acetic acid 1.0 N Aqueous potassium hydroxide (2.66 mL, 2.66 mmol) was added to a stirred suspension of [2,6-dibromo-4-(6-bromo-benzo[b]naphtho[2,3-d]thiophen-11-yl)-phenoxy]-acetic acid, methyl ester (1.51 g, 2.37 mmol) in THF (13 mL) and methanol (4 mL). Dissolution occurred. After 2.5 h at ambient temperature, the reaction mixture was diluted with water and extracted with ether (100 mL). The aqueous phase was acidified with 10% aqueous HCl and filtered. The solid was washed with water and triturated with pet. ether. The solid was dried in vacuo at 70° C. to provide the title compound as a white solid (1.34 g, 91%): mp 259–261° C.: NMR (DMSO-d6): δ8.29 (dd, J=8, 1 Hz, 1 H), 8.06 (dd, J=8, 1 Hz, 1 H), 7.82 (s, 2 H), 7.79 (ddd, J=8, 6, 2 Hz, 1 H), 7.61 (m, 2 H), 7.52 (ddd, J=8, 7, 1 Hz, 1 H), 7.32 (ddd, J=8, 7, 1 Hz, 1 H), 6.73 (dd, J=8, 1 Hz, 1 H), 4.78 (s, 2 H); MS (EI): [M+], 3 bronine isotope pattern, 618 (30%), 620 ( 90%) 622 (100%) 624 (50%); Anal. Calc. for C24H13Br3O3S: C, 46.41, H, 2.11, N, 0.00. Found: C, 46.38, H, 1.99, N, 0.01.

EXAMPLE 80

[2,6-Dibromo-4-(6-bromo-benzo[b]naphtho[2,3-d]thiophen-11-yl)-phenoxy]-acetic acid, sodium salt Aqueous sodium hydroxide (1.00 N, 0.315 mL, 0.315 mmol) was added to a stirred solution of [2,6-dibromo-4-(6-bromo-benzo[b]naphtho[2,3-d]thiophen-11-yl)-phenoxy]-acetic acid (194 mg, 0.315 mmol) in THF (1 mL)/methanol (1 mL). The reaction mixture was concentrated, water (2.5 mL) was added and the solid was filtered (101 mg) . The aqeous phase was extracted with ether (25 mL) and the ether phase was evaporated to dryness to provide a second solid (77 mg). The solids were combined and triturated with toluene and benzene and dried in vacuo to provide the title compound as a tan solid (152 mg, 76%): mp 315–317° C.: NMR (DMSO-d6);, δ8.28 (d, J=8.5 Hz, 1 H), 8.07 (d, J=8 Hz, 1 H), 7.79 (ddd, J=8, 7, 2 Hz, 1 H), 7.76 (s, 2 H), 7.62 (m, 2 H), 7.52 (ddd, J=8, 8, 1 Hz, 1 H), 7.33 (ddd, J=8, 8, 1 Hz, 1 H), 6.69 (d, J=8 Hz, 1 H), 4.27 (s, 2 H); MS (−FAB): [M−Na], 3 bromine isotope pattern, 617, 619, 621, 622; Anal. Calc. for C24H12Br3O3SNa.0.75 H2O:C, 43.90, H, 2.07, N, 0.00. Found: C, 44.09, H, 2.18, N, 0.03.

EXAMPLE 81

[(4-Benzo[b]naphtho[2,3-d]thiophen-11 -yl)-2,6-dicyano-phenoxy]-acetic acid 5-(Benzo[b]naphtho[2,3-d]thiophen-11-yl)-2-hydroxy-isophthalonitrile (0.455 g, 1.21 mmol), methyl bromoacetate (0.351 mL, 3.63 mmol), potassium carbonate (0.251 g, 1.81 mmol) and N,N-dimethylformamide (5.0 mL) were combined and stirred at ambient temperature for two days. The reaction mixture was diluted with water (60 mL) and acidified with 10% aqueous HCl to pH 1 and aqueous was extracted with ethyl acetate (100 mL). The ethyl acetate extract was washed with water, dried with brine and anhydrous MgSO4, and concentrated to provide a white solid. The solid was dissolved in ethyl acetate (60 mL) and silica gel was added. Solvent was removed and the adsorbate was flash chromatographed (eluent 8:2 petroleum ether:ethyl acetate) to provide the methyl ester as a white solid (0.370 g, 83%): Aqueous potassium carbonate (170 mg in 5 mL of water, 1.23 mmol) was added to a stirred solution of this methyl ester (0.275 g, 0.613 mmol) in THF (10 mL) at ambient temperature. After 31 h the reaction mixture was diluted with water (100 mL) and acidified with 10% aqueous HCl to pH 1 and aqueous was extracted with ethyl acetate (150 mL). The ethyl acetate extract was washed with water, dried with brine and anhydrous MgSO4, and concentrated to provide the title compound as a white solid (0.207 g, 78%): mp 134–136° C.: NMR (CDCl3); δ8.43 (s, 1 H), 7.98 (dd J=8, 1 Hz, 1 H), 7.91 (s, 2 H), 7.8 (dd J=8, 1 Hz, 1 H), 7.58 (ddd, J=8, 7, 1 Hz, 1 H), 7.49-7.42 (m, 3 H), 7.36 (dd, J=8, 1 Hz, 1 H), 7.18 (ddd, J=8, 7, 1 Hz, 1 H), 6.70 (dd, J=8 ,1 Hz, 1 H), 4.47 (s, 2 H); MS (EI): 434 (100%, MI); High resolution MS (EI) Calc. for C26H14N2O3S: High resolution MS (EI) Calc. for C26H14N2O3S: 434.072516, Found: 434.078475; Anal. Calc. for C26H14N2O3S: C, 71.88, H, 3.25, N, 6.45. Found: C, 70.80, H, 3.14, N, 6.18.

EXAMPLE 82

[(4-benzo[b]naphtho[2,3-d]thiophen-11 -yl)-2-cyano-phenoxy]-acetic acid 5-(Benzo[b]naphtho[2,3-d]thiophen-11-yl)-2-hydroxy-benzonitrile (0.386 g, 1.1 mmol), methyl bromoacetate (0.266 mL, 2.75 mmol), potassium carbonate (0.228 g, 1.65 mmol) and N,N-dimethylformamide (5.0 mL) were combined and stirred at ambient temperature for 1.5 h. The reaction mixture was diluted with water (120 mL) and acidified with 10% aqueous HCl to pH 1 and aqueous mixture was extracted with ethyl acetate (150 mL). The ethyl acetate extract was washed with water, dried with brine and anhydrous MgSO4, and concentrated to provide a white solid. The solid was dissolved in ethyl acetate (60 mL) and silica gel was added. Solvent was removed and the adsorbate was flash chromatographed (eluent 7:3 petroleum ether: ethyl acetate) to provide the methyl ester as a white solid (0.195 g, 42%). Aqueous potassium carbonate (124 mg in 4 mL of water, 0.90 mmol) was added to a stirred solution of this methyl ester (0.190 g, 0.45 mmol) in THF (5 mL) at ambient temperature. After 23 h the reaction mixture was diluted with water (80 mL) and acidified with 10% aqueous HCl to pH 1 and aqueous was extracted with ethyl acetate (100 mL). The ethyl acetate extract was washed with water, dried with brine and anhydrous MgSO4, and concentrated to provide the title compound as a white solid (0.116 g, 63%): mp 235–236° C.: NMR (CDCl3); δ8.38 (s, 1 H), 7.96 (d J=8 Hz, 1 H), 7.81 (dd, J=8, 1 Hz, 1 H), 7.72 (d, J=2 Hz, 1 H), 7.61 (dd J=8, 1 Hz, 1 H), 7.55 (ddd, J=8, 7, 1 Hz, 1 H), 7.45-7.38 (m, 3 H), 7.19 (d, J=8 Hz, 1 H), 7.12 (ddd, J=8, 7, 1 Hz, 1 H), 6.73 (d, J=8 Hz, 1 H), 5.04 (s, 2 H); MS (EI): 409 (100%, MI); Anal. Calc. for C25H15NO3S: C, 73.33, H, 3.69, N, 3.42. Found: C, 71.66, H, 3.33, N, 3.31.

EXAMPLE 83

(4-Benzo[b]naphtho[2,3-d]thiophen-11-yl-2,6-diiodo-phenoxy)-acetic acid 4-(Benzo[b]naphtho[2,3-d]thiophen-11-yl)-2,6-diiodo-phenol (0.543 g, 0.94 mmol), methyl bromoacetate (0.181 mL, 1.88 mmol), potassium carbonate (0.141 g, 1.03 mmol) and N,N-dimethylformamide (5.4 mL) were combined and stirred at ambient temperature for 1 h. The reaction mixture was added to water and filtered. The solid was washed with water and dried in vacuo to provide the (4-benzo [b]naphtho [2,3-d]thiophen-11-yl-2,6-diiodo-phenoxy)-acetic acid methyl ester as a white solid (0.537 g, 88%): mp 203–205 ° C. Aqueous potassium hydroxide (0.5 N, 2.54 mL, 1.28 mmol) was added to a stirred solution of this methyl ester (0.55 g, 0.85 mmol) in THF (5.0 mL) at ambient temperature. After 1 h the solution was concentrated, diluted with water (75 mL) and acidified with 10% aqueous HCl. The solid was filtered and washed with water to provide the title compounds as a white solid (0.428 g, 80%): mp 250–252° C.: NMR (DMSO-d6); δ8.66 (s, 1 H), 8.07 (d, J=8 Hz, 1 H), 8.01 (d, J=8 Hz, 1 H), 7.93 (s, 2 H), 7.61 (ddd, J=8, 7, 1 Hz, 1 H), 7.54-7.48 (m, 2 H), 7.47 (ddd, J=8, 7, 1 Hz, 1 H), 7.27 (ddd, J=8, 7, 1 Hz, 1 H), 6.71 (d, J=8 Hz, 1 H), 4.69 (s, 2 H); MS (EI): 636 (100%, MI); Anal. Calc. for C24H14I2O3S: C, 45.31, H, 2.22, N, 0.00. Found: C, 44.95, H, 1.99, N, 0.23.

The compounds in Examples 84–95 were prepared using the procedure in Example 83 and the appropriate starting material.

EXAMPLE 84

[4-Benzo[b]naphtho[2,3-d]thiophen- 11 -yl-phenoxy]-acetic acid

From 4-benzo[b]naphtho[2,3-d]thiophen-1 1-yl-phenol (Example 14). White solid: mp 221–223° C.: NMR (DMSO-d6); δ13.05 (broad s, 1 H), 8.61 (s, 1 H), 8.05 (d, J =8 Hz, 1 H), 7.96 (d, J=7 Hz, 1 H), 7.58 (ddd, J=8, 7, 1 Hz, 1 H), 7.51-7.40 (m, 3 H), 7.33 (d, J=9 Hz, 2 H), 7.23 (d, J=9 Hz, 2 H), 7.12 (ddd, J=8, 7, 1 Hz, 1 H), 6.71 (ddd, J=8, 1, 1 Hz, 1 H), 4.86 (s, 2 H); MS (EI): [M+], 384 (100%); Anal. Calc. for C24H16O3S: C, 74.98, H, 4.20, N, 0.00. Found: C, 74.62, H, 4.14, N, 0.08.

EXAMPLE 85

(4-Benzo[b]naphtho[2,3-d]thiophen-11-yl-2-iodo-phenoxy)-acetic acid

From 4-(benzo[b]naphtho[2,3-d]thiophen-11 -yl)-2-iodo-phenol (Example 27). White solid: mp 248–249° C.: NMR (DMSO-d6); δ8.63 (s, 1 H), 8.05 (d, J=8 Hz, 1 H), 7.98 (d, J=7 Hz, 1 H), 7.81 (d, J=2 Hz, 1 H), 7.61-7.56 (m, 1 H), 7.49-7.48 (m, 2 H), 7.44 (ddd, J=8, 7, 1 Hz, 1 H), 7.41 (dd, J=8, 2 Hz, 1 H), 7.20 (d, J=8, Hz, 1 H), 7.17 (ddd, J=8, 7, 1 Hz, 1 H), 6.75 (d, J=8, Hz, 1 H), 4.96 (s, 2 H); MS (EI): 510 (100%, MI); Anal. Calc. for C24H15IO3S: C, 56.48, H, 2.96, N, 0.00. Found: C, 56.35, H, 2.84, N, 0.27.

EXAMPLE 86

{2,6-Dimethyl-4-[6-methyl-(benzo[b]naphtho[2,3-d] thiophen- 11-yl)]-phenoxy}-acetic acid From {2,6-dimethyl-4-[6-methyl-(benzo[b]naphtho[2,3-d]thiophen- 11-yl)]-phenoxy }-acetic acid methyl ester (Example 25). White solid: mp 155–181° C.; NMR (DMSO-d6); δ12.95 (broad s, 1 H), 8.23 (d, J=8 Hz 1 H), 7.97 (d, J=8 Hz, 1 H), 7.63 (d, J=8, 7, 1 Hz, 1 H), 7.58 (d, J=8 Hz, 1 H), 7.47 (ddd, J=8, 7, 1 Hz, 1 H), 7.41 (ddd, J=8, 8, 1 Hz, 1 H), 7.15 (ddd, J=8, 7, 1 Hz, 1 H), 7.05 (s, 2 H), 6.67 (d, J=8 Hz, 1 H), 4.59 (s, 2 H), 2.92 (s, 3 H), 2.34 (s, 6 H).MS (EI): [M+] 426 (100%); Anal. Calc. for C27H22O3S: C, 76.03, H, 5.20, N, 0.00. Found: C, 75.64, H, 5.31, N, 0.02.

EXAMPLE 87

[(4-(6-Bromo-benzo[b]naphtho[2,3-d]thiophen-11-yl)-phenoxy]-acetic acid

From [4-(6-bromo-benzo[b]naphtho[2,3-d]thiophen-11-yl)-phenoxy]-acetic acid, methyl ester (Example 41). White solid: mp 198–200° C.: NMR (CDCl3); δ8.34 (ddd, J=8, 1, 1 Hz, 1 H), 7.80 (ddd, J=8, 1, 1 Hz, 1 H), 7.66-7.61 (m, 2 H), 7.45-7.38 (m, 2 H), 7.36 (d, J=9 Hz, 2 H), 7.22 (d, J=9 Hz, 2 H), 7.09 (ddd, J=8, 7,1 Hz, 1 H), 6.71 (ddd, J=8, 1, 1 Hz, 1 H), 4.89 (s, 2 H); MS (EI): [M+], 1 bromine isotope pattern, 462 (95%), 464 (100%); Anal. Calc. for C24H15BrO3S.0.6CH3CO2 H.0.28H2O: C, 60.00, H, 3.37, N, 0.00. Found: C, 59.82, H, 3.42, N, 0.03.

EXAMPLE 88

[2,6-Dibromo-4-(6-cyano-benzo[b]naphtho[2,3-d] thiophen- 1-yl)-phenoxyl-acetic acid From [2,6-dibromo-4-(6-cyano-benzo[b]naphtho[2,3-d] thiophen-11-yl)-phenoxy ]-acetic acid, methyl ester (Example 58). White solid: mp 259–261° C.: NMR (DMSO-d6); δ13.2 (broads s, 1 H), 8.27 (d, J=8 Hz, 1 H), 8.16 (d, J=8, 1H), 7.91 (ddd, J=8, 7, 1 Hz, 1 H),7.89 (s, 2 H), 7.74-7.65 (m, 2 H), 7.59 (ddd, J=8, 7, 1 Hz, 1 H), 7.38 (ddd, J=8, 7, 1 Hz, 1 H), 6.75 (d, J=8 Hz, 1 H), 4.78 (s, 2 H); MS (EI): [M+], 2 bromine isotope pattern, 565 (45%), 567 (100%) 569 (50%); Anal. Calc. for C25H13Br32NO3S: C, 52.93, H, 2.31, N, 2.47. Found: C, 51.96, H, 2.07, N, 2.31.

EXAMPLE 89

[4-(6-Bromo-benzo[b]naphtho[2,3-d]thiophen-11-yl)-2,6-diisopropyl-phenoxy)-acetic acid From 4-(6-bromo-benzo[b]naphtho [2,3-d]thiophen- 11 -yl)-2,6-diisopropyl-phenol (Example 40). White solid: mp: 220–221° C.; NMR (CDCl3); δ8.37 (ddd, J=8, 1, 1, 1H), 7.81 (ddd, J=8, 1, 1 Hz, 1 H), 7.69 (ddd, J=8, 1, 1 Hz, 1 H), 7.66 (ddd, J=8, 8, 1, 1H), 7.48 (ddd, J=8, 8, 1 Hz, 1 H), 7.38 (ddd, J=8, 8, 1 Hz, 1 H), 7.19 (s, 2 H), 7.02 (ddd, J=8, 8, 1 Hz, 1 H), 6.54 (d, J=8 Hz, 1 H), 4.69 (s, 2 H), 3.42 (septuplet, J=7 Hz, 2 H), 1.28 (d, J=7 Hz, 6 H), 1.23 (d, J=7 Hz, 6 H); MS (+FAB): 546 (90%), 548 (100); Anal. Calc. for C3OH27BrO3S: C, 65.81, H, 4.97, N, 0.00. Found: C, 65.56, H, 4.89, N, 0.10.

EXAMPLE 90

[3-(6-Bromo-benzo[b]naphtho[2,3-d]thiophen- 11 -yl)-phenoxyl]-acetic acid

From 3-(6-bromo-benzo [b]naphtho [2,3-d]thiophen- 11 -yl)-phenol (Example 42). White solid: mp 180–181° C.: MS (+FAB): [M+], 462; Anal. Calc. for C24H15BrO3S: C, 62.21, H, 3.26, N, 0.00. Found: C, 61.90, H, 3.19, N, 0.13.

EXAMPLE 91

[2-Bromo-5-(6-bromo-benzo[b]naphtho[2,3-d] thiophen- 11 -yl)-phenoxyl]-acetic acid From 2-bromo-5-(6-bromo-benzo[b]naphtho[2,3-d]thiophen-11-yl)-phenol (Example 68). White solid: mp 174–175° C.: MS (+FAB): [M+], 2 bromine isotope pattern, 540, 542, 544; Anal. Calc. for C24H14Br2O3S: C, 53.16, H, 2.60, N, 0.00. Found: C, 52.91, H, 2.75, N, 0.48.

EXAMPLE 92

[2,4-Dibromo-5-(6-bromo-benzo[b]naphtho[2.3-d] thiophen- 1-yl)-phenoxyl]-acetic acid From 2,4-dibromo-5-(6-bromo-benzo[b]naphtho[2,3-d]thiophen- 11 -yl)-phenol (Example 69). White solid: mp 256–258 C.: MS (+FAB): [M+], 618; Anal. Calc. for C24H13Br3O3S: C, 46.41, H, 2.11, N, 0.00. Found: C, 46.26, H, 2.17, N, 0.07.

EXAMPLE 93

5-(6-Bromo-benzo[b]naphtho[2,3-d]thiophen- 11- yl)-2-carboxymethoxy-phenoxyl]-acetic acid From 4-(6-bromo-benzo[b]naphtho[2,3-d]thiophen- 11 -yl)-benzene- 1,2-diol (Example 42). White solid: mp 222–224° C.: MS (+FAB): [M+], 536; Anal. Calc. for C26H17BrO6S: C, 58.11, H, 3.19, N, 0.00. Found: C, 57.58, H, 3.00, N, 0.15.

EXAMPLE 94

3-Bromo-5-(6-bromo-benzo[b]naphtho[2,3-d] thiophen-1-yl)-2-carboxymethoxy-phenoxyl ]-acetic acid From 3-bromo-5-(6-bromo-benzo[b]naphtho[2,3-d]thiophen-11-yl)-benzene-1, 2-diol (Example 70). White solid: mp 135–137° C.: MS (EI): [M+], 2 bromine isotope pattern, 614, 616, 618; Anal. Calc. for C26H16Br2O6S: C, 50.67, H, 2.26, N, 0.00. Found: C, 49.45, H, 2.73, N, 0.11.

EXAMPLE 95

4-Bromo-5-(6-bromo-benzo[b]naphtho[2,3-d] thiophen-11-yl)-2-carboxymethoxy-phenoxyl ]- acetic acid From 4-Bromo-5-(6-bromo-benzo[b]naphtho[2,3-d]thiophen-11-yl)-benzene-1, 2-diol (Example 71). White solid: mp 256–257° C.: MS (EI): [M+], 2 bromine isotope pattern, 614, 616, 618; Anal. Calc. for C26H16Br2O6S: C, 50.67, H, 2.26, N, 0.00. Found: C, 50.88, H, 2.96, N, 0.04.

EXAMPLE 96

(S)-2-Hydroxy-3-phenylpropionic acid, methyl ester

A solution of commercially available (S)-2-hydroxy-3-phenylpropionic acid (5.0 g, 30.1 mmol) and p-toluenesulfonic acid hydrate (1 g) in methanol (125 mL) was refluxed with removal of water using 3A molecular sieves for 17 h. The solution was concentrated and dissolved in ether. The ether solution was washed with saturated sodium bicarbonate, brine and concentrated to provide the title compound as a white solid (5.32 g, 98%): NMR (CDCl3); δ7.36-7.20 (m, 5 H), 4.47 (ddd, J=5, 6, 7 Hz, 1 H), 3.78 (s, 3 H), 3.14 (dd, J=5, 14 Hz, 1 H), 2.97 ( dd, J=7, 14 Hz), 2.69 (d, J=6 Hz, 1 H).

EXAMPLE 97

(R)-2-Hydroxy -3-phenylpropionic acid, methyl ester

Prepared from commercially available (R)-2-hydroxy-3-phenylpropionic acid according to the procedure in Example 96. White solid: NMR (CDCl3); δ7.34-7.20 (m, 5 H), 4.47 (ddd, J=5, 6, 7 Hz, 1 H), 3.78 (s, 3 H), 3.14 (dd, J=5, 14 Hz, 1 H), 2.97 (dd, J=7, 14 Hz), 2.69 (d, J=6 Hz, 1 H).

EXAMPLE 98

D,L-Indole-3-lactic acid methyl ester

Prepared from commercially available D, L-indole-3-lactic acid according to the procedure in Example 96. White solid: mp 42–44 ° C.: NMR (CDCl3); δ8.07 (m, 1 H, NH), 7.61 (d, J=8 Hz, 1 H), 7.34 (d, J=8 Hz, 1 H), 7.19-7.10 (m, 3 H), 5.45 (q, J=6 Hz, 1 H), 3.72 (s, 3 H), 3.25 (dd, J=7, 6 Hz, 2 H), 2.75 (d, J=6 Hz, 1 H, OH); MS (EI): [M+], 219.

EXAMPLE 99

(S)-(+)-α-Hydroxy-1,3-dioxo-2-isoindolinebutyric acid, methyl ester

Prepared from commercially available (S)-(+)-α-hydroxy-1,3dioxo-2-isoindolinebutyric acid according to the procedure in Example 9. White solid: mp 123–124.5° C.: MS (EI): [M+], 263; Anal. Calc. for C13H13NO5: C, 59.31, H, 4.98, N, 5.32. Found: C, 59.04, H, 5.02, N, 5.06.

EXAMPLE 100

L-β-Imidazolelactic acid, methyl ester, hydrochloride

Thionyl chloride (4.8 mL, 68.4 mmol) was added dropwise to a stirred, ambient temperature suspension of commercially available L-β-imidazolelactic acid, hydrochloride (1.11 g, 5.7 mmol) in methanol (7 mL) under a dry nitrogen atmosphere over a period of 10 min. The solution was heated in an 60° C. oil bath for 2 days. Upon cooling to room temperature, the reaction mixture was concentrated, chased with ethyl ether to provide the title compound as a sticky white solid (1.07 g, 90%); NMR (DMSO-d6); δ8.63 (s, 1 H), 7.23 (s, 1 H), 4.35 (t, J=6 Hz, 1 H), 3.62 (s, 3 H, OCH3), 2.90 (d, J=6 Hz, 2 H); MS (EI): 170 (10%, MI), 111(40%), 81(100%).

EXAMPLE 101

N-t-BOC-L-β-Imidazolelactic acid, methyl ester

Triethylamine (0.878 mL, 6.3 mmol) was added dropwise to a stirred, ambient temperature solution of L-β-imidazolelactic acid, methyl ester, hydrochloride (0.87 g, 4.2 mmol) in methanol (12 mL) under a dry nitrogen atmosphere. The stirring was continued at ambient temperature for 40 min. After 6 h., the reaction mixture was concentrated to yield an oil and dichloromethane (150 mL) was added. The dichloromethane was washed with water and brine. Silica gel (12 mL) was added. Solvents were removed and the silica adsorbate was flash chromatographed (eluent 4: 6 petroleum ether:ethyl acetate) to provide the title compound as an oil (0.86 g, 75%): MS (EI): [M+], 270.

EXAMPLE 102

(S)-2-[4-Nitrobenzoyl]-4-phenylbutyric acid, ethyl ester

To a cold (ice bath) solution of commercially available (R)-2-hydroxy-4-phenyl-butyrate, ethyl ester (1.86 mL, 9.60 mmole), p-nitrobenzoic acid (6.42 g, 38.4 mmole, 4 eq) and triphenylphosphine (10.07 g, 38.4 mmole, 4 eq.) in anhydrous tetrahydrofuran (110 mL) was added diethyl azodicarboxylate (6.05 mL, 38.4 mmole, 4 eq) dropwise over a period of 40 minutes keeping the internal temperature between 4 and 5° C. After stirring for one additional hour, the ice bath was removed and the solution was allowed to stir at ambient temperature for 5 days. The solvents were removed and the residue was redissolved in a mixture of ether and ethyl acetate (600 mL). Silica gel (200 mL) was added and the solvents removed. The adsorbate was flash chromatographed (gradient: 80/20- 70/30 petroleum ether/ethyl acetate) to give the title compound as a yellow oil (4.03 g): NMR (CDCl3); δ8.30 (d, J=9 Hz, 2 H), 8.18 (d, J=9 Hz, 2 H), 7.38 - 7.18 (m, 5 H), 5.28 (t, J=2 Hz, 1 H), 4.23 (q, J=7 Hz, 2 H), 2.85 (t, J=8Hz, 2 H), 2.40 - 2.33(m, 2 H), 1.29 (t, J=7 H, 3 H); MS [(+) FAB]: [M +H] m/z =358.

EXAMPLE 103

(S)-2-Hydroxy-4-phenylbutyric acid, ethyl ester

To a suspension of potassium cyanide (0.176 g, 2.70 mmole) in absolute ethanol (43mL) was added a solution of (S)-2-[4-nitrobenzoyl]-4-phenylbutyrate, ethyl ester (3.86 g, 10.8 mmole) in absolute ethanol (38 mL) dropwise over a period of 0.5 hours. After stirring 2.25 hours the solvent was removed and the reside was diluted with water and acidified with dilute hydrochloric acid. The organics were extracted with ether. The extracts were combined, silica gel (60 mL) was added and the solvent was removed. The adsorbate was flash chromatographed, eluent (gradient 90/10- 80/20petroleum ether/ethyl acetate) and the solvents were chased with benzene to give the title compound as a yellow oil (1.67 g, 74%): [a]25D +178.23 (10.98 mg/L CHCl3); NMR (CDCl3); δ7.38 - 7.16 (m, 5 H), 4.30 - 4.10 (m, 3 H), 2.9 - 2.6 (m, 3 H), 2.2 - 1.9 (m, 2 H), 1.15 (t, 4 Hz, 3 H);.

EXAMPLE 104

3-Pyridin-3-yl-propionic acid, ethyl ester

According to the procedure of B. A. Lefker, W. A. Hada, P. J. McGarry *Tetrahedron Lett.* 1994, 35, 5205–5208, a solution of sodium bis(trimethylsilyl)amide (1.0 N in THF, 44.3 mL, 44.3 mmol) was added dropwise at a rate to keep the temperature below −50° C. to a stirred solution of 3-pyridine carboxaldehyde (4.41 mL, 46.7 mmol), ethyl chloroacetate (4.93 mL, 46.7 mmol) and THF (34 mL) under a dry nitrogen atmosphere. After 45 min at −78° C., the reaction mixture was warmed to 0° C. and then quenched with water and concentrated. The residue was partitioned between ether and water. The ether phase was dried with brine and concentrated. The residue was dissolved in erthyl acetate and palladium hydroxide on carbon (wet, Degussa type, 20% Pd content, 1 g) was added. The mixture was hydrogenated at 45 psi hydrogen pressure for 2 h. The reaction mixture was filtered thru sulka floc and the solvent was removed. The residue was flash chromatographed (2:3 petroleum ether:ethyl acetate, eluent) to provide the title compound as an oil (3.83 g, 42%): NMR (CDCl3); 8.24 (m, 2 H), 7.60 (d, 1 H), 7.22 (dd, 1 H), 4.45 (t, 1 H), 4.22 (q, 2 H), 3.15 (dd, 1 H), 2.95 (dd, 1 H), 1.27 (t, 3 H).

EXAMPLE 105

(S)-(+)-α,3-Dihydroxy-1-oxo-2-isoindolinebutyric acid, methyl ester

Sodium borohydride (0.474 g, 12.54 mmol) was added portionwise to a −20° C., stirred solution of (s)-(+)-α-hydroxy-1,3-dioxo-2-isoindolinebutyric acid methyl ester (3.0 g, 11.4 mmol) in THF/water (30/1.38 mL) for 6 hours. Upon cooling to room temperature, the reaction mixture was carefully quenched and acidified with 10% aqueous HCl. Aqueous mixture was extracted with ethyl acetate (300 mL). The ethyl acetate extract was washed with water and brine. Silica gel (15 mL) was added. Solvents were removed and the silica adsorbate was flash chromatographed (eluent 95: 5 petroleum ether: dichloromethane) to provide the title compound as an oil (0.96 g, 32%): MS (EI): [M+], 265.

EXAMPLE 106

(s)-(+)-α-Hydroxy-1-oxo-2-isoindolinebutyric acid, methyl ester

Trifluoroacetic anhydride (1.1 mL, 7.66 mmol) was added dropwise to a stirred suspension of (s)-(+)-α,3-dihydroxy-1-oxo-2-isoindolinebutyric acid, methyl ester (0.84 g, 3.19 mmol) in chloroform (10 mL) under a try N2 atmosphere for 2 hours. After the reaction mixture was concentrated to yield an oil, trifluoroacetic acid (3.4 mL) and triethylsilane (1.1 mL, 3.83 mmol) were added at ambient temperature under a dry nitrogen atmosphere. After 6 hours, the reaction mixture was carefully quenched with 10% aqueous sodium bicarbonate. Aqueous mixture was extracted with dichloromethane (150 mL). The dichloromethane extract was washed with water and brine. Silica gel (12 mL) was added. Solvents were removed and the silica adsorbate was flash chromatographed (eluent 15:85 petroleum ether:ethyl acetate) to provide an oil (0.50 g, 63%): mp 73.5–74.5° C.: MS (EI): [M+], 247.

EXAMPLE 107

(R)-2-[2,6-Dibromo-4-(6-bromo-benzo[b]naphtho[2,3-d]thiophen-11-yl)-phenoxy]-3-phenyl-propionic acid, methyl ester Diethylazodicarboxylate (0.437 mL, 2.74 mmol) was added dropwise to a stirred, room temperature suspension of 2,6-dibromo-4-(6-bromo-benzo [b]naphtho[2,3-d]thiophen-11-yl)-phenol (1.00 g, 1.83 mmol), (S)-2-hydroxy-3-phenylpropionic acid, methyl ester (0.494 g, 2.74 mmol), triphenylphosphine (0.72 g, 2.74 mmol) and benzene (12 mL) under a dry nitrogen atmosphere. Dissolution occurred and the solution was heated in an 80° C. oil bath for 3.5 h. Upon cooling to room temperature, the reaction mixture was diluted with dichloromethane and silica gel (30 mL) was added. The reaction mixture was concentrated and the silica adsorbate was flash chromatographed (96:4 petroleum ether-:ethyl acetate) to provide the title compound as a white solid (1.20 g, 90%): mp 138–139.5° C.: NMR (CDCl3); δ8.36 (ddd, J=8, 1, 1 Hz, 1 H), 7.83 (ddd., J=8, 1, 1 Hz, 1 H), 7.68 (ddd, J =8, 7, 1 Hz, 1 H), 7.60 (dd, J=5, 2 Hz, 2 H), 7.60-7.48 (m, 2 H), 7.46-7.28 (m, 6 H), 7.18 (ddd, J=8, 7, 1 Hz, 1 H), 6.74 (ddd, J=8, 1, 1 Hz, 1 H), 5.26 ( t, J=8 Hz, 1 H), 3.76 (s, 3 H), 3.59 (dd, J=8, 5 Hz, 2 H); MS (FAB+): [M+], 3 bromine isotope pattern, 722 (30%), 724 ( 70%) 726 (100%) 728 (35%); Anal. Calc. for C32H21Br3O3S: C, 52.99, H, 2.99, N, 0.00. Found: C, 52.60, H, 2.68, N, 0.07.

EXAMPLE 108

(R)-2-[2,6-Dibromo-4-(6-bromo-benzo[b]naphtho[2,3-d]thiophen-11-yl)-phenoxy]-3-phenyl-propionic acid Aqueous potassium hydroxide (1 N, 6.37 mL, 6.37 mmol) was added to a stirred solution of (R)-2-[2,6-dibromo-4-(6-bromo-benzo[b]naphtho[2,3-d]thiophen-11 -yl)-phenoxy]-3-phenyl-propionic acid, methyl ester (2.31 g, 3.19 mmol) in THF (22 mL)/methanol (15 mL). After 2 h the solution was concentrated, diluted with water (100 mL) and acidified with 10% aqueous HCl. The solid was filtered, washed with water and triturated with petroleum ether. It was then recrystalyzed from methanol to provide the title compound as a white solid (1.52 g, 67%): mp 140–142° C.: [a]D25=+25.66 (10.52 mg/mL CHCl3); NMR (DMSO-d6);δ13.26 (broad s, 1 H), 8.29 (d, J=8 Hz, 1 H), 8.07 (d, J=8 Hz, 1 H), 7.80 (m, 1 H), 7.79 (dd, J=7, 3 Hz, 2 H), 7.63 (ddd, J=8, 7, 1 Hz, 1 H), 7.55 (d, J=8 Hz, 1 H), 7.51 (ddd, J=8, 7, 1 Hz, 1 H), 7.41 (d, J=7 Hz, 2 H), 7.38-7.32 (m, 3 H), 7.31-7.22 (m, 3 H), 6.64 (d, J=8 Hz, 1 H), 5.32 (t, J =7 Hz, 1 H), 3.41 (d, J=7 Hz, 2 H); MS (EI): [M+], 3 bromine isotope pattern, 708 (35%), 710 (90%) 712 (100%) 714 (40%); Anal. Calc. for C31H19Br3O3S: C, 52.35, H, 2.69, N, 0.00. Found: C, 52.46, H, 2.59, N, 0.10. Chiral analytical HPLC determined that this compound had approx. 100% EE [column:Chirobiotic V, 5 micron (4.6 ×250 mm); isocratic, 1:1 ethanol:hexane; flow rate =0.80 mL/min; injection volume =0.3 μL; sample conc. =0.25 mg/mL; retention time, R-enantiomer =21 min; retention time, S-enantiomer =16 min.].

EXAMPLE 109

(R)-2-[2,6-Dibromo-4-(6-bromo-benzo[b]naphtho[2,3-d]thiophen- 11-yl)-phenoxy]-3-phenyl-propionic acid, sodium salt Sodium hydroxide (1 N, 0.417 mL, 0.417 mmol) was added to a stirred room temperature solution of (R)-2-[2,6-dibromo-4-(6-bromo-benzo [b]naphtho [2,3-d]thiophen-11-yl)-phenoxy]-3-phenyl-propionic acid (0.297 g, 0.418 mmol) in THF (1.3 mL)/methanol (1.3). After 30 min, the solvent was removed and the solvent was repeatedly chased with benzene via rotoevaporation and dried overnight at 70° C. to provide the title compound as a white solid (0.31 g, 100%): mp 261–265° C.: NMR (DMSO-d6); δ8.27 (d, J=8 Hz, 1 H), 8.03 (d, J=8 Hz, 1 H), 7.79 (ddd, J=8, 8, 1 Hz, 1 H), 7.63 (ddd, J=8, 7, 1 Hz, 1 H), 7.58-7.47 (m, 4 H), 7.41 (d, J=7 Hz, 2 H), 7.35-7.32 (m, 1 H), 7.22 (t, J=7 Hz, 1 H), 6.77 (d, J=8 Hz, 1 H), 5.42 (dd, J=8, 4 Hz, 1 H), 3.4 (m, 2 H); MS (ESI): [M–H]-, 3 bromine isotope pattern, 707, 709, 711, 713; Anal. Calc. for C31H18Br3O3SNa: C, 50.78, H, 2.47, N, 0.00. Found: C, 50.82, H, 2.79, N, 0.02.

EXAMPLE 110

(S)-2-[2,6-Dibromo-4-(6-bromo-benzo[b]naphtho[2,3-d]thiophen-11-yl)-phenoxy]-3-phenyl-propionic acid, methyl ester Diethylazodicarboxylate (0.839 mL, 5.50 mmol) was added dropwise to a stirred, room temperature suspension of 2,6-dibromo-4-(6-bromo-benzo [b]naphtho[2,3-d]thiophen-11-yl)-phenol (2.00 g, 3.55 mmol), (R)-2-hydroxy-3-phenylpropionic acid, methyl ester (0.96 g, 5.50 mmol), triphenylphosphine (1.40 g, 5.50 mmol) and benzene (15 mL) under a dry nitrogen atmosphere. Dissolution occurred and the solution was heated in an 80° C. oil bath for 19 h. Upon cooling to room temperature, the reaction mixture was diluted with ether and silica gel (60 mL) was added. The reaction mixture was concentrated and the silica adsorbate was flash chromatographed (95:5 petroleum ether:ethyl acetate) to provide the title compound as a white solid (2.48 g, 94 %): mp 140–143° C.: [a]D25=-56.87° (10.02 mg/mL CHCl3); NMR (CDCl3); δ8.36 (ddd, J=8, 1, 1 Hz, 1 H), 7.83 (ddd, J=8, 1, 1 Hz, 1 H), 7.68 (ddd, J=8, 7, 1 Hz, 1 H), 7.60 (dd, J=5, 2 Hz, 2 H), 7.60-7.49 (m, 2 H), 7.46-7.27 (m, 6 H), 7.18 (ddd, J=8, 7, 1 Hz, 1 H), 6.74 (ddd, J=8, 1, 1 Hz, 1 H), 5.26 ( dd, J =8, 6 Hz, 1 H), 3.76 (s, 3 H), 3.59 (dd, J=8, 5 Hz, 2 H); MS (FAB+): [M+], 3 bromine isotope pattern, 722 (31%), 724 (94%) 726 (100%) 728 (40%); Anal. Calc. for C32H21Br3O3S: C, 52.99, H, 2.99, N, 0.00. Found: C, 52.99, H, 2.85, N, 0.03.

EXAMPLE 111

(S)-2-[2,6-Dibromo-4-(6-bromo-benzo[b]naphtho[2,3-d]thiophen-11-yl)-phenoxy]-3-phenyl-propionic acid Aqueous potassium hydroxide (1 N, 2.40 mL, 2.40 mmol) was added to a stirred solution of (S)-2-[2,6-dibromo-4-(6-bromo-benzo[b]naphtho[2,3-d]thiophen-11 -yl)-phenoxy]-3-phenyl-propionic acid, methyl ester (0.88 g, 1.21 mmol) in THF (12 mL)/methanol (8 mL). After 2 h the solution was concentrated, diluted with water (50 mL) and acidified with 10% aqueous HCl. The reaction mixture was then partitioned between water and ether. The ether phase was concentrated and triturated with ether and pet. ether. It was then recrystalized from methanol to provide the title compound as a white solid (0.54 g, 63%): [a]D25 =-24.81° (10.08 mg/mL CHCl3); NMR (CDCl3); δ8.36 (d, J=8 Hz, 1 H), 7.81 (d, J=8 Hz, 1 H), 7.68 (ddd, J=8, 5, 3 Hz, 1 H), 7.58 (dd, J=10, 2 Hz, 2 H), 7.54-7.48 (m, 2 H), 7.44-7.27 (m, 6 H), 7.16 (ddd, J=8, 7, 1), 6.72 (d, J=8 Hz, 1 H), 5.45 (t, J=7 Hz, 1 H), 3.59 (d, J=7 Hz, 2 H); MS (EI): [M+], 3 bromine isotope pattern, 708 (24%), 710 ( 80%) 712 (100%) 714 (40%); Anal. Calc. for C31H19Br3O3S: C, 52.35, H, 2.69, N, 0.00. Found: C, 52.05, H, 2.59, N, 0.10. Chiral analytical HPLC determined that this compound had approx. 100% EE [column:Chirobiotic V, 5 micron (4.6 ×250 mm); isocratic, 1:1 ethanol:hexane; flow rate =0.80 mL/min; injection volume =0.3 pL; sample conc. =0.25 mg/mL; retention time, R-enantiomer =21 min; retention time, S-enantiomer =16 min.]

EXAMPLE 112

(R)-2-[2,6-Dibromo-4-(6-methoxy-benzo[b]naphtho [2,3-d]thiophen-11-yl)-phenoxy]-3 -phenyl-propionic acid, methyl ester Prepared from 2,6-dibromo-4-(6-methoxy-benzo[b]naphtho[2,3-d]thiophen-11-yl )-phenol (Example 63) and (S)-2-hydroxy-3-phenylpropionic acid, methyl ester (Example 96) according to the procedure of Example 107. White solid (0.608 g, 96%): NMR (THF-d8); δ8.29-8.26 (m, 1 H), 7.87 (d., J=8 Hz, 1 H), 7.72 - 7.68 (dd, 2 H, J=4, 2 Hz), 7.60 - 7.56 (m, 2 H), 7.48-7.37 (m, 4 H), 7.32 - 7.28 (m, 2 H), 7.25-7.23 (m, 2 H), 7.20 - 7.15 (m, 2 H), 6.85 - 6.82 (m, 1 H), 5.22(dd, 1 H, J=14, 2, Hz), 4.17 (s, 1 H), 3.71 (s, 1 H), 3.58(s, 6 H), ; MS (FAB+): [M+], 2 bromine isotope pattern, 674 (40%), 676 ( 66%), 678 (45%); Anal. Calc. for C33H24Br2O4S: C, 58.60, H, 3.58, N, 0.00. Found: C, 58.11, H, 3.53, N, 0.19.

EXAMPLE 113

(R)-2-[2,6-Dibromo-4-(6-bromo-benzo[b]naphtho [2.3-d]thiophen-11-yl)-phenoxy]-3-phenyl-butyric acid Diethylazodicarboxylate (DEAD, 0.210 mL, 1.33 mmol) was added to a stirred, room temperature solution of 2,6-dibromo-4-(6-bromo-benzo[b]naphtho[2,3-d ]thiophen-11-yl)-phenol (0.500 g, 0.888 mmol), (S)-2-hydroxy-4-phenyl-butyrate, ethyl ester (0.277 g, 1.33 mmol), triphenylphosphine (0.350 g, 1.33 mmol) and benzene (3.8 mL) under a dry nitrogen atmosphere. Dissolution occurred and the solution was heated in an 80° C. oil bath for 2 h. Upon cooling to room temperature, the reaction mixture was diluted with ether and silica gel was added. The reaction mixture was concentrated and the silica adsorbate was flash chromatographed (95:5 petroleum ether:ethyl acetate) to provide a white solid (0.570 g, 85%). Aqueous potassium hydroxide (1 N, 1.4 mL, 1.4 mmol) was added to a stirred solution of this solid (0.562 g, 0.746 mmol) in THF (12 mL)/methanol (5 mL). After 3h the solution was concentrated, diluted with water and acidified with 10% aqueous HCl. The solid was filtered, washed with water and triturated with petroleum ether to provide the title compound as a white solid (0.526 g, 97%): mp 115–120° C.: NMR (DMSO-d6); δ13.3 (broad s, 1 H), 8.29 (d, J=8 Hz, 1 H), 8.07 (d, J=8 Hz, 1 H), 7.83 (d, J=2 Hz, 1 H), 7.81 (d, J=2 Hz, 1 H), 7.80 (ddd, J=8, 7, 1 Hz, 1 H), 7.65-7.58 (m, 2 H), 7.51 (ddd, J =8, 8, 1 Hz, 1 H), 7.33-7.20 (m, 6 H), 6.67 (d, J=8 Hz, 1 H), 5.15 (dd, J=6 Hz, 1 H), 3.00 (m, 1 H), 2.79 (m, 1 H), 2.34 (m, 2 H); MS (FAB+): [M+], 3 bromine isotope pattern, 722, 724, 726, 728; Anal. Calc. for C32H21Br3O3S: C, 52.99, H, 2.92, N, 0.00. Found: C, 52.49, H, 2.69, N, 0.17.

The compounds in Examples 114–144 were prepared using the procedure in Example 113 and the appropriate starting materials.

EXAMPLE 114

(S)-2-[4-(6-bromo-benzo[b]naphtho[2,3-d]thiophen-11-yl)-phenoxy]-3-phenyl-propionic acid Prepared from 4-(6-bromo-benzo[b]naphtho[2,3-d] thiophen-11-yl)-phenol (Example 41) and (R)-2-hydroxy-3-phenylpropionic acid, methyl ester (Example 97). White solid: [a]D25=+17.94° (10.30 mg/mL CHCl3): NMR (CDCl3); δ8.31 (ddd, J=8, 1, 1 Hz, 1 H), 7.76 (ddd., J=8, 1, 1 Hz, 1 H), 7.60 (ddd, J=8, 8, 1 Hz, 1 H), 7.54 (d, J=8 Hz, 1 H), 7.44-7.29 (m, 6 H), 7.24-7.20 (m, 4 H), 7.19-7.04 (m, 3 H), 6.62 (d, J=8 Hz, 1 H), 5.08 ( dd, J=7, 5 Hz, 1 H), 3.44 (d, J=5 Hz, 1 H), 3.43 (d, J=7 Hz, 1 H); MS (FAB+): [M+H], bromine isotope pattern, 553 (11%), 569 ( 12%); Anal. Calc. for C31H21BrO3S: C, 67.27, H, 3.82, N, 0.00. Found: C, 65.17, H, 3.64, N, 0.04. Analytical HPLC determined that this compound was 98.9% pure [column:novapak, 5 micron (4.6 ×250 mm); isocratic, 7:3 accetonitrile: 0.01 M potassium dihydrogen phosphate, pH =3.5; flow rate =1.0 mL/min].

EXAMPLE 115

(S)-2-[2,6-Dibromo-4-(6-cyano-benzo[b]naphtho[2, 3-d]thiophen-11-yl)-phenoxy]-3-phenyl-propionic acid Prepared from 11-(3, 5-dibromo-4-hydroxy-phenyl)-benzo[b]naphtho[2,3-d ]thiophene-6-carbonitrile (Example 58) and (R)-2-hydroxy-3-phenylpropionic acid, methyl ester (Example 97). White solid: mp 176–178° C.: NMR (CDCl3); δ8.36 (ddd, J =8,1,1 Hz, 1 H), 7.85 (d, J=8 Hz, 1 H), 7.77 (ddd, J=8, 8, 2 Hz, 1 H), 7.58 (d, J=2 Hz, 1 H), 7.61-7.54 (m, 2 H), 7.56 (d, J=2 Hz, 1 H), 7.47 (ddd, J=8, 8, 1 Hz, 1 H), 7.41 (ddd, J=8, 1, 1, 2 H ), 7.36-7.26 (m, 3 H), 7.20 (ddd, J=8, 8, 1, 1 H), 6.75 (ddd, J =8, 1, 1 Hz, 1 H), 5.46 (t, J=7 Hz, 1 H), 3.59 (d, J=7 Hz, 2 H); MS (-FAB): [M–H]-, 2 bromine isotope pattern, 654 (2%), 656 ( 4%) 658 (2%); Anal. Calc. for C32H19Br2NO3S: C, 58.47, H, 2.91, N, 2.13 Found: C, 58.23, H, 2.69, N, 2.03.

EXAMPLE 116

(R)-2-[4-(6-Cyano-benzo[b]naphtho[2,3-d]thiophen-11-yl)-phenoxy]-3-phenyl-propionic acid Prepared from 11-(4-hydroxy-phenyl)-benzo [b]naphtho [2,3-d]thiophene-6-carbonitrile (Example 44) and (S)-2-hydroxy-3-phenylpropionic acid, methyl ester (Example 96). White solid: mp 145–148° C.: [a]D25=–2.03° (7.883 mg/mL CHCl3); NMR (CDCl3); δ8.31 (ddd, J=8, 1, 1 Hz, 1 H), 7.78 (ddd., J=8, 1, 1 Hz, 1 H), 7.70 (ddd, J=8, 8, 1 Hz, 1 H), 7.56 (ddd, J=8, 1, 1 Hz, 1 H), 7.47-7.37 (m, 6 H), 7.32 (ddd, J=8, 7, 1 Hz, 1 H), 7.20 (dd., J=8, 2 Hz, 1 H),7.14-7.05 (m, 4 H), 6.62 (ddd, J=8, 1, 1 Hz, 1 H), 5.06 (dd, J=7, 5 Hz, 1 H), 3.44 (d, J=5 Hz, 1 H), 3.42 (d, J=7 Hz, 1 H); MS (EI): [M+], 499 (100%); Anal. Calc. for C32H21NO3S: C, 76.93, H, 4.24, N, 2.80. Found: C, 75.77, H, 4.22, N, 2.70.

EXAMPLE 117

(R)-2-[4-(Benzo[b]naphtho[2,3-d]thiophen-11-yl)-phenoxy]-3-phenyl-propionic acid Prepared from 4-benzo[b]naphtho[2,3-d]thiophen-11-yl-phenol (Example 14) and (S)-2-hydroxy-3-phenylpropionic acid, methyl ester (Example 96). White solid: [a]25/D =–19.09° (8.538 mg/mL, CHCl3); NMR (CDCl3); δ8.30 (s, 1 H), 7.91 (d, J=8 Hz, 1 H), 7.73 (d, J=8 Hz, 1 H), 7.55-7.24 (m, 10 H), 7.14-7.09 (m, 2 H), 7.05 (ddd, J =8, 7, 1 Hz, 1 H), 6.70 (d, J=8 Hz, 1 H), 5.09 (dd, J=8,5 Hz, 1 H,), 3.42 (m, 2 H); MS (EI): [M+] 474 (100%); Anal Calc. for C31H22O3S: C, 78.46, H, 4.67, N, 0.00. Found: C, 77.09, H, 4.60, N, 0.03 Analytical HPLC purity (98.5%).

EXAMPLE 118

(S)-2-[2,6-Dibromo-4-(6-bromo-benzo[b]naphtho[2, 3-d]thiophen-11-yl)-phenoxy]-3-phenyl-butyric acid Prepared from of 2,6-dibromo-4-(6-bromo-benzo[b] naphtho[2,3-d]thiophen-11 -yl)-phenol (Example 21) and commercially available (R)-2-hydroxy-4-phenyl-butyrate, ethyl ester. White solid: mp 180–181° C.: [a]D25=+5.83° (10.3 mg/mL CHCl3); NMR (CDCl3); δ8.36 (d, J=8 Hz, 1 H), 7.83 (d, J=8 Hz, 1 H), 7.67 (ddd, J =8, 7, 1 Hz, 1 H), 7.64 (dd, J=5, 2 Hz, 2 H), 7.63-7.49 (m, 2 H), 7.42 (ddd, J=8, 7, 1 Hz, 1 H), 7.34-7.22 (m, 5 H), 7.12 (ddd, J=8, 7, 1 Hz, 1 H), 6.76 ( d, J=8 Hz, 1 H), 5.30 (t, 1 H), 3.21-2.87(m, 2 H), 2.59-2.49 (m, 2 H); MS (FAB–): [M–H]-, 3 bromine isotope pattern, 721, 723, 725, 727; Anal. Calc. for C32H21Br3O3S: C, 53.00, H, 2.92, N, 0.00. Found: C, 52.63, H, 2.68, N, 0.09.

EXAMPLE 119

(R)-2-[4-(3-Carboxymethoxy-benzo[b]naphtho[2,3-d]thiophen-11-yl)-phenoxy-3-phenyl-propionic acid Prepared from of [11 -(4-hydroxy-phenyl)-benzo[b] naphtho[2,3-d]thiophen-3-yloxy ]-acetic acid methyl ester (Example 72) and (S)-2-hydroxy-3-phenylpropionic acid, methyl ester (Example 96). White solid: mp: 191–201° C.: NMR (DMSO-d6); δ13.1 (broad s, 2 H), 8.45 (s, 1 H), 8.01 (d, J=8 Hz, 1 H), 7.55-7.25 (m, 11H), 7.16 (d, J =9 Hz, 2 H), 6.67 (dd, J=9, 2Hz, 1 H), 6.49 (d, J=9 Hz, 1 H), 5.18 (dd, J=7,4Hz, 1 H), 4.74 (s, 2 H), 3.28 (dd, J=7, 4 Hz, 1 H), 3.21 (dd, J=14, 7 Hz, 1 H); MS (EI): 458 (80%, M+); Anal. Calc. for C33H24O6S: C, 72.25, H, 4.41, N, 0.00. Found: C, 69.57, H, 4.15, N, 0.32; Analytical HPLC :92% purity.

EXAMPLE 120

(R)-2-[2,6-Dibromo-4-(6-bromo-benzo[b]naphtho[2,3-d]thiophen-11-yl)-phenoxy]-3-(1 H-imidazol-4-yl)-propionic acid, hydrochloride Prepared from of 2,6-dibromo-4-(6-bromo-benzo[b]naphtho[2,3-d]thiophen-11 -yl)-phenol (Example 21) and N-t-BOC-L-β-imidazolelactic acid, methyl ester (Example 101). White solid: mp >265° C. (dec): NMR (CDCl3); δ9.00 (s, 1 H), 8.29 (d, J=8 Hz, 1 H), 8.08 (d, J=8 Hz, 1 H), 7.84-7.78 (m, 3 H), 7.65-7.51 (m, 4 H), 7.28 (dd, J =8, 1 Hz, 1 H), 6.68 (d, J=8 Hz, 1 H), 5.40 (t, J=7 Hz, 1 H), 3.49-3.47 (m, 2 H); MS (+FAB): [M+H]+, 3 bromine isotope pattern, 699, 701, 703, 705; Anal. Calc. for C28H17Br3N2O3S: C, 45.59, H, 2.46, N, 3.80. Found: C, 45.69, H, 2.38, N, 3.76.

EXAMPLE 121

(R)-2-[2,6-Dibromo-4-(6-bromo-benzo[b]naphtho[2,3-d]thiophen- 11-yl)-phenoxy]-propionic acid Prepared from of 2,6-dibromo-4-(6-bromo-benzo[b]naphtho[2,3-d]thiophen-11-yl)-phenol (Example 21) and commercially available (S)-lactic acid, methyl ester. White solid: mp 131–133 ° C.: NMR (CDCl3);δ8.37 (d, J=9 Hz, 1 H), 7.84 (d, J=8 Hz, 1 H), 7.71-7.65 (m, 3 H), 7.57-7.50(m, 2 H), 7.45 (ddd, J=8, 7, 1 Hz, 1 H), 7.18 (ddd, J=8,7, 1 Hz, 1 H), 6.73 (d, J=8 Hz, 1 H), 5.36 (q, J=7 Hz, 1 H), 1.82 (d, J=7 Hz, 3 H); MS (EI): [M–H]+, 3 bromine isotope pattern, 631 (14%), 633 (44 %), 635 (42%), 637 (16%); Anal. Calc. for C25H15Br3O3S: C, 47.27, H, 2.38, N, 0.00. Found: C, 47.57, H, 2.33, N, 0.03.

EXAMPLE 122

(R,S)-2-[2.6-Dibromo-4-(6-bromo-benzo[b]naphtho[2,3-d]thiophen-11-yl)-phenoxy]-3 -(1 H-indol-3-yl)-propionic acid Prepared from of 2,6-dibromo-4-(6-bromo-benzo[b]naphtho[2,3-d]thiophen-11 -yl)-phenol (Example 21) and D,L-indole-3-lactic acid methyl ester (Example 98). White solid: mp 146–147 ° C.: NMR (CDCl3): δ8.36 (d, J=9 Hz, 1 H), 8.04-8.03 (m, 1 H, NH), 7.81 (d, J=8 Hz, 1 H), 7.72-7.65 (m, 2 H), 7.60 (s, 2 H), 7.59-7.59 (m, 2 H), 7.42-7.37 (m, 2 Hz), 7.28 (d, 2 Hz, 1 H), 7.22 (ddd, J=8, 7, 1 Hz, 1 H), 7.16 (dd, J=8,1 Hz, 1 H), 7.12 (dd, J=8, 1 Hz, 1 H), 6.73 (d, J=8 Hz, 1 H), 5.45 (t, J=6 Hz, 1 H), 3.75 (d, J=7 Hz, 2 H); MS (FAB+): [M+], 3 bromine isotope pattern, 747, 749, 751, 753; Anal. Calc. for C33H2OBr3NO3S: C, 52.83, H, 2.69, N, 1.87. Found: C, 53.08, H, 2.73, N, 1.19.

EXAMPLE 123

2-[2,6-Dibromo-4-(6-bromo-benzo[b]naphtho[2,3-d]thiophen-11-yl)-phenoxy]-hexanoic acid Prepared from of 2,6-dibromo-4-(6-bromo-benzo[b]naphtho [2,3-d]thiophen-11-yl)-phenol (Example 21) and commercially available (R,S)-2-hydroxypentanoic, methyl ester. White solid: mp 212–213° C.: NMR (CDCl3); δ8.36 (d, J=8 Hz, 1 H), 7.83 (d, J=8 Hz, 1 H), 7.67 (ddd, J=8, 5, 1 Hz, 1 H), 7.63 (dd, J=2, 1 Hz, 2 H), 7.58-7.42 (m, 3 H), 7.16 (t, J=8, 1H), 6.75 (d, J=8 Hz, 1 H), 5.23 (t, J=5 Hz, 1 H), 2.26 -2.16 (m, 2 H), 1.8 - 1.73 (m, 1 H), 1.60 - 1.41 (m, 3 H), 0.99 (t, 3 H,); MS (EI): [M+], 3 bromine isotope pattern, 674 (35%), 676 ( 90%) 678 (100%) 680 (35%); Anal. Calc. for C28H21Br3O3S: C, 49.66, H, 3.12, N, 0.00. Found: C, 49.28, H, 2.90, N, 0.09.

EXAMPLE 124

(2R)-2-[2,6-Dibromo-4-(6-bromo-benzo[b]naphtho[2,3-d]thiophen-11-yl)-phenoxy]-4-(1-oxo-1,3-dihydro-isoindol-2-yl)-butyric acid Prepared from of 2,6-dibromo-4-(6-bromo-benzo[b]naphtho[2,3-d]thiophen-1 1-yl)-phenol (Example 21) and (S)-(+)-α-hydroxy-1-oxo-2-isoindolinebutyric acid methyl ester (Example 106). White solid: mp 239–241° C.: NMR (CDCl3); δ8.34 (d, J =8 Hz, 1 H), 7.90 (d, J=8 Hz, 1 H), 7.80 (d, J=8 Hz, 1 H), 7.66 (ddd, J=8, 7, 1 Hz, 1 H), 7.62-7.58 (m, 4 H), 7.52-7.47 (m, 3 H), 7.39 (ddd, J=8, 7, 1 Hz, 1 H), 7.14 (ddd, J =8, 7, 1 Hz, 1 H), 6.72 (d, J=8, Hz, 1 H), 5.39 (t, J=7 Hz, 1 H), 4.59 (m, 2 H), 4.22-3.93 (m, 2 H), 2.65 (t, J=6 Hz, 2 H); MS (+FAB): [M+H]+, 3 bromine isotope pattern, 778, 780, 782, 784); Anal. Calc. for C34H22Br3NO4S: C, 52.33, H, 2.84, N, 1.79. Found: C, 52.11, H, 2.73, N, 1.79.

EXAMPLE 125

(R)-2-[2,6-Dibromo-4-(6-trifluoromethyl-benzo[b]naphtho[2,3-d]thiophen-11-yl)-phenoxy ]-3-phenyl-propionic acid Prepared from of 2,6-dibromo-4-(6-trifluoromethyl-benzo[b]naphtho[2,3-d ]thiophen-11-yl)-phenol (Example 61) and (S)-2-hydroxy-3-phenylpropionic acid, methyl ester (Example 96). White solid: mp 109–143° C.; [a]D25=+ 47.99° (10.002 mg/mL CH3OH); NMR (DMSO-d6); δ13.26 (s, 1 H), 8.30 - 8.27 (m, 1 H), 8.06 (d, J =7 Hz, 1 H), 7.87 - 7.81 (m, 3 H), 7.71 - 7.60 (m, 2 H), 7.52 (dd, J=8, 1 Hz, 1 H), 7.43 -7.24 (m, 6 H), 6.60 (d, J=8 Hz, 1 H), 5.33 (t, J=7 Hz, 1 H), 3.41 (d, J=7 Hz, 2 H); MS (EI): [M+], 2 bromine isotope pattern, 698 (8%), 700 ( 20%) 702 (15%); Anal. Calc. for C32H19Br2F3O3S: C, 54.88, H, 2.74, N, 0.00. Found: C, 55.29, H, 3.11, N, 0.10.

EXAMPLE 126

(R)-2-[2,6-Dibromo-4-(6-methoxy-benzo[b]naphtho[2,3-d]thiophen-11-yl)-phenoxy]-3 -phenyl-propionic acid Prepared from of 2,6-dibromo-4-(6-methoxybenzo[b]naphtho[2,3-d]thiophen-11 -yl-phenol (Example 63) and (S)-2-hydroxy-3-phenylpropionic acid, methyl ester (Example 96). White solid: mp 102–110° C.: NMR (DMSO-d6); δ13.2 (broad peak, 1 H), 8.23 (d, J=8 Hz, 1 H), 8.02 (d, J=8 Hz, 1 H), 7.74 (dd, J=6, 2 Hz, 2 H), 7.56 (ddd, J=8, 7, 1, 1H), 7.56 (ddd, J=8, 7, 1 1H), 7.51-7.45 (m, 2 H), 7.42-7.40 (m, 2 H), 7.36 - 7.32 (m, 4 H), 7.30 - 7.20 (m, 2 H), 6.68 (d, J=8Hz, 1 H), 5.30(t, J=7 Hz, 1 H), 4.13(s, 3 H), 3.41 (d, J=7 Hz, 2 H); MS (EI): [M+], M/z 660 (46%), 662 (100%), 664 (54%); Hi Res MS, Calc. Sample Mass for C32H22Br2O4S: 659.960553, Measured Mass: 659.953875, Mass deviation 6.7 nam; Anal. Calc. for C32H22Br2O4S.0.23C6 H6: C, 58.08, H, 3.37 N, 0.00. Found: C, 59.34, H, 3.24, N, 0.04.

EXAMPLE 127

(R)-2-{ 2,6-Dibromo-4-(6-chloro-benzo[b]naphtho[2,3-d]thiophen-11-yl)-phenoxy}-3-phenyl-propionic acid Prepared from of 2,6-dibromo-4-(6-chloro-benzo[b]naphtho[2,3-d]thiophen-11 -yl)-phenol (Example 60) and (S)-2-hydroxy-3-phenylpropionic acid, methyl ester (Example 96). White solid: [a]25/D=+19.63° (8.805 mg/mL, CHCl3); NMR (DMSO-d 6); δ13.25-13.22 (broad singlet, 1 H), 8.32 (d, J=8 Hz, 1 H,), 8.70 (d, J=8 Hz, 1 H), 7.81-7.79 (ddd, J=8,7, 1 Hz, 1 H), 7.79 (dd, J 10, 2 Hz, 2 H), 7.64 (ddd, J=8,7, 1 Hz, 1 H), 7.58-7.49 (m, 2 H), 7.42-7.32 (m, 4 H, ), 7.29-7.24 (m, 2 H), 6.66 (d, J=8 Hz, 1 H), 5.32 (t, J=6 Hz, 1 H,), 3.41 (d, J=7 Hz, 2 H); MS (-ESI): [(M-H)+], 2 bromine, 1 chlorine isotope pattern, 663 (40%),665 (100%), 667 (60%), 669 (17%); Anal Calc. for C31H19Br2ClO3S: C, 55.84, H, 2.87, N, 0.00. Found: C, 56.95; H, 3.00, N, 0.24.

EXAMPLE 128

(R)-2-[2,6-Dibromo-4-(6-phenylsulfanyl-benzo[b]naphtho[2,3-d]thiophen-11 -yl)-phenoxy]-3-phenyl-propionic acid Prepared from of 2,6-dibromo-4-(6-phenylsulfanyl-benzo[b]naphtho[2,3-d ]thiophen-11-yl)-phenol (Example 64) and (S)-2-hydroxy-3-phenylpropionic acid, methyl ester (Example 96). White solid: NMR (DMSO-d6); δ8.50 (d, J=8 Hz, 1 H), 7.98 (d, J=8 Hz, 1 H), 7.83 (d, J=2 Hz, 1 H), 7.81 (d, J=2 Hz, 1 H),7.71 (ddd, J=6, 5, 2 Hz, 2 H), 7.58 (m, 2 H), 7.47 (ddd, J=8, 8, 1 Hz, 1 H), 7.42 (d, J=8 Hz, 2 H), 7.34 (t, J=7 Hz, 2 H), 7.29-7.20 (m, 4 H), 7.17-7.08 (m, 3 H), 6.67 (d, J=8 Hz, 1 H), 5.35 (t, J=7 Hz, 1 H, CH), 3.41 (d, J=7 Hz, 2 H); MS (+FAB): [M+], 2 bromine isotope pattern, 738 (35%), 740 ( 90%) 742 (60%); Anal. Calc. for C37H24Br2O3S2: C, 60.01, H, 3.27, N, 0.00. Found: C, 58.57, H, 3.04, N, 0.22.

EXAMPLE 129

(R)-2-[2,6-Dibromo-4-(6-phenylsulfanyl-benzo[b]naphthor[2,3-d]thiophen-11 -yl)-phenoxy]-propionic acid Prepared from of 2,6-dibromo-4-(6-phenylsulfanyl-benzo[b]naphtho[2,3-d]thiophen-11-yl)-phenol (Example 64) and commercially available (S)-lactic acid, methyl ester. White solid: mp 232–234° C.: NMR (DMSO-d6); δ8.51 (d, J=8 Hz, 1 H), 8.00 (d, J=8 Hz, 1 H), 7.89 (d, J=2 Hz, 1 H), 7.89 (d, J=2 Hz, 1 H), 7.71 (ddd, J =8, 7, 1 Hz, 1 H), 7.65 (d, J=8 Hz, 1 H), 7.60 (ddd, J=8, 7, 1 Hz, 1 H), 7.49 (ddd, J=8, 7, 1 Hz, 1 H), 7.28-7. (m, 4 H), 7.17-7.09 (m, 4 H), 6.68 (d, J=8 Hz, 1 H), 5.13 (dd, J =7, 14 Hz, 1 H), 1.64 (d, J=7 Hz, 2 H); MS (+FAB): [M+], 2 bromine isotope pattern, 662 (35%), 664 ( 100%) 666 (60%); Anal. Calc. for C31H20Br2O3S2: C, 56.04, H, 3.03, N, 0.00. Found: C, 55.53, H, 2.86, N, 0.24.

EXAMPLE 130

(R)-2-[2,6-Dichloro-4-(6-bromo-benzo[b]naphtho[2,3-d]thiophen-11-yl)-phenoxy]l-3-phenyl-propionic acid Prepared from of 2,6-dichloro-4-(6-bromo-benzo[b]naphtho[2,3-d]thiophen-11 -yl)-phenol (Example 67) and (S)-2-hydroxy-3-phenylpropionic acid, methyl ester (Example 96). White solid: NMR (DMSO-d6); δ13.25 (broad s, 1 H), 8.29 (d, J=8 Hz, 1 H), 8.07 (d, J=8 Hz, 1 H), 7.80 (ddd, J=8, 8, 1, 1H), 7.65-7.61 (m, 1 H) 7.63 (d, J=2 Hz, 1 H), 7.61 (d, J=2 Hz, 1 H), 7.55 (dd, J=8, 1, 1 H), 7.51 (dd, J=8, 1, 1H), 7.41 (dd, J=8, 1, 2H), 7.34 (ddd, J=8, 8, 1, 2H), 7.27 (ddd, J=8, 8, 1, 2H), 6.66 (d, J=8 Hz, 1 H), 5.28 (t, J=7 Hz, 1 H), 3.44-3.30 (m, 2 H); MS (+FAB): [M+], 1 bromine, 2 chlorine isotope pattern, 620, 622, 624; Anal. Calc. for C31H19BrCl2O3S: C, 59.83, H, 3.08, N, 0.00. Found: C, 59.31, H, 2.93, N, 0.40.

EXAMPLE 131

(R)-Benzo[b]naphtho[2,3-d]thiophen-11-yl-2,6-diiodo-phenoxy)-3-phenyl-propionic acid Prepared from of 4-(benzo[b]naphtho[2,3-d]thiophen-11-yl)-2,6-diiodo-phenol (Example 26) and (S)-2-hydroxy-3-phenylpropionic acid, methyl ester (Example 96). White solid: mp 115–117° C.: NMR (CDCl3); δ8.36 (s, 1 H), 7.95 (dd J=8, 1 Hz, 1 H), 7.87 (d, J=2 Hz, 1 H), 7.85 (d, J=2 Hz, 1 H), 7.78 (dd, J=8, 1 Hz, 1 H), 7.58-7.27 (m, 9 H), 7.12 (ddd, J=8, 7, 1 Hz, 1 H), 6.77 (d, J=8, 1 Hz, 1 H), 5.56 (t, J=7 Hz, 1 H), 3.67-3.55 (m, 2 H); MS (EI): [M+], 726; Anal. Calc. for C31H20I2O3S: C, 51.26, H, 2.77, N, 0.00. Found: C, 51.49, H, 2.87, N, 0.13.

EXAMPLE 132

(R)-2-(4-Benzo[b]naphtho[2,3-d]thiophen-11-yl-2,6-diiodo-phenoxy)-propionic acid Prepared from of 4-(benzo[b]naphtho[2,3-d]thiophen-11-yl)-2,6-diiodo-phenol (Example 26) and commercially available (S)-lactic acid, methyl ester. White solid: mp 134–136: NMR (CDCl3): δ8.38 (s, 1 H), 7.95 (dd J=8, 6 Hz, 1 H), 7.93 (d, J=1 Hz, 2 H), 7.81 (d, J=8 Hz, 1 H), 7.58 (ddd, J=8, 7, 1 Hz, 1 H), 7.59-7.54 (m, 2 H), 7.49-7.40 (m, 2 H), 7.15(ddd, J=8, 7, 1 Hz, 1 H), 6.77 (d, J=8, 1 Hz, 1 H), 5.48 (q, J =7 Hz, 1 H), 1.82 (d, J=7 Hz, 2 H); MS (+FAB): [M+H]+, 651; Anal. Calc. for C26H16I2O3S: C, 46.18, H, 2.48, N, 0.00. Found: C, 46.60, H, 2.50, N, 0.21.

EXAMPLE 133

(R)-2-{2,6-Dibromo-4-[6-(2-dimethylamino-ethylsulfanyl)-benzo[b]naphtho[2,3-d]thiophen-11 -yl]-phenoxy}-3-phenyl-propionic acid Prepared from of 2,6-dibromo-4-[6-(2-dimethylaminoethylsulfanyl)-benzo [b]naphtho[2,3-d]thiophen-11-yl]-phenol (Example 66) and (S)-2-hydroxy-3-phenylpropionic acid, methyl ester (Example 96). White solid: mp 169–174° C.; NMR (DMSO-d6); δ13.3 (broad s, 1 H), 8.64 (d, J=8 Hz, 1 H), 8.04 (d, J=8 Hz, 1 H), 7.81 (ddd, J=8,7,1 Hz, 1 H), 7.76 (dd, J=16,1 Hz), 7.72-7.48 (m, 4 H), 7.42-7.22 (m, 7 H), 6.64 (d, J=8 Hz, 1 H), 5.32 (t, J=7 Hz, 1 H), 3.36-3.14 (m, 6 H); 2.64 (s, 6 H); MS (+FAB): [(M+H)+], 2 bromine isotope pattern, 734-(55%), 736 (100%), 738 (70%). Anal. calc. for C35H29Br2NO3S2; C, 54.45, H, 3.92, N, 1.81. Found: C, 54.46, H, 3.76, N, 1.66.

EXAMPLE 134

(R)-2-{2,6-Dibromo-4-[6-(pyridin-4-ylsulfanyl)-benzo[b]naphtho[2,3-d]thiophen-11-yl]-phenoxy }-3-phenyl-propionic acid Prepared from of 2,6-dibromo-4-[6-(pyridin-4-ylsulfanyl)-benzo [b]naphtho[2,3-d]thiophen-11-yl]-phenol (Example 65) and (S)-2-hydroxy-3-phenylpropionic acid, methyl ester (Example 96). White solid: NMR (DMSO- d6);

δ13.3 (broad singlet, 1 H), 8:45 (m, 2 H), 8.37 (d, J=8 Hz, 1 H), 7.99 (d, J=8 Hz, 1 H), 7.85 (dd, J=7, 2 Hz, 2 H), 7.77-7.74 (m, 1 H), 7.66-7.65 (m, 2 H), 7.50 (t, J 7 Hz, 1 H), 7.43-7.25 (m, 8H), 6.68 (d, J=8 Hz, 1 H), 5.35 (dd, J 8 ,2 Hz, 1 H), 3.43 (d, J=7 Hz, 2 H); MS [+FAB]: [(M+H)+], 739.9 (70%), 741.9 (100%), 743.9 (90%); MS High resolution (FAB)+ve, calc mass for C36H24Br2NO3S2 739.95644; measured mass 739.96224, mass deviation 5.80 mmu. Anal. Calc. for C36H23Br2NO3S2: C, 55.58, H, 3.11, N, 1.80. Found: C, 55.38, H, 3.37, N, 1.92.

EXAMPLE 135

(R)-2-[2,6-Dibromo-4-(6-iodo-benzo[b]naphtho[2,3-d]thiophen-11-yl]-phenoxy]-propionic acid Prepared from of 2,6-dibromo-4-(6-iodo-benzo[b]naphtho[2,3-d]thiophen-11-yl )-phenol (Example 59) and commercially available (S)-lactic acid, methyl ester. White solid: mp 129–196° C. dec; Opt. rot. [a]25/D=+4.312° (8.812 mg/mL, CHCl3); NMR (DMSO-d6); δ13.12 (broad s, 1 H), 8.12 (d, J=8, 1 Hz, 1 H), 8.06 (d, J =7 Hz, 1 H), 7.82 (q, J=Hz, 2 H), 7.75 (ddd, J=8,7, 1 Hz, 1 H), 7.62-7.49 (m, 3 H), 7.27 (ddd, J=8, 7, 1 Hz, 1 H), 6.61 (d, J=8 Hz, 1 H), 5.12 (q, J=7 Hz, 1 H), 1.63 (d, J =7 Hz, 3 H); MS (+FAB): [M+], 2 bromine isotope pattern, 680 (45%), 682 (100%), 684 (60%); Anal. Calc. for C25H15Br2IO3S: C, 44.02, H, 2.22, N, 0.00; Found: C, 44.66, H, 2.54, N, 0.21.

EXAMPLE 136

(R)-2-[2,6-Dibromo-4-(6-iodo-benzo[b]naphtho[2,3-d]thiophen-11-yl]-phenoxyl-3-phenyl-propionic acid Prepared from of 2,6-dibromo-4-(6-iodo-benzo[b]naphtho[2,3-d]thiophen-11 -yl)-phenol (Example 59) and (S)-2-hydroxy-3-phenylpropionic acid, methyl ester (Example 96). White solid: [a]25/D=+31.791° (9.940 mg/mL CHCl3); NMR (CDCl3); δ8.23 (ddd, J=8, 1, 1 Hz), 7.81 (ddd, J=8, 1, 1 Hz, 1 H), 7.64 (ddd, J=8,7, 1 Hz, 1 H), 7.58 (dd, J=9, 2Hz, 2 H), 7.52-7.39 (m, 7 H), 7.37-7.28 (m, 2 H), 6.68 (ddd, J=8,1, 1 Hz, 1 H), 5.48 (t, J=7 Hz, 1 H, -CH), 3.5 (d, J=7 Hz, 2 H); MS (+FAB): [M+], 2 bromine isotope pattern, 756 (65%), 758 (100%), 760 (90%); Anal. calc. for C31H19Br2IO3S: C, 49.10, H, 2.53, N, 0.00. Found: C, 50.75, H, 3.00, N, 0.09.

EXAMPLE 137

2-[2,6-Dibromo-4-(6-bromo-benzo[b]naphtho[2,3-d]thiophen-11-yl)-phenoxy]-3-pyridin-3 -yl-propionic acid Prepared from 2,6-dibromo-4-(6-bromo-benzo[b]naphtho[2,3-d]thiophen- 1 -yl)-phenol (Example 21) and 3-pyridin-3-yl-propionic acid, ethyl ester (Example 104). White solid: NMR (DMSO-d6); δ8.98 (s, 1 H), 8.82 (d., J=5 Hz, 1 H), 8.57 (d, J=8 Hz, 1 H), 8.28 (d, J=8 Hz, 1 H), 8.07 (d, J=8 Hz, 1 H), 7.96 (dd, J=8, 6 Hz, 1 H), 7.82 (d, J=2 Hz, 1 H), 7.79 (m, 1 H), 7.78 (d, J=2 Hz, 1 H),7.62 (dd, J=8, 1 Hz, 1 H), 7.57-7.50 ( m, 2 H), 7.27 (dd, J=8, 1 Hz, 1 H), 6.67 (d, J=8 Hz, 1 H), 5.45 (dd, J=6, 2, 1 H), 3.60 (m, 2 H); MS (+FAB): [M+H]+, 3 bromine isotope pattern, 710, 712, 714, 716; Anal. Calc. for C30H18Br3NO3S.HCl: C, 48.13, H, 2.56, N, 1.87. Found: C, 48.12, H, 2.86, N, 1.65.

EXAMPLE 138

(R)-2-[2,6-Dimethyl-4-(6-methyl-benzo[b]naphtho[2,3-d]thiophen-11-yl)-phenoxy]-3-phenyl-propionic acid Prepared from of 2,6-dimethyl-4-(6-methyl-benzo[b]naphtho [2,3-d]thiophen-11-yl)-phenol (Example 25) and (S)-2-hydroxy-3-phenylpropionic acid, methyl ester (Example 96). White solid: NMR (DMSO-d6); δ13.0 (broad band, 1 H), 8.18 (d, J=8 Hz, 1 H), 7.91(d, J=8 Hz, 1 H), 7.61 - 7.53 (m, 2 H), 7.43 (ddd, J=8, 7, 1 Hz, 1 H), 7.45 - 7.28(m, 5 H), 7.25 - 7.21 m, 1 H), 7.01 (ddd, J=8, 7, 1 Hz, 1 H), 6.95 (d, J=5 Hz, 2 H), 6.53 (d, J=8Hz, 1 H), 4.75 (t, J=7 Hz, 1 H), 3.32 - 3.24 (m, 2 H), 2.87 (s, 3 H), 2.56 (s, 3 H), 2.18 (s, 3 H): MS(EI): [M+] 516; Anal. Calc. for C34H28O3S: C, 79.04, H, 5.46, N, 0.00. Found: C, 79.13, H, 5.41, N, 0.11.

EXAMPLE 139

(2R)-2-[4-(6-Bromo-benzo[b]naphtho[2,3-d]thiophen-11-yl)-2,6-diisopropyl-phenoxy)-3-phenyl-propionic acid Prepared from of 4-(6-bromo-benzo[b]naphtho[2,3-d]thiophen-11-yl)-2,6-diisopropyl-phenol (Example 40) and (S)-2-hydroxy-3-phenylpropionic acid, methyl ester (Example 96). White solid: NMR (DMSO-d6); δ13.08 (broad s, 1 H), 8.27 (d, J=8 Hz, 1 H), 8.00 (d, J=8 Hz, 1 H), 7.76 (ddd, J=8, 8, 1, 1H), 7.66-7.58 (m, 2 H), 7.43 (ddd, J=8, 8, 1 Hz, 1 H), 7.40-7.34 (m, 4 H), 7.31-7.25 (m, 1 H), 7.12 (s, 2 H), 7.08 (ddd, J=8, 8, 1, 1H), 6.36 (d, J=8 Hz, 1 H), 4.55 (t, J=7 Hz, 1 H), 3.45 (septuplet, J=7 Hz, 2 H), 3.32 (d, J=7 Hz, 2 H), 1.14 (d, J=7 Hz, 3 H), 1.09 (d, J=7 Hz, 3 H), 1.05 (d, J=7 Hz, 3 H), 1.03 (d, J=7 Hz, 3 H); MS (+FAB): [M+] 636 (95%), 638 (100%); Anal. Calc. for C37H33BrO3S: C, 69.70, H, 5.11, N, 0.00. Found: C, 69.48, H, 5.11, N,0.11.

EXAMPLE 140

(R)-2-[4-(6-Bromo-benzo[b]naphtho[2,3-d]thiophen-11-yl)-2,6-diisopropyl-phenoxy)-propionic acid Prepared from of 4-(6-bromo-benzo[b]naphtho[2,3-d]thiophen-11-yl)-2,6-diisopropyl-phenol (Example 40) and commercially available (S)-lactic acid, methyl ester. White solid: mp: 214–215° C.; NMR (CDCl3); δ8.37 (ddd, J=8, 1, 1, 1H), 7.80 (d, J=8 Hz, 1 H), 7.70 (ddd, J=8, 1, 1 Hz, 1 H), 7.66 (ddd, J=8, 8, 1, 1 H), 7.48 (ddd, J=8, 8, 1 Hz, 1 H), 7.37 (ddd, J=8, 8, 1 Hz, 1 H), 7.18 (s, 2 H), 7.01 (ddd, J=8, 8, 1 Hz, 1 H), 6.53 (d, J=8 Hz, 1 H), 4.75 (q, J=7 Hz, 1 H), 3.47 (septuplet, J=7 Hz, 1 H), 3.41 (septuplet, J=7 Hz, 1 H), 1.71 (d, J=7 Hz, 3 H), 1.25 (d, J=7 Hz, 6 H), 1.20 (d, J =7 Hz, 3 H), 1.19 (d, J=7 Hz, 3 H); MS (EI): 560 (90%), 562 (100); Anal. Calc. for C31H29BrO3S: C, 66.31, H, 5.21, N, 0.00. Found: C, 65.90, H, 5.18, N, 0.02.

EXAMPLE 141

(R)-2-[2,6-Dibromo-4-(6-methyl-benzo[b]naphtho[2,3-d]thiophen-11-yl)-phenoxyl-3-phenyl-propionic acid Prepared from 2,6-dibromo-4-(6-methyl-benzo[b]naphtho[2,3-d]thiophen- 11-yl)-phenol (Example 62) and (S)-2-hydroxy-3-phenylpropionic acid, methyl ester (Example 96). White solid: mp 117–122° C.: [a]D25=+34.13° (9.963 mg/mL CHCl3); NMR (DMSO-d6): δ8.17 (d, J=8 Hz, 1 H), 7.81 (d, J=8 Hz, 1 H), 7.63-7.58 (m, 1 H), 7.57 (dd, J=6, 2 Hz, 2 H), 7.52-7.46 (m, 2 H), 7.42-7.38 (m, 3 H), 7.37-7.28 (m, 3 H), 7.16-7.10 (dt, J=1, 6 Hz, 1 H), 6.76 (d, J=8 Hz, 1 H), 5.45 (t, J=7 Hz, 1 H, CH), 3.59 (d, J=7 Hz, 2 H), 2.98 (s, 3 H); MS (EI): [M+], 643.6 (20%), 644.4 ( 50%), 645.5 (100%) 647.7 (30%); Anal. Calc. for C32H22Br2O3S: C, 59.46, H, 3.43, N, 0.00. Found: C, 59.34, H, 3.24, N, 0.04.

EXAMPLE 142

(R)-[2,6-Dibromo-4-(6-bromo-benzo[b]naphtho[2,3-d]thiophen-11-yl)-phenoxy]-phenyl-acetic acid Prepared from 2,6-dibromo-4-(6-bromo-benzo[b]naphtho [2,3-d]thiophen-11 -yl)-phenol (Example 21) and commercially avialable methly (s)-(+)-mandelate. White solid: mp 135–137° C.: MS (FAB–): [M–H]–, 693; Anal. Calc. for C30H17Br3O3S: C, 51.68, H, 2.46, N, 0.00. Found: C 51.57, H, 2.89, N, 0.14.

EXAMPLE 143

(S)-2-[2-Bromo-5-(6-bromo-benzo[b]naphtho[2,3-d]thiophen-11-yl)-phenoxyl]-propionic acid Prepared from of 2-bromo-5-(6-bromo-benzo[b]naphtho[2,3-d]thiophen-11-yl)-phenol (Example 68) and commercially available (R)-lactic acid, methyl ester. White solid: mp 132–134° C.: MS (+EI): [M+], 2 bromine isotope pattern, 554, 556, 558; Anal. Calc. for C25H16Br2O3S: C, 53.98, H, 2.90, N, 0.00. Found: C,52.97, H, 2.98, N, 0.04.

EXAMPLE 144

(R)-2-[2-bromo-5-(6-Bromo-benzo[b]naphtho[2,3-d]thiophen-11-yl)-phenoxyl]-propionic acid Prepared from of 2-bromo-5-(6-bromo-benzo[b]naphtho[2,3-d]thiophen- 11-yl)-phenol (Example 68) and commercially available (R)-lactic acid, methyl ester. White solid: mp 133–134.5° C.: MS (–ESI): [M–H]–, 2 bromine isotope pattern 553, 555, 557; Anal. Calc. for C25H16Br2O3S: C, 53.98, H, 2.90, N, 0.00. Found: C, 53.18, H, 2.82, N, 0.04.

EXAMPLE 145

(R)-2-[2,6-Dibromo-4-(6-bromo-benzo[b]naphtho[2,3-d]thiophen-11-yl)-phenoxy]-4-(1, 3-dioxo-1,3-dihydro-isoindol-2-yl)-butyric acid, methyl ester Diethylazodicarboxylate (0.293 mL, 1.86 mmol) was added dropwise to a stirred, ambient temperature suspension of 2,6-dibromo-4-(6-bromo-benzo [b]naphtho[2,3-d]thiophen-11-yl)-phenol (0.700 g, 1.24 mmol), (S)-(+)-2-hydroxy-1,3-dioxo-2-isoindolinebutyric acid, methyl ester (0.490 g, 1.86 mmol), triphenylphosphine (0.488 g, 1.86 mmol) and benzene (5.5 mL) under a dry nitrogen atmosphere. Dissolution occurred and the solution was heated in an 80° C. oil bath for 1.5 h. Upon cooling to room temperature, the reaction mixture was diluted with dicloromethane and silica gel (20 mL) was added. The reaction mixture was concentrated and the silica adsorbate was flash chromatographed (83:17 petroleum ether:ethyl acetate) to provide the title compound as a white solid (0.822 g, 81%): mp 221–222° C.; NMR (DMSO-d6); δ8.29 (d, J=8 Hz, 1 H), 8.08 (d., J=8 Hz, 1 H), 7.98 (ddd, J=8, 7, 1 Hz, 2 H), 7.87-7.83 (m, 4 H), 7.80 (ddd, J=8, 7, 1 Hz, 1 H), 7.66-7.58 (m, 2 H), 7.53 (ddd, J=8, 7, 1 Hz, 1 H), 7.29 (ddd, J=8, 7, 1 Hz, 1 H), 6.71 (d, J=8 Hz, 1 H), 5.16 (t, 1 H), 3.94 (m, 2 H), 3.71 (s, 3 H), 2.50 (m, 2 H); MS (FAB+): [M+], 3 bromine isotope pattern, 805 (22%), 807 ( 88%), 809 (100%), 811 (42 %); Anal. Calc. for C35H22Br3NO5S: C, 52.01, H, 2.74, N, 1.73. Found: C, 52.02, H, 2.70, N, 1.73.

EXAMPLE 146

(R)-2-(4-Benzo[b]naphtho[2,3-d]thiophen-11-yl-2,6-dibromo-phenoxy)-4-(1, 3-dioxo-1 , 3-dihydro-isoindol-2-yl)-butyric acid Iodotrimethylsilane (0.203 mL, 1.43 mmol) was added to a rt, stirred solution of (R)-2-[2,6-dibromo-4-(6-bromo-benzo[b]naphtho[2,3-d]thiophen-11-yl)-phenoxy]-4-(1,3-dioxo-1,3-dihydro-isoindol-2-yl)-butyric acid, methyl ester (0.770 g, 0.953 mmol) in methylene chloride (8 mL) under a dry nitrogen atmosphere. After 2 h, iodotrimethylsilane (3×0.203 mL, 4.29 mmol) was added to the resulted dark brown solution at rt three times every 12 h. The solution was quenched with water (0.4 mL), concentrated, chased with benzene (3×50 mL). The resulted residue was dissolved in ethyl acetate (60 mL) and silica gel (acid washed, 8 mL) was added. Solvent was removed and the adsorbate was flash chromatographed (eluent 7:3 pet. ether:ethyl acetate) to provide the title compound as a yellow solid (0.304 g, 45%): mp: 222–223° C.; NMR (CDCl3); δ8.37 (s, 1 H), 7.95(d, J=8 Hz, 1 H),7.89-7.85 (m, 2 H), 7.79 (dd, J=8,1 Hz, 1 H), 7.78-7.71 (m, 2 H), 7.64 (d, J=10 Hz, 1 H), 7.62 (d, J=10 Hz, 1 H), 7.59 (dd, J=8, 1 Hz, 1 H), 7.55 (ddd, J=8, 7, 1 Hz, 1 H), 7.46 (ddd, J=8, 7, 1 Hz, 1 H), 7.40 (ddd, J=8, 7, 1 Hz, 1 H), 7.19(ddd, J=8, 7, 1 Hz, 1 H), 6.88(d, J=8 Hz, 1 H), 5.27 (t, J=7 Hz, 1 H, 1 H, CH), 4.12 (m, 2 H), 2.65 (t, J=6 Hz, 2 H); MS (FAB–): [M–H]–, 2 bromine isotope pattern, 713, 714, 716; Anal. Calc. for C34H21Br2NO5S: C, 57.08, H, 2.96, N, 1.96. Found: C, 56.43, H, 2.74, N, 1.90.

EXAMPLE 147

(R)-2-[2,6-Dibromo-4-(6-bromo-benzo[b]naphtho[2, 3-d]thiophen-11-yl)-phenoxy]-4-(1, 3-dioxo-1, 3-dihydro-isoindol-2-yl)-butyric acid Iodotrimethylsilane (2.8 mL, 1 N in methylene chloride) was added dropwise to a –10° C., stirred solution of (R)-2-[2,6-dibromo-4-(6-bromo-benzo[b]naphtho[2,3-d]thiophen-11-yl)-phenoxy]-4-(1, 3-dioxo-1, 3-dihydro-isoindol-2-yl)-butyric acid, methyl ester (0.770 g, 0.953 mmol) in methylene chloride (14 mL) under a try N2 atmosphere. The solution was allowed to warm to ambient temperature and was stirred overnight. The reaction mixture was quenched, further diluted with water (100 mL), and partitioned between water and methylene chloride (2×75 mL). Methylene chloride extracts were concentrated and triturated with pet. ether. It was then recrystallized from acetic acid to provide the title compound as a grey solid (0.228 g, 52%): mp 215–217° C.: NMR (CDCl3): δ8.35 (d, J=8 Hz, 1 H), 7.89-7.86 (m, 2 H), 7.82 (dd, J=8, 1 Hz, 1 H), 7.76-7.71 (m, 2 H), 7.67(ddd, J=8, 7, 1 Hz, 1 H), 7.63-7.59 (m, 3 H), 7.58 (ddd, J=8, 7, 1 Hz, 1 H), 7.42 (ddd, J=8, 7, 1 Hz, 1 H), 7.20 (ddd, J=8, 7, 1 Hz, 1 H), 6.81(d, J=8 Hz, 1 H), 5.27 (t, J=7 Hz, 1 H, 1 H), 4.12 (m, 2 H), 2.65 (t, J =7 Hz, 2); MS (EI): [M+], 3 bromine isotope pattern, 791 (75%), 793 (98%), 795 (100%), 797 (38%); Anal. Calc. for C34H2OBr3NO5S: C, 51.41, H, 2.54, N, 1.76. Found: C, 51.65, H, 2.37, N, 1.70.

EXAMPLE 148

(R)-2-(4-benzo[b]naphtho[2,3-d]thiophen-11-yl)-phenoxy)-4-(1, 3-dioxo-1, 3-dihydro-isoindol-2-yl)-butyric acid Iodotrimethylsilane (1.31 mL, 9.23 mmol) was added dropwise to a 0° C., stirred solution of (R)-2-(4-benzo[b]naphtho[2,3-d]thiophen-11-yl)-phenoxy)-4-(1, 3-dioxo- 1, 3-dihydro-isoindol-2-yl)-butyric acid, methyl ester (1.17 g, 2.05 mmol) in methylene chloride (15 mL) under a try N2 atmosphere. After 1 h. the solution was allowed to warm to ambient temperature. After 1 h. the reaction mixture was quenched with 10% aqueous sodium bisulfide and further diluted with water (100 mL). Aqueous mixture was extracted with ethyl acetate (150 mL). The ethyl acetate extract was washed with water, dried with brine and anhydrous MgSO4, and concentrated to provide a white solid. The solid was recrystallized from aqueous acetic acid and purified by HPLC (Dynamax C18 Column, 90:10 acetonitrile:water (both with 0.1% TFA) to provide the title compound as a light yellow solid (0.420 g, 32%): mp 145–14° C. 7: NMR (CDCl3); δ8.31 (s, 1 H), 7.92 (d, J=8 Hz, 1 H), 7.87-7.84 (2 distored d, J=8 Hz, 2 H), 7.75 (d, J=8 Hz, 1 H), 7.72-7.69 (2 distored d, J=8 Hz, 2 H), 7.59 (d, J=8 Hz, 1 H), 7.49 (ddd, J=8, 7, 1 Hz, 1 H), 7.39-7.33 (m, 2 H), 7.29-7.22 (m, 2 H), 7.15 (ddd, J=8, 7,1 Hz, 1 H), 7.05 (dd, J=9, 8 Hz, 1 H), 7.01 (dd, J=9, 8 Hz, 1 H), 6.75 (d, J=8 Hz, 1 H), 4.99 (t, J=6 Hz, 1 H), 4.09 (t, J=6 Hz, 2 H), 2.52 (q, J=6 Hz, 2 H); MS (+FAB): [M+H]+, 558; Anal. Calc. for C34H23NO5S: C, 73.23, H, 4.16, N, 2.51. Found: C, 71.82, H, 4.00, N, 2.61.

EXAMPLE 149

(R)-2-[4-(3-Carboxymethoxy-benzo[b]naphtho[2,3-d]thiophen-11-yl)-phenoxy-4-(1, 3-dioxo-1, 3-dihydro-isoindol-2-yl)-butyric acid Diethylazodicarboxylate (DEAD, 0.133 mL, 0.845 mmol) was added to a stirred, room temperature solution of 11-(4-hydroxy-phenyl)-benzo[b]naphtho[2,3-d ]thiophen-3-yloxy]-acetic acid methyl ester ( 0.140 g, 0.338 mmol), L-3-phenyllactic acid, methyl ester (0.133 g, 0.845 mmol), triphenylphosphine (0.222 g, 0.845 mmol) and benzene (1.5 mL) under a dry nitrogen atmosphere. Dissolution occurred and the solution was heated in an 80° C. oil bath for 6 h. More diethylazodicarboxylate (DEAD, 0.053 mL, 0.338 mmol), L-3-phenyllactic acid, methyl ester (0.070 g, 0.338 mmol) and triphenylphosphine (0.103 g, 0.338 mmol) were added. The reaction mixture was cooled to room temperature after 5.5 h. The reaction mixture was diluted with ether and silica gel was added. The reaction mixture was concentrated and the silica adsorbate was flash chromatographed (gradient 99:1 to 98:2 dichloromethane:acetonitrile) to provide a white solid (0.190 g). This solid was recrystalized from acetonitrile containing 0.1% of trifluoroacetic acid to provide a white solid (144 mg). 1.0 M solution of boron tribromide (1.4 mL, 1.4 mmol) in dichloromethane was added to a stirred, −78° C. solution of this solid in dichloromethane (3.0 mL). After 45 min the reaction mixture was warmed to room temperature. Afer 3.5 h ,the reaction mixture was recooled to −78° C. and an additional amount of 1.0 N boron tribromide (0.8 mL, 0.8 mmol) was added. The reaction mixture was warmed to room temperature. After an additional 2 h, water was added and the reaction mixture was extracted with ethyl acetate. The ethyl acetate phase was concentrated and purified by prep HPLC (reverse phase: 7:3 acetonitrile:water with 0.1% trifluoroacetic acid). The resultant compound (13 mg) was recrystalized from acetic acid/water to provide the tilte compound as a white solid (0.005 g, 2%): mp: 259–260° C.: NMR (DMSO-d6); δ13.2 (broad s, 2 H), 8.54 (s, 1 H), 8.02 (d, J=8 Hz, 1 H), 7.88-7.81 (m, 4 H), 7.55-7.44 (m, 4 H), 7.25 (dd, J =9, 2 Hz, 2 H),7.11-7.04 (m, 2 H) 6.79 (dd, J=9, 2 Hz, 1 H), 6.52 (d, J=9 Hz, 1 H), 5.03 (dd, J=8, 2 Hz, 1 H), 4.75 (s, 2 H), 3.92 (m, 2 H), 2.32 (m, 2 H); MS (FAB+): 632 (10%, M+H); Analytical HPLC: 98.8% pure.

EXAMPLE 150

(R)-2-[4-(6-Bromo-benzo[b]naphtho[2,3-d]thiophen-11-yl)-phenoxyl-4-(1, 3-dioxo-1, 3-dihydro-isoindol-2-yl)-butyric acid Boron tribromide (1 M solution in methylene chloride, 10.4 mL, 10.4 mmol) was added dropwise to a −10° C., stirred solution of (R)-2-[4-(6-bromo-benzo [b]naphtho[2,3-d]thiophen-11-yl)-phenoxy]-4-(1,3-dioxo-1,3-dihydro-isoindol-2-yl)-butyric acid, methyl ester (1.35 g, 2.08 mmol) in methylene chloride (35 mL) under a try N2 atmosphere. After 1 h. the solution was allowed to warm to ambient temperature. After 1 h. the reaction mixture was quenched, further diluted with water (100 mL), and partitioned between water and methylene chloride. Methylene chloride extracts were concentrated to give a solid, The solid was separated and purified by HPLC (Dynamax C18 Column, 95:5 acetonitrile:water (both with 0.1% TFA) to provide the title compound as a light yellow solid (0.420 g, 32%): mp >69° C. (dec): NMR (CDCl3): δ8.32 (d, J=8 Hz, 1 H), 7.86-7.84 (2 d, J=8 Hz, 2 H), 7.77 (d, J=8 Hz, 1 H), 7.72-7.70 (d, J=8 Hz, 2 H), 7.64-7.59 (m, 2 H), 7.43-7.36 (m, 2 H), 7.25-7.16 (m, 3 H), 7.05 (dd, J=9, 8 Hz, 1 H), 7.01 (dd, J=9, 8 Hz, 1 H), 6.68(d, J=8 Hz, 1 H), 4.99 (t, J=6 Hz, 1 H), 4.09 (t, J=6 Hz, 2 H), 2.52 (q, J=6 Hz, 2 H); MS (EI): [M+], 1 bromine isotope pattern, 635 (90%), 637 (100%); Anal. Calc. for C34H22BrNO5S: C, 64.16, H, 3.48, N, 2.20. Found: C, 64.19, H, 4.04, N, 2.08.

EXAMPLE 151

(R)-2-[2,6-Dibromo-4-(6-bromo-benzo[b]naphtho[2, 3-d]thiophen- 11-yl)-phenoxyl-succinic acid dimethyl ester Diethylazodicarboxylate (0.254 mL, 1.61 mmol) was added dropwise to a stirred, room temperature suspension of 2,6-dibromo-4-(6-bromo-benzo [b]naphtho[2,3-d]thiophen-11-yl)-phenol (0.600 g, 1.10 mmol), dimethyl (S)-(−)-malate (0.213 mL, 1.61 mmol) and triphenylphosphine (0.421 g, 1.61 mmol) in benzene (7.5 mL) under a dry nitrogen atmosphere. The solution was heated in an 79° C. oil bath for 23 h. Additional Dimethyl (S)-(−)-malate (0.043 mL, 0.321 mmol) and triphenylphosphine (0.084 g, 0.321 mmol) and diethylazodicarboxylate (0.050 mL, 0.321 mmol) were added and the reaction mixture was heated for an additional 10 hours. The reaction mixture was cooled to room temperature, diluted with methylene chloride combined with silica gel (20 mL) and concentrated. The silica adsorbate was flash chromatographed (92:8 petroleum ether:ethyl acetate) to provide the title compound as a white solid (0.389 g, 51%): mp 118–121° C.: NMR (CDCl3); δ8.36 (dd, J=8, 0.5 Hz, 1 H), 7.83 (dd, J=8, 0.5 Hz, 1 H), 7.68 (ddd, J=8, 7, 1 Hz, 1 H), 7.61 - 7.59 (m, 3 H), 7.55 -7.43 (m, 2 H), 7.26 - 7.21 (m, 1 H), 6.79 (d, J=8 Hz, 1 H), 5.46 (t, J=6 Hz, 1 H), 3.90 (s, 3 H), 3.77 (s, 3 H), 3.32 - 3.30 (m, 1 H); MS (EI): [M+], 3 bromine isotope pattern, 704 (5%), 706 ( 15%), 708 (15%), 710 (4%); Anal. Calc. for C28H19Br3O5S: C, 47.55, H, 2.71, N, 0.00. Found: C, 47.93, H, 2.65, N, 0.14.

EXAMPLE 152

(R)-2-[2,6-Dibromo-4-(6-bromo-benzo[b]naphtho[2, 3-d]thiophen-11-yl)-phenoxy]-succinic acid A solution of (R)-2-[2,6-Dibromo-4-(6-bromo-benzo[b] naphtho[2,3-d ]thiophen-11-yl)-phenoxy]-succinic acid, dimethly ester (0.317 g, 0.448 mmol) in 4M HCl in dioxane (5 mL) was combined with water (5 mL) and concentrated HCl (1 mL) in a sealed pressure bottle and heated for 9 hours. After remaining at ambient temperature for an additional 14 hours the reaction mixture was partitioned between water and ether. The layers were separated and acid treated silica gel (7 mL) was added to the ether layer. The solvent was removed and the adsorbate was purified by flash chromatography (acid treated silica gel, eluant 80:20 pet. ether-:ethyl acetate) to provide the title compound as a white solid (0.142 g, 47%), mp 163–164° C.; [a]D25=+14.16° (8.825 mg/mL, methanol); NMR (DMSO-d6); δ13.6 - 13.2 (broad singlet, 1 H,), 12.7 - 12.6 (broad singlet, 1 H), 8.28 (d, J=8 Hz, 1 H), 8.07 (d, J=8 Hz, 1 H), 7.82 - 7.78(m, 3 H), 7.65 - 7.57(m, 2 H,), 7.52(dd, J=7, 1 Hz, 1 H), 7.31(dd, J=7, 1, 1H), 6.70(d, J=8 Hz, 1 H), 5.32 (t, J=8 Hz), 3.67(m, 2 H); MS (-FAB) [M-H]-; 3 bromine pattern detected, 675(25%), 677(10%), 679(25%), 681(10%); Anal. Calc. for C26H15Br3O5S: C, 45.78, H, 2.23, N, 0.00. Found: C, 46.42, H, 2.40, N, 0.05.

EXAMPLE 153

2-[2,6-Dibromo-4-(6-bromo-benzo[b]naphtho[2,3-d]thiophen-11-yl)-phenoxy]3-(4-fluoro-phenyl-propionic acid tert-butyl ester Diisopropylamine (distilled over CaH2, 0.169 mL, 1.2 mmol) was added to anhydrous tetrahydrofuran (0.65 mL) and cooled to −74° C. under a dry argon atmosphere. n-Butyllithium (2.5 M in hexane, 0.516 mL, 1.29 mmole) was added dropwise and the mixture was warmed to 0° C. for 10 minutes then recooled to −74° C. Hexamethylphosphorarnide (0.83 mL) was added followed 5 minutes later by the slow (0.5 hour) dropwise addition of a solution of (R)-2-[2,6-dibromo-4-(6-bromo-benzo [b]naphtho[2,3-d]thiophen-11-yl)-phenoxy]-propionic acid, tert-butyl ester (0.715g, 1.06 mmole) in anhydrous tetrahydrofuran (2.8 mL). After stiring one hour at −75° C., 4-fluorobenzylbromide (0.158 mL, 1.29 mmol) was added dropwise. After stirring 1 hour at −80° C. the reaction mixture was allowed to warm to room temperature overnight. The reaction mixture was quenched with dilute aqueous ammonium chloride and was partitioned between water (100 mL) and a 1:1 methylene chloride: ether solution (130 mL). After one more extraction with methylene chloride (50 mL) the organic layers were combined, silica gel was added, and the solvents removed. The adsorbate was purified by flash chromatography (eluent 7:3 pet ether:methylene chloride) and HPLC (Column: Waters Silica Prep Pak; gradient, 99:1 to 95:5 petroleum ether:ethyl acetate; Flow rate=225 mL/min) to provide the title compound as a white solid (0.265 g, 32%): mp: 80–100° C.; NMR(CDCl3); δ8.35 (dd, J =8, 1 Hz, 1 H), 7.83 (dd, J=6, 1 Hz, 1 H), 7.66 (ddd, J=6, 5, 1 Hz, 1 H), 7.58 (dd, J =4, 2 Hz, 2 H), 7.53 -7.38 (m, J=2 Hz, 5 H), 7.18 (ddd, J=7, 1, 1, 1H), 7.04 (t, J=9 Hz, 2 H), 6.83 (d, J=8 Hz, 1 H), 5.31 (t, J=6 Hz, 1 H), 3.49 (t, J=6 Hz, 2 H), 1.40 (s, 9 H); MS (FAB+): [M+], 3 bromine pattern, 782 (20%), 784 (70%), 786 (80%), 788 (35%); Anal. Calc. for C35H26Br3FO3S: C, 53.53, H, 3.34, N, 0.00.Found: C, 53.25; H, 3.21, N, 0.04.

EXAMPLE 154

(R)-2-[2,6-Dibromo-4-(6-bromo-benzo[b]naphtho[2,3-d]thiophen-11-yl)-phenoxyl-3-napthalen-2-yl-propionic acid tert-butyl ester Diisopropylamine (distilled over CaH2, 0.233 mL, 1.78 mmol) was added to anhydrous tetrahydrofuran (0.91 mL) and cooled to −74° C. under a dry argon atmosphere. n-Butyllithium (2.5 M in hexane, 0.71 mL, 1.78 mmole) was added dropwise and the mixture was warmed to 0° C. for ca. 20 minutes then recooled to −75° C. Hexamethylphosphoramide (2 mL) was added followed 10 minutes later by the slow (0.5 hour) dropwise addition of a solution of (R)-2-[2,6-dibromo-4-(6-bromo-benzo [b]naphtho[2,3-d]thiophen-11-yl)-phenoxy]-propionic acid, tert-butyl ester (1.004 g, 1.48 mmole) in anhydrous tetrahydrofuran (3 mL). After stirring one hour at −75° C., 2 bromomethylnaphthalene (0.393 g, 1.78 mmol) was added dropwise. After stirring 0.5 hour at −80° C. the reaction mixture was allowed warm to room temperature overnight. The reaction mixture was quenched with dilute aqueous ammonium chloride and was partitioned between water (100 mL) and a 1:1 methylene chloride: ether solution (200 mL). After one more extraction with methylene chloride the organic layers were combined, washed with water (100 mL) and purification by flash chromatographed (eluent 7:3 pet ether:ethyl acetate) and HPLC (2 times) (First column:Waters Silica Prep Pak; isocratic, 98:2 hexane:ethyl acetate; Flow rate =225 mL/min; Second column: Waters Silica Prep Pak; gradient, 75:25 to 60:40 petroleum ether:methylene chloride) to provide the title compound as a white solid (0.280 g, 23%); NMR (CDCl3); δ8.35 (d, J=8 Hz, 1 H), 7.88-7.80 (m, 5 H), 7.66 (ddd, J=6, 5, 1 Hz, 1 H), 7.61 (d, J=2 Hz, 1 H), 7.60 (d, J=2 Hz 1 H) 7.58-7.56 (m, 2 H), 7.51-7.41 (m, 4 H), 7.18 (ddd, J=7, 1, 1 Hz, 1 H), 6.83 (dd, J=7, 1 Hz, 1 H) 5.44 (t, J =8 Hz, 1 H), 1.34 (s, 9 H); MS (FAB+): [M+], 3 bromine pattern, 814 (30%) 816 (95%) 818 (100%) 820 (42%); Anal. Calc. for C39H29Br3O3S: C, 57.30; H, 3.58, N, 0.00. Found: C, 57.55; H, 3.75, N, 0.02.

EXAMPLE 155

2-[2,6-Dibromo-4-(6-bromo-benzo[b]naphtho[2,3-d]thiophen-11-yl)-phenoxy]-3-(4-fluoro-phenyl )-propionic acid A suspension of 2-[2,6-dibromo-4-(6-bromo-benzo[b]naphtho[2,3-d]thiophen-11 -yl)-phenoxy]-3-(4-fluoro-phenyl)-propionic acid tert-butyl ester (0.232 g 0.295 mmol) in trifluoroacetic acid (5 mL) was heated at 55° C. for 11 hours. After cooling to room temperature the reaction mixture was poured into water (60 mL) and extracted with ether. The combined ether extracts were washed with water and brine, concentrated, and dried in vacuo at 60° C. to provide the title compound as an off white solid (0.187 g, 98%): NMR (CDCl3); δ8.36 (d, J=7 Hz, 1 H), 7.82 (d, J=7 Hz, 1 H), 7.68 (ddd, J=8, 6, 2 Hz, 1 H), 7.58 (dd, J=8, 2 Hz, 2 H), 7.55-7.48 (m, 2 H), 7.45-7.35 (m, 3 H), 7.15 (dt, J=7, 1, 1H), 7.03 (tt J=10, 3, 1, 2H), 6.71 (d, J=8 Hz, 1 H), 5.44 (t, J=6 Hz, 1 H), 3.56 (d, J=7 Hz, 2 H); MS (+FAB): [M+], 3 bromine isotope pattern, 726 (15%), 728 ( 30%) 730 (35%) 732 (15%); Anal. Calc. for C31H18Br3FO3S: C, 51.06, H, 2.49, N, 0.00. Found: C, 50.80, H, 2.46, N, 0.10.

EXAMPLE 156

2-[2,6-Dibromo-4-(6-bromo-benzo[b]naphtho[2,3-d]thiophen-11-yl)-phenoxy]-3-naphthalen-2yl-propionic acid A solution of 2-[2,6-dibromo-4-(6-bromo-benzo[b]naphtho[2,3-d]thiophen-11-yl)-phenoxy ]-3-naphthalen-2yl—propionic acid, tert butyl ester (0.221 g, 0.270 mmol) in trifluoroacetic acid (10 mL) was heated to 50° C. for 15 hours. The mixture was cooled to room temperature and combined with water. Ether was added and the resulting organic suspension was separated from the water layer and concentrated. The residue was dried in vacuo at 46 C. to provide the title compound as an off white solid (0.186 g, 90%) mp 270–271° C.; NMR (DMSO-d6); δ13.25 (broad singlet, 1 H), 8.28 (d, J=8 Hz, 1 H,), 8.06 (d, J=8 Hz, 1 H), 7.91(m, 4 H), 7.81(d, J=2 Hz, 1 H), 7.79(d, J =2 Hz, 1 H) 7.82-7.77(m, 1 H), 7.63-7.47(m, 6 H), 7.25 (dd, J=7, 1 Hz,, 1 H), 6.64 (d, J=8 Hz, 1 H) 5.42 (t, J=7 Hz, 1 H), 3.59 (d, J=7 Hz, 2 H); MS (FAB+): [M+], 3 bromine pattern, 757.8 (21%) 759.8 (100%) 761.8 (100%) 763.8 (50%); Anal.

Calcd. for C31H19Br3O3S: C, 55.07; H,3.04, N, 0.00. Found: C, 55.36; H, 2.89, N, 0.06.

EXAMPLE 157

Diethyl Trifluoromethanesulfonoxymethylphosphonate

Prepared according to the procedure of D. P. Phillion and S. S. Andrew *Tet. Lett.* 1986, 1477–1480. A solution of trifluoromethanesulfonic anhydride (11.6 mL, 68.9 mmol) in methylene chloride (45 mL) was added dropwise to a stirred, –10 ° C. solution of diethyl hydroxymethylphosphonate (10.82 g, 64.4 mmol) and pyridine (5.76 mL, 68.9 mmol) in methylene chloride (170 mL) under N2 over a period of 20 min. The mixture was stirred at –10° C. for 1 h. and placed in the freezer (–15 to –20 ° C.) overnight. The reaction mixture was diluted with cold methylene chloride and washed with cold 1 N HCl and ice water. The organic layer was separated, dried with brine, anhydrous MgSO4 and concentrated to provide an oil (12.58 g, 65 %): MS (+FAB): [M+H]+, 423 .

EXAMPLE 158

{2,6-Dibromo-4-[6-bromo-benzo[b]naphtho[2,3-d]thiophen-11-yl)]-phenoxymethyl}-phosphonic acid diethyl ester A solution of 2,6-dibromo-4-(6-bromo-benzo[b]naphtho[2,3-d]thiophen-11-yl)-phenol (1.00 g, 1.78 mmol) in THF (5 mL) was added dropwise to a stirred, 0° C. solution of 80% sodium hydride (0.08 g, 2.67 mmol) in THF (10 mL) under a dry nitrogen atmosphere over a period of 15 min. After the mixture was stirred in an 0° C. oil bath for 40 min., a solution of diethyl trifluoromethanesulfonoxymethylphosphonate (0.80 g, 2.67 mmol) was added dropwise over a period of 15 min. The reaction mixture was then warmed to, and stirred at, ambient temperature for 1 h. The reaction mixture was quenched and diluted with water (80 mL). The resulting solid was filtered, washed with water and triturated with pet. ether. The solid was dried in vacuo at 50° C. to provide the title compound as a white solid (1.12 g, 88%): mp 178–180° C.: NMR (CDCl3); δ8.36 (d, J=9 Hz, 1 H), 7.84 (d, J=8 Hz, 1 H), 7.68 (ddd, J=7, 6, 1 Hz, 1 H), 7.62 (s, 2 H), 7.57-7.49 (m, 2 H), 7.45 (ddd, J=8, 7, 1 Hz, 1 H), 7.18 (ddd, J=8, 7, 1 Hz, 1 H), 6.73 (d, J=8, Hz, 1 H), 4.61 (s, 2 H), 4.41 (q, 4 H), 1.49 (t, 6 H, CH3); MS (EI): [M+], 3 bromine isotope pattern, 710 (35%), 712 (95%) 714 (100%), 716 (40%); Anal. Calc. for C27H22Br3O4PS: C, 45.47, H, 3.11, N, 0.00. Found: C, 45.30, H, 2.95, N, 0.07.

EXAMPLE 159

[4-(Benzo[b]naphtho[2,3-d]thiophen-11-yl)-phenoxymethyl]-phosphonic acid diethyl ester A solution of 4-(benzo[b]naphtho[2,3-d]thiophen-11-yl)-phenol (1.00 g, 3.06 mmol) in THF (5 mL) was added dropwise to a stirred, 0° C. solution of 80% sodium hydride (0.138 g, 4.95 mmol) in THF (10 mL) under a dry nitrogen atmosphere over a period of 15 min. After the mixture was stirred in an 0° C. oil bath for 1 h., a solution of diethyl trifluoromethanesulfonoxymethylphosphonate (1.4 g, 4.95 mmol) was added dropwise over a period of 15 min. The reaction mixture was then warmed to and stirred at ambient temperature for 2 h. The reaction mixture was quenched and diluted with water (150 mL). Aqueous mixture was extracted with ethyl acetate (2×150 mL). The ethyl acetate extracts were washed with water, dried with brine and anhydrous MgSO4, and concentrated to provide a white solid. The solid was purified by flash chromatography (eluent 7:3 pet. ether:ethyl acetate) to provide the title compound as a white solid (0.922 g, 63%): mp 129–130° C.; MS (EI): [M+], 476 (100% MI); Anal. Calc. for C27H25O4PS: C, 68.05, H, 5.29, N, 0.00. Found: C, 66.58, H, 5.34, N, 0.00.

EXAMPLE 160

3-Phenyl-1-hydro-1-propylphosphonic acid, diethyl ester

Aluminum oxide (15 g) was added to a stirred, ambient temperature solution of hydrocinnamaldehyde (3.93 mL, 28.3 mmol) and diethylphosphite (3.72 mL, 28.3 mmol) in methylene chloride (30 mL). The mixture was stirred at ambient temperature for 2 days. The reaction mixture was filtered and dichloromethane filtrate was concentrated and triturated with petroleum ether to provide the title compound as a white solid (4.10 g, 53%): mp 60–61° C.: MS (+FAB): [M+H]+, 273 (100%, MI); Anal. Calc. for C13H21O4P: C, 57.35, H, 7.77, N, 0.00. Found: C, 57.48, H, 7.87, N, 0.04.

EXAMPLE 161

{1-2,6-Dibromo-4-(6-bromo-benzo[b]naphtho[2,3-d]thiophen-11-yl)-phenoxyl-3-phenyl-propyl }-phosphonic acid, diethyl ester Diethylazodicarboxylate (0.420 mL, 2.67 mmol) was added dropwise to a stirred, ambient temperature suspension of 2,6-dibromo-4-(6-bromo-benzo [b]naphtho[2,3-d]thiophen-11-yl)-phenol (1.00 g, 1.78 mmol), 3-phenyl-1-hydro-1 -propylphosphonic acid, diethyl ester (0.730 g, 2.67 mmol), triphenylphosphine (0.700 g, 2.67 mmol) and benzene (9 mL) under a dry nitrogen atmosphere. The solution was heated in an 80° C. oil bath for 4 h. Upon cooling to room temperature, the reaction mixture was partitioned between water (80 mL) and dichloromethane ( 100 mL). Dichloromethane phase was washed with 10% aq HCl ( 80 mL) and silica gel (20 mL) was added. Solvent was removed and the silica adsorbate was flash chromatographed (95:5 Dichloromethane:acetonitrile) to provide the title compound as a white solid (1.17 g, 73%): mp 161–162° C.: MS (EI+): [M+], 3 bromine isotope pattern, 814, 816, 818, 820; Anal. Calc. for C35H30Br3O4PS: C, 51.43, H, 3.70, N, 0.00. Found: C, 51.36, H, 3.67, N, 0.03.

EXAMPLE 162

[2,6-Dibromo-4-(6-bromo-benzo[b]naphtho[2,3-d]thiophen-11-yl)-phenoxymethyl]-phosphonic acid Iodotrimethylsilane (0.63 mL, 4.41 mmol) was added dropwise to a stirred, 0° C. solution of {2,6-dibromo-4-[6-bromo-benzo[b]naphtho[2,3-d]thiophen-11-yl)]-phenoxymethyl }-phosphonic acid diethyl ester (1.05 g, 1.47 mmol) in methylene chloride (29 mL) under a dry nitrogen atmosphere over a period of 10 min. After 1 h at 0° C., the reaction mixture was quenched with water (0.5 mL), stirred at ambient temperature for 30 min., and then diluted with water (50 mL). The solid was filtered and partitioned in ethyl acetate (100 mL) and 20% aquous HCl (60 mL) with stirring for 3 h. The solid was filtered, washed with water and triturated with pet. ether. The solid was dried in vacuo at 100° C. to provide the title compound as an off-white solid (0.428 g, 44%): mp 334–335° C.: NMR (DMSO-d6); δ8.28

(d, J=9 Hz, 1 H), 8.07 (d, J=8, Hz, 1 H), 7.84 (s, 2 H), 7.79 (ddd, J=8, 7, 1 Hz, 1 H), 7.65-7.57 (m, 2 H), 7.52 (dd, J=7, 1 Hz, 1 H), 7.32 (ddd, J=8, 7, 1 Hz, 1 H), 6.67 (d, J=8 Hz, 1 H), 4.32 (d, J=1 Hz, 2 H); MS (ESI): [M–H]-, 3 bromine isotope pattern; Anal. Calc. for C23H14Br3O4PS: C, 42.04, H, 2.15, N, 0.00. Found: C, 41.26, H, 2.12, N, 0.05; Karl Fischer: 0.58 mol H2O.

EXAMPLE 163

[4-(Benzo[b]naphtho[2,3-d]thiophen-11-yl)-phenoxymethyl]-phosphonic acid

Iodotrimethylsilane (0.78 mL, 5.49 mmol) was added to a 0–5° C., stirred solution of [4-(benzo[b]naphtho [2,3-d] thiophen-11-yl)-phenoxymethyl]-phosphonic acid diethyl ester (0.871 g, 1.83 mmol) in methylene chloride (24 mL) under a try N2 atmosphere over a period of 10 min. After 1 h, the solution was quenched with water (0.6 mL), 10% aqueous sodium carbonate (100 mL) was added and mixture was washed with methylene chloride. The aqueous layer was acidified with 10% aqueous HCl. The solid was filtered and recrystallized from methanol (75 mL) to provide the title compound as a white solid (0.65 g, 85%): mp 240–242° C.: MS (EI): [M+], 420; Anal. Calc. for C23H17O4PS: C, 65.17, H, 4.08, N, 0.00. Found: C, 63.95, H, 3.89, N, 0.41.

EXAMPLE 164

{1-[2,6-Dibromo-4-(6-bromo-benzo[b]naphtho[2,3-d]thiophen-11-yl)-phenoxy]-3-phenyl-propyl-phosphonic acid Iodotrimethylsilane (0.56 mL, 3.93 mmol) was added dropwise to a stirred, 0° C. solution of {1-[2,6-dibromo-4-(6-bromo-benzo[b]naphtho[2,3-d]thiophen-11-yl)-phenoxy ]-3-phenyl-propyl}-phosphonic acid, diethyl ester (1.07 g, 1.31 mmol) in methylene chloride (26 mL) under a dry nitrogen atmosphere over a period of 10 min. After 1 h at 0° C., the reaction mixture was quenched with 10% aq sodium bisulfite (1 mL), stirred at ambient temperature for 30 min. The mixture was partitioned in methylene chloride (100 mL) and water (100 mL). The methylene chloride phase was washed with 18% aq HCl (100 mL), concentrated, and triturated with pet. ether to afford a crude solid (0.894 g). The solid was then recrystalized from 85% aq. acetic acid (50 mL) to provide the title compound as a off-white solid (0.466 g, 47%): NMR (CDCl3); δ8.33 (d, J=9 Hz, 1 H), 7.76 (d, J=7 Hz, 1 H), 7.59 (ddd, J=8, 7, 1 Hz, 1 H), 7.48-7.40 (m, 3 H), 7.36-7.28 (m, 2 H), 7.06-6.98 (m, 5 H), 6.91-6.83 (m, 1 H), 6.77 (d, J=8 Hz, 1 H), 5.47-5.42(m, 1 H), 4.50 (s, 2 H), 3.05-2.85 (m, 2 H), 2.59-2.41 (m, 2 H); MS (FAB–): [M–H]-, 3 bromine isotope pattern, 756; Anal. Calc. for C31H22Br3O4PS: C, 48.91, H, 2.91, N, 0.00. Found: C, 49.29, H, 2.90, N, -0.02.

EXAMPLE 165

2-[2,6-Dibromo-4-(6-bromo-benzo[b]naphtho[2,3-d]thiophen-11-yl)-phenoxyl-acetamide Methanol (10 mL) was purged with ammonia gas for 10 min at 0° C. [2,6-dibromo-4-(6-bromo-benzo[b]naphtho[2, 3-d]thiophen-11-yl)-phenoxy]-acetic acid, methyl ester (0.50 g, 0.787 mmol) was added and the vessel was sealed, warmed to room temperature and stirred for two days. The reaction mixture was concentrated, diluted with ether and filtered. The solid was boiled in ethyl acetate (8 mL), hot filtered and washed with ethyl acteate and pentane and dried in vacou to provide the title compound as an off white solid (0.22 g, 45%): mp 263–265° C.: NMR (DMSO-d6); δ8.29 (d, J=8 Hz, 1 H), 8.09 (d, J=8 Hz, 1 H), 7.88 (s, 2 H), 7.80 (ddd, J=8, 7, 1 Hz, 1 H), 7.67-7.51 (m, 5 H), 7.30 (ddd, J=8, 7, 1 Hz, 1 H), 6.71 (d, J=8 Hz, 1H), 4.56 (s, 2 H); MS (EI): [M+], 3 bromine isotope pattern, 617 (30%), 619 ( 90%) 621 (100%) 623 (40%); Anal. Calc. for C24H14Br3NO2S: C, 46.48, H, 2.28, N, 2.26. Found: C, 45.69, H, 2.02 , N, 2.14.

EXAMPLE 166

(R)-2-[2,6-Dibromo-4-(6-bromo-benzo[b]naphtho[2, 3-d]thiophen-11-yl)-phenoxyl-3-phenyl-propionamide Three drops of DMF were added to a stirred, room temperature solution of (R)-2 -[2,6-dibromo-4-(6-bromo-benzo[b]naphtho[2,3-d]thiophen-11-yl)-phenoxy]-3-phenyl-propionic acid (2.09 g, 2.94 mmol), oxalyl chloride (0.31 mL, 3.53 mmol) and dichloromethane (31 mL) under a dry nitrogen atmosphere. Oxalyl chloride (0.10 mL, 51.14 mmol) was added after 2.5 h and again (0.10 mL, 1.14 mmol) at 6 h. After 6.5 h, the reaction mixture was concentrated and dried in vacuo. The solid was dissolved in dichloromethane (25 mL) and added over a 2 minute period to stirred, cold (0° C.) concentrated ammonium hydroxide (50 mL). The dichloromethane was removed and the resulting solid was filtered and washed with water and dried in vacuo to provide the title cmpound as a white solid (1.99 g, 95%): mp 220–222° C.: NMR (DMSO-d6); δ8.28 (d, J=8 Hz, 1 H), 8.07 (d, J=8 Hz, 1 H), 7.80 (ddd, 8, 7, 1 Hz, 1 H), 7.75 (d, J=2 Hz, 1 H), 7.74 (d, J=2 Hz, 1 H), 7.67-7.62 (m, 2 H), 7.53-7.48 (m, 2 H), 7.41-7.24 (m, 7 H), 6.69 (d, J=8 Hz, 1 H), 5.74 (s, 1 H, 0.5 eq CH2Cl2), 5.23 (t, J=6 Hz, 1 H), 3.46-3.27 (m, 2 H); MS (+FAB): [M+], 3 bromine isotope pattern, 707 (30%), 709 ( 75%) 711 (100%) 713 (40%); Anal. Calc. for C31H20Br3NO2S.0.56CH2Cl2: C, 50.02, H, 2.82, N, 1.85. Found: C, 49.67, H, 2.67, N, 1.96.

EXAMPLE 167

(R)-2-[2,6-Dibromo-4-(6-bromo-benzo[b]naphtho[2, 3-d]thiophen-11-yl)-phenoxyl-N-hydroxy-3-phenyl-propionamide DMF (2 drops) was added to a stirred solution of (R)-2-[2,6-dibromo-4-(6-bromo-benzo[b]naphtho[2,3-d]thiophen-11-yl)-phenoxy]-3-phenyl-propionic acid (0.736 g, 1.03 mmol), oxalyl chloride (0.11 mL, 1.27 mmol) and dichloromethane (11 mL). After 1 h, the solvent was removed. The residue was dissolved in chloroform (3.5 mL) and added dropwise to a rapidly stirred, 0° C. suspension of hydroxylamine hydrochloride (0.097 g, 1.34 mmol), sodium carbonate (0.191, 1.65 mmol), water (3.5 mL) and chloroform (3.5 mL). This stirred suspension was warmed to room temperature and stirred overnight. Water was added and the reaction mixture was extracted with chloroform. 2% phosphoric acid/methanol treated silica gel was added to the chloroform phase and the solvent was removed. The adsorbate was flashed on 2% phosphoric acid/methanol treated silica gel (gradient: 4:1 to 3:2 petroleum ether:ethyl acetate) to provide the title compounds as a white solid (0.464 g, 64%): mp 143–144° C.: NMR (DMSO-d6); δ9.03 (d, J=2 Hz, 1 H), 8.29 (d, J=8 Hz, 1 H), 8.07 (d, J=8 Hz, 1 H), 7.81 (ddd, J=8, 1,1 Hz, 1 H), 7.78 (s, 2 H), 7.63 (ddd, J=8, 7, 1 Hz, 1 H), 7.56 (d, J=8 Hz, 1 H), 7.52 (ddd, J=8, 7, 1 Hz, 1 H), 7.36-7.25 (m, 6 H), 6.71 (d, J=8 Hz, 1 H), 5.32 (dd, J=9, 5 Hz, 1 H), 3.51-3.39 (m, 2 H); MS (FAB+): [M+], 3 bromine isotope pattern, 723 (20%), 725 ( 55%) 727 (50%) 729 (30%); Anal.

Calc. for C31H20NBr3O3S: C, 51.27, H, 2.78, N, 1.93. Found: C, 51.19, H, 2.69, N, 1.86.

EXAMPLE 168

(R)-2-[2,6-Dibromo-4-(6-bromo-benzo[b]naphtho[2, 3-d]thiophen-11-yl)-phenoxyl-N-(3-nitrolo-propyl)3-phenyl-propionamide Dicyclohexylcarbodiimide (0.605 g, 2.926 mmol) was added to a 0° C. stirred solution of (R)-2-[2,6-dibromo-4-(6-bromo-benzo[b]naphtho[2,3-d]thiophen-11-yl)-phenoxy]-3-phenyl-propionic acid (2.08 g, 2.926 mmol), 2-aminopropionitrile (0.215 mL, 2.926 mmol), HOBT (0.448 g, 2.926 mmol) in DMF (7.2 mL) undera dry nitrogen atmosphere. After 16.5 h, the reaction mixture was added to water and partitioned between water/ethyl acetate and THF. Silica gel was added to the organic phase and the solvent was removed. The adsorbate was flashed (7:3, petroleum:ethyl acetate) to provide an off-white solid (2.23 g). This solid was dissolved in dichloromethane and silica gel was added. The solvent was removed and the adsorbate was flashed (gradient:dichloromethane to 97.5:2.5 dichloromethane:acetonitrile) to provide the title compound as a white solid (1.89 g, 85%): mp 194–195° C.: NMR (DMSO-d6); δ8.70 (t, J=6 Hz, 1 H), 8.28 (ddd, J=8, 1, 1 Hz, 1 H), 8.07 (dd, J=8, 1 Hz, 1 H), 7.80 (ddd, J=8, 7, 1 Hz, 1 H), 7.76 (s, 2 H), 7.63 (ddd, J=8, 7, 1 Hz, 1 H), 7.52 (ddd, J=8, 7, 1 Hz, 1 H), 7.48 (dd, J=8, 1, 1 Hz, 1 H), 7.37-7.24 (m, 6 H), 6.74 (d, J=8 Hz, 1 H), 5.16 (t, J=6 Hz, 1 H), 3.51-3.26 (m, 2 H), 2.62 (t, J=6 Hz, 1 H); MS (EI): [M+], 3 bromine isotope pattern, 760, 762, 764, 766; Anal. Calc. for C34H23Br3N2O2S: C, 53.50, H, 3.04, N, 3.67. Found: C, 53.24, H, 2.86, N, 4.02.

EXAMPLE 169

[2,6-Dibromo-4-(6-bromo-benzo[b]naphtho[2.3-d] thiophen- 11-yl)-phenoxy]-acetonitrile Bromoacetonitrile (0.25 mL, 3.56 mmol) was added to a room temperature, stirred suspension of 2,6-dibromo-4-(6-bromo-benzo[b]naphtho[2,3-d]thiophen-11-yl)-phenol (1.0 g, 1.78 mmol) and potassium carbonate (0.615 g, 4.45 mmol) in DMF (5 mL). After 2.5 h, the reaction mixture was added to water, filtered, washed with water and triturated with petroleum ether. The solid was dried in vacuo at 80° C. to provide the title compound as a white solid (1.03 g, 96%): NMR (DMSO-d6); δ8.29 (d, J=8 Hz, 1 H), 8.08 (d, J=8 Hz, 1 H), 7.92 (s, 2 H), 7.80 (ddd, J=8, 7, 1 Hz, 1 H), 7.65-7.51 (m, 3 H), 7.27 (ddd, J=8, 7, 1 Hz, 1 H), 6.68 (d, J=8 Hz, 1 H), 5.36 (s, 2 H); MS (+FAB): [M+], 3 bromine isotope pattern, 599, 601, 603, 605; Anal. Calc. for C24H12Br3NOS: C, 47.87, H, 2.01, N, 2.33. Found: C, 47.83, H, 1.92, N, 2.32.

EXAMPLE 170

(R)-2-[2,6-Dibromo-4-(6-bromo-benzo[b]naphtho[2, 3-d]thiophen-11-yl)-phenoxy]-3-phenyl-propionitrile Trifluoroacetic anhydride (0.375, 2.65 mmol) was added to a stirred, room temperature suspension of (R)-2- [2,6-dibromo-4-(6-bromo-benzo[b]naphtho [2,3-d ]thiophen-11-yl)-phenoxy]-3-phenyl-propionamide (1.68 g, 2.37 mmol), pyridine (0.393 mL, 4.74 mmol) and dioxane (5.4 mL). Dissolution occurred and the solution was heated in a 105° C. oil bath for 2 h. The reaction mixture was cooled to room temperature, diluted with ether, washed with 5% HCl and brine. Silica gel was added to the ether phase and the solvent was removed. The adsorbate was flash chromatographed (ether as eluent) to provide the title compound as a white solid (1.38 g, 84%): mp 160–165° C.: NMR (DMSO-d6): δ8.29 (d, J=8 Hz, 1 H), 8.07 (d, J=8 Hz, 1 H), 7.93 (d, J=2 Hz, 1 H), 7.91 (d, J=2 Hz, 1 H), 7.80 (ddd, 8, 7, 1 Hz, 1 H), 7.65-7.33 (m, 8 H), 7.23 (ddd, 8, 7, 1 Hz, 1 H), 6.65 (d, J=8 Hz, 1 H), 5.87 (t, J=7 Hz, 1 H), 3.58 (m, 2 H); MS (EI): [M+], 3 bromine isotope pattern, 689 (30%), 691 (95%) 693 (100%) 695 (40%); Anal. Calc. for C31H18Br3NOS: C, 53.74, H, 2.62, N, 2.02. Found: C, 53.60, H, 2.60, N, 1.83.

EXAMPLE 171

5-[2,6-Dibromo-4-(6-bromo-benzo[b]naphtho[2,3-d] thiophen-11-yl)-phenoxymethyl]-1 H-tetrazole Trimethylaluminum (2.55 mL, 3.84mmol, 2.0 M solution in toluene) was added to [2,6-dibromo-4-(6-bromo-benzo [b]naphtho[2,3-d]thiophen-11-yl)-phenoxy]-acetonitrile (0.615 g, 1.02 mmol) under a dry nitrogen atmosphere. Trimethylsilyl azide (0.510 mL, 3.84 mmol) was then added and the solution was heated in a 80° C. oil bath. After 16.5 h the reaction mixture was cooled to room temperature and water was cautiously added. The mixture was partitioned between dilute aqueous HCl and ethyl acetate. The layers were separated and the 2% phosphoric acid in methanol washed silica gel was added to the organic phase. The solvent was removed and the adsorbate was flashed using 2% phosphoric acid in methanol washed silica gel (eluent:gradient: 4:1 to 7:3 petroleum ether:ethyl acetate) to provide the title compound as a white solid, which was recrystallized from cyclohexane (0.365 g, 55%): mp 243–245° C.: NMR (DMSO-d6); δ8.29 (d, J=8 Hz, 1H), 8.09 (d, J=8 Hz, 1 H), 7.89 (s, 2 H), 7.80 (ddd, J =8, 7, 1 Hz, 1 H), 7.66-7.57 (m, 2 H), 7.55 (ddd, J=8, 7, 1 Hz, 1 H), 7.40 (ddd, J=8, 7, 1 Hz, 1 H), 6.71 (d, J=8 Hz, 1 H), 5.64 (s, 2 H), 1.34 (cyclohexane, 0.3 mole eq); MS (EI): [M+], 3 bromine isotope pattern, 642, 644, 646, 648; Anal. Calc. for C24H13Br3N4S.0.33 C6 H12: C, 46.39, H, 2.55, N, 8.32. Found: C, 46.28, H, 2.43, N, 7.90.

EXAMPLE 172

(R)-5-{1-[2,6-Dibromo-4-(6-bromo-benzo[b] naphtho[2,3-d]thiophen- 11-yl)-phenoxy]-2-phenyl-ethyl}-1 H-tetrazole Trimethylaluminum (7.24 mL, 14.4 mmol, 2.0 M solution in toluene) was added to (R)-2-[2,6-dibromo-4-(6-bromo-benzo[b]naphtho[2,3-d]thiophen-11-yl)-phenoxy ]-3-phenyl-propionamide (1.33 g, 1.93 mmol) under a dry nitrogen atmosphere. Trimethylsilyl azide (1.92 mL, 14.4 mmol) was then added and the solution was heated in a 85° C. oil bath. After 7 h the reaction mixture was cooled to room temperature and diluted with ether. Water was cautiously added and after bubbling subsided, the mixture was partitioned between dilute aqueous HCl and ether. The ether phase was concentrated and triturated with petroleum ether, a small amount of methanol, a small amount of ether and finally petroleum ether to provide the title compound as a white solid (0.802 g, 57%): mp 238–239° C.: NMR (DMSO-d6); δ8.28 (d, J=8 Hz, 1 H), 8.07 (d, J=8 Hz, 1 H), 7.81-7.74 (m, 3 H), 7.62 (ddd, 8, 7, 1 Hz, 1 H), 7.57-7.53 (m, 2 H), 7.44 (ddd, 8, 7, 1 Hz, 1 H), 7.38-7.22 (m, 5 H), 6.60 (d, J=8 Hz, 1 H), 5.87 (dd, J=9, 7 Hz, 1 H), 3.90 (dd, J=13, 7, 1H), 3.80 (dd, J=13, 8, 1H); MS (-ESI): [M–H], 3 bromine isotope pattern, 731 (60%), 733 ( 90%) 735 (100%) 737 (60%); Anal. Calc. for C31H19Br3N4OS: C, 50.64, H, 2.61, N, 7.62. Found: C, 49.65, H, 2.434, N, 7.16.

EXAMPLE 173

(R)-6-Bromo-11-[3,5-dibromo-4-(1-hydroxymethyl-2-phenyl-ethoxy)-phenyl]-benzo[b]naphtho[2,3-d]thiophene A solution of R)-2-[2,6-dibromo-4-(6-bromo-benzo[b]naphtho[2,3-d]thiophen-11-yl)-phenoxy]-3-phenyl-propionic acid, methyl ester (0.30 g, 0.414 mmol) in THF (4.2 mL) was added dropwise to a −78 ° C., stirred solution of mixed hydride (0.435 mL, 0.414 mmol) of lithium aluminum hydride/aluminum chloride (1.0 M solution in THF) in THF (3 mL) under a dry nitrogen atmosphere over a period of 5 min. After 1 h., the solution was allowed to warm to ambient temperature. After 2 h. the reaction mixture was quenched carefully with methanol (3 mL) and further diluted with water (80 mL). Aqueous mixture was extracted with ethyl acetate (2×80 mL). The ethyl acetate extracts were washed with water, dried with brine and anhydrous MgSO4, and concentrated to provide the title compound as a white solid (0.28 g, 97%): mp 83–85: MS (EI): [M+], 3 bromine isotope pattern, 694, 696, 698, 700.

EXAMPLE 174

(R)-6-Bromo-11-[3,5-dibromo-4-( 1-bromomethyl-2-phenyl-ethoxy)-phenyl]-benzo[b]naphtho[2,3-d]thiophene Diethylazodicarboxylate (0.151 mL, 0.96 mmol) was added dropwise to a 0° C., stirred solution of triphenylphosphine (0.257 g, 0.98 mmol) in THF (6 mL) under a dry nitrogen atmosphere. After 20 min., lithium bromide was added to a nearly colorless reation mixture, followed by adding a solution of (R)-6-bromo-1 1-[3,5-dibromo-4-(1-hydroxymethyl-2-phenyl-ethoxy)-phenyl]-benzo[b]naphtho[2,3-d]thiophene (0.273 g, 0.392 mmol) in THF (3 mL). After 1 h, the solution was allowed to warm to ambient temperature. After 2 h, the reaction mixture was quenched with water (0.2 mL) and further diluted with ethyl ether (50 mL). Silica gel ( 8 mL) was added. Solvent was removed and the silica adsorbate was flash chromatographed (eluent 98:2 petroleum ether:ethyl acetate) to provide the title compound as a white solid (0.23 g, 73%): mp >90° C. (dec.): MS (EI): [M+], 4 bromine isotope pattern, 756, 758, 760, 762, 764; Anal. Calc. for C28H17Br3N2O3S.0.25 hexane: C, 49.97, H, 2.97, N, 0.00. Found: C, 49.97, H, 2.83, N, 0.02.

EXAMPLE 175

5-[2,6-Dibromo-4-(6-bromo-benzo[b]naphtho[2,3-d]thiophen-11-yl)-phenoxy]-thiazolidinedione-2.4-dione Lithium (bis)trimethylsilylamide (1.0 M in THF, 5.32 mL, 5.32 mmol) was added dropwise over a 20 min period to a −78° C. stirred solution of 2,6-dibromo-4-(6-bromo-benzo[b]naphtho[2,3-d]thiophen-11-yl)-phenol (1.50 g, 2.66 mmol), 5-bromothiazolidine dione (Zask, et al., *J. Med Chem,* 1990, 33, 1418–1423, 0.522 g, 2.66 mmol) and THF (20 mL) under a dry nitrogen atmosphere. After 45 min, the reaction mixture was warmed to room temperature. After 2 h, the reaction mixture was added to water and acidified with 10% HCl and extracted with ether. Silica gel was added to the ether phase and the solvent was removed. The adsorbate was flashed (7:3 petroleum ether:ethyl acetate) to provide the title compound a white solid (0.882 g, 49%): NMR (DMSO-d6); δ12.75 (s, 1H), 8.30 (dd, J=8, 1 Hz, 1 H), 8.09 (ddd, J =8, 1, 1 Hz, 1 H), 7.92 (s, 2 H), 7.81 (ddd, J=8, 7, 1 Hz, 1 H), 7.67-7.59 (m, 2 H), 7.54 (ddd, J=8, 7, 1 Hz, 1 H), 7.27 (ddd, J=8, 7, 1 Hz, 1 H), 6.96 (s, 1 H), 6.65 (d, J=8 Hz, 1 H); MS (−ESI): [M−H]-, 3 bromine isotope pattern, 674, 676, 678, 680; Anal. Calc. for C25H12Br3NO3S2: C, 44.27, H, 1.78, N, 2.07. Found: C, 44.20, H, 1.90, N, 2.14.

EXAMPLE 176

Phosphoric acid Di-tert-Butyl ester 2,6-Dibromo-4-(6-bromo-benzo[b]naphtho[2,3-d ]thiophen-11-yl)-phenyl ester Tetrazole (0.215 g, 3.0 mmol) was added in one portion to a stirred suspension of 2,6-dibromo-4-(6-bromo-benzo[b]naphtho[2,3-d]thiophen-11-yl)-phenol (0.527 g, 1.0 mmol), di-tert-butyl N,N-diethyhlphosporamidate (93%, 0.353 mL, 1.0 mmol) in THF at room temperature under a dry nitrogen atmosphere. Dissolution occurred. After 1 h, the solution was cooled to −40° C. and a suspension occurred. A solution of meta-chlorobenzoic aid (80%, 0.26 g, 1.2 mmol) was added slowly so as not to raise the temperature. The resultant suspension was slowly warmed to room temperature where dissolution occurred. Aqueous 10% sodium bisulfite was added and the biphasic mixture was stirred for 20 min. The reaction mixture was taken up in ether and wasshed with aqeous sodium bisulfite and saturated aqueous sodium bicarbonate. The ether phase was concentrated and filtered. The white solid was triturated with ether and then flash chromatographed (gradient: dichloromethane to 97.5:2.5 dichloromethane:acetonitrile) to provide the title compound as a white solid (0.324 g, 43%): NMR (DMSO-d6);: δ8.25 (d, J=9 Hz, 1 H), 8.06 (d, J=8 Hz, 1 H), 7.86 (s, 2 H), 7.75 (ddd, J=8, 7, 1 Hz, 1 H), 7.56 (ddd, J=8, 7, 1 Hz, 1 H), 7.50 (ddd, J=8, 7, 1 Hz, 1 H), 7.44 (d, J 8 Hz, 1 H), 7.14 (ddd, J=8, 7, 1 Hz, 1 H), 6.77 (d, J=8 Hz, 1 H), 1.51 (s, 18 H); MS (+FAB): [M+], 3 bromine isotope pattern, 752, 754, 756, 758; Anal. Calc. for C30H28Br3O4PS: C, 47.71, H, 3.74, N, 0.00. Found: C, 47.87, H, 3.69, N, 0.10.

EXAMPLE 177

Phosphoric acid Mono-[2,6-dibromo-4-(6-bromo-benzo[b]naphtho[2,3-d]thiophen-11-yl)-phenyl ]ester HCl (4 N in dioxane, 1.5 mL, 6 mmol) was added to a room temp[erature, stirred solution of phosphoric acid di-tert-butyl ester 2,6-dibromo-4-(6-bromo-benzo[b]naphtho[2,3-d]thiophen-11-yl)-phenyl ester (0.290 g, 0.384 mmol) in dioxane (6 mL). After 4.5 h, the solvent was removed and the solid was triturated with ether, petroleum ether and dried in vacuo to provide the title compound as a white solid (0.220, 86%): NMR (DMSO-d6); δ8.29 (d, J=8 Hz, 1 H), 8.08 (d, J=8 Hz, 1 H), 7.83 (s, 2 H), 7.80 (ddd, J=8, 7, 1 Hz, 1 H), 7.64 (ddd, J=8, 7, 1 Hz, 1 H), 7.56-7.51 (m, 2 H), 7.26 (ddd, J=8, 7, 1 Hz, 1 H), 6.71 (d, J=8 Hz, 1 H); MS (+FAB): [M+], 3 bromine isotope pattern, 640, 642, 644, 646; Anal. Calc. for C22H12Br3O4PS: C, 41.09, H, 1.88, N, 0.00. Found: C, 41.71, H, 2.22, N, 0.07.

EXAMPLE 178

2-[2,6-Dibromo-4-(6-bromo-benzo[b]naphtho[2,3-d]thiophen-11-yl)-phenoxy]-2-methyl-propionic acid Solid sodium hydroxide (0.682 g, 17.05 mmol) was added in three equal portions to a 0° C., stirred suspension of 2,6-dibromo-4-(6-bromo-benzo[b]naphtho[2,3-d ]thiophen-11-yl)-phenol (0.800 g, 1.421 mmol), 1,1,1 -trichloro-2- methyl-2-propanol tetrahydrate (1.06 g, 4.263 mmol) in acteone (7.5 mL) over 3 h period. The resulting suspension was warmed to room temperature and stirred for 15 h. The reaction mixture was added to water, acidified with 10% aqueous HCl and extracted with ether. To the ether phase was added acid washed (2% phosphoric acid in methanol) silica gel and the solvent was removed. The adsorbate was flash chromatographed (2% phosphoric acid in methanol treated silica gel; eluent: gradient: 9:1 to 8:2 petroleum ether:ethyl acetate) to provide the title compound as an white solid (0.620g, 67%): mp 197–199° C.: NMR (DMSO-d6); δ13.00 (broad s, 1 H), 8.29 (d, J=8 Hz, 1 H), 8.09 (d, J=8 Hz, 1 H), 7.85 (s, 2 H), 7.81 (ddd, J=7, 6, 1 Hz, 1 H), 7.67-7.60 (m, 2 H), 7.52 (ddd, J=8, 7, 1 Hz, 1 H), 7.23 (ddd, J=8, 7, 1 Hz, 1 H), 6.60 (d, J=8 Hz, 1 H), 1.70 (s, 6 H); MS (-ESI): [M–H], 3 bromine isotope pattern, 645 (20%), 647 ( 60%) 649 (1000%) 651 (30%); Anal. Calc. for C26H17Br3O3S: C, 48.10, H, 2.64, N, 0.00. Found: C, 47.78, H, 2.76 , N, 0.31.

EXAMPLE 179

3-[2,6-Dibromo-4-(6-bromo-benzo[b]naphtho[2,3-d]thiophen-11-yl )-phenoxyl-propionic acid β-Propiolactone ( 0.186 mL, 2.66 mmol) was added to a stirred, room temperature solution of 2,6-dibromo-4-(6-bromo-benzo[b]naphtho[2,3-d]thiophen- 11 -yl)-phenol (1.5 g, 2.66 mmol), potassium tert-butoxide (0.314 g, 2.66 mmol) in THF (33 mL) under a dry nitrogen atmosphere. After 2 days the reaction mixture was added to water, acidified with 10% aqueous HCl and extracted with ethyl acetate. To the ethyl acetate phase was added acid washed (2% phosphoric acid in methanol) silica gel and the solvent was removed. The adsorbate was flash chromatographed (2% phosphoric acid in methanol treated silica gel ; eluent: gradient: 9:1 to 8:2 petroleum ether:ethyl acetate) to provide the title compound as an off-white solid (0.748 g, 44%): mp 218–220° C.: NMR (DMSO-d6);δ12.48 (broad s, 1H), 8.28 (d, J=8 Hz, 1H), 8.08 (d, J=8 Hz, 1H), 7.83 (s, 2 H), 7.79 (ddd, J=7, 6, 1 Hz, 1 H), 7.64-7.57 (m, 2 H), 7.52 (ddd, J=8, 7, 1 Hz, 1H), 7.31 (ddd, =8, 7, 1 Hz, 1 H), 6.69 (d, J=8 Hz, 1 H), 4.44 (t, J=6 Hz, 2 H), 2.89 (t, J=6 Hz, 2 H); MS (+FAB): [M+], 3 bromine isotope pattern, 632 (30%), 634 ( 70%) 636 (80%) 638 (40%); Anal. Calc. for C25H15Br3O3S: C, 47.27, H, 2.38, N, 0.00. Found: C, 47.68, H, 2.36, N, 0.01.

EXAMPLE 180

(R)-3-[2,6-Dibromo-4-(6-bromo-benzo[b]naphtho[2,3-dlthiophen- 11 -yl)-phenoxyl-butyric acid Diethylazodicarboxylate (0.420 mL, 2.66 mmol) was added dropwise to a stirred, ambient temperature suspension of 2,6-dibromo-4-(6-bromo-benzo [b]naphtho[2,3-d] thiophen-11-yl)-phenol (0.50 g, 0.89 mmol), methyl-(S)-(+)-3-hydroxybutyrate (0.30 mL, 2.66 mmol), and triphenylphosphine (0.70 g, 2.66 mmol) in benzene (6 mL) under a dry nitrogen atmosphere. Dissolution occurred and the solution was heated in an 80° C. oil bath for 4.0 h. Upon cooling to room temperature, the reaction mixture was diluted with dichloromethane and silica gel (15 mL) was added. Solvents were removed and the silica adsorbate was flash chromatographed (eluent 9:1 petroleum ether: ethyl acetate) to provide the methyl ester as a white solid (0.345 g, 52 %): mp 143–144° C.: 10% Aqueous hydrochloride (3.0 mL) was added to a stirred solution of this methyl ester (0.308 g, 0.464 mmol) in 4.0 M hydrogen chloride/dioxane (6.0 mL) at ambient temperature. The suspension in a presure reactor was immersed in an 80° C. oil bath for 2.0 h. The solution was concentrated and ethyl ether (40 mL) was added to the resulted residue. Silica gel (3 mL) was added. Solvents were removed and the silica adsorbate was flash chromatographed (eluent: ethyl acetate) to provide the title compound as a white solid (0.143 g, 48%): mp 175–176° C.: NMR (CDCl3); δ8.36 (d, J=8 Hz, 1 H), 7.83 (d, J=8 Hz, 1 H), 7.68 (ddd, J =8, 7, 1 Hz, 1 H), 7.61-7.58 (m, 3 H), 7.52 (dd, J=8 Hz, 1 H), 7.43 (ddd, J=8, 7, 1 Hz, 1 H), 7.17 (ddd, J=8, 7, 1 Hz, 1 H), 6.78 (d, J=8 Hz, 1 H), 5.29 (q, J=7 Hz, 1 H,), 3.20 (dd, J=6 Hz, 1 H), 2.91 (dd, J=6 Hz, 1 H), 1.62 (d, J=7 Hz, 3 H); MS (EI): M+, 3 bromine isotope pattern, 646, 648, 650, 652; Anal. Calc. for C26H17Br3O3S: C, 48.10, H, 2.64, N, 0.00. Found: C, 48.49, H, 2.63, N, 0.16.

EXAMPLE 181

(R)-2-[4-(6-Hdroxy-benzo[b]naphtho[2,3-d]thiophen-11-yl)-2,6-dibromo-phenoxy]-3-phenyl-propionic acid, methyl ester To a cold (–70° C. dry ice/isopropanol bath) solution of (R)-2-[4-(6-methoxy-benzo [b]naphtho[2,3-d]thiophen-1 1-yl)-2,6-dibromo-phenoxy]-3-phenyl-propionic acid, methyl ester (1.10 g, 1.63 mmol) in dry methylene chloride (11 mL) was added a 1 M solution of boron tribromide in methylene chloride (5.20 mL, 5.20 mmol, 3.2 eq) dropwise over a period of 25 minutes under a dry nitrogen atmosphere. After standing at –55° C. overnight the reaction mixture was kept stirring between –20° and –30° C. for five hours, then poured into water (50 mL) and the organics were extracted with diethyl ether (100 mL). The diethyl ether layer was washed with water and brine, concentrated, and chased with petroleum ether to the title compound as a yellow solid (1.10, 100%).

EXAMPLE 182

(R)-2-[4-(6-Benzyloxy-benzo[b]naphtho[2,3-d]thiophen-11-yl]-2,6-dibromo-phenoxyl-3-phenyl-propionic acid, methyl ester To a solution of (R)-2-[4-(6-hydroxy-benzo[b]naphtho[2, 3-d]thiophen-11-yl]-2,6-dibromo-phenoxy]-3-phenyl-propionic acid, methyl ester (0.50 g, 0.755 mmol) in dry N,N-dimethylformamide (5 mL) was added benzyl bromide (0.27 mL, 2.27 mmol, 3 eq) dropwise at room temperature under a dry nitrogen atmosphere. After stirring about 17 hours the reaction was quenched with water (50 mL) and the organics were extracted with ether. The extracts were washed with water, and brine and combined with silica gel. The solvent was removed and the adsorbate was flash chromatographed (⁹⁄₃ petroleum ether/ethyl acetate) and the solvents chased with benzene and petroleum ether to provide the title compound as a pale yellow solid (0.572 g, 84%): NMR (CDCl3); δ8.30 (ddd, J=8, 1, 1 Hz, 1 H), 7.82 (ddd, J=8,1,1 Hz, 1 H), 7.68 (ddd, J=8, 1, 1 Hz, 2 H), 7.62 (dd, J=3, 2 Hz, 2 H), 7.60-7.55 (m, 2 H), 7.51-7.26 (m, 10 H), 7.16 (ddd, J=8, 7,1 Hz, 1 H), 6.81 (ddd, J=8, 1, Hz, 1 H), 5.34 (s, 2 H), 5.25 (dd, J=6, 2 Hz, 1 H), 3.76 (s, 3 H), 3.59 (septet, J =Hz, 2 H); MS (EI): [M+], 2 bromine isotope pattern, 750 (2%), 752 (3.5%), 754 (2.5%); Anal Calc. for C39H28Br2O4S: C, 62.25, H, 3.75, N, 0.00; Found C, 61.66, H, 3.53, N, 0.25.

EXAMPLE 183

(R)-2-[2,6-Dibromo-4-(6-methoxycarbonylmethoxy-benzo[b]naphtho[2,3-d]thiophen-11 -yl)-phenoxyl-3-phenyl-propionic acid methyl ester To a solution of (R)-2-[2,6-dibromo-4-(6-hydroxy-benzo [b]naphtho[2,3-d ]thiophen-11-yl)-phenoxy]-3-phenylpropionic acid methyl ester (0.60 g, 0.906 mmol) in anhydrous N,N-dimethylformamide was added potassuim carbonate (0.376 g, 2.72 mmol, 3 eq) and methylbromoacetate (0.26 mL, 2.72 mmol, 3 eq) at room temperature under a dry nitrogen atmosphere. After stirring for 24 hours the reaction mixture was combined with water (60 mL) the organics were extracted with diethyl ether (2×100 mL). The extracts were combined and washed with water (2×100 mL) and brine (100 mL). Silica gel was added and the solvents removed. The adsorbate was twice flash chromatographed (eluent 88/12 petroleum ether/ethyl acetate and 85/15 ethyl ether/ethyl acetate) to provide the title compound as a white solid (0.493 g, 73%): NMR (CDCl3); δ8.38 (d, J=8 Hz, 1 H), 7.81 (d, J =Hz, 1 H), 7.64-7.59 (m, 3 H), 7.55 (d, J=8 Hz, 1 H), 7.48 (ddd, J=8, 7, 1 Hz, 1 H), 7.43-7.26 (m, 6 H), 7.16 (ddd, J=8,7,1 Hz, 1 H), 6.79 (d, J=8 Hz, 1 H), 5.25 (dd, J=8, 6 Hz, 1 H), 4.94 (s, 2 H), 3.92 (s, 3 H), 3.76 (s, 3 H), 3.57 (septet, J=7 Hz, 2 H); MS (EI): [M+], 2 bromine isotope pattern, 732 (1.8%), 734 (4%), 736 (0.8%); Anal. Calc. for C35H26Br2O6S:, 57.24, H, 3.57, N, 0.00. Found: C, 57.01, H, 3.42, N, -0.07.

EXAMPLE 184

(R)-2-[4-(6-Benzyloxy-benzo[b]naphtho[2,3-d] thiophen-11-yl]-2-6-dibromo-phenoxy }-3-phenyl-propionic acid To a solution of (R)-2-[4-(6-benzyloxy-benzo[b]naphtho [2,3-d]thiophen-11-yl ]-2-6-dibromo-phenoxy}-3-phenyl-propionic acid methyl ester (0.484 g, 0.644 mmol) in tetrahydrofuran (9 mL) and methanol (3 mL) was added an aqueous solution of potassuim hydroxide (1 N, 1.29 mL, 1.29 mmol, 2 eq) dropwise at room temperature. After stirring 2.5 hours the solvents were removed and the residue was partitioned between dilute aqueous hydrochloric acid and ether. This biphasic system was shaken vigorously and the layers were separated. The ether layer was washed with water and brine and combined with acid treated (2% phosphoric acid in methanol) silica gel. The ether was removed and the adsorbate was flash chromatographed (acid treated silica gel, 9⁰/10 petroleum ether/ethyl acetate) to provide the title compound as a white solid (0.354 g, 74.5%): [a]25/D =+24.77° (10.091 mg/mL, CHCl3); NMR (CDCl3); δ8.29 (d, J=8 Hz, 1 H), 7.80 (d, J=8 Hz, 1 H), 7.68 (d, J=8 Hz, 2 H), 7.61 (dd, J=10, 2 Hz, 2 H), 7.59-7.56 (m, 1 H), 7.51-7.47 (m, 3 H), 7.46-7.27 (m, 8H), 7.15 (ddd, J=8, 7, 1 Hz, 1H), 6.80 (d, J =Hz, 1H), 5.47 (t, J=7 Hz, 1 H), 5.34 (s, 2 H), 3.59 (d, J=7 Hz, 2 H); MS (CI): [(M+H)+], 2 bromine isotope pattern, 737 (6%), 739 (10%), 741 (4%); Anal. Calc. for C38H26Br2O4S: C, 61.80, H, 3.55, N, 0.00. Found: C, 62.15, H, 3.52, N, 0.07.

EXAMPLE 185

(R)-2-[2,6-Dibromo-4-(6-carboxymethoxy-benzo[b] naphtho[2,3-d]thiophen-11-yl)-phenoxyl-3-phenyl-propionic acid To a solution of (R)-2-[2,6-dibromo-4-(6-carboxymethoxy-benzo [b]naphtho[2,3-d]thiophen-11-yl)-phenoxy]-3-phenyl-propionic acid, methyl ester (0.436 g, 0.594 mmol) in tetrahydrofuran (9 mL) and methanol (3 mL) was added an aqueous solution of potassuim hydroxide (1 N, 2.37 mL, 2.37 mmol, 4 eq) dropwise at room temperature. After stirring 3.5 hours the solvents were removed and the residue was combined with water. The suspension was acidified with 10% aqueous hydrochloric acid and diethyl ether was added. The biphasic mixture was shaken well before the layers were separated. The organic phase was washed with water and concentrated. The residue was triturated with petroleum ether and dried in vacuo to provide the title compound as a white solid (0.366 g, 87%): mp 110–120° C.; [a]25/D =+49.620 (10.076 mg/mL, methanol); NMR (DMSO-d6): δ13.21 (broad s, 2 H), 8.40 (d, J=8 Hz, 1H), 8.03 (d, J=8 Hz, 1H), 7.74 (dd, J=2, 8 Hz, 2 H), 7.68 (ddd, J=8, 7, 1 Hz, 1 H), 7.57 (ddd, J=8, 7, 1 Hz, 1H), 7.52 - 7.45 (m, 2 H), 7.43 - 7.38 (m, 2 H), 7.37 -7.11 (m, 2 H), 7.10–7.20 (m, 2 H), 6.69 (d, J=8Hz, 1H), 5.30 (t, J=7 Hz, 1 H), 4.90 (s, 2 H), 3.41 (d, J=7 Hz, 2 H); MS (+FAB): [M+], 2 bromine isotope pattern, 704 (9%), 706 (22%), 708 (22%); Anal. Calc. for C33212Br2O6S: C, 56.11, H, 3.14, N, 0.00. Found: C, 55.93, H, 3.28, N, 0.09.

EXAMPLE 186

[2,6-Dibromo-4-(6-bromo-5,5-dioxo-5 H-6-benzo[b] naphtho[2,3-d]thiophen-11-yl)]-phenoxy]-acetic acid To a stirred suspension of [2,6-dibromo-4-(6-bromo-benzo[b]naphtho[2,3-d ]thiophen-11-yl)-phenoxy]-acetic acid (0.050 g, 0.0805 mmol) in glacial acetic acid (2 mL) was added a 30% aqueous solution of hydrogen peroxide (0.082 mL, 0.805 mmol, 10 eq) dropwise at room temperature. The suspension was heated at 105–107° C. for 2.5 hours. The reaction mixture was cooled to room temperature and the white solid was filtered, and washed with petroleum ether to give the title compound (0.042 g, 79%): mp 281–282.5° C.; NMR (DMSO-d6): δ8.42 (d, J=8Hz, 1 H), 7.66-7.61 (m, 2 H), 7.50 (d, J=8Hz, 1 H), 6.51-6.48 (m, 1 H), 4.75 (s, 2 H), 1.90 (s, 3 H); MS (EI): M+], 3 bromine isotope pattern, 650 (32%), 652 (95%), 654 (100%), 656 (38%); Anal. Calc. for C24H13Br3O5S - CH3COOH: C, 43.79, H, 2.40, N, 0.00. Found: C, 43.66, H, 2.26, N, 0.08.

EXAMPLE 187

[2,6-Dibromo-4-[6-bromo-5-oxo-5 H-4-benzo[b] naphtho[2,3-d]thiophen-11-yl)l-phenoxyl-acetic acid To a stirred suspension of [2,6-dibromo-4-(6-bromo-benzo[b]naphtho[2,3-d ]thiophen-11-yl)]-phenoxy]-acetic acid (0.450 g, 0.725 mmol) in glacial acetic acid (4 mL) was added a 30% aqueous solution of hydrogen peroxide (0.75 mL, 7.25 mmol, 10 eq) dropwise at room temperature. The suspension was heated to 105° C. and when dissolution did not occur an additional 15 mL of acetic acid was added. Dissolution occurred rapidly and the solution was heated at 105° C. for 5.5 hours. On cooling to room temperature a yellow solid precipitated. The solid was removed and combined with the diethyl ether extracts taken from the diluted filtrate. The solid did not completely dissolve in the diethyl ether nor when ethyl acetate was added and was removed by filtration. The solid was recrystallized from acetic acid with hot filtration to the title compound as a yellow solid (0.055g, 12%): mp 287–289° C.; NMR (DMSO-d 6); δ13.3 (broad band, 1 H), 8.39 (d, J=8, 1H), 8.14 (ddd, J=8, 1, 1 Hz, 1 H), 7.91 (d, J=2 Hz, 1 H), 7.84 (ddd, J=8, 7, 1 Hz, 1 H), 7.77-7.72 (m, 2 H), 7.60-7.50 (m, 3 H), 6.45 (ddd, J=8, 1, 1 Hz, 1 H), 4.75 (s, 2 H); MS (EI): [M+], 3 bromine isotope pattern, 634 (25%), 636 (70%), 638 (75%), 640 (30%); Anal. calc. for C24H13Br3O4S: C, 45.24, H, 2.06, N, 0.00. Found: C, 44.89, H, 1.76, N, 0.06.

EXAMPLE 188

R)-2-[2,6-Dibromo-4-(6-bromo-5.5-dioxo-5 H-5 (λ.6)-benzo[b]naphtho[2,3-d]thiophen-1 1-yl)-phenoxyl-3-phenyl-propionic acid, methyl ester A stirred suspension of (R)-2-[2,6-Dibromo-4-(6-bromo-benzo[b]naphtho[2,3-d ]thiophen-11-yl)-phenoxy]-3- phenyl-propionic acid, methyl ester (0.94g, 1.30 mmol) in glacial acetic acid (38 mL) and a 30% solution of hydrogen peroxide (1.5 mL, 13 mmol) was heated at 100–110° C. (dissolution occurred) for 5.5 hours and then remained at ambient temperature overnight. The solvents were removed. The solid residue was dissolved in methylene chloride and silica gel was added. The solvent was removed and the adsorbate was flash chromatographed (80:20 Petroleum ether:ethyl acetate) to the title compound as a yellow solid 0.937 g, 95%): mp 156–157° C.: [a]D25 =+47.920 (10.017 mg/mL CHCl3); NMR (CDCl3); δ8.48 (d, J=7 Hz, 1 H), 7.89 (d, J=6 Hz, 1H), 7.74 (ddd, J=8, 7, 1 Hz, 1 H,), 7.64 (ddd, J=8, 7, 1 Hz, 1 H), 7.54 (dd,J =7, 4, Hz, 2 H), 7.50-7.27 (m, 8 H), 6.44 (dd, J=7, 1 Hz), 5.27 (dd, J=6, 8 Hz, 1 H), 3.75 (s, 3 H), 3.56 (m, 2 H); MS (+FAB): [M+H]+, 3 Bromine pattern, 755 (8%), 757 (20%), 759 (30%), 761 (10%); Anal. Calcd. for C32H21Br3O5S: C, 50.75, H, 2.80, N, 0.00. Found: C, 50.75, H, 2.61, N, -0.04.

EXAMPLE 189

(R)-2-[2,6-Dibromo-4-(6-bromo-5,5-dioxo-5 H-5 (λ6)-benzo[b]naphtho[2,3-d]thiophen-11-yl)-phenoxyl-3-phenyl-propionic acid Aqueous potassium hydroxide (1 N, 2.22 mL, 2.22 mmol) was added to a stirred solution of (R)-2-[2,6-dibromo-4-(6-bromo-5,5-dioxo-5 H-5(λ6)-benzo [b]naphtho[2,3-d] thiophen-11-yl)-phenoxy]-3-phenyl-propionic acid, methyl ester (0.832 g, 1.11 mmol) in tetrahydrofuran (7.5 mL)/ methanol (5.5 mL). After 1 h the solution was concentrated, diluted with water and acidified with 10% aqueous HCl. The organics were extracted with ether. The ether was removed and the residue was dried in vacuo overnight at 53 C. to give the title compound as a white solid (0.534 g, 65%): mp 173–193° C.: [a]D25=+42.73; NMR (CDCl3); δ8.47 (dd, J=8, 1 Hz, 1 H), 7.76 (dd, J=8, 1 Hz, 1 H), 7.74 (ddd, J=7, 3, 1 Hz, 1 H,), 7.64 (ddd, J=7, 3, 1 Hz, 1H), 7.55 - 7.46 (m, 3 H,), 7.41 - 7.27 (m, 7 H), 6.42 (d, J=8 Hz, 1H), 5.44 (t, J=7 Hz, 1 H), 3.57 (d, J=7 Hz, 2 H); MS (EI): [M+] 3 bromine pattern 740 (2%), 742 (8%), 744 (6% ), 746 (2%); Anal. Calc. for: C31H19Br3O5S: C, 50.09, H, 2.58, N 0.00. Found: C, 50.18, H, 2.71, N, 0.00.

EXAMPLE 190

5'-Benzo[b]naphtho[2,3-d]thiophen-11-yl-[1,1':3', 1Δ]terphenyl-2'-ol

A solution of 4-(benzo[b]naphtho[2,3-d]thiophen-11-yl)-2,6-diiodo-phenol (1.26 g, 2.18 mmol), phenylboronic acid (0.584 g, 4.80 mmol), barium hydroxide octahydrate (2.75 g, 8.72 mmol), palladium acetate (10 mg, 0.087 mmol) and 6:1 dimethoxyethane:water (49 ml) was heated to 80° C. overnight. An additional amount of phenylboronic acid (0.29 g, 2.40 mmol) and a catalytic amount of palladium acetate were added, and the solution was heated for four additional hours. The reaction mixture was acidified to pH 1 with conc. HCl, diluted with ethyl acetate and washed with water. The solvents was removed and the crude product was flash chromatographed (99:1 ethyl acetate:pet. ether) to provide the title compound as a white solid (0.948 g, 91%): NMR (DMSO-d6); δ8.76 (s, 1 H), 8.61 (s, 1 H), 8.05 (d, J =8 Hz, 1 H), 7.99 (d, J=8 Hz, 1 H), 7.77 (d, J=9 Hz, 1 H), 7.63-7.30 (m, 13H), 7.25 (s, 2 H), 7.22 (ddd, J=8, 8, 1 Hz, 1 H), 7.08 (d, J=9 Hz, 1 H); MS (EI): 492 (100%, MI); Anal. Calc. for C34H22OS.1.6H2O: C, 80.48, H, 5.01, N, 0.00. Found: C, 80.26, H, 4.63, N, 0.05.

EXAMPLE 191

(5'-Benzo[b]naphtho[2,3-d]thiophen-11-yl)-[1,1'; 3', 1"]terphenyl-2'yloxy)-acetic acid 5'-Benzo[b]naphtho[2,3-d]thiophen-11-yl-[1,1';3',1"] terphenyl-2'-ol (0.145 g, 0.30 mmol), methyl bromoacetate (0.057 mL, 0.61 mmol), potassium carbonate (0.046 g, 0.33 mmol) and N,N-dimethylformamide (5 mL) were combined and stirred at ambient temperature for 3 day. The reaction mixture was added to water and extracted with ethyl acetate. The ethyl acetate layer was washed with aqueous 1 N Hcl, sat. sodium bicarbaonte and dried *(magnesium sulfate). The ethyl acetate was removed and and the crude product was flash chromatographed (95:5 ethyl acetate:pet. ether) to provide (5'-benzo[b]naphtho[2,3-d]thiophen-11-yl)-[1,1';3', 1"]terphenyl-2'-yloxy)-acetic acid, methyl ester as a white solid (0.177 g). Aqueous potassium hydroxide (1 N, 1.61 mL, 1.61 mmol) was added to a stirred solution of this methyl ester in 3:2 THF:methanol (5.0 mL) at ambient temperature. After 2 h the solution was concentrated, diluted with water (75 mL) and acidified with 10% aqueous HCl. The solid was filtered and washed with water to provide the title compound as a white solid (0.119 g, 69%): mp>132° C. (dec): NMR (DMSO-d6); δ12.60 (s, 1H), 8.63 (s, 1 H), 8.07 (d, J=8 Hz, 1 H), 7.99 (d, J=8 Hz, 1H), 7.76 (d, J=8 Hz, 1H), 7.67-7.41 (m, 11 H), 7.40-7.33 (m, 2 H), 7.24 (ddd, J=8, 8, 1 Hz, 1 H), 6.91 (d, J=9 Hz, 1 H); MS (EI): 536 (100%, MI); Anal. Calc. for C36H24O3S.0.5H2O: C, 79.24, H, 4.62, N, 0.00. Found: C, 78.80, H, 4.57, N, 0.09.

EXAMPLE 192

3-Bromo-5-(6-bromo-benzo[b]naphtho[2,3-d] thiophen-11-yl)-2-benzyloxy-phenol

A suspension of 3-bromo-5-(6-bromo-benzo[b]naphtho [2,3-d]thiophen-11-yl)-benzene-1,2-diol (0.390 g, 0.78 mmol) and potassium carbonate (0.108 g, 0.78 mmol) in DMF (4 mL) was stirred at 0 ° C. under a dry N2 atmosphere for 20 min. Benzyl bromide (0.093 mL, 0.78 mmol) was added dropwise to this mixture over a period of ten minutes. After the mixture was stirred at 0 ° C. for 6.5 h., the reaction mixture was quenched with aqueous hydrochloric acid to pH 1 and further diluted with water (60 mL) and aqueous mixture was extracted with methylene chloride (2×60 mL). The combined organic extracts were washed with water and dried with brine. Silica gel (5 mL) was added. Solvent was removed and the adsorbate was flash chromatographed (eluents: petroleum ether:methylene chloride 6:4 to petroleum ether:ethyl acetate 6:4) to provide a mixture (271 mg, 59%) of the title compound (87%) and 2-bromo-4-(6) -bromo-benzo[b]naphtho[2,3-d]thiophen- 11 -yl)-6-benzyloxy-phenol (13%). The mixture was used for next reaction without separation: NMR (CDCl3): δ8.35 (d, J=8 Hz, 1 H), 7.79 (d, J=8 Hz, 1 H), 7.72-7.33 (m, 9 H), 7.18 (d, J=2 Hz, 1 H), 7.17 (ddd, J=8, 7, 1 Hz, 1 H), 6.93 (d, J=2 Hz, 1H), 6.87 (d, J=8 Hz, 1 H), 5.71 (s, 1H), 5.32 (t, J=7 Hz,2 H).

EXAMPLE 193

2-Bromo-4-(6-bromo-benzo[b]naphtho[2,3-d] thiophen-11yl)-6-methoxy-phenol

Iodomethane (0.086 mL, 1.38 mmol) was added dropwise to a room temperature, stirred light suspension of a mixture [3-bromo-5-(6-bromo-benzo [b]naphtho[2,3-d]thiophen-11-yl)-2-benzyloxy-phenol (87% pure, contaminated with 2-bromo-4-(6-bromo-benzo[b]naphtho[2,3-d]thiophen-11-yl)-6-benzyloxy-phenol (13%), 0.271 g, 0.46 mmol), potassium carbonate (0.191 g, 1.38 mmol) in DMF (2 mL) over a period of twenty minutes. After the mixture was stirred at ambient temperature for 3 h., the reaction mixture was quenched with aqueous hydrochloride to pH 1 and further diluted with water (40 mL) and aqueous mixture was extracted with methylene chloride (80 mL). The organic extract was washed with water, dried with brine and anhydrous MgSO4, and concentrated to provide a mixture (279 mg, 100%) of 11-(3-methoxy-4-benzyloxy-5-bromo-phenyl)-6-bromo-benzo[b]naphtho[2,3-d]thiophene (87%) and 11-(4-methoxy-3-benzyloxy-5-bromo-phenyl)-6-bromo-benzo[b]naphtho[2,3-d]thiophene(13%). This mixture was used for next reaction without separation. A solution of a this mixture (279 mg, 0.49 mmol) and 10% palladium on carbon (28 mg) in ethyl acetate: ethanol (1.5:10, 15 mL) was hydrogenated in a Parr vessel at 51 psi at ambient temperature for 6 h. The reaction mixture was filtered through a bed of Solka Floc and washed with hot ethyl acetate: ethanol (1.5:10). Silica gel (5 mL) was added to the filtrate. Solvent was removed and the adsorbate was flash chromatographed (eluents:petroleum ether:methylene chloride 6:4 to petroleum ether:ethyl acetate 7:3) to provide a white solid (145 mg) that contained about 73% 2-bromo-4-(benzo[b]naphtho[2,3-d]thiophen-11-yl)-6-methoxy-phenol and 27% of the title compound. The bromine was re-introduced to the 6 position of the majority (73%) of the crude according to the procedures outlined by methods in Examples 34 (acetylation of the phenol), Example 37 (bromination in the 6 position) and Example 41 (saponification of the acetyl moiety) to provide the title compound as a white solid: mp 216–218° C.; NMR (CDCl3); δ8.36 (d, J=8 Hz, 1 H), 7.83 (d, J=8 Hz, 1 H), 7.68-7.64 (m, 2 H), 7.50-7.43 (m, 2 H), 7.21 (d, J=2 Hz, 1 H), 7.18 (d, J=8 Hz, 1H), 6.93 (d, J=8 Hz, 1 H), 6.87 (d, J=8 Hz, 1H), 6.20 (s, 1 H), 3.86 (s, 3 H); MS (+FAB): [M+], 2 bromine isotope pattern; 512.

EXAMPLE 194

(R)-2-[2-Bromo-4-(6-bromo-benzo[b]naphtho[2,3-d]thiophen-11-yl)-6-methoxy-phenoxy]-3-phenyl-propionic acid Prepared from 2-bromo-4-(6-bromo-benzo [b]naphtho [2,3-d]thiophen-11-yl)-6-methoxy-phenol (Example 193) and (S)-2-hydroxy-3-phenylpropionic acid, methyl ester (Example 96) according to the procedure in Example 113. White solid: mp >103° C. (dec.): NMR (CDCl3); δ8.36 (ddd, J=8, 1, 1 Hz, 1 H), 7.83 (ddd, J=8, 7, 1 Hz, 1 H), 7.67 (ddd, J=8, 7, 1 Hz, 1 H), 7.57-7.26 (m, 9 H), 7.18 (ddd, J=8, 7, 1 Hz, 1 H), 6.89 (ddd, J=8, 1, 1 Hz, 1H), 6.79 (ddd, J=8, 7, 1 Hz, 1H), 5.29 (t, 1H), 3.76, 3.74 (ds, 3 H), 3.39–3.46 (m, 2 H); MS (EI): [M+], 2 bromine isotope pattern, 660; Anal. Calc. for C32H22Br2O4S: C, 58.02, H, 3.35, N, 0.00. Found: C, 58.04, H, 3.73, N, 0.02.

EXAMPLE 195

3-Bromo-5-(6-bromo-benzo[b]naphtho[2,3-d]thiophen-11-yl)-2-methoxy-phenol

Iodomethane (0.074 mL, 1.2 mmol) was added dropwise to a rt, stirred light suspension of 3-bromo-5-(6-bromo-benzo [b]naphtho [2,3 -d]thiophen-11 -yl)-benzene-1, 2-diol (0.30 g, 0.60 mmol), potassium carbonate (0.083 g, 0.6 mmol) in DMF (1.5 mL) over a period of five minutes. After the mixture was stirred at ambient temperature for 1.5 h., the reaction mixture was quenched with aqueous hydrochloric acid to pH 1 and further diluted with water (80 mL) and aqueous mixture was extracted with methylene chloride (120 mL). The organic extract was washed with water and dried with brine. Silica gel (5 mL) was added. Solvent was removed and the adsorbate was flash chromatographed (eluents:petroleum ether:methylene chloride 7:3 to 1:1 and then petroleum ether: ethyl acetate 7:3) to provide the title compound as a white solid (85 mg, 29%): mp 233–234° C.: NMR (CDCl3); δ8.35 (ddd, J=8, 1, 1 Hz, 1 H), 7.82 (ddd, J=8, 1, 1 Hz, 1 H), 7.66 (ddd, J=8, 7, 1 Hz, 1H), 7.65 (dd, J=8, 1, Hz, 1 H), 7.48 (ddd, J=8, 7, 1 Hz, 1 H), 7.43 (ddd, J=8, 7, 1 Hz, 1 H), 7.17 (ddd, J=8, 7, 1 Hz, 1 H), 7.15 (d, J=2 Hz, 1 H), 7.00 (d, J=2 Hz, 1 H), 6.87 (ddd, J=8, 1, 1 Hz, 1 H), 5.93 (s, 1 H), 4.14 (s, 3); MS (EI): [M+], 2 bromine isotope pattern, 512; Anal. Calc. for C23H14Br2O2S: C, 53.72, H, 2.74, N, 0.00. Found: C, 53.85, H, 2.98, N, 0.02.

EXAMPLE 196

(R)-2-[3-Bromo-5-(6-bromo-benzo[b]naphtho[2,3-d]thiophen-11-yl)-2-methoxy-phenoxy]-3-phenyl-propionic acid Prepared from 3-Bromo-5-(6-bromo-benzo[b]naphtho[2,3-d]thiophen-11-yl)-2-methoxy-phenol (Example 195) and (S)-2-hydroxy-3-phenylpropionic acid, methyl ester (Example 96) according to the procedure in Example 113. White solid: mp >99° C. (dec.): NMR (CDCl3); δ8.34 (ddd, J=8, 1, 1 Hz, 1 H), 7.79 (ddd, J=8, 7, 1 Hz, 1 H), 7.64 (ddd, J=8, 7, 1 Hz, 1 H), 7.52(dd, J=8, 1, Hz, 1 H), 7.45 (ddd, J=8, 7, 1 Hz, 1 H), 7.39 (ddd, J=8, 7, 1 Hz, 1 H), 7.28-7.07 (m, 7 H), 6.67 (ddd, J=8, 7, 1 Hz, 1 H), 6.63 (d, J=2 Hz, 1 H), 4.91-4.84 (m, 1 H), 3.33-3.20 (m, 2 H), 3.95, 3.89 (ds, 3 H);

MS (+FAB): [M+H]+, 2 bromine isotope pattern, 660, 662, 664; Anal. Calc. for C32H22Br2O4S: C, 58.02, H, 3.35, N, 0.00. Found: C, 58.37, H, 3.63, N, 0.03.

EXAMPLE 197

2,4-Difluoro-3-methoxy-benzoic acid

A solution of 5-bromo-1,3-difluoro-2-methoxy-benzene (12.35 g, 55.4 mmole, L. I. Kruse, et al., *Biochemistry* 1986, 25, 7271–7278) in anhydrous tetrahydrofuran (350 mL) was transferred via canulla into a 1 L flask which had been flame dried. The solution was cooled to −80° C. and a solution of n-butyl lithium (2.5 M in hexanes, 24.35 mL, 60.9 mmol) was added dropwise via syringe pump over a 1 hour period with stirring under a dry nitrogen atmosphere. After stirring 2.5 hours, dry carbon dioxide gas was bubbled into the cold reaction mixture for 0.5 hour. The solution was then poured onto crushed dry ice and strirred for 0.5 hours. The mixture was causiously added to water (600 mL) and acidified with 10% HCl. The organics were extracted with ether. The extracts were combined and washed with brine. After concentrating and standing at room temperature for two days the residue was redissolved in ether and combined with acid treated (2% H3PO4 in methanol) silica gel. The solvent was removed and the adsorbate was flash chromatographed to give the title compound as an off-white solid: mp 191–192° C.: NMR (400 MHz, DMSO-d6); δ13.37 (broad singlet, 1 H), 7.63-7.58 (m, 1 H,), 7.25 - 7.20 (m, 1 H), 3.92(s, 3 H); MS (+FAB): (M+H): 189 (12%), 154 (100%), 136 (75%); Anal. Calc. for C8H6F2O3: C, 51.08; H, 3.21. Found: C, 50.98, H, 3.15.

Concentration of less polar fractions gave 6-bromo-2,4-difluoro-3-methoxy-benzoic acid (3.44 g, 23%) as a white solid: mp 92–94° C.: NMR (400MHz, DMSO-d6); δ14.18 (broad singlet, 1 H), 7.65 (dd, J=3, 1 Hz, 1 H), 3.94 (s, 3 H); MS: (+FAB) (M +H: 267/269 (38%), 91 (100%); Anal. calc. for C8H5BrF2O3: C, 35.98, H, 1.89, N, 0.00.

Found: C, 36.26, H, 1.79, N 0.03.

EXAMPLE 198

(2-Benzyl-benzo[b]thiophen-3-yl)-(2-4-difluoro-3-methoxy-phenyl)-methanone

To a suspension of 2,4-difluoro-3-methoxy-benzoic acid (3.55 g., 18.9 mmol) and N,N-dimethylformamide (3 drops)

in anhydrous methylene chloride (70 mL) was added oxalyl chloride (2.80 mL, 32.1 mmol) dropwise under a dry nitrogen atmosphere. After stirring 3 hours additional oxalyl chloride (1.6 mL, 16.1 mmol) was added. After stirring another hour the solvents and excess oxalyl chloride were removed to give a semi-solid residue which was used in the following reaction.

To a thick suspension of 2 benzylbenzo[b]thiophene (3.85 g, 17.2 mmole) and the above acid chloride (3.90 g, 18.9 mmole) in methylene chloride (56 mL) cooled to −80° C. was added tin IV chloride (4.43 mL, 37.8 mmol) dropwise over a period of 55 minutes under a dry nitrogen atmosphere. After stirring for an additional hour the ice-bath was removed. Dissolution occurred as the solution warmed to room temperature. After stirring ca. 15 hours the reaction mixture was added to water (200 mL) and the organics were extracted with ether. The extracts were combined, washed with brine and combined with silica gel. The solvents were removed and the adsorbate was flash chromatographed (gradient 100% petroleum ether to $^{97}/_3$ petroleum ether/ethyl acetate) to give the title compound as a yellow oil (2.19 g, 34% yield): NMR (400 MHz, DMSO-d6): δ7.97-7.94 (m, 1 H), 7.77-7.20 (m, 10 H), 4.33 (s, 2 H), 4.24 (s, 3 H); MS (EI) (M+): 394 (100%).

EXAMPLE 199

3-(Benzo[b]naphtho[2,3-d]thiophen-11-yl)-2.6 difluoro-phenol

To a cold (−78° C.) solution of (2-benzyl-benzo[b]gthiophen-3-yl)-(2-4-difluoro-3-methoxy-phenyl)-methanone (2.07g, 5.28 mmole) in anhydrous methylene chloride (20 mL) was added boron tribromide (1.60 mL, 16.9 mmol) dropwise via syringe pump over a period of 43 minutes under a dry nitrogen atmosphere. After stirring an additional 14 minutes the ice bath was removed and the reaction was allowed to stir at room temperature for about 4 hours. The dark red mixture was cooled in an ice bath and causiously quenched with water and the organics were extracted with ether. The extract was washed with brine and concentrated to give the crude product as a yellow foam (2.2 g). The solid was redissolved in a mixture of ether, tetrahydrofuran, and methylene chloride and combined with silica gel (60 mL). The solvents were removed and the adsorbate was flash chromatographed ($^{90}/_{10}$ petroleum ether/ethyl acetate) to give the title compound as a white solid (1.4g, 74%): NMR (300 MHz, DMSO-d6); δ10.57 (s, 1 H), 8.69 (s, 1 H), 8.09 (d, J=8 Hz, 1 H), 8.02 (d, J=8 Hz, 1 H), 7.64-7.23 m, 6 H), 6.94-6.83 (m, 2 H).

EXAMPLE 200

3-(6-Bromo-benzo[b]naphtho[2,3-d]thiophen-11-yl)-2,6 difluoro-phenol

To a cold (−23° C. dry ice/carbon tetrachloride bath) stirred solution of 3-(benzo [b]naphtho[2,3-d]thiophen-11-yl)-2,6 difluoro-phenol (1.38 g, 3.81 mmol) in methylene chloride (35 mL) was added a solution of bromine (0.22 mL, 4.19 mmol) in methylene chloride (7 mL) dropwise, very slowly, over a period of 28 minutes. After stirring an additional 1.5 h the reaction was quenched with dilute sodium bisulfite and the organics were extracted with ether. The extract was concentrated to give a yellow solid (1.64 g, 98% crude yield). A small portion was taken up in methylene chloride and combined with silica gel. The solvent was removed and the adsorbate was flash chromatographed ($^{85}/_{15}$ petroleum ether/ethyl acetate) to give the title compound as an off white solid: mp 180–182° C.; NMR (400 MHz, DMSO-d6); δ10.64 (s, 1 H), 8.30 (d, J=9 Hz, 1 H), 8.09 (d, J=9 Hz, 1 H), 7.82-7.78 (m, 1 H), 7.64-7.51 (m, 3 H), 7.42-7.37 (m, 1 H), 7.33-7.29 (m, 1 H), 6.96-6.91 (m, 1 H), 6.81-6.78 (m, 1 H); MS (FAB): (M−H): one bromine pattern observed; $^{439}/_{441}$ (8%); Anal. Calc. for C22H11BrF2OS: C, 59.88, H, 2.51, N, 0.00%. Found: C, 59.82, H, 2.59, N, 0.06.

EXAMPLE 201

[3-(6-Bromo-benzo[b]naphtho[2,3-d]thiophen-11-yl)-2.6-difluoro-phenoxy]-acetic acid To a suspension 3-(6-bromo-benzo[b]naphtho[2,3-d]thiophen- 11-yl)-2,6 difluoro-phenol (0.200 g, 0.453 mmol) and potassium carbonate (0.085, 0.612 mmol) in N,N-dimethylformamide (2 mL) was added methyl bromoacetate (0.086 mL, 0.906 mmol) dropwise at room temperature under a dry nitrogen atmosphere. After stirring 2.5 hours the reaction mixture was combined with water (50 mL) and the organics were extracted with ether. The extract was combined with silica gel, the solvent was removed and the adsorbate was flash chromatographed ($^{90}/_{10}$ petroleum ether/ethyl acetate). The solvents were chased with benzene (2×) and petroleum ether to give [3-(6-bromo-benzo[b]naphtho[2, 3-d]thiophen-11-yl)-2, 6-difluoro-phenoxy]-acetic acid, methyl ester as a white solid (0.198 g, 85%). To a solution of this methyl ester (0.190 g, 0.370 mmol) in tetrahydrofuran (3 mL) and methanol (1 mL) was added a 1 N aqueous solution of potassium hydroxide (0.55 mL, 0.55 mmol) dropwise at room temperature. After stirring 1 hour the solvents were removed and water was added to the solid residue. The aqueous mixture was acidified with 10% HCl and the organics were extracted with ether. After several minutes of vigorous shaking the layers were separated and the organic layer was washed with water and concentrated. The residue was chased with benzene and dried in vacuo to give the title compound as a white solid (0.177g, 95%): mp 195–197° C.: NMR (400 MHz, DMSO-d6): 8 13.11 (broad s, 1 H), 8.31 (d, J=8 Hz, 1 H), 8.09 (d, J=8 Hz, 1 H), 7.83-7.79 (m, 1 H), 7.64-7.46 (m, 4 H), 7.31-7.27 (m, 1 H), 7.23-7.17 (m, 1 H), 6.81 (d, J=8 Hz, 1 H), 4.89 (s, 2 H); MS(−FAB): (M−H): one bromine pattern observed: $^{497}/_{499}$ (35%138%); HRMS: Calc. for C24H13BrF2O3S M+: 497.97368, measured mass: 497.97787, mass deviation 4.19 mmu; Anal. HPLC 97% pure; Anal. Calc. for C24H13BrF2O3S: C, 57.72, H, 2.62% N, 0.00. Found: C, 56.77, H, 2.79% N, 0.00.

EXAMPLE 202

(R)-2-[3-(6-Bromo-benzo[b]naphtho[2,3-d]thiophen-11-yl)-2,6-difluoro-phenoxyl-propionic acid To a solution of 3-(6-bromo-benzo[b]naphtho[2,3-d]thiophen-11-yl)-2,6 difluoro-phenol (0.570 g, 1.29 mmol), commercially available (S)-lactic acid, methyl ester. (0.246 mL, 2.58 mmol) and triphenylphosphine (0.677g, 2.58 mmol) in dry benzene (7 mL) was added diethylazodicarboxylate (0.406 mL, 2.58 mmol) dropwise at room temperature under a dry nitrogen atmosphere. The reaction mixture was sealed in a pressure bottle and immersed in a pre-heated oil bath at 105° C. After heating for 2.5 hours the mixture was stirred at ambient temperature for about 14 hours. The reaction mixture was then diluted with methylene chloride and combined with silica gel. The solvents were removed and the adsorbate was flash chromatographed ($^{90}/_{10}$ petroleum ether/ethyl acetate) to give (R)-2-[3-(6-bromo-benzo

[b]naphtho[2,3-d ]thiophen-11-yl)-2,6-difluoro-phenoxy]-propionic acid, methyl ester as a white solid (0.59 g, 86%). To a solution of this methyl ester (0.46 g, 0.929 mmol) in tetrahydrofuran (18 mL) and methanol (6 mL) was added a 1 N aqueous solution of potassuim hydroxide (1.39 mL, 1.39 mmol) dropwise at room temperature. After stirring for 2 hours the solvents were removed and the residue was combined with water (50 mL) and acidified with 10% HCl. The solid was extracted into ether. The layers were shaken together well, separated, and the organic layer was washed with water and concentrated to give the title compound as a white solid (0.396 g, 88%): [a]D25=+13.22 (9.383 mg/mL methanol); NMR (400 MHz, DMSO-d6): δ13.11 (s, 1 H), 8.31 (d, J=8 Hz, 1H), 8.10-8.08 (m, 1H), 7.83-7.78 (m, 1H), 7.65-7.46 (m, 4 H), 7.32-7.19 (m, 2 H), 6.82-6.75 (m, 1 H), 4.98-4.93 (m, 1 H), 1.53-1.50 (m, 3 H); MS (-FAB): (M-H): one bromine pattern observed: 511/513 (2%); Anal. Calc. for C25H15BrF2O3S: C, 58.49, H, 2.95, N, 0.00. Found: C, 58.41, H, 3.44, N, 0.02.

EXAMPLE 203

(R)-2-[]3-(6-Bromo-benzo[b]naphtho[2,3-d] thiophen11-yl)-2.6-difluoro-phenoxyl-3-phenyl-propionic acid To a solution of 3-(6-bromo-benzo[b]naphtho[2,3-d] thiophen-11-yl)-2,6 difluoro-phenol (0.700, 1.59 mmol), (S)-2-hydroxy-3-phenylpropionic acid, methyl ester (0.572g, 3.17mmol) and triphenylphosphine (0.831g, 3.17 mmol) in dry benzene (10 mL) was added diethylazodicar-boxylate (0.50 mL, 3.17 mmol) dropwise at room temperature under a dry nitrogen atmosphere. The reaction mixture was sealed in a pressure bottle and immersed in a pre-heated oil bath at 105° C. and heated for 2.5 hours. After stirring at ambient temperature for 14 hours the reaction mixture was diluted with methylene chloride and combined with silica gel. The solvents were removed and the adsorbate was flash chromatographed (90/10 petroleum ether/ethyl acetate) to give (R)-2-[3-(6-bromo-benzo[b]naphtho[2,3-d]thiophen-11-yl)-2,6-difluoro-phenoxy ]-3-phenyl-propionic acid, methyl ester as an off white solid (0.73g., 76%). To a solution of this methyl ester (0.66g, 1.09 mmol) in tetrahydrofuran (2 mL) and methanol (7 mL) was added a 1 N aqueous solution of potassium hydroxide (1.64mL, 1.64mmol). After stirring for two hours the solvents were removed and the residue was combined with water (50 mL) and acidified with 10% HCl. The solid was extracted into ether and the layers were shaken well together for several minutes before they were separated. The organic layer was washed with water and concentrated to give the title compound as a white solid (0.613 g, 95%): [a]D25 =-13.81 (9.413 mg/mL chloroform); NMR (400 MHz, DMSO-d6): δ13.21 (s, 1H), 8.30 (d, J=8 Hz, 1 H), 8.08 (d, J=8 Hz, 1 H), 7.82 - 7.78 (m, 1 H), 7.62 - 7.41 (m, 4 H), 7.35 - 7.14 (m, 7 H), 6.74 (dd, J=8, 9 Hz, 1 H), 5.17 - 5.11 (m, 1 H), 3.32 - 3.24 (m, 1 H), 3.19 -3.12(m, 1H), NMR indicates that 0.22 mole eq. of benzene is present; MS (+FAB): (M:+): one bromine pattern observed, 588/590 (78%, 75%); Anal. Calc. for C31H19BrF2O3S.0.22 C6 H6: C, 63.99, H, 3.38, N, 0.00. Found: C, 64.52, H, 3.48. N, 0.06.

EXAMPLE 204

2-B enzofuranylphenyl-methanone

According to the procedure in Syn. Comm. 1987, 17, 341–354, salicylaldehyde (21.3 mL, 0.20 mol), 2-bromoacetophenone (39.8 g, 0.20 mol), potassium carbonate (30%, 300 g in 700 mL water), tetrabutylammonium sulfate ( 3.5 g, 5 mol%) and dichloromethane (1.5 L) were stirred vigorously for 19 h. The layers were separated, the dichloromethane phase was washed with water and brine. It was then concentrated and the residue was recrytallized from ethanol (200 mL) to provide the title compound as white crystals (37.9 g, 85%): mp 88–90° C.: NMR (DMSO-d6); δ8.00 (m, 2 H), 7.86 (ddd, J=8, 1.5, 0.5 Hz, 1H), 7.80 (d, J=1 Hz, 1 H), 7.77 (ddd, J=8, 2, 1 Hz, 1 H), 7.77 (ddd, J=8, 2, 1 Hz, 1 H), 7.72 (m, 1 H), 7.63-7.55 (m, 3 H), 6.73 (dd, J=8, 1 Hz, 1 H), 7.39 (ddd, J=8, 7, 1 Hz, 1 H); MS (EI): [M+], 222 (100%); Anal. Calc. for C15H10O2: C, 81.07, H, 4.54, N, 0.00. Found: C, 81.05, H, 4.44, N, -0.09.

EXAMPLE 205

2-Benzyl-benzofuran

A suspension of 2-benzofuranylphenyl-methanone (34.8 g, 0.157 mol), hydrazine monohydrate (31 mL, 0.639 mol) and diethylene glycol (72 mL) was heated to reflux for 10 min and cooled to room temperature. Potassium hydroxide (22.9 g, 0.408 mol) was added. The reaction mixture was heated in 130° C. oil bath for 1 h., cooled to room temperature and added to water. The oil was extracted with ether. Silica ge was added to the ether phase and the solvent was removed. The adsorbate was flash chromatographed eluent: (petroleum ether) to provide the title compound as an oil (23.9 g, 90%): NMR (CDCl3); δ7.5-7.1 (m, 9 H), 6.38 (s, 1 H), 4.10 (s, 2 H).

EXAMPLE 206

(2-Benzyl-benzofuran-3-yl)-(4-methoxy-phenyl)-methanone

Tin tetrachloride (6.5 mL, 55.5 mmol) was added dropwise over a 30 minute period to a stirred solution of 2-benzyl-benzofuran (10.0 g, 48.01 mmol), anisoyl chloride (8.51 g, 49.93 mmol) and carbon disulfide (53 mL) at room temperature under a dry nitrogen atmosphere. After 15 h the reaction mixture was added to water and extracted with dichloromethane. Silica gel was added to the dichloromethane phase and the solvent was removed. The adsorbate was flash chromatographed (95:5 petroleum ether:ethyl acetate as eluent) to provide the title compond as a white solid (13.84 g, 84%): mp 84–85° C.: NMR (CDCl3); δ7.87 (dm, J=9 Hz, 2 H), 7.46 (dm, 1 H), 7.36-7.12 (m, 8 H), 6.97 (dm, J=9 Hz, 2 H), 4.29 (s, 2 H), 3.90 (s, 3 H): MS (EI): 342 (100%, MI); Anal. Calc. for C23H18O3: C, 80.68, H, 5.30, N, 0.00. Found: C, 80.61, H, 5.25, N, 0.10.

EXAMPLE 207

(2-Benzyl-benzofuran-3-yl)-(2, 4-dimethoxy-phenyl)-methanone

Prepared from 2-benzyl-benzofuran and 2, 4-dimethoxybenzoyl chloride according to the procedure in Example 207. White solid (6.88g): mp 74–76C.; NMR (CDCl3); δ7.47(d, J=8Hz, 1 H), 7.40 (dd, J=2,1 Hz, 1 H), 7.31 - 7.24 (m, 5 H), 7.24 -7.19 (m, 2 H), 7.16 - 7.12 (m, 1 H), 6.55 (d, J=2, Hz, 1 H), 6.48 (s, 1 H), 4.29 (s, 2 H), 3.89 (s, 3 H), 3.58 (s, 3 H), MS (EI): [M*+m/z] 372(55%), 165(100%), 234(88%), Anal. Calc. for C24H20O4, C,77.40, H, 5.41, N, 0.00. Found: C, 77.48, H, 5.44, N, 0.09.

EXAMPLE 208

4-Benzo[b]naphtho[2,3-d]furan-11yl)-phenol

Boron tribromide (1.0 M in dichloromethane, 130 mL, 130 mmol) was added dropwise over a 30 minute period to a stirred, −78° C. solution of (2-benzyl-benzofuran-3-yl)-(4-methoxy-phenyl)-methanone (12.0 g, 35.05 mmol) in dichloromethane (140 mL) under a dry nitrogen atmosphere. The solution was warmed to room temperature. After 23 h, water was cautiously added. The layers were separated and the dichloromethane layer was washed with water (3×), brine and silica gel was added to it. The solvent was removed and the adsorbate was flash chromatographed (gradient: 9:1 to 1:1 petroleum ether:ethyl acetate) to provide the title compound as an off-white solid (4.56 g, 42%): mp 137–138° C.: NMR (CDCl3); δ8.01 (dt, J=8 Hz, 1 H), 7.94 (s, 1 H) , 7.89 (dm, J=8 Hz, 1 H), 7.53 (m, 2 H), 7.44-7.36 (m, 2 H), 7.38 (d, J=9 Hz, 2 H), 7.10 (d, J=9 Hz, 2 H), 7.13-7.06 (m, 1 H), 7.01 (dm, J =8 Hz, 1 H); MS (EI): 310 (100%, MI); High Resolution MS (EI) Calc. for C22H14O2: 310.0993803, Found:310.09878; Anal. Calc. for C22H14O2: C, 85.14, H, 4.55, N, 0.00. Found: C, 84.33, H, 4.30, N, 0.03.

EXAMPLE 209

4-(Benzo[b]naphtho[2,3-d]furan-11-yl)-benzene-1,3-diol

To a cold (−76° C. dry ice, isopropanol bath) solution of (2-benzyl-benzofuran-3-yl)-( 2,4-dimethoxy-phenyl)-methanone (6.13 g, 16.5 mmol) in anhydrous methylene chloride (60 mL) was added a 1 M solution of boron tribromide in methylene chloride (100 mL, 100 mmol, 6.06 eq) dropwise over a period of 20 minutes under a dry nitrogen atmosphere. The dry ice bath was removed and the reaction mixture was stirred at ambient temperature for 45 hours. After cooling in an ice bath water was carefully added and after quenching the reaction mixture was further diluted with water (300 mL). The organics were extracted with diethyl ether and methylene chloride. The extracts were combined, washed with water and brine, and combined with silica gel. The solvents were removed and the adsorbate was flash chromatographed ($^{80}/_{20}$ petroleum ether/ethyl acetate) to provide the title compound as a white solid (2.07 g, 38%): mp 201 –202° C.; NMR (CDCl3); δ8.03 (ddd, J=8, 7, 1 1 H), 8.01 (s, 1 H), 7.82 - 7.79 (m, 1 H), 7.58 - 7.54 (m, 2 H), 7.48 - 7.43 (m, 2 H), 7.20 (d, J=8 Hz, 1 H), 7.18 - 7.15 (m, 2 H), 6.70 (m, 2 H), 5.00 (s, 1 H), 4.70 (s, 1 H); Hi Res MS, Calc. Sample Mass for C22H14O3, 326.0942951, Measured Mass 326.09019, mas deviation 4 mmu. Anal. Calc. for C22H14O3: C, 80.97, H, 4.32, N, 0.00. Found: C, 79.80, H, 4.10, N, 0.07.

EXAMPLE 210

2,6-Dibromo-4-(6-bromo-benzo[b]naphtho[2,3-d]furan-11ly)-phenol

A stirred suspension of 4-benzo[b]naphtho[2,3-d]furan-11yl)-phenol (3.0 g, 9.67 mmol) in acetic acid (85 mL) and water (6 mL) was heated slightly to effect dissolution. Bromine (1.8 mL, 34.01 mmol) in acetic acid (20 mL) was then added dropwise over a 10 minute period. The resultant suspension was stirred at room temperature for 2 h. Water and solid sodium thiosulfite were added and the reaction mixture was filtered. The solid was wasshed with water and triturated with petroleum ether to provide a white solid (4.37 g, 83%). A portion (1.0 g) of this solid was recrystallized from acetic acid (45 mL) and then hexane to provide the title compound as a white solid: mp 175–176° C.; NMR (CDCl3); δ8.45 (ddd, J=8, 1, 1 Hz, 1 H),7.74 (ddd, J=8, 1, 1 Hz, 1 H), 7.70-7.65 (m, 2 H), 7.62 (s, 2 H), 7.53-7.48 (m, 2 H), 7.20 (ddd, J=8, 7, 1 Hz, 1 H), 7.02 (ddd, J=8, 1, Hz, 1 H), 6.17 (s, 1 H); MS (EI): [M+], 3 bromine isotope pattern, 544 (30%), 546 (100%), 548 (100%) 550 (30%); Anal. Calc. for C22H11Br3O2: C, 48.30, H, 2.03, N, 0.00. Found: C, 48.22, H, 1.79, N, 0.11.

EXAMPLE 211

2,6-Dibromo-4-(6-bromo-benzo[b]naphtho[2,3-d]furan-11-yl)-3-hydroxy-phenol

To a solution of the 4-(benzo [b]naphtho [2,3 -d]furan-11 -yl)-benzene- 1,3-diol (1.48g, 4.55 mmole) and acetic acid potassium salt (4.46 g, 45.5 mmole) in glacial acetic acid (15 mL) was added bromine (0.75 mL, 14.6 mmole) dropwise over a period of 20 minutes at room temperature. After stirring, 0.5 hours the mixture was concentrated and the residue was diluted with water (20 mL). The resulting solid was filtered, washed with water and petroleum ether and dried in vacuo at 40 C. to give the crude product (2.5 g). The solid was taken up in ethyl acetate, combined with silica gel and the solvent was removed. The adsorbate was flash chromatographed (gradient $^{85}/_{15}$ petroleum ether/ethyl acetate) to give a yellow solid (0.990 g, mixture of di and tri brominated products). To a cold (−10° C.,) solution of this solid (0.437 g, 1.11 mmol) in anhydrous methylene chloride (10 mL) was added a solution of bromine (0.057 mL, 1.11 mmol) in anhydrous methylene chloride (2 mL) dropwise over a period of 30 minutes under nitrogen. After stirring in the warming bath overnight the reaction mixture was poured into water (80 mL) and extracted with diethyl ether. The extracts were combined, washed well with a dilute aqueous solution of sodium bisulfite and brine and silica gel was added. The solvents were removed and the adsorbate was flash chromato graphed ($^{87}/_{13}$ petroleum ether/ethyl acetate) to give the title compound as an off-white solid (0.429 g): mp 226–228° C.; NMR (CDCl3); δ8.48 (ddd, J=8, 1, 1 Hz, 1 H), 7.73-7.69 (m, 2 H), 7.66 (ddd, J =8, 1, 1 Hz, 1 H), 7.51 (ddd, J=8, 1, 1 Hz, 2 H), 7.49 (s, 1 H), 7.22 (ddd, J=8, 7, 1 Hz, 1 H), 7.04 (ddd, J=8, 1, 1 Hz, 1 H), 6.18 (s, 1 H), 5.47 (s, 1 H); MS (EI): [M+], 3 bromine isotope pattern, 560 (20%), 562 (75%), 564 (44%), 566 (25%); Anal. Calc. for C22H11Br3O3: C, 46.93, H, 1.97, N, 0.00. Found: C, 46.63, H, 1.93, N, 0.09.

EXAMPLE 212

4-(Benzo[b]naphtho[2,3-d]furan-11-yl-phenoxy)-acetic acid methy ester

Methyl bromoacetate (0.554 mL, 5.8 mmol) was added to a stirred, room temperature suspension of 4-benzo[b]naphtho[2,3-d]furan-11yl)-phenol (0.90 g, 2.90 mmol), potassium carbonate (0.81 g, 5.8 mmol) and dimethylformamide (7 mL). After 20 h, the reaction mixture was added to water and extracted with ether. Silica gel was added to the ether phase and the solvent was removed. The adsorbate was flash chromatographed (9:1 petroleum ether:ethyl acetate as eluent) to provide the title compound as a white solid (0.845 g, 76%): mp 146–147° C.: NMR (DMSO-d6); δ8.19 (s, 1 H) 8.13 (d, J=8 Hz, 1 H) , 7.69 (d, J=8 Hz, 1 H), 7.67 (d, J=8 Hz, 1 H), 7.58 (ddd, J=8,7,1 Hz, 1 H), 7.50 (ddd, J=8,7,1 Hz, 1 H), 7.47-7.43 (m, 1 H), 7.43 (d, J=9 Hz, 2 H), 7.24 (d, J=9 Hz, 2 H), 7.17 (ddd, J=8,7,1 Hz, 1 H), 6.88 (dd, J=8, 0.5 Hz, 1 H), 4.98 (s, 2 H), 3.76 (s, 3 H); MS (EI): 382 (100%, MI); Anal. Calc. for C25H18O4: C, 78.52, H, 4.74, N, 0.00. Found: C, 77.88, H, 4.71, N, 0.07.

EXAMPLE 213

4-(Benzo[b]naphtho[2,3-d]furan-11-yl-phenoxy)-acetic acid

Potassium hydroxide (1.0 M, 2.85 mL, 2.85 mmol) was added to a stirred solution of 4-(benzo[b]naphtho[2,3-d]

furan-11-yl-phenoxy)-acetic acid methyl ester (0.80 g, 2.09 mmol) in THF (9 mL) and methanol (9 mL). After 2 h, the solvents were removed, water was added and the reaction mixture was acidified with 10% HCl. After stirring overnight, the solid was filtered and washed with water, triturated with hexane and dried in vacuo at 100° C. to provide a white solid (0.735 g, 95%). This solid was recrystalized from acetic acid and then hexane/ethyl acetate to provide the title compound as a white solid (0.338 g, 44%): mp 205–207° C.: NMR (CDCl3); δ8.01 (d, J=8, 1, 0.5 Hz, 1 H), 7.95 (s, 1 H), 7.76 (ddd, J=8, 1, 0.5 Hz, 1 H), 7.55-7.36 (m, 4 H), 7.47 (d, J=9 Hz, 2 H), 7.21 (d, J=9 Hz, 2 H), 7.08 (ddd, J=9,8,1 Hz, 1 H), 6.88 (ddd, J=8, 1, 0.5 Hz, 1 H), 4.89 (s, 2 H); MS (EI): 368 (100%, MI); High Resolution MS (EI) Calc. for C24H16O4: 368.10486 Found:368.10867. Anal. Calc. for C24H16O4: C, 78.25, H, 4.38, N, 0.00. Found: C, 77.84, H, 4.30, N, 0.14.

EXAMPLE 214

[2, 6-Dibromo-4-(6-bromo-benzo[b]naphtho[2,3-d]furan-11-yl)-phenoxy-acetic acid methyl ester Methyl bromoacetate (0.554 mL, 5.8 mmol) was added to a stirred, room temperature suspension of 2, 6-dibromo-4-(6-bromo-benzo[b]naphtho[2,3-d]furan-11yl)-phenol (1.6 g, 2.92 mmol), potassium carbonate (0.81 g, 5.8 mmol) and dimethylformamide (7 mL). After 21 h, the reaction mixture was added to water and filtered. The solid was taken up in THF and silica gel was added. The solvent was removed. The adsorbate was flash chromatographed (9:1 petroleum ether:ethyl acetate as eluent) to provide the title compound as a white solid (0.987 g, 55%): mp 188–189° C.: NMR (DMSO-d6); δ8.37 (d, J=8 Hz, 1 H), 7.91 (s, 2 H), 7.84 (d, J=8 Hz, 1 H), 7.80 (ddd, J=8, 7, 1 Hz, 1 H), 7.70 (d, J=8 Hz, 1 H), 7.64-7.58 (m, 2 H), 7.31 (t, J=8 Hz, 1 H), 6.92 (d, J=8, 1 H), 4.88 (s, 2 H), 3.80 (s, 3 H); MS (EI): [M+], 3 bromine isotope pattern, 616 (30%), 618 (100%) 620 (100%) 622 (30%); Anal. Calc. for C25H15Br3O4: C, 48.50, H, 2.44, N, 0.00. Found: C, 48.53, H, 2.29, N, 0.00.

EXAMPLE 215

[2,6-Dibromo-4-(6-bromo-benzo[b]naphtho[2,3-d]furan-11-yl)-phenoxy]-acetic acid

Potasium hydroxide (1.0 M, 1.60 mL, 1.60 mmol) was added to a stirred solution of [2, 6-dibromo-4-(6-bromo-benzo[b]naphtho[2,3-d]furan-11-yl)-phenoxy]-acetic acid methyl ester (0.90 g, 1.45 mmol) in THF (9 mL) and methanol (5 mL). After 3 h, the solvent was removed, water was added and the reaction mixture was acidified with 10% HCl. After stirring overnight, the solid was filtered and washed with water, triturated with hexane and dried in vacuo at 100° C. to provide the title compound as a white solid (0.821 g, 94%): mp 250–252° C.: NMR (DMSO-d6); δ8.37 (d, J=8 Hz, 1 H), 7.90 (s, 2 H), 7.84 (d, J=8 Hz, 1 H), 7.70 (ddd, J=8, 6, 1 Hz, 1 H), 7.61 (ddd, J=8, 1, 1 Hz, 1 H)), 7.62-7.58 (m, 2 H), 7.31 (ddd, J=8, 7, 1 Hz, 1 H), 6.92 (ddd, J=8, 1,1 Hz, 1 H), 4.75 (s, 2 H); MS (EI): [M+], 3 bromine isotope pattern, 602 (40%), 604 ( 95%) 606 (100%) 608 (40%); Anal. Calc. for C24H13Br3O4: C, 47.64, H, 2.17, N, 0.00. Found: C, 47.33, H, 1.95, N, 0.04.

EXAMPLE 216

(R)-2-[2,6-Dibromo-4-(6-bromo-benzo[b]naphtho[2, 3-d]furan-11-yl)-phenoxy]-3-phenyl-propionic acid Diethylazodicarboxylate (DEAD, 0.108 mL, 0.686 mmol) was added to a stirred, room temperature solution of 2, 6-dibromo-4-(6-bromo-benzo[b]naphtho[2,3-d ]furan-11yl)-phenol (0.250 g, 0.457 mmol), (S)-2-hydroxy-3-phenylpropionic acid, methyl ester (0.124 g, 0.686 mmol), triphenylphosphine (0.180 g, 0.686 mmol) and benzene (2 mL) under a dry nitrogen atmosphere. Dissolution occurred and the solution was heated in an 80° C. oil bath for 4.5 h. Upon cooling to room temperature, the reaction mixture was diluted with ether and silica gel was added. The reaction mixture was concentrated and the silica adsorbate was flash chromatographed (95:5 petroleum ether:ethyl acetate) to provide a white solid (0.266 g, 82%). Aqueous potassium hydroxide (1 N, 1.3 mL, 1.3 mmol) was added to a stirred solution of this oil in THF (3 mL)/methanol (1.3 mL). After 1.5 h the solution was concentrated, diluted with water (100 mL) and acidified with 10% aqueous HCl. The solid was filtered, washed with water and triturated with petroleum ether to provide the title compound as a white solid (0.256 g, 98%): NMR (DMSO-d6); 13.25 (broad s, 1 H), 8.36 (d, J=8 Hz, 1 H), 7.84-7.77 (m, 3 H), 7.67-7.56 (m, 3 H), 7.40 (d, J=8 Hz, 2 H), 7.33 (t, J=8 Hz, 2 H), 7.27 (t, J=8 Hz, 2 H), 6.85 (ddd, J=8, 1, 1 Hz, 1 H), 5.31 (t, J =7 Hz, 1 H), 3.41 (d, J=7 Hz, 2 H); MS (+FAB): [M+], 3 bromine isotope pattern, 692 (35%), 694 ( 90%) 696 (100%) 698(50%); Anal. Calc. for C31H19Br3O4: C, 53.56, H, 2.75, N, 0.00. Found: C, 52.44, H, 2.82, N, -0.13.

EXAMPLE 217

[2,6-Dibromo-4-(6-bromo-benzo[b]naphtho[2,3-d]furan-11-yl)-3-hydroxy-phenoxyl-acetic acid To a solution of [2,6-dibromo-4-(6-bromo-benzo[b]naphtho[2,3-d]furan-1 1-yl)-3-hydroxy-phenol (1.28 g, 2.27 mmole) in anhydrous tetrahydrofuran (64 mL) was added triphenylphosphine (1.193 g, 4.55 mmole), methyl glycolate (0.351 mL, 4.55 mmol) and diethylazodicarboxylate (0.305mL, 4.55 mmole) at room temperature under a dry nitrogen atmosphene. After stiring at room temperature for 8 days the reaction was quenched with water (10 mL) and the solvents were removed. The yellow residual solid was taken up in a mixture of methylene chloride, ether, and ethyl acetate and combined with silica gel. The solvents were removed and the adsorbate was flash chromatographed (40/60 petroleum ether/methylene chloride) to provide a white solid (0.342 g, 24%). To a solution of this solid (0.490 g, 0.772 mmol) in tetrahydrofuran (6 mL) and methanol (2 mL) was added a 0.5 M aqueous solution of potassuim hydroxide (3.24 mL, 1.62 mmol, 2.1 eq) dropwise at room temperature. After stirring 1.5 hours at room temperature the solvents were removed and the residue was combined with water. After removing impurities with diethyl ether (20 mL), the aqueous phase was acidified with 10% aqueous hydrochloric acid. The organics were extracted with diethyl ether. The extracts were combined, concentrated, and chased several times with benzene and dried in vacuo at 60° C. to provide the title compound as an off-white solid (0.380 g, 79%): mp 194–240° C.; NMR (DMSO, d6): δ 13.15 (s, 1 H), 9.58 (s, 1 H, OH), 8.35 (d, J=8 Hz, 1 H), 7.83 (d, J=8 Hz, 1 H), 7.78 (ddd, J=8, 7, 1 Hz, 1 H), 7.67 - 7.57 (m, 4 H), 7.31 (t, J=8 Hz, 1 H), 6.94 - 6.92 (m, 1 H), 4.70 (s, 2 H); MS (+FAB): [M+], 3 bromine isotope pattern, 618 (34%), 620 (100%), 622 (100%), 624 (34%); Anal. Calc. for C24H13Br3O5: C, 46.41, H, 2.11, N, 0.00. Found: C, 46.78, H, 2.05,

What is claimed is:
1. A compound of formula I having the structure

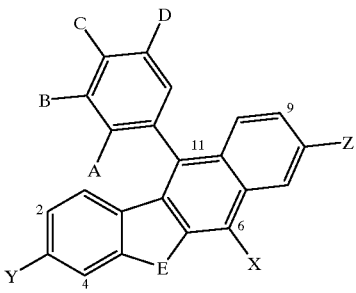

(I)

wherein
A is hydrogen, halogen, or OH;
B and D are each, independently, hydrogen, halogen, CN, alkyl of 1–6 carbon atoms, aryl, aralkyl of 6–12 carbon atoms, nitro, amino or OR;
R is hydrogen, alkyl of 1–6 carbon atoms, -COR$^1$, -CH$_2$CO$_2$R$^1$, -CH(R$^{1a}$)CO$_2$R$^1$, or -SO$_2$R$^1$;
R$^1$ and R$^{1a}$ are each, independently, hydrogen, alkyl of 1–6 carbon atoms, aralkyl of 6–12 carbon atoms or aryl;
E is S, SO, SO$_2$, O;
X is hydrogen, halogen, alkyl of 1–6 carbon atoms, CN, perfluoroalkyl of 1–6 carbon atoms, alkoxy of 1–6 carbon atoms, aryloxy, arylalkoxy of 6–12 carbon atoms, nitro, amino, alkylsulfanyl of 1–6 carbon atoms, arylsulfanyl, pyridylsulfanyl, 2-N,N-dimethylaminoethylsulfanyl, or -OCH$_2$CO$_2$R$^{1b}$;
R$^{1b}$ is hydrogen or alkyl of 1–6 carbon atoms;
Y and Z are each, independently, hydrogen or OR$^2$;
R$^2$ is hydrogen, alkyl of 1–6 carbon atoms, aralkyl of 6–12 carbon atoms, or -CH$_2$CO$_2$R$^3$;
R$^3$ is hydrogen or alkyl of 1–6 carbon atoms;
C is hydrogen, halogen or OR$^4$;
R$^4$ is hydrogen, alkyl of 1–6 carbon atoms, -CH(R$^5$)W, -C(CH$_3$)$_2$CO$_2$R$^6$, 5-thiazolidine-2,4-dione, -CH(R$^7$)CH$_2$CO$_2$R$^6$, -COR$^6$, PO$_3$(R$^6$)$_2$, or -SO$_2$R$^6$;
R$^5$ is hydrogen, alkyl of 1–6 carbon atoms, aralkyl, aryl, CH$_2$(1 H-imidazol-4-yl), -CH$_2$(3-1 H - indolyl), -CH$_2$CH$_2$(1,3-dioxo-1,3-dihydro-isoindol-2-yl), -CH$_2$CH$_2$(1-oxo-1,3-dihydro-isoindol-2-yl), -CH$_2$(3-pyridyl), or -CH$_2$CO$_2$H;
W is -CO$_2$R$^6$, -CONH$_2$, -CONHOH, CN, -CONH(CH$_2$)$_2$CN, 5-tetrazole, -PO$_3$(R$^6$)$_2$, -CH$_2$OH, or -CH$_2$Br, -CONR$^6$CHR$^7$CO2R$^8$,
R$^6$ is hydrogen, alkyl of 1–6 carbon atoms, aryl or aralkyl;
R$^7$ is hydrogen, alkyl of 1–6 carbon atoms, aryl or aralkyl;
R$^8$ is hydrogen, alkyl of 1–6 carbon atoms, aryl or aralkyl;
with the proviso that at least one of A,B,C, and D is not hydrogen or a pharmaceutically acceptable salt thereof.
2. The compound according to claim 1, wherein
A and B are each, independently, hydrogen, or bromine;
C and D are OH;
E is S, or O;
X is hydrogen, halogen, alkyl of 1–6 carbon atoms, CN, alkoxy of 1–6 carbon atoms, aryloxy of 6–12 carbon atoms; arylalkoxy of 6–12 carbon atoms, arylsulfanyl, or pyridylsulfanyl;
Y and Z are H;
or a pharmaceutically acceptable salt thereof.
3. The compound according to claim 1, wherein
A is hydrogen;
B and D are each, independently, halogen, alkyl of 1–6 carbon atoms, aryl or aralkyl of 6–12 carbon atoms, or alkoxy of 1–6 carbon atoms;
C is OR$^4$
E is S, O;
X is hydrogen, halogen, alkyl of 1–6 carbon atoms, perfluoroalkyl of 1–6 carbon atoms, CN, alkoxy of 1–6 carbon atoms, aryloxy, arylalkoxy of 6–12 carbon atoms, arylsulfanyl, pyridylsulfanyl;
Y and Z are H;
R$^4$ is H, alkyl of 1–6 carbon atoms, -CH(R$^5$)W, or 5-thiazolidine-2,4-dione;
R$^5$ is H, alkyl of 1–6 carbon atoms, aralkyl of 6–12 carbon atoms, aryl, -CH$_2$(3-1 H-indolyl ), -CH$_2$CH$_2$(1,3-dioxo-1,3-dihydro-isoindol-2-yl), -CH$_2$CH$_2$(1-oxo-1,3-dihydro-isoindol-2-yl), or -CH$_2$(3-pyridyl);
W is -CO$_2$R$^6$, -CONH$_2$, -CONHOH, -5-tetrazole, or -PO$_3$(R$^6$)$_2$;
R$^6$ is hydrogen or alkyl of 1–6 carbon atoms;
or a pharmaceutically acceptable salt thereof.
4. The compound of claim 1, which is (R)-2-[2,6-dibromo-4-(6-bromo-benzo [b]naphtho[2,3-d]furan-11-yl)-phenoxy]-3-phenyl-propionic acid or a pharmaceutically acceptable salt thereof.
5. The compound of claim 1, which is (R)-2-[2,6-dibromo-4-(6-bromo-benzo [b]naphtho[2,3-d]thiophen-11-yl)-phenoxy]-3-phenyl-propionic acid or a pharmaceutically acceptable salt thereof.
6. The compound of claim 1, which is (5'-benzo[b]naphtho[2,3-d]thiophen-11-yl )-[1,1';3', 1"]terphenyl-2'-yloxy)-acetic acid or a pharmaceutically acceptable salt thereof.
7. The compound of claim 1, which is (R)-2-[2,6-dibromo-4-(6-iodo-benzo [b]naphtho[2,3-d]thiophen-11-yl]-phenoxyl-3-phenyl-propionic acid or a pharmaceutically acceptable salt thereof.
8. The compound of claim 1, which is 2-[2,6-dibromo-4-(6-bromo-benzo [b]naphtho[2,3-d]thiophen-11-yl)-phenoxyl-3-(4-fluoro-phenyl)-propionic acid or a pharmaceutically acceptable salt thereof.
9. The compound of claim 1, which is (R)-2-[2-bromo-4-(6-bromo-benzo [b]naphtho[2,3-d]thiophen-11-yl)-6-methoxy-phenoxy]-3-phenyl-propionic acid or a pharmaceutically acceptable salt thereof.
10. The compound of claim 1, which is (R)-2-[2,6-dibromo-4-(6-bromo-benzo [b]naphtho[2,3-d]thiophen-1-yl)-phenoxy]-propionic acid or a pharmaceutically acceptable salt thereof.
11. The compound of claim 1, which is (R)-2-[2,6-dibromo-4-(6-iodo-benzo [b]naphtho[2,3-d]thiophen-11-yl]-phenoxy]-propionic acid or a pharmaceutically acceptable salt thereof.
12. The compound of claim 1, which is 2-[2,6-dibromo-4-(6-bromo-benzo [b]naphtho[2,3-d]thiophen-11-yl)-phenoxy]-hexanoic acid or a pharmaceutically acceptable salt thereof.
13. The compound of claim 1, which is (R)-2-[2,6-dibromo-4-(6-methoxy-benzo [b]naphtho[2,3-d]thiophen-11-yl)-phenoxy]-3-phenyl-propionic acid or a pharmaceutically acceptable salt thereof.
14. The compound of claim 1, which is (R)-2-{2,6-dibromo-4-(6-chloro-benzo [b]naphtho[2,3-d]thiophen-11- yl]-phenoxy}-3-phenyl-propionic acid or a pharmaceutically acceptable salt thereof.

15. The compound of claim 1, which is (R)-2-[2,6-dibromo-4-(6-phenylsulfanyl-benzo [b]naphtho[2,3-d]thiophen-11-yl)-phenoxy]-3-phenyl-propionic acid or a pharmaceutically acceptable salt thereof.

16. The compound of claim 1, which is (R)-2-[2,6-dibromo-4-(6-phenylsulfanyl-benzo [b]naphtho[2,3-d]thiophen-11-yl)-phenoxy]-propionic acid or a pharmaceutically acceptable salt thereof.

17. The compound of claim 1, which is (R,S)-2-[2,6-dibromo-4-(6-bromo-benzo [b]naphtho[2,3-d]thiophen-11-yl)-phenoxy]-3-( 1H-indol-3-yl)-propionic acid or a pharmaceutically acceptable salt thereof.

18. The compound of claim 1, which is (R)-benzo[b]naphtho[2,3-d]thiophen-11-yl-2, 6-diiodo-phenoxy)-3-phenyl-propionic acid or a pharmaceutically acceptable salt thereof.

19. The compound of claim 1, which is (R)-2-[2,6-dibromo-4-(6-bromo-benzo [b]naphtho[2,3-d]thiophen-11-yl)-phenoxy]-3-phenyl-butyric acid or a pharmaceutically acceptable salt thereof.

20. The compound of claim 1, which is (R)-2-[2,6-dibromo-4-(6-trifluoromethyl-benzo [b]naphtho[2,3-d]thiophen-11-yl)-phenoxy]-3-phenyl- propionic acid or a pharmaceutically acceptable salt thereof.

21. The compound of claim 1, which is (S)-2-[2,6-dibromo-4-(6-bromo-benzo [b]naphtho[2,3-d]thiophen-11-yl)-phenoxyl-3-phenyl-butyric acid or a pharmaceutically acceptable salt thereof.

22. The compound of claim 1, which is (R)-2-(4-benzo[b]naphtho[2,3-d]thiophen-11-yl-2,6-dibromo-phenoxy)-4-(1, 3-dioxo- 1, 3-dihydro-isoindol-2-yl)-butyric acid or a pharmaceutically acceptable salt thereof.

23. The compound of claim 1, which is (R)-2-[2,6-dibromo-4-(6-bromo-benzo [b]naphtho[2,3-d]thiophen-11-yl)-phenoxy]-4-(1, 3-dioxo- 1, 3-dihydro-isoindol-2-yl)-butyric acid or a pharmaceutically acceptable salt thereof.

24. The compound of claim 1, which is {1-[2,6-dibromo-4-(6-bromo-benzo [b]naphtho[2,3-d]thiophen-11-yl)-phenoxy]-3-phenyl-propyl }-phosphonic acid, diethyl ester or a pharmaceutically acceptable salt thereof.

25. The compound of claim 1, which is (R)-2-{2,6-dibromo-4-[6-(pyridin-4-ylsulfanyl )-benzo[b]naphtho[2,3-d]thiophen-11-yl]-phenoxy }-3-phenyl-propionic acid or a pharmaceutically acceptable salt thereof.

26. The compound of claim 1, which is (R)-2-[4-(6-benzyloxy-benzo [b]naphtho[2,3-d]thiophen-11-yl]-2-6-dibromo-phenoxy }-3-phenyl-propionic acid or a pharmaceutically acceptable salt thereof.

27. The compound of claim 1, which is (S)-2-[2,6-dibromo-4-(6-bromo-benzo [b]naphtho[2,3-d]thiophen-11-yl)-phenoxy]-3-phenyl-propionic acid, methyl ester or a pharmaceutically acceptable salt thereof.

28. The compound of claim 1, which is (R)-[2,6-dibromo-4-(6-bromo-benzo [b]naphtho[2,3-d]thiophen-11-yl)-phenoxy]-phenyl-acetic acid or a pharmaceutically acceptable salt thereof.

29. The compound of claim 1, which is [2,6-dibromo-4-(6-bromo-benzo [b]naphtho[2,3-d]thiophen-11-yl)-phenoxy]-acetic acid or a pharmaceutically acceptable salt thereof.

30. The compound of claim 1, which is [2,6-dibromo-4-(6-bromo-benzo [b]naphtho[2,3-d]thiophen-11-yl)-phenoxymethyl]-phosphonic acid or a pharmaceutically acceptable salt thereof.

31. The compound of claim 1, which is [2,6-dibromo-4-(6-cyano-benzo [b]naphtho[2,3-d]thiophen-11-yl)-phenoxy]-acetic acid or a pharmaceutically acceptable salt thereof.

32. The compound of claim 1, which is 2-[2,6-dibromo-4-(6-bromo-benzo [b]naphtho[2,3-d]thiophen-11-yl)-phenoxy]-3-naphthalen-2yl-propionic acid or a pharmaceutically acceptable salt thereof.

33. The compound of claim 1, which is (2R)-2-[2,6-dibromo-4-(6-bromo-benzo [b]naphtho[2,3-d]thiophen-11 -yl)-phenoxy]-4-( 1 -oxo- 1, 3-dihydro-isoindol-2-yl)-butyric acid or a pharmaceutically acceptable salt thereof.

34. The compound of claim 1, which is (R)-2-[2,6-dibromo-4-(6-methyl-benzo [b]naphtho[2,3-d]thiophen-11-yl)-phenoxyl-3-phenyl-propionic acid or a pharmaceutically acceptable salt thereof.

35. The compound of claim 1, which is (R)-5-{l-[2,6-dibromo-4-(6-bromo-benzo [b]naphtho[2,3-d]thiophen-11-yl)-phenoxyl-2-phenyl-ethyl }- 1H-tetrazole or a pharmaceutically acceptable salt thereof.

36. The compound of claim 1, which is (R)-2-[2,6-dibromo-4-(6-bromo-benzo [b]naphtho[2,3-d]thiophen-11-yl)-phenoxy]-N-hydroxy-3-phenyl-propionamide or a pharmaceutically acceptable salt thereof.

37. The compound of claim 1, which is 5-[2,6-dibromo-4-(6-bromo-benzo [b]naphtho[2,3-d]thiophen-11-yl)-phenoxy]-thiazolidinedione-2,4-dione or a pharmaceutically acceptable salt thereof.

38. The compound of claim 1, which is (R)-2-(4-benzo[b]naphtho[2,3-d]thiophen-11-yl-2,6-diiodo-phenoxy)-propionic acid or a pharmaceutically acceptable salt thereof.

39. The compound of claim 1, which is 2-[2,6-dibromo-4-(6-bromo-benzo [b]naphtho[2,3-d]thiophen-11-yl)-phenoxy]-3-pyridin-3-yl-propionic acid.

40. The compound of claim 1, which is (2R)-2-[4-(6-bromo-benzo[b]naphtho[2,3-d ]thiophen-11 -yl)-2,6-diisopropyl-phenoxy)-3-phenyl-propionic acid or a pharmaceutically acceptable salt thereof.

41. The compound of claim 1, which is 4-(6-bromo-benzo [b]naphtho[2,3-d ]thiophen-11-yl)-2,6-diisopropyl-phenol or a pharmaceutically acceptable salt thereof.

42. The compound of claim 1, which is 4-(6-bromo-benzo [b]naphtho[2,3-d ]thiophen-11-yl)-benzene-1,2-diol or a pharmaceutically acceptable salt thereof.

43. The compound of claim 1, which is 3-bromo-5-(6-bromo-benzo[b]naphtho[2,3-d ]thiophen-11-yl)-benzene-1,2-diol or a pharmaceutically acceptable salt thereof.

44. The compound of claim 1, which is 4-bromo-5-(6-bromo-benzo[b]naphtho[2,3-d ] thiophen-11-yl)-benzene-1,2-diol or a pharmaceutically acceptable salt thereof.

45. The compound of claim 1, which is [2, 6-dibromo-4-(6-bromo-benzo [b]naphtho[2,3-d]furan-11-yl)-phenoxy]-acetic acid or a pharmaceutically acceptable salt thereof.

46. The compound of claim 1, which is 2, 6-dibromo-4-(6-bromo-benzo [b]naphtho[2,3-d]furan-11yl)-phenol or a pharmaceutically acceptable salt thereof.

47. The compound of claim 1, which is [4-(6-bromo-benzo[b]naphtho[2,3-d ]thiophen-11-yl)-2,6-diisopropyl-phenoxy)-acetic acid or a pharmaceutically acceptable salt thereof.

48. The compound of claim 1, which is
4-benzo[b]naphtho[2,3-d]thiophen-11-yl-phenol;
11-(4-hydroxy-phenyl)-benzo[b]naphtho[2,3-d]thiophen-3-ol;
4-(6-benzo[b]naphtho[2,3-d]thiophen-11-yl)-2,6-diisopropyl-phenol;
3-benzo[b]naphtho[2,3-d]thiophen-11-yl)-phenol;
4-(benzo[b]naphtho[2,3-d]thiophen-11-yl)-benzene-1,2-diol;
8-methoxy-11-(4-methoxy-phenyl)-benzo[b]naphtho[2,3-d]thiophene;

11-(4-hydroxy-phenyl)-benzo[b]naphtho[2,3-d]thiophen-8-ol;

2,6-dibromo-4-(6-bromo-benzo[b]naphtho[2,3-d]thiophen-11-yl)-phenol;

11-(3,5-dibromo-4-methoxy-phenyl)-benzo[b]naphtho[2,3-d]thiophene;

11-(4-methoxy-phenyl)-benzo[b]naphtho[2,3-d]thiophene;

11-(4-methoxy-3,5-dimethyl-phenyl)-6-methyl-benzo[b]naphtho[2,3-d]thiophene;

2,6-dimethyl-4-(6-methyl-benzo[b]naphtho[2,3-d]thiophen-11-yl)-phenol;

4-(benzo[b]naphtho [2,3-d]thiophen-11-yl)-2,6-diiodo-phenol;

4-(benzo[b]naphtho[2,3-d]thiophen-11-yl)-2-iodo-phenol;

11-(4-methoxy-3,5-diiodo-phenyl)-benzo[b]naphtho[2,3-d]thiophene;

11-(3-iodo-4-methoxy-phenyl)-benzo[b]naphtho[2,3-d)thiophene;

5-benzo[b]naphtho[2,3-d]thiophen-11-yl-2-methoxy-isophthalonitrile;

5-(benzo[b]naphtho[2,3-d]thiophen-11-yl)-2-methoxy-benzonitrile;

5-benzo[b]naphtho[2,3-d]thiophen-11-yl-2-hydroxy-isophthalonitrile;

5-benzo[b]naphtho[2,3-d]thiophen-11-yl-2-hydroxy-benzonitrile;

4-(benzo[b]naphtho[2,3-d]thiophen-11-yl-phenol) acetate ester;

acetic acid 3-benzo[b]naphtho[2,3-d]thiophen-11-yl)-phenyl ester;

acetic acid 2-acetoxy-4-(benzo[b]naphtho[2,3-d]thiophen-11-yl )-phenyl ester;

4-(6-bromo-benzo [b]naphtho [2,3-d]thiophen-11-yl-phenol) acetate;

acetic acid 3-(6-bromo-benzo[b]naphtho[2,3-d]thiophen-1-yl)-phenyl ester;

acetic acid 2-acetoxy-4-(6-bromo-benzo[b]naphtho [2,3-d]thiophen-11-yl)-phenyl ester;

4-(6-bromo-benzo[b]naphtho[2,3-d]thiophen-11-yl)-phenol;

3(6-bromo-benzo [b]naphtho[2,3-d]thiophen-11-yl)-phenol;

11-(4-hydroxy-phenyl)-benzo [b]naphtho[2,3-d]thiophene-6-carbonitrile;

methanesulfonic acid 4-benzo[b]naphtho[2,3-d]thiophen-11-yl-phenyl ester;

methanesulfonic acid 4-(6-chloro-benzo[b]naphtho[2,3-d]thiophen-11-yl)-phenyl ester;

methanesulfonic acid 4-(6-iodo-benzo[b]naphtho[2,3-d]thiophen-11-yl)-phenyl ester;

methanesulfonic acid 4-(6-trifluoromethyl-benzo[b]naphtho[2,3-d] thiophen-11-yl)-phenyl ester;

methanesulfonic acid 4-(6-methyl-benzo[b]naphtho[2,3-d]thiophen-11-yl)-phenyl ester;

4-(6-chloro-benzo[b]naphtho[2,3-d]thiophen-11-yl)-phenol;

4-(6-iodo-benzo[b]naphtho[3,3-d]thiophen-11-yl)-phenol;

4-(6-trifluoromethyl-benzo[b]naphtho[2,3-]thiophen-11-yl)-phenol;

4-(6-methyl-benzo[b]naphtho[2,3-d]thiophen-11-yl)-phenol;

4-(6-methoxy-benzo[b]naphtho[2,3-d]thiophen-11-yl)-phenol;

4-(6-phenylsufanyl-benzo[b]naphtho[2,3-d]thiophen-11-yl)-phenol;

4-[6-(2-dimethylamino-ethylsulfanyl)-benzo[b]naphtho[2,3-d]thiophen-11-yl]-phenol;

4-[6-(pyridin-4-ylsulfanyl)-benzo[b]naphtho[2,3-d]thiophen-11-yl]-phenol;

11-(3, 5-dibromo-4-hydroxy- phenyl)-benzo[b]naphtho[2,3-d]thiophene-6-carbonitrile;

2,6-dibromo-4-(6-iodo-benzo[b]naphtho[2,3-d]thiophen11-yl)-phenol;

2,6-dibromo-4-(6-chloro-benzo[b]naphtho[2,3-d]thiophen-11-yl)-phenol;

2,6-dibromo-4-(6-trifluoromethyl-benzo[b]naphtho[2,3-d]thiophen-11-yl)-phenol;

2,6-dibromo-4-(6-methyl-benzo[b]naphtho[2,3-d]thiophen-11-yl)-phenol;

2,6-dibromo-4-(6-methoxybenzo[b]naphtho[2,3-d]thiophen-11-yl-phenol;

2,6-dibromo-4-(6-phenylsulfanyl-benzo[b]naphtho[2,3-d]thiophen-11-yl)-phenol;

2,6-dibromo-4-[6-(pyridin-4-ylsulfanyl)-benzo[b]naphtho[2,3-d]thiophen-11-yl]-phenol;

2,6-dibromo-4-[6-(2-dimethylamino-ethylsulfanyl)-benzo[b]naphtho[2,3-d]thiophen-11 -yl]-phenol;

2,6-dichloro-4-(6-hromo-benzo[b]naphtho[2,3-d]thiophen-11-yl)-phenol;

2-bromo-5-(6-bromo-benzo[b]naphtho[2,3-d]thiophen-11-yl)-phenol;

2,4-dibromo-5-(6-bromo-benzo[b]naphtho[2,3-d]thiophen-11-yl)-phenol;

[11-(4-hydroxy-phenyl)-benzo[b]naphtho[2,3-d]thiophen-3-yloxy]-acetic acid methyl ester;

[11-(4-methoxycarbonylmethoxy-phenyl)-benzo[b]naphtho[2,3-d]thiophen-3-yloxy]-acetic acid methyl ester;

[1-(4-carboxymethoxy-phenyl)-benzo[b]naphtho[2,3-d]thiophen-3-yloxyl-acetic acid;

[1-(4-methoxycarbonylmethoxy-phenyl)-benzo[b]naphtho[2,3-d]thiophen-8-yloxy]-acetic acid, methyl ester;

[11-(4-carboxymethoxy-phenyl)-benzo[b]naphtho[2,3-d]thiophen-8-yloxy]-acetic acid;

[2,6-dibromo-4-(6-bromo-benzo[b]naphtho[2,3-d]thiophen-11-yl)-phenoxy]-acetic acid, methyl ester;

[2,6-dibromo-4-(6-bromo-benzo[b]naphtho[2,3-d]thiophen-11-yl)-phenoxy]-acetic acid, tert-butyl ester;

[2,6-dibromo-4-(6-bromo-benzo[b]naphtho[2,3-d]thiophen-11-yl)-phenoxy]-acetic acid, sodium salt;

[(4-benzo[b]naphtho[2,3-d]thiophen-11-yl)-2,6-dicyano-phenoxy]-acetic acid;

[(4-benzo[b]naphtho[2,3-d]thiophen-11-yl)-2-cyano-phenoxy]-acetic acid;

[4-benzo[b]naphtho[2,3-d]thiophen-11-yl-2,6-diiodo-phenoxy]-acetic acid;

[4-benzo[b]naphtho[2,3-d]thiophen-11-yl-phenoxy]-acetic acid;

[4-benzo[b]naphtho[2,3-d]thiophen-11-yl-2-iodo-phenoxy]-acetic acid;

{2,6-dimethyl-4-[6-methyl-(benzo[b]naphtho[2,3-d]thiophen-11-yl)]-phenoxy}-acetic acid;

[4-(6-bromo-benzo[b]naphtho[2,3-d]thiophen-11-yl)-phenoxy]-acetic acid;

[3-(6-bromo-benzo [b]naphtho[2,3-d]thiophen-11 -yl)-phenoxyl]-acetic acid;

[2-bromo-5-(6-bromo-benzo[b]naphtho[2,3-d]thiophen-11-yl)-phenoxyl]-acetic acid;

[2,4-dibromo-5-(6-bromo-benzo[b]naphtho[2,3-d]thiophen-11-yl)-phenoxyl]-acetic acid;

5-(6-bromo-benzo[b]naphtho[2,3-d]thiophen-11-yl)-2-carboxymethoxy-phenoxyl]-acetic acid;

3-bromo-5-(6-bromo-benzo[b]naphtho[2,3-d]thiophen-11-yl)-2-carboxymethoxy-phenoxyl ]-acetic acid;

4-bromo-5-(6-bromo-benzo[b]naphtho[2,3-d]thiophen-11-yl)-2-carboxymethoxy-phenoxyl ]-acetic acid;

(R)-2-[2,6-dibromo-4-(6-bromo-benzo[b]naphtho[2,3-d]thiophen-11-yl)-phenoxy]-3-phenyl-propionic acid, methyl ester;

(R)-2-[2,6-dibromo-4-(6-bromo-benzo[b]naphtho[2,3-d]thiophen-11-yl)-phenoxy]-3-phenyl-propionic acid, sodium salt;

S)-2-[2,6-dibromo-4-(6-bromo-benzo[b]naphtho[2,3-d]thiophen-11-yl)-phenoxy]-3-phenyl-propionic acid;

R)-2-[2,6-dibromo-4-(6-methoxy-benzo[b]naphtho[2,3-d]thiophen-11-yl)-phenoxy]-3-phenyl-propionic acid, methyl ester;

(S)-2-[4-(6-bromo-benzo[b]naphtho[2,3-d]thiophen-11-yl)-phenoxy]-3-phenyl-propionic acid;

(S)-2-[2,6-dibromo-4-(6-cyano-benzo[b]naphtho[2,3-d]thiophen-11-yl)-phenoxy]-3-phenyl-propionic acid;

(R)-2-[4-(6-cyano-benzo[b]naphtho[2,3-d]thiophen-11-yl)-phenoxy]-3-phenyl-propionic acid;

(R)-2-[4-(benzo[b]naphtho[2,3-d]thiophen-11-yl)-phenoxy]-3-phenyl-propionic acid (R)-2-[4-(3-carboxymethoxy-benzo[b]naphtho[2,3-d]thiophen-11-yl)-phenoxy-3-phenyl-propionic acid;

(R)-2-[2,6-dibromo-4-(6-bromo-benzo[b]naphtho[2,3-d]thiophen-11-yl)-phenoxy]-3-(1 H-imidazol-4-yl)-propionic acid, hydrochloride;

(R)-2-[2,6-dichloro-4-(6-bromo-benzo[b]naphtho[2,3-d]thiophen-11-yl)-phenoxy]-3-phenyl-propionic acid;

(R)-2-{2,6-dibromo-4-[6-(2-dimethylamino-ethylsulfanyl)-benzo[b]naphtho[2,3-d ]thiophen-11-yl]-phenoxy}-3-phenyl-propionic acid;

(R)-2-[2,6-dimethyl-4-(6-methyl-benzo[b]naphtho[2,3-d]thiophen-11-yl)-phenoxy]-3-phenyl-propionic acid;

(R)-2-[4-(6-bromo-benzo[b]naphtho[2,3-d]thiophen-11-yl)-2,6-diisopropyl-phenoxy)-propionic acid;

(S)-2-[2-bromo-5-(6-bromo-benzo[b]naphtho[2,3-d]thiophen-11-yl)-phenoxyl]-propionic acid;

(R)-2-[2-bromo-5-(6-Bromo-benzo[b]naphtho[2,3-d]thiophen-11-yl)-phenoxyl]-propionic acid;

(R)-2-[2,6-dibromo-4-(6-bromo-benzo[b]naphtho[2,3-d]thiophen-11-yl)-phenoxy]-4-(1, 3-dioxo-1,3-dihydro-isoindol-2-yl)-butyric acid, methyl ester;

(R)-2-(4-benzo[b]naphtho[2,3-d]thiophen-11-yl)-phenoxy)-4-(1, 3-dioxo- 1, 3-dihydro-isoindol-2-yl)-butyric acid;

(R)-2-[4-(3-carboxymethoxy-benzo[b]naphtho[2,3-d]thiophen-11-yl)-phenoxy-4-(1, 3-dioxo-1, 3-dihydro-isoindol-2-yl)-butyric acid;

(R)-2-[4-(6-bromo-benzo[b]naphtho[2,3-d]thiophen-11-yl)-phenoxy] -4-(1, 3-dioxo-1, 3-dihydro-isoindol-2-yl)-butyric acid;

(R)-2-[2,6-dibromo-4-(6-bromo-benzo[b]naphtho[2,3-d]thiophen-11-yl)-phenoxy]-succinic acid dimethyl ester;

(R)-2-[2,6-dibromo-4-(6-bromo-benzo[b]naphtho[2,3-d]thiophen-11-yl)-phenoxy]-succinic acid;

2-[2,6-dibromo-4-(6-bromo-benzo[b]naphtho[2,3-d]thiophen-11-yl)-phenoxy]-3-(4-fluoro-phenyl-propionic acid tert-butyl ester;

(R)-2-[2,6-dibromo-4-(6-bromo-benzo[b]naphtho[2,3-d]thiophen-11-yl)-phenoxy]-3-napthalen-2-yl-propionic acid tert-butyl ester;

{2,6-dibromo-4-[6-bromo-benzo[b]naphtho[2,3-d]thiophen-11-yl)]-phenoxymethyl }-phosphonic acid diethyl ester;

[4-(benzo[b]naphtho[2,3-d]thiophen-11-yl)-phenoxymethyl]-phosphonic acid diethyl ester;

[4-(benzo[b]naphtho[2,3-d]thiophen-11-yl)-phenoxymethyl]-phosphonic acid;

{1-[2,6-dibromo-4-(6-bromo-benzo[b]naphtho[2,3-d]thiophen-11-yl)-phenoxy]-3-phenyl-propyl}-phosphonic acid;

2-[2,6-dibromo-4-(6-bromo-benzo[b]naphtho[2,3-d]thiophen-11-yl)-phenoxy]-acetarnide;

(R)-2-[2,6-dibromo-4-(6-bromo-benzo[b]naphtho[2,3-d]thiophen-11-yl)-phenoxyl-3-phenyl-propionamide;

(R)-2-[2,6-dibromo-4-(6-bromo-benzo[b]naphtho[2,3-d]thiophen-11-yl)-phenoxy]-N-(3-nitrolo-propyl)3-phenyl-propionamide;

[2,6-dibromo-4-(6-bromo-benzo[b]naphtho[2,3-d]thiophen-11-yl)-phenoxy]-acetonitrile;

(R)-2-[2,6-dibromo-4-(6-bromo-benzo[b]naphtho[2,3-d]thiophen-11-yl)-phenoxy]-3-phenyl-propionitrile;

5-[2,6-dibromo-4-(6-bromo-benzo[b]naphtho[2,3-d]thiophen-11-yl)-phenoxymethyl]-1H-tetrazole;

(R)-6-bromo-11-[3,5-dibromo-4-(1-hydroxymethyl-2-phenyl-ethoxy)-phenyl]-benzo [b]naphtho[2,3-d]thiophene;

(R)-6-bromo-1 -[3,5-dibromo-4-( 1 -bromomethyl-2-phenyl-ethoxy)-phenyl]-benzo [b]naphtho[2,3-d]thiophene;

phosphoric acid di-tert-butyl ester 2,6-dibromo-4-(6-bromo-benzo[b]naphtho[2,3-d ]thiophen-11-yl)-phenyl ester;

phosphoric acid mono-[2,6-dibromo-4-(6-bromo-benzo[b]naphtho[2,3-d]thiophen-1-yl)-phenyl ] ester;

2-[2,6-dibromo-4-(6-bromo-benzo[b]naphtho[2,3-d]thiophen-11-yl)-phenoxy]-2-methyl-propionic acid;

3-[2,6-dibromo-4-(6-bromo-benzo[b]naphtho[2,3-d]thiophen-11-yl)-phenoxy]-propionic acid;

(R)-3-[2,6-dibromo-4-(6-bromo-benzo[b]naphtho[2,3-d]thiophen-11-yl)-phenoxy]-butyric acid;

(R)-2-[4-(6-fydroxy-benzo[b]naphtho[2,3-d]thiophen-11-yl)-2,6-dibromo-phenoxy]-3-phenyl-propionic acid, methyl ester;

(R)-2-[4-(6-benzyloxy-benzo[b]naphtho[2,3-d]thiophen-11-yl]-2,6-dibromo-phenoxy]-3 -phenyl-propionic acid, methyl ester;

(R)-2-[2,6-dibromo-4-(6-methoxycarbonylmethoxy-benzo[b]naphtho[2,3-d]thiophen-11 -yl)-phenoxy]-3-phenyl-propionic acid methyl ester;

(R)-2-[2,6-dibromo-4-(6-carboxymethoxy-benzo[b]naphtho[2,3-d]thiophen-11-yl)-phenoxy ]-3-phenyl-propionic acid;

[2,6-dibromo-4-(6-bromo-5,5-dioxo-5 H-6-benzo[b]naphtho[2,3-d]thiophen-11-yl)]-phenoxy ]-acetic acid;

[2,6-dibromo-4-[6-bromo-5-oxo-5H-4-benzo[b]naphtho[2,3-d]thiophen-11-yl)]-phenoxy ]-acetic acid;

(R)-2-[2,6-dibromo-4-(6-bromo-5,5- dioxo-5 H-5(λ6)-benzo[b]naphtho[2,3-d]thiophen-11 -yl)-phenoxy]-3-phenyl-propionic acid, methyl ester;

(R)-2-[2,6-dibromo-4-(6-bromo-5,5- dioxo-5 H-5(λ6)-benzo[b]naphtho[2,3-d]thiophen-11 -yl)-phenoxy]-3-phenyl-propionic acid;

5'-benzo[b]naphtho[2,3-d]thiophen-11-yl-[1,1';3',1"]terphenyl-2'-ol 3-bromo-5-(6-bromo-benzo[b]naphtho[2,3-d]thiophen-11-yl)-2-benzyloxy-phenol;

2-bromo-4-(6-bromo-benzo[b]naphtho[2,3-d]thiophen-11-yl)-6-methoxy-phenol;

3-bromo-5-(6-bromo-benzo[b]naphtho[2,3-d]thiophen-11-yl)-2-methoxy-phenol;

(R)-2-[3-bromo-5-(6-bromo-benzo[b]naphtho[2,3-d]thiophen-11-yl)-2-methoxy-phenoxy ]-3-phenyl-propionic acid;

3-(benzo[b]naphtho[2,3-d]thiophen-11-yl)-2,6 difluoro-phenol;

3-(6-bromo-benzo[b]naphtho[2,3-d]thiophen-11-yl)-2,6 difluoro-phenol;

[3-(6-bromo-benzo[b]naphtho[2,3-d]thiophen-11-yl)-2,6-difluoro-phenoxy]-acetic acid;

(R)-2-[3-(6-bromo-benzo[b]naphtho[2,3-d]thiophen-11-yl)-2,6-difluoro-phenoxy]-propionic acid;

(R)-2-[3-(6-bromo-benzo[b]naphtho[2,3-d]thiophen-11-yl)-2,6-difluoro-phenoxy]-3-phenyl-propionic acid;

4-benzo[b]naphtho[2,3-d]furan-11yl)-phenol;

4-(benzo[b]naphtho[2,3-d]furan-11-yl)-benzene-1,3-diol;

2,6-dibromo-4-(6-bromo-benzo[b]naphtho[2,3-d]furan-11-yl)-3-hydroxy-phenol;

4-(benzo[b]naphtho[2,3-d]furan-11-yl-phenoxy)-acetic acid methy ester;

4-(benzo[b]naphtho[2,3-d]furan-11-yl-phenoxy)-acetic acid;

[2,6-dibromo-4-(6-bromo-benzo[b]naphtho[2,3-d]furan-11-yl)-phenoxy]-acetic acid methyl ester; or

[2,6-dibromo-4-(6-bromo-benzo[b]naphtho[2,3-d]furan-11-yl)-3-hydroxy-phenoxy]-acetic acid;

or a pharmaceutically acceptable salt thereof.

49. A method of treating metabolic disorders mediated by insulin resistance or hyperglycemia in a mammal in need thereof which comprises administering to said mammal, a compound of formula I having the structure

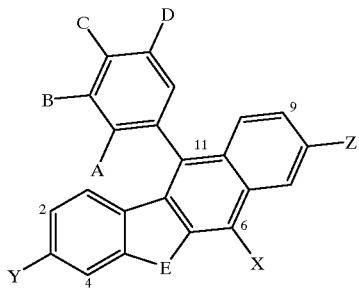

(I)

wherein

A is hydrogen, halogen, or OH;

B and D are each, independently, hydrogen, halogen, CN, alkyl of 1–6 carbon atoms, aryl, aralkyl of 6–12 carbon atoms, nitro, amino or OR;

R is hydrogen, alkyl of 1–6 carbon atoms, -COR$^1$, -CH$_2$CO$_2$R$^1$, -CH(R$^{1a}$)CO$_2$R$^1$, or -SO$_2$R$^1$;

R$^1$ and R$^{1a}$ are each, independently, hydrogen, alkyl of 1–6 carbon atoms, aralkyl of 6–12 carbon atoms or aryl;

E is S, SO, SO$_2$, O;

X is hydrogen, halogen, alkyl of 1–6 carbon atoms, CN, perfluoroalkyl of 1–6 carbon atoms, alkoxy of 1–6 carbon atoms, aryloxy, arylalkoxy of 6–12 carbon atoms, nitro, amino, alkylsulfanyl of 1–6 carbon atoms, arylsulfanyl, pyridylsulfanyl, 2-N,N-dimethylaminoethylsulfanyl, or -OCH$_2$CO$_2$R$^{1b}$;

R$^{1b}$ is hydrogen or alkyl of 1–6 carbon atoms;

Y and Z are each, independently, hydrogen or OR$^2$;

R$^2$ is hydrogen, alkyl of 1–6 carbon atoms, aralkyl of 6–12 carbon atoms, or -CH$_2$CO$_2$R$^3$;

R$^3$ is hydrogen or alkyl of 1–6 carbon atoms;

C is hydrogen, halogen or OR$^4$;

R$^4$ is hydrogen, alkyl of 1–6 carbon atoms, -CH(R$^5$)W, -C(CH$_3$)$_2$CO$_2$R$^6$, 5-thiazolidine-2,4-dione, -CH(R$^7$)CH$_2$CO$_2$R$^6$, -COR$^6$, PO$_3$(R$^6$)$_2$, or -SO$_2$R$^6$;

R$^5$ is hydrogen, alkyl of 1–6 carbon atoms, aralkyl, aryl, CH$_2$(1 H-imidazol-4-yl), -CH$_2$( 3-1 H - indolyl), -CH$_2$CH$_2$(1,3-dioxo-1,3-dihydro-isoindol-2-yl), -CH$_2$CH$_2$(1-oxo-1,3-dihydro-isoindol-2-yl), -CH$_2$(3-pyridyl), or -CH$_2$CO$_2$H;

W is -CO$_2$R$^6$, -CONH$_2$, -CONHOH, CN, -CONH(CH$_2$)$_2$CN, 5-tetrazole, -PO$_3$(R$^6$)$_2$, -CH$_2$OH, or -CH$_2$Br, -CONR$^6$CHR$^7$CO2R$^8$, R$^6$ is hydrogen, alkyl of 1–6 carbon atoms, aryl or aralkyl;

R$^7$ is hydrogen, alkyl of 1–6 carbon atoms, aryl or aralkyl;

R$^8$ is hydrogen, alkyl of 1–6 carbon atoms, aryl or aralkyly.

50. A method of treating or inhibiting type II diabetes in a mammal in need thereof which comprises administering to said mammal, a compound of formula I having the structure

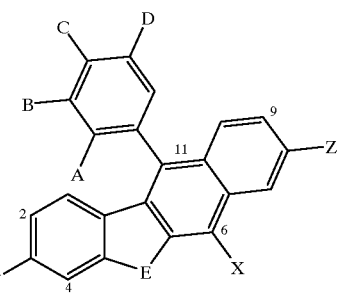

(I)

wherein

A is hydrogen, halogen, or OH;

B and D are each, independently, hydrogen, halogen, CN, alkyl of 1–6 carbon atoms, aryl, aralkyl of 6–12 carbon atoms, nitro, amino or OR;

R is hydrogen, alkyl of 1–6 carbon atoms, —COR$^1$, —CH$_2$CO$_2$R$^1$, —CH(R$^{1a}$)CO$_2$R$^1$, or —SO$_2$R$^1$;

R$^1$ and R$^{1a}$ are each, independently, hydrogen, alkyl of 1–6 carbon atoms, aralkyl of 6–12 carbon atoms or aryl;

E is S, SO, SO$_2$, O;

X is hydrogen, halogen, alkyl of 1–6 carbon atoms, CN, perfluoroalkyl of 1–6 carbon atoms, alkoxy of 1–6 carbon atoms, aryloxy, arylalkoxy of 6–12 carbon atoms, nitro, amino, alkylsulfanyl of 1–6 carbon atoms, arylsulfanyl, pyridylsulfanyl, 2—N,N-dimethylaminoethylsulfanyl, or —OCH$_2$CO$_2$R$^{1b}$;

R$^{1b}$ is hydrogen or alkyl of 1–6 carbon atoms;

Y and Z are each, independently, hydrogen or OR$^2$;

R$^2$ is hydrogen, alkyl of 1–6 carbon atoms, aralkyl of 6–12 carbon atoms, or —CH$_2$CO$_2$R$^3$;

R$^3$ is hydrogen or alkyl of 1–6 carbon atoms;

C is hydrogen, halogen or OR$^4$;

R$^4$ is hydrogen, alkyl of 1–6 carbon atoms, —CH(R$^5$)W, —C(CH$_3$)$_2$CO$_2$R$^6$, 5-thiazolidine-2,4-dione, —CH(R$^7$)CH$_2$CO$_2$R$^6$, —COR$^6$, PO$_3$(R$^6$)$_2$, or —SO$_2$R$^6$;

R$^5$ is hydrogen, alkyl of 1–6 carbon atoms, aralkyl, aryl, CH$_2$(1H-imidazol-4-yl), —CH$_2$(3-1 H - indolyl), —CH$_2$ CH$_2$( 1,3-dioxo-1,3-dihydro-isoindol-2-yl), —CH$_2$CH$_2$(1-oxo-1,3-dihydro-isoindol-2-yl), —CH$_2$(3-pyridyl), or —CH$_2$CO$_2$H;

W is —CO$_2$R$^6$, —CONH$_2$, —CONHOH, CN, —CONH(CH$_2$)$_2$CN, 5-tetrazole, —PO$_3$(R$^6$)$_2$, —CH$_2$OH, or —CH$_2$Br, —CONR$^6$CHR$^7$CO2R$^8$, R$^6$ is hydrogen, alkyl of 1–6 carbon atoms, aryl or aralkyl;

R$^7$ is hydrogen, alkyl of 1–6 carbon atoms, aryl or aralkyl;

R$^8$ is hydrogen, alkyl of 1–6 carbon atoms, aryl or aralkyl;

or a pharmaceutically acceptable salt thereof.

51. A method of modulating glucose levels in a mammal in need thereof which comprises administering to said mammal, a compound of formula I having the structure

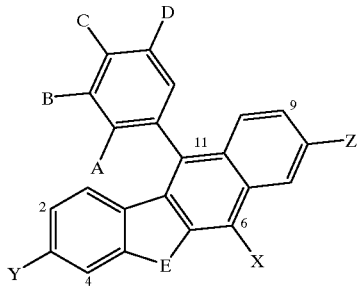

(I)

wherein

A is hydrogen, halogen, or OH;

B and D are each, independently, hydrogen, halogen, CN, alkyl of 1–6 carbon atoms, aryl, aralkyl of 6–12 carbon atoms, nitro, amino or OR;

R is hydrogen, alkyl of 1–6 carbon atoms, —COR$^1$, —CH$_2$CO$_2$R$^1$, —CH(R$^{1a}$)CO$_2$R$^1$, or —SO$_2$R$^1$;

R$^1$ and R$^{1a}$ are each, independently, hydrogen, alkyl of 1–6 carbon atoms, aralkyl of 6–12 carbon atoms or aryl;

E is S, SO, SO$_2$, O;

X is hydrogen, halogen, alkyl of 1–6 carbon atoms, CN, perfluoroalkyl of 1–6 carbon atoms, alkoxy of 1–6 carbon atoms, aryloxy, arylalkoxy of 6–12 carbon atoms, nitro, amino, alkylsulfanyl of 1–6 carbon atoms, arylsulfanyl, pyridylsulfanyl, 2—N,N-dimethylaminoethylsulfanyl, or —OCH$_2$CO$_2$R$^{1b}$;

R$^{1b}$ is hydrogen or alkyl of 1–6 carbon atoms;

Y and Z are each, independently, hydrogen or OR$^2$;

R$^2$ is hydrogen, alkyl of 1–6 carbon atoms, aralkyl of 6–12 carbon atoms, or —CH$_2$CO$_2$R$^3$;

R$^3$ is hydrogen or alkyl of 1–6 carbon atoms;

C is hydrogen, halogen or OR$^4$;

R$^4$ is hydrogen, alkyl of 1–6 carbon atoms, —CH(R$^5$)W, —C(CH$_3$)$_2$CO$_2$R$^6$, 5-thiazolidine-2,4-dione, —CH(R$^7$)CH$_2$CO$_2$R$^6$, —COR$^6$, PO$_3$(R$^6$)$_2$, or —SO$_2$R$^6$;

R$^5$ is hydrogen, alkyl of 1–6 carbon atoms, aralkyl, aryl, CH$_2$(1 H-imidazol-4-yl), —CH$_2$(3-1 H -indolyl), —CH$_2$ CH$_2$(1,3-dioxo-1,3-dihydro-isoindol-2-yl), —CH$_2$CH$_2$(1-oxo-1,3-dihydro-isoindol-2-yl), —CH$_2$(3-pyridyl), or —CH$_2$CO$_2$H;

W is -CO$_2$R$^6$, -CONH$_2$, -CONHOH, CN, -CONH(CH$_2$)$_2$CN, 5-tetrazole, -PO$_3$(R$^6$)$_2$, —CH$_2$OH, or —CH$_2$Br, —CONR$^6$CHR$^7$CO2R$^8$, R$^6$ is hydrogen, alkyl of 1–6 carbon atoms, aryl or aralkyl;

R$^7$ is hydrogen, alkyl of 1–6 carbon atoms, aryl or aralkyl;

R$^8$ is hydrogen, alkyl of 1–6 carbon atoms, aryl or aralkyl;

or a pharmaceutically acceptable salt thereof.

52. A pharmaceutical composition which comprises a compound of formula I having the structure

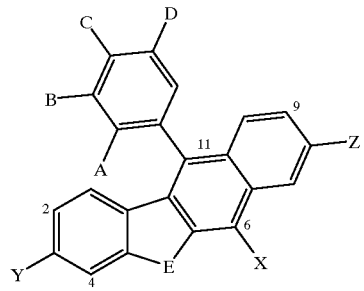

(I)

wherein

A is hydrogen, halogen, or OH;

B and D are each, independently, hydrogen, halogen, CN, alkyl of 1–6 carbon atoms, aryl, aralkyl of 6–12 carbon atoms, nitro, amino or OR;

R is hydrogen, alkyl of 1–6 carbon atoms, —COR$^1$, —CH$_2$CO$_2$R$^1$, —CH(R$^{1a}$)CO$_2$R$^1$, or —SO$_2$R$^1$;

R$^1$ and R$^{1a}$ are each, independently, hydrogen, alkyl of 1–6 carbon atoms, aralkyl of 6–12 carbon atoms or aryl;

E is S, SO, SO$_2$, O;

X is hydrogen, halogen, alkyl of 1–6 carbon atoms, CN, perfluoroalkyl of 1–6 carbon atoms, alkoxy of 1–6 carbon atoms, aryloxy, arylalkoxy of 6–12 carbon atoms, nitro, amino, alkylsulfanyl of 1–6 carbon atoms, arylsulfanyl, pyridylsulfanyl, 2—N,N-dimethylaminoethylsulfanyl, or —OCH$_2$CO$_2$R$^{1b}$;

R$^{1b}$ is hydrogen or alkyl of 1–6 carbon atoms;

Y and Z are each, independently, hydrogen or OR$^2$;

R$^2$ is hydrogen, alkyl of 1–6 carbon atoms, aralkyl of 6–12 carbon atoms, or —CH$_2$CO$_2$R$^3$;

R$^3$ is hydrogen or alkyl of 1–6 carbon atoms;

C is hydrogen, halogen or OR$^4$;

R$^4$ is hydrogen, alkyl of 1–6 carbon atoms, —CH(R$^5$)W, —C(CH$_3$)$_2$CO$_2$R$^6$, 5-thiazolidine-2,4-dione, —CH(R$^7$)CH$_2$CO$_2$R$^6$, —COR$^6$, PO$_3$(R$^6$)$_2$, or —SO$_2$R$^6$;

$R^5$ is hydrogen, alkyl of 1–6 carbon atoms, aralkyl, aryl, $CH_2$(1H-imidazol-4-yl), —$CH_2$( 3-1 H -indolyl), —$CH_2$ $CH_2$(1,3-dioxo-1,3-dihydro-isoindol-2-yl), —$CH_2CH_2$(1-oxo-1,3-dihydro-isoindol-2-yl), —$CH_2$ (3-pyridyl), or —$CH_2CO_2H$;

W is —$CO_2R^6$, —$CONH_2$, —CONHOH, CN, —CONH$(CH_2)_2$CN, 5-tetrazole, —$PO_3(R^6)_2$, —$CH_2OH$, or —$CH_2Br$, —$CONR^6CHR^7CO2R^8$, $R^6$ is hydrogen, alkyl of 1–6 carbon atoms, aryl or aralkyl;

$R^7$ is hydrogen, alkyl of 1–6 carbon atoms, aryl or aralkyl;

$R^8$ is hydrogen, alkyl of 1–6 carbon atoms, aryl or aralkyl;

or a pharmaceutically acceptable salt thereof, and a pharmaceutical carrier.

* * * * *